US012543711B2

(12) United States Patent
McWhirter et al.

(10) Patent No.: US 12,543,711 B2
(45) **Date of Patent: *Feb. 10, 2026**

(54) NON-HUMAN ANIMALS EXPRESSING pH-SENSITIVE IMMUNOGLOBULIN SEQUENCES

(71) Applicant: Regeneron Pharmaceuticals, Inc., Tarrytown, NY (US)

(72) Inventors: John McWhirter, Greenville, NC (US); Lynn Macdonald, Harrison, NY (US); Joel H. Martin, Putnam Valley, NY (US); Andrew J. Murphy, Croton-on-Hudson, NY (US)

(73) Assignee: Regeneron Pharmaceuticals, Inc, Tarrytown, NY (US)

( * ) Notice: Subject to any disclaimer, the term of this patent is extended or adjusted under 35 U.S.C. 154(b) by 1048 days.

This patent is subject to a terminal disclaimer.

(21) Appl. No.: 17/545,099

(22) Filed: Dec. 8, 2021

(65) Prior Publication Data

US 2022/0217955 A1 Jul. 14, 2022

Related U.S. Application Data

(63) Continuation of application No. 15/703,490, filed on Sep. 13, 2017, now Pat. No. 11,224,207, which is a continuation of application No. 13/834,129, filed on Mar. 15, 2013, now Pat. No. 9,801,362.

(60) Provisional application No. 61/736,930, filed on Dec. 13, 2012, provisional application No. 61/613,352, filed on Mar. 20, 2012, provisional application No. 61/612,126, filed on Mar. 16, 2012, provisional application No. 61/611,950, filed on Mar. 16, 2012.

(51) Int. Cl.

| | |
|---|---|
| ***A01K 67/0275*** | (2024.01) |
| ***A01K 67/0278*** | (2024.01) |
| ***C07K 16/00*** | (2006.01) |
| ***C12N 15/85*** | (2006.01) |

(52) U.S. Cl.

CPC ...... *A01K 67/0275* (2013.01); *A01K 67/0278* (2013.01); *C07K 16/00* (2013.01); *C12N 15/8509* (2013.01); *A01K 2217/072* (2013.01); *A01K 2217/075* (2013.01); *A01K 2217/15* (2013.01); *A01K 2227/105* (2013.01); *A01K 2267/01* (2013.01); *C07K 2317/10* (2013.01); *C07K 2317/21* (2013.01); *C07K 2317/92* (2013.01); *C07K 2317/94* (2013.01); *C12N 2800/204* (2013.01)

(58) Field of Classification Search

None

See application file for complete search history.

(56) References Cited

U.S. PATENT DOCUMENTS

| | | | |
|---|---|---|---|
| 5,545,806 | A | 8/1996 | Lonberg et al. |
| 5,545,807 | A | 8/1996 | Surani et al. |
| 5,603,931 | A | 2/1997 | Raso |
| 5,667,988 | A | 9/1997 | Barbas et al. |
| 5,999,908 | A | 12/1999 | Abelow |
| 6,096,551 | A | 8/2000 | Barbas et al. |
| 6,162,963 | A | 12/2000 | Kucherlapati et al. |
| 6,586,251 | B2 | 7/2003 | Economides et al. |
| 6,596,541 | B2 | 7/2003 | Murphy et al. |
| 6,673,986 | B1 | 1/2004 | Kucherlapati et al. |
| 6,774,279 | B2 | 8/2004 | Dymecki |
| 6,946,548 | B2 | 9/2005 | Sarkar et al. |
| 7,052,873 | B2 | 5/2006 | Tsuchiya |
| 7,067,284 | B1 | 6/2006 | Barbas et al. |
| 7,105,348 | B2 | 9/2006 | Murphy et al. |
| 7,183,076 | B2 | 2/2007 | Arathoon et al. |

(Continued)

FOREIGN PATENT DOCUMENTS

| | | | |
|---|---|---|---|
| CN | 1277632 | A | 12/2000 |
| CN | 1484707 | A | 3/2004 |

(Continued)

OTHER PUBLICATIONS

UniPro Accession No. P01619, Human KV3-20, downloaded from https://www.uniprot.org/uniprotkb/P01619/entry#sequences on Apr. 17, 2025.*

(Continued)

*Primary Examiner* — Christopher M Babic
*Assistant Examiner* — Kimberly A Aron
(74) *Attorney, Agent, or Firm* — FisherBroyles, LLP; Rita S. Wu; Margarita Zippin

(57) ABSTRACT

Genetically modified non-human animals are provided that express an immunoglobulin variable domain that comprises at least one histidine, wherein the at least one histidine is encoded by a substitution of a non-histidine codon in the germline of the animal with a histidine codon, or the insertion of a histidine codon in a germline immunoglobulin nucleic acid sequence. Immunoglobulin genes comprising histidines in one or more CDRs, in an N-terminal region, and/or in a loop 4 region are also provided. Immunoglobulin variable domains comprising one or more histidines (e.g., histidine clusters) substituted for non-antigen-binding non-histidine residues. Non-human animals that are progeny of animals comprising modified heavy chain variable loci (V, D, J segments), modified light chain variable loci (V, J segments), and rearranged germline light chain genes (VJ sequences) are also provided. Non-human animals that make immunoglobulin domains that bind antigens in a pH-sensitive manner are provided.

27 Claims, 57 Drawing Sheets

Specification includes a Sequence Listing.

(56) References Cited

U.S. PATENT DOCUMENTS

| | | | |
|---|---|---|---|
| 7,262,028 | B2 | 8/2007 | Van Berkel et al. |
| 7,276,585 | B2 | 10/2007 | Lazar et al. |
| 7,294,754 | B2 | 11/2007 | Poueymirou et al. |
| 7,435,871 | B2 | 10/2008 | Green et al. |
| 7,501,552 | B2 | 3/2009 | Lonberg et al. |
| 7,576,259 | B2 | 8/2009 | Poueymirou et al. |
| 7,659,442 | B2 | 2/2010 | Poueymirou et al. |
| 7,879,985 | B2 | 2/2011 | Ursøet al. |
| 7,910,798 | B2 | 3/2011 | Tanamachi et al. |
| 8,062,640 | B2 | 11/2011 | Sleeman et al. |
| 8,080,243 | B2 | 12/2011 | Liang et al. |
| 8,158,419 | B2 | 4/2012 | Lonberg et al. |
| 8,502,018 | B2 | 8/2013 | Murphy et al. |
| 8,642,835 | B2 | 2/2014 | Macdonald et al. |
| 9,301,510 | B2 | 4/2016 | McWhirter et al. |
| 9,332,742 | B2 | 5/2016 | McWhirter et al. |
| 9,334,334 | B2 | 5/2016 | McWhirter et al. |
| 9,422,370 | B2 | 8/2016 | McWhirter et al. |
| 2002/0088016 | A1 | 7/2002 | Bruggemann |
| 2003/0078385 | A1 | 4/2003 | Arathoon et al. |
| 2003/0108925 | A1 | 6/2003 | Dix et al. |
| 2004/0018626 | A1 | 1/2004 | Murphy et al. |
| 2005/0170398 | A1 | 8/2005 | Van Berkel et al. |
| 2006/0015949 | A1 | 1/2006 | Lonberg et al. |
| 2006/0015957 | A1 | 1/2006 | Lonberg et al. |
| 2006/0088838 | A1 | 4/2006 | Murray et al. |
| 2006/0099207 | A1 | 5/2006 | Wu et al. |
| 2006/0141456 | A1 | 6/2006 | Edwards et al. |
| 2006/0199204 | A1 | 9/2006 | Dix et al. |
| 2007/0061900 | A1 | 3/2007 | Murphy et al. |
| 2007/0280945 | A1 | 12/2007 | Stevens et al. |
| 2008/0069822 | A1 | 3/2008 | Jensen et al. |
| 2008/0078000 | A1 | 3/2008 | Poueymirou et al. |
| 2009/0035836 | A1 | 2/2009 | Datta et al. |
| 2009/0181855 | A1 | 7/2009 | Vasquez et al. |
| 2010/0069614 | A1 | 3/2010 | Houtzager et al. |
| 2010/0146647 | A1 | 6/2010 | Logtenberg et al. |
| 2010/0310586 | A1 | 12/2010 | Dolcetti et al. |
| 2010/0331527 | A1 | 12/2010 | Davis et al. |
| 2011/0076275 | A1 | 3/2011 | Igawa et al. |
| 2011/0098450 | A1 | 4/2011 | Igawa et al. |
| 2011/0111406 | A1 | 5/2011 | Igawa et al. |
| 2011/0145937 | A1 | 6/2011 | McWhirter et al. |
| 2011/0195454 | A1 | 8/2011 | McWhirter et al. |
| 2011/0229489 | A1 | 9/2011 | Pons et al. |
| 2012/0021409 | A1 | 1/2012 | McWhirter et al. |
| 2012/0167237 | A1 | 6/2012 | Bradley et al. |
| 2012/0192300 | A1 | 7/2012 | Babb et al. |
| 2012/0204278 | A1 | 8/2012 | Bradley et al. |
| 2012/0322108 | A1 | 12/2012 | Macdonald et al. |
| 2013/0011866 | A1 | 1/2013 | Igawa et al. |
| 2013/0045492 | A1 | 2/2013 | Babb et al. |
| 2013/0145484 | A1 | 6/2013 | Logtenberg et al. |
| 2013/0185821 | A1 | 7/2013 | Babb et al. |
| 2013/0198880 | A1 | 8/2013 | Babb et al. |
| 2013/0247234 | A1 | 9/2013 | McWhirter et al. |
| 2013/0247235 | A1 | 9/2013 | McWhirter et al. |
| 2013/0302836 | A1 | 11/2013 | McWhirter et al. |
| 2014/0013456 | A1 | 1/2014 | McWhirter et al. |
| 2014/0329711 | A1 | 11/2014 | McWhirter et al. |
| 2015/0059009 | A1 | 2/2015 | McWhirter et al. |
| 2015/0119556 | A1 | 4/2015 | McWhirter et al. |
| 2015/0250151 | A1 | 9/2015 | McWhirter et al. |
| 2015/0313193 | A1 | 11/2015 | McWhirter et al. |
| 2016/0219847 | A1 | 8/2016 | McWhirter et al. |
| 2016/0229906 | A1 | 8/2016 | McWhirter et al. |
| 2016/0311899 | A1 | 10/2016 | McWhirter et al. |
| 2017/0369593 | A1 | 12/2017 | McWhirter et al. |
| 2019/0021295 | A1 | 1/2019 | Babb et al. |
| 2019/0029237 | A1 | 1/2019 | McWhirter et al. |
| 2019/0040123 | A1 | 2/2019 | McWhirter et al. |
| 2019/0071519 | A1 | 3/2019 | McWhirter et al. |
| 2019/0077884 | A1 | 3/2019 | McWhirter et al. |
| 2019/0090462 | A1 | 3/2019 | Babb et al. |

FOREIGN PATENT DOCUMENTS

| | | | |
|---|---|---|---|
| CN | 1560081 | A | 1/2005 |
| EP | 1439234 | A1 | 7/2004 |
| EP | 0843961 | B1 | 1/2007 |
| EP | 1605058 | B1 | 5/2009 |
| EP | 2147594 | A1 | 1/2010 |
| EP | 2275443 | A1 | 1/2011 |
| EP | 2505654 | A1 | 10/2012 |
| EP | 2517556 | A2 | 10/2012 |
| EP | 2517557 | A2 | 10/2012 |
| EP | 2556747 | A2 | 2/2013 |
| EP | 2564695 | A1 | 3/2013 |
| EP | 2825036 | B1 | 5/2018 |
| WO | 1992/003918 | A1 | 3/1992 |
| WO | 1994/002602 | A1 | 2/1994 |
| WO | 1996/034096 | A1 | 10/1996 |
| WO | 1998/046645 | A2 | 10/1998 |
| WO | 1998/050431 | A2 | 11/1998 |
| WO | 2002/020767 | A2 | 3/2002 |
| WO | 2002/036789 | A2 | 5/2002 |
| WO | 2004/009618 | A2 | 1/2004 |
| WO | 2004/106375 | A1 | 12/2004 |
| WO | 2005/007696 | A2 | 1/2005 |
| WO | 2006/117699 | A2 | 11/2006 |
| WO | 2007/117410 | A2 | 10/2007 |
| WO | 2008/043822 | A2 | 4/2008 |
| WO | 2008/054606 | A2 | 5/2008 |
| WO | 2008/076379 | A2 | 6/2008 |
| WO | 2008/112922 | A2 | 9/2008 |
| WO | 2009/125825 | A1 | 10/2009 |
| WO | 2009/157771 | A2 | 12/2009 |
| WO | 2010/039900 | A2 | 4/2010 |
| WO | 2010/053751 | A1 | 5/2010 |
| WO | 2010/070263 | A1 | 6/2010 |
| WO | 2010/128897 | A1 | 11/2010 |
| WO | 2011/004192 | A1 | 1/2011 |
| WO | 2011/072204 | A1 | 6/2011 |
| WO | 2011/097603 | A1 | 8/2011 |
| WO | 2011/111007 | A2 | 9/2011 |
| WO | 2011/122011 | A2 | 10/2011 |
| WO | 2011/158009 | A1 | 12/2011 |
| WO | 2011/163314 | A1 | 12/2011 |
| WO | 2012/141798 | A1 | 10/2012 |
| WO | 2012/148873 | A2 | 11/2012 |
| WO | 2013/022782 | A1 | 2/2013 |
| WO | 2013/046722 | A1 | 4/2013 |
| WO | 2013/079953 | A1 | 6/2013 |
| WO | 2013/134263 | A1 | 9/2013 |
| WO | 2013/184761 | A1 | 12/2013 |
| WO | 2014/130690 | A1 | 8/2014 |
| WO | 2010/136598 | A1 | 12/2020 |

OTHER PUBLICATIONS

Adderson, E. et al., Restricted immunoglobulin VH usage and VDJ combinations in the human response to Haemophilus influenzae type b capsular polysaccharide. Nucleotide sequences of monospecific anti-Haemophilus antibodies and polyspecific antibodies cross-reacting with self antigens, J Clin Invest., 91(6):2734-43 (1993).

Arnold et al., (1994) "Development of B-1 cells: Segregation of Phosphatidyl Choline-specific B Cells to the B-1 Population Occurs after Immunoglobulin Gene Expression," J. Exp. Med., 179:1585-1595.

Aucouturier et al., (1992) "Human rearranged IgK mRNA VJC region," GenBank Accession No. M87478 1 page, first referenced Mar. 3, 1992, first seen at NCBI Apr. 27, 1993.

Aucouturier et al., (1993) "Monoclonal Ig L chain and L chain V domain fragment crystallization in myeloma-associated Fanconi's syndrome," J. Immunol., 150(8):3561-3568.

Auerbach et al., (2000) "Establishment and Chimera Analysis of 129/SvEv- and C57BL/6-Derived Mouse Embryonic Stem Cell Lines," BioTechniques 29:1024-1032.

Basu, (1984) "Receptor-mediated endocytosis: An overview of a dynamic process," J. Biosci. 6(4):535-542.

(56) References Cited

OTHER PUBLICATIONS

Bauer et al., (1988) "Structure and pre-B lymphocyte restricted expression of the VpreB gene in humans and conservation of its structure in other mammalian species," The EMBO Journal, 7(1):111-116.
Beguinot et al., (1984) "Down-regulation of the epidermal growth factor receptor in KB cells is due to receptor internalization and subsequent degradation in lysosomes," PNAS, 81:2384-2388.
Bostrom et al., (2009) "Variants of the Antibody Herceptin That Interact with HER2 and VEGF at the Antigen Binding Site," Science, 323(5921):1610-1614 and supplementary pages (8 pages).
Bot et al., (1996) "$V_\lambda$-Light Chain Genes Reconstitute Immune Responses to Defined Carbohydrate Antigens or Haptens by Utilizing Different $V_H$ Genes," Molecular Immunology, 33(17/18):1359-1368.
Brevini et al., (2010) "No shortcuts to pig embryonic stem cells," Theriogenology 74:544-550.
Brezinschek et al., (1998) "Pairing of Variable Heavy and Variable κ Chains in Individual Naïve and Memory B Cells," J. Immunol., 160(10):4762-4767.
Brown et al., (1983) "Recycling Receptors: The Round-Trip Itinerary of Migrant Membrane Proteins," Cell, 22:663-667.
Bruggemann (1997) "The Preparation of Human Antibodies from Mice Harbouring Human Immunoglobulin Loci," (Edited by L. M. Houdebine) Transgenic Animals: Generation and Use, Amsterdam: Harwood Acedemic Publishers, pp. 397-403.
Cao et al., (2009) "Isolation and Culture of Primary Bovine Embryonic Stem Cell Colonies by a Novel Method," Journal of Experimental Zoology, 311A:368-376.
Carmack et al., (1991) "Influence of a V κ 8 L chain transgene on endogenous rearrangements and the immune response to the HA(Sb) determinant of influenza virus," J. Immunol., 147(6):2024-2033.
Carter, (2001) "Bispecific human IgG by design," Journal of Immunological Methods, 248(1-2):7-15.
Cascalho et al., (1996) "A Quasi-Monoclonal Mouse," Science, 272(5268):1649-1652.
Chaparro-Riggers et al., (2012) "Increasing Serum Half-life and Extending Cholesterol Lowering in Vivo by Engineering Antibody with pH-sensitive Binding to PCSK9," J. Biol. Chem. 287(14):11090-11097.
Chen et al., (1994) "Deletion and Editing of B Cells that Express Antibodies to DNA," Journal of Immunology, 152:1970-1982.
Choi et al., (2004) "Characterization and comparative genomic analysis of intronless Adams with testicular gene expression," Genomics 83(4): 636-646.
Clark et al., "Trends in Antibody Sequence Changes during the Somatic Hypermutation Process," J. Immunol., 2006, 177:333-340.
Corbett et al., (1997) "Sequence of the Human Immunoglobulin Diversity (D) Segment Locus: A Systematic Analysis Provides No Evidence for the Use of DIR Segments, Inverted D Segments, "Minor" D Segments or D-D Recombination," J. Mol. Biol. 270:587-597.
Dall'Acqua et al., (2006) "Properties of Human IgG1s Engineered for Enhanced Binding to the Neonatal Fc Receptor (FcRn)," J. Biol. Chem. 281:23514-23524.
Davies et al., (1993) "Creation of Mice Expressing Human Antibody Light Chains by Introduction of a Yeast Artificial Chromosome Containing the Core Region of the Human Immunoglobulin κ Locus," Nature Biotechnology 11:911-914.
De Kruif et al., (2009) "Human Immunoglobulin Repertoires against Tetanus Toxoid Contain a Large and Diverse Fraction of High-Affinity Promiscuous VH Genes," J. Mol. Biol., 387:548-558.
De Wildt et al., (1999) "Analysis of heavy and light chain pairings indicates that receptor editing shapes the human antibody repertoire," J. Mol. Biol., 285(3): 895-901.
Dechiara et al., (2009) Chapter 16: VelociMouse: Fully ES Cell-Derived FO Generation Mice Obtained from the Injection of ES Cells into 8-Cell Stage Embryos, Gene Knockout Protocols: Second Edition, vol. 530, Humana Press.
Deng et al., (2010) "Pharmacokinetics of Humanized Monoclonal Anti-Tumor Necrosis Factor-a Antibody and Its Neonatal Fc Receptor Variants in Mice and Cynomolgus Monkeys, Drug Metabolism and Disposition," 38(4):600-605.
Dennis (2002) "Welfare issues of genetically modified animals," ILAR Journal, 43(2):100-109.
Desienhofer, (1981) "Crystallographic Refinement and Atomic Models of a Human Fc Fragment and Its Complex with Fragment B of Protein A from *Staphylococcus aureus* at 2.9- and 2.8-Å Resolution," Biochemistry, 20(9):2361-2370.
Donohoe et al., (2000) "Transgenic Human 5 Rescues the Murine Lambda5 Nullizygous Phenotype," J. Immunol., 164:5269-5276.
Dunn et al., (1989) "Iterative Fractionation of Recycling Receptors from Lysosomally Destined Ligands in an Early Sorting Endosome," J. Cell. Biol. 109(6/2):3303-3314.
Edwards et al., (2008) "The ADAM Metalloproteinases", Molecular Aspects of Medicine, 29(5):258-289.
Fallon et al., (2000) "Increased Endosomal Sorting of Ligand to Recycling Enhances Potency of an Interleukin-2 Analog," J. Biol. Chem. 275(10):6790-6797.
Featherstone et al., (2010) "The Mouse Immunoglobulin Heavy Chain V-D Intergenic Sequence Contains Insulators That May Regulate Ordered V(D)J Recombination," J. Biol. Chem., 285(13):9327-9338.
Festing et al., (1999) "Revised nomenclature for strain 129 mice," Mammalian Genome, 10:836.
Fishwild et al., (1996) "High-avidity human IgGk monoclonal antibodies from a novel train of mililocus transgenic mice," Nat. Biotech., 14(7):845-851.
Fraenkel et al., (2007) "Allelic 'choice' governs somatic hypermutation in vivo at the immunoglobulin kappa-chain locus," Nat. Immunol., 8(7):715-722.
Gan et al., (2009) "Analyses of the recycling receptor, FcRn, in live cells reveal novel pathways for lysosomal delivery," Traffic 10(5):600.
Gay et al., (1993) "Receptor editing: an approach by autoreactive B cells to escape tolerance," J. Exp. Med., 177(4):999-1008.
Giallourakis et al., (2010) "Elements between the IgH variable (V) and diversity (D) clusters influence antisense transcription and lineage-specific V(D)K recombination," PNAS, 107(51):22207-22212.
Goldstein and Brown, (2009) "The LDL Receptor," Arterioscler. Thromb. Vasc. Biol. 29:431-438.
Goletz et al., (2002) "Selection of Large Diversities of Antiidiotypic Antibody Fragments by Phage Display", J. Mol. Biol. 315:1087-1097.
Gonnet et al., (1992) "Exhaustive Matching of the Entire Protein Sequence Database," Science 256:1443-1445.
Gonzalez-Fernandez et al., (1993) "Analysis of somatic hypermutation in mouse Peyer's patches using immunoglobulin κ light-chain transgenes," PNAS, 90:9862-9866.
Goodhardt et al., (1987), "Rearrangement and Expression of rabbit immunoglobulin K light chain gene in transgenic mice," PNAS, 84:4229-4233.
Goyenechea et al., (1996) "Modifying the sequence of an immunoglobulin V-gene alters the resulting pattern of hypermutation," PNAS, 93:13979-13984.
Goyenechea et al., (1997) "Cells strongly expressing Ig(kappa) transgenes show clonal recruitment of hypermutation: a role for both MAR and the enhancers," EMBO J., 16(13):3987-94.
Green et al., (1994) "Antigen-specific human monoclonal antibodies from mice engineered with human Ig heavy and light chain YACs," Nat. Genet., 7(1):13-21.
Green et al., (1998) "Regulation of B cell development by variable gene complexity in mice reconstituted with human immunoglobulin yeast artificial chromosomes," J. Exp. Med., 188(3):483-495.
Green et al., (1999) "Antibody engineering via geneitc engineering of the mouse: XenoMouse strains are a vehicle for the facile generation of therapeutic human monoclonal antibodies," J. Immunol. Methods, 231:11-23.
Han et al., 2009) "Comprehensive Analysis of Reproductive ADAMs: Relationship of ADAM4 and ADAM6; with an ADAM Complex Required for Fertilization in Mice", Biol. Reprod., 80(5):1001-1008.

(56) References Cited

OTHER PUBLICATIONS

Hardy and Hayakawa, (2001) "B cell development pathways," Annu. Rev. Immunol., 19:595-621.
Hartley and Goodnow (1993) "Censoring of self-reactive B cells with a range of receptor affinities in transgenic mice expressing heavy chains for a lysozyme-specific antibody," International Immunology, 6(9):1417-1425.
Hendricks et al., (2010) "Organization of the variable region of the immunoglobin heavy-chain gene locus of the rat," Immunogenetics, 62:479-486.
Hengstschlager et al., (1994) "A lambda 1 transgene under the control of a heavy chain promoter and enhancer does not undergo somatic hypermutation," Eur. J. Immunol., 24:1649-1656.
Hochedlinger et al., (2002) "Monoclonal Mice Generated by Nuclear Transfer from Mature B and T Donor Cells," Nature 415(6875):1035-1038.
Hoi and Ippolito (2013) Intrinsic bias and public rearrangements in the human immunoglobulin Vλ light chain repertoire, Genes and Immunity, 14:271-276.
Hömig-Hölzel et al., (2008) "Constitutive CD40 signaling in B cells selectively activates the noncanonical NF-kappaB pathway and promotes lymphomagenesis," J. Exp. Med., 205(6):1317-1329.
Houdebine (2009) Methods to Generate Transgenic Animals, Genetic Engineering in Livestock, New Applications and Interdisciplinary Perspectives, Engelhard M, et al., 2009, XVI, 1 46 p. 8 illus., pp. 31-47, see p. 36.
Igawa et al., (2010) "Reduced elimination of IgG antibodies by engineering the variable region," Protein Engineering, Design & Selection, 23(5):385-392.
Igawa et al., (2010) "Antibody recycling by engineered pH-dependent antigen binding improves the duration of antigen neutralization," Nature Biotech., 28(11):1203-1208 and supplement.
Igawa et al., (2011) "Engineering the variable region of therapeutic IgG antibodies," mAbs, 3(3):243-252.
Inlay et al., (2002) "Essential roles of the kappa light chain intronic enhancer and 3' enhancer in kappa rearrangement and demethylation," Nat. Immunol., 3(5):463-468.
Ippolito, (2006) "Forced usage of positively charged amino acids in immunoglobulin CDR-H3 impairs B cell development and antibody production," J. Exp. Med. 203(6):1567-1578.
Ito et al. (1992) "The His-probe method: effects of histidine residues introduced into the complementary-determining regions of antibodies on antigen-antibody interactions at different pH values," FEBS Lett. 309(1):85-88.
Ivanov et al., (2002) on the Hydropathicity and Sequence Composition of HCDR3 are Conserved Across Evolution, The Antibodies, vol. 7, M. Zanetti and J. D. Capra, eds.Taylor & Francis Group, London, Chapter 3, pp. 43-67.
Jakobovits, (1995) "Production of fully human antibodies by transgenic mice," Curr. Opin. Biotechnol., 6(5):561-566.
Jakobovits et al., (2007) "From XenoMouse technology to panitumumab, the first fully human antibody product from transgenic mice," Nature Biotech., 25(10):1134-1143.
Janeway's Immunobiology, (2008) Seventh Edition, Murphy, Travers and Walpot, eds., Garland Science, New York and London, Ch. 4, pp. 145-155.
Jendeberg et al., (1997) "Engineering of Fc1 and Fc3 from human immunoglobulin G to analyse subclass specificity for staphylococcal protein A1," Journal of Immunologial Methods, 201:25-34.
Jolly et al., (1997) "Rapid methods for the analysis of immunoglobulin gene hypermutation: application to transgenic and gene targeted mice," Nucleic Acids Research, 25(10):1913-1919.
Kabat and Wu, (1991) "Identical V region amino acid sequences and segments of sequences in antibodies of different specificities. Relative contributions of VH and VL genes, minigenes, and complementarity-determining regions to binding of antibody-combining sites," J. Immunol., 147(5):1709-1719.
Kaushik, (1990) "Stochastic pairing of heavy-chain and x light-chain variable gene families occurs in polyclonally activated B cells," Proc. Natl. Acad. Sci. USA, 87: 4932-4936.
Kim et al., (2006) "Expression and relationship of mail reproductive ADAMs in mouse," Biol. Reprod., 74:744-750.
Klöhn et al., (2013) "IBC's 23rd Annual Antibody Engineering, 10th Annual Antibody Therapeutics international conferences and the 2012 Annual Meeting of The Antibody Society: Dec. 3-6, 2012," San Diego, CA, Mabs, 5(2):178-201.
Klotz et al., (1996) "Somatic Hypermutation of a lambda 2 Transgene Under the Control of the lambda Enhancer or the Heavy Chain Intron Enhancer," J. Immunol., 157:4458-4463.
Klotz et al. (1998)"Somatic Hypermutation of an Artificial Test Substrate Within an Igκ Transgene," J. Immunol., 161:782-790.
Knappik et al. (2000) "Fully Synthetic Human Combinatorial Antibody Libraries (HuCAL) Based on Modular Consensus Frameworks and CDRs Randomized with Trinucleotides," JMB, 296:57-86.
Kong et al., (1998) "A lambda 3' enhancer drives active and untemplated somatic hypermutation of a lambda 1 transgene," J. Immunol., 161:294-301.
Kufer et al., (2004) "A revival of bispecific antibodies," Trends Biotechnol. 22(5):238-244.
Lee and Owen, (2012) "The application of transgenic mice for therapeutic antibody discovery," Methods in Mol. Biol. 901:137-148.
Lencer, et al. (2005) "A passionate kiss, then run: exocytosis and recycling of IgG by FcRn," Trends in Cell Biol. 15(1):5-9.
Lefranc, (2000) "Nomenclature of the Human Immunoglobulin Genes," Current Protocols in Immunology, Supplement 40, pp. A.1P.1-A.1P.37.
Lefranc et al. (2003) "IMGT unique numbering for immunoglobulin and T cell receptor variable domains and Ig superfamily V-like domains," Dev. Comp. Immunol. 27:55-77, www.imgt.org.
Leitzgen et al., (1997) "Assembly of immunoglobulin Light Chains as a Prerequisite for Secretion," J. Biol. Chem., 272(5):3117-3123.
Lindhofer et al., (1995) "Preferential Species-Restricted Heavy/Light Chain Pairing in Rat/Mouse Quadromas," J. Immunol., 155:219-225.
Link and Schroeder, (2002) Clues to the etiology of autoimmune diseases through analysis of immunoglobulin genes, Arthritis Research, 4(2):80-83 (Available online http://arthritisresearch.com/content/4/2/080).
Logtenberg, (2007) "Antibody cocktails: next-generation biopharmaceuticals with improved potency," Trends Biotechnol., 25(9):390-394.
Lonberg et al., (1994) "Antigen-specific Human Antibodies from Mice Comprising Four Distinct Genetic Modifications," Nature 368:856-859.
Lonberg, (2005) "Human antibodies from transgenic animals," Nature Biotech., 23(9):1117-1125.
Longo et al., (2008) "Characterization of immunoglobulin gene somatic hypermutation in the absence of activation-induced cytidine deaminase," J. Immunol., 181(2):1299-1306.
Macdonald et al. (2006) "Velocigene Technology Extended to Humanization of Several Megabases of complex Gene Loci," First International MUGEN Conference of Animal Models for Human Immunological Disease, Sep. 10-13, 2006—Athens, Greece, Abstract 21 and Poster, 11 pages.
Maeda et al., (2002) "pH-dependent receptor/ligand dissociation as a determining factor for intracellular sorting of ligands for epidermal growth factor receptors in rat hepatocytes," J. Controlled Release, 82:71-82.
Marten Hofker , (2003) "Transgenic mouse methods and protocols," Methods in Molecular Biology, 209:51-58.
Marvin et al., (2005) "Recombinant approaches to IgG-like bispecific antibodies," Acta Pharmacologica Sinica, 26(6):649-658.
Meijer et al., (2006) "Isolation of Human Antibody Repertoires with Preservation of the Natural and Heavy Light Chain Pairing," J. Mol. Biol., 358:764-772.
Mellman, (1992) "The Importance of Being Acidic: The Role of Acidification in Intracellular Membrane Traffic," J. Exp. Biol. 172:39-45.
Mendez et al., (1997) "Functional Transplant of Megabase Human Immunoglobulin Loci Recapitulates Human Antibody Response in Mice," Nat. Genetics 15(2)146-156.

(56) References Cited

OTHER PUBLICATIONS

Merchant et al., (1998) "An efficient route to human bispecific IgG," Nature Biotech., 16(7):677-681.
Moran, (2013) "Mouse Platforms Jostle for Slice of Humanized Antibody Market," Nature Biotech., 3:267-268.
Murtaugh et al., (2011) "A combinatorial histidine scanning library approach to engineer highly pH-dependent protein switches," Protein Sci. 20(9):1619-1631.
Nagle, (2007) "Regeneron helps make Sanofi VelocImmune to its "weak pipeline,"" <http://www.outsourcing-pharma.com>—Published Dec. 3, 2007.
Nakasako et al., (1999) "The pH-dependent Structural Variation of Complementarity-determining Region H3 in the Crystal Structures of the Fv Fragment from an Anti-dansyl Monoclonal Antibody," J. Mol. Biol. 291:117-134.
Nemazee, (2006) "Receptor editing in lymphocyte development and central tolerance," Nat. Rev. Immunol., 6(10):728-740.
News In Brief Article (2007) "Big Pharma vies for mice," Nature Biotechnology, 25(6):613—Published Jun. 2007.
Nicholson et al., (1999) "Antibody Repertoires of Four- and Five-Feature Translocus Mice Carrying Human Immunoglobulin Heavy Chain and kappa and lambda Light Chain Yeast Artificial Chromosomes," J. Immunol., 163:6898-6906.
No Author Listed, Additional post-filing data and letter filed by the Applicant/Patentee for corresponding European application 09075279.1, now opposed patent EP 2147594 B1, 4 pages (Jun. 13, 2013).
No Author Listed, "Next generation transgenic mice for therapeutic human antibodies, Description of MeMoTM," filed by the Applicant/Patentee in prosecution for corresponding European application 09075279.1, now opposed patent EP 2147594 B1, 2 pages (Dec. 22, 2011).
No Author Listed, (2011) Chapter 8: The Development and Survival of Lymphocytes, Janeway's Immunobiology, 8th Edition, Eds. Kenneth Murphy et al, Garland Science (ISBN: 9780815342434), whole document, in particular paqe 279 and Fiqure 8.4.
O'Brien et al., (1987) "Somatic hypermutation of an immunoglobulin transgene in K mice," Nature, 326(6111):405-409.
Orban et al., (1992) "Tissue- and site-specific DNA recombination in transgenic mice," PNAS, 89(15):6861-6865.
Ozato, et al. "Comment on Gene Disruption Study Reveals a Nonredundant Role for TRIM21/Ro52 in NF-κB-Dependent Cytokine Expression in Fibroblasts," The Journal of Immunology, 2009, 183:7619-7621.
Panka et al., (May 1988) "Variable region framework differences result in decreased or increased affinity of variant anti-digoxin antibodies," PNAS, 85:3080-3084.
Paris and Stout (2010) "Equine embryos and embryonic stem cells: Defining reliable markers of pluripotency," Theriogenology 74:516-524.
Paul, (1993) Fundamental Immunology, 3rd ed., Raven Press, NY, Chapter 9, pp. 292-295.
Pelanda et al., (1996) "A prematurely Expressed Igκ Transgene, but Not VκJκ Gene Aegment Targeted into the Igκ Locus, Can Rescue B Cell Development in λ5-Deficient Mice," Immunity, 5(3):229-239.
Petkova et al., (2006) "Enhanced half-life of genetically engineered human IgG1 antibodies in a humanized FcRn mouse model: potential application in humorally mediated autoimmune disease," Intl. Immunol. 18(12):1759-1769.
Phan et al. (2003) "B Cell Receptor-independent Stimuli Trigger Immunoglobulin (Ig) Class Switch Recombination and Production of IgG Autoantibodies by Anergic Self-Reactive B Cells," J. Exp. Med., 197(7):845-860.
Phan et al. (2005) "Altered Migration, Recruitment, and Somatic Hypermutation in the Early Response of Marginal Zone B Cells to T Cell-Dependent Antigen," J. Immunology, 174:4567-4578.
Phan et al. (2006) "High affi nity germinal center B cells are actively selected into the plasma cell compartment," JEM, 203(11):2419-2424.
Popov et al., (1999) "A human immunoglobulin lambda locus is similarly well expressed in mice and humans," J. Exp. Med., 189(10):1611-1620.
Poueymirou et al., (2007) "F0 generation mice that are essentially fully derived from the donor gene-targeted ES cells allowing immediate phenotypic analyses," Nature Biotech. 25(1):91-99.
Poulsen et al., (2011) "Limits for Antibody Affinity Maturation and Repertoire Diversification in Hypervaccinated Humans," J. Immunol., 187:4229-4235.
Prak et al., (1995) "Light chain replacement: a new model for antibody gene rearrangement," J. Exp. Med., 182(2):541-548.
Presta, (2008) "Molecular engineering and design of therapeutic antibodies," Curr. Opin. Immunol. 20(4):460-470.
Rabquer et al., (2005) "Immunoglobulin light chain variable region, partial [*Homo sapiens*]," GenBank Accession No. ABA26122, 2 pages, first reference Dec. 31, 1995.
Raso et al., (1997) "Intracellular Targeting with Low pH-triggered Bispecific Antibodies," J. Biol. Chem. 272(44):27623-27628.
Rickert et al., (1997) "B lymphocyte-specific, Cre-mediated mutagenesis in mice," Nucleic Acids Res., 25(6):1317-1318.
Ritchie et al. (1984) "Allelic exclusion and control of endogenous immunologlobulin gene rearrangement in κ transgenic mice," Nature, 312:517-520.
Roberts et al., (1990) "Isolation and Characterization of the Fc Receptor from Fetal Yolk Sac of the Rat," J. Cell. Biol. 111:1867-1876.
Rojas et al., (2002) "Phage antibody fragments library combining a single human light chain variable region with immune mouse heavy chain variable regions," J. Biotech., 94:287-298.
Roopenian and Sun, (2010) "Clinical Ramifications of the MHC Family Fc Receptor FcRn," J. Clin. Immunol. 30(6):790-797.
Roopenian et al., (Sep. 2007) FcRn: the neonatal Fc receptor comes of age, Nature Rev. Immunol. 7:715-725.
Rudikoff et al., (1982) "Single amino acid substitution altering antigen-binding specificity," PNAS, 79:1979-1983.
Sarkar et al., (2002) "Rational cytokine design for increased lifetime and enhanced potency using pH-activated histidine switching," Nature Biotech. 20:908-913.
Sasaki et al., (2006) "Canonical NF-x13 Activity, Dispensable for B Cell Development, Replaces BAFF-Receptor Signals and Promotes B Cell Proliferation upon Activation," Immunity, 24:729-739.
Schroeder et al., (2010) Genetic control of $D_H$ reading frame and its effect on B cell development and antigen-specific antibody production, Crit. Rev. Immunol., 30(4):327-344.
Schroeder et al., (2006) "Similarity and divergence in the development and expression of the mouse and human antibody repertoires," Developmental and Comparative Immunol. 30(1-2):119-135.
Scott, (2007) "Mice with a human touch," Nature Biotechnology, 25(10): 1075-1077.
Seals et al., (2003) "the ADAMs family of metalloproteases: multidomain; proteins with multiple functions," Genes and Development, 17(1):7-30.
Sharpe et al., (1991) "Somatic hypermutation of immunoglobulin kappa may depend on sequences 3' of C kappa and occurs on passenger transgenes," EMBO J., 10(8):2139-2145.
Shriner et al., (2006) "Comparison of the human immune response to conjugate and polysaccharide pneumococcal vaccination using a reconstituted SCID mouse model," Vaccine, 24:7197-7203.
Shriner et al., (2006) "Immunoglobulin light chain variable region, partial (*Homo sapiens*)," Direct Submission GenBank ABG38383, May 9, 2006, pp. 1-2.
Simister et al., (1989) An Fc receptor structurally related to MHC class I antigens, Nature 337:184-187.
Simon and Rajewsky, (1990), "Antibody domain mutants demonstrate autonomy of the antigen binding site," EMBO J., 9(4):1051-1056.
Singer et al. (1998) "Genes and genomes," Moscow, "Mir" 1:63-64 (English translation).
Sirac et al., (2006) "Role of the monoclonal kappa chain V domain and reversibility of renal damage in a transgenic model of acquired Fanconi syndrome," Blood, 108(2):536-543.
Sirac et al. (2011) "Toward Understanding Renal Fanconi Syndrome: Step by Step Advances through Experimental Models," Exp.

(56) References Cited

OTHER PUBLICATIONS

Models for Renal Diseases: Pathogenesis and Diagnosis, Contrib. Nephrol. Basel, Karger, 169:247-261.
Smith et al., (2010) "The unique and immunoglobulin-like regions of surrogate light chain component lambda5 differentially interrogate immunoglobulin heavy-chain structure," Mol. Immunol., 47:1195-1206.
Soriano, (1999) "Generalized lacZ expression with the ROSA26 Cre reporter strain," Nat. Genet., 21(1):70-71.
Stevens et al. (2006) "Velocimmune: Humanization of Immunoglobulin Loc Using Velocigene Technology," First International MUGEN Conference of Animal Models for Human Immunological Disease, Sep. 10-13, 2016—Athens, Greece, Abstract 4 and Poster, 11 pages.
Stevens et al., (2008) "Human Antibody Discovery, VelocImmune—A novel platform, Pharma Focus Asia," Issue 8:72-74.
Storb et al., (1986) "Transgenic Mice with μ and κ Genes Encoding Antiphosphorycholine Antibodies", J. Exp. Med., 164:627-641.
Suzuki et al., (2010) "Importance of Neonatal FcR in REgulation the Serum Half-Life of Therapeutic Proteins Containing the Fc Domain of Human IgG1: A Comparative Study of the Affinity of Monoclonal Antibodies and Fc-Fusion Proteins to Human Neonatal FcR," J. Immunol. 184:1968-1976.
Tabrizi et al., (2006) "Elimination mechanisms of therapeutic monoclonal antibodies," Drugs Discovery Today 11(1/2):81-88.
Taylor et al., (1992) "A Transgenic Mouse that Expresses a Diversity of Human Sequence Heavy and Light Chain Immunoglobulins," Nucleic Acid Research, 20(23):6287-6295.
Taylor et al., (1993) "Human immunoglobulin transgenes undergo rearrangement, somatic mutation and class switching in mice that lack endogenous IgM," Int. Immunol. 6:579-591.
Tiegs et al. (1993) "Receptor Editing in Self-reactive Bone Marrow B Cells," J. Exp. Med., 177:1009-1020.
Torres and Kuhn, (1997) "Laboratory Protocols for Conditional Gene Targeting," Oxford University Press, 978-0-19-963677-8, 42-53.
Tsubata et al., (1990) "The Products of the Pre-B Cell-specific Genes (Lambda5 and VpreB) and the Immunoglobulin mu Chain Form a Comples that is Transported onto the Cell Surface," J. Exp. Med., 172:973-976.
Tuaillon et al., (1995) "Analysis of direct and inverted DJH rearrangements in a human Ig heavy chain transgenic minilocus," J. Immunol., 154(12):6453-6465.
Tutt et al., (1991) "Trispecific F(ab')3 Derivatives That Use Cooperative Signaling Via the TCR/CD3 Complex and CD2 to Activate and Redirect Resting Cytotoxic T Cells," J. Immunol. 147(1):60-69.
Tzaban et al., (2009) "The recycling and transcytotic pathways for IgG transport by FcRn are distinct and display an inherent polarity," J. Cell Biol. 185(4):673-684.
Uson et al., (1997) "X-ray crystallography reveals stringent conservation of protein fold after removal of the only disulfide bridge from a stabilized immunoglobulin variable domain," Folding & Design, 2(6):357-361.
Valenzuela et al., (2003) "High-throughput engineering of the mouse genome coupled with high-resolution expression analysis," Nature Biotech. 21(6):652-659.
Vaughn and Bjorkman, (1998) "Structural basis of pH-dependent antibody binding by the neonatal receptor," Structure 6:63-73.
Vaughan et al., (1996) "Human antibodies with sub-nanomolar affinities isolated from a large non-immunized phage display library," Nat. Biotechnol., 14(3):309-314.
Wang, X. et al., Ab-origin: an enhanced tool to identify the sourcing gene segments in germline for rearranged antibodies. BMC Bioinformatics, 9(Suppl 12), 9 pages (2008).
Wang et al., (2008) "Monoclonal Antibody Pharmacokinetics and Pharmacodynamics," Clinical Pharmacology & Therapeutics, 84(5):548-558.
Watanabe et al., (2009) "Optimizing pH Response of Affinity between Protein G and IgG Fc: How Electrostatic Modulations Affect Protein-Protein Interactions," J. Biol. Chem. 284(18):12373-12383.
Winter et al., (1997) "Insertion of 2 kb of bacteriophage DNA between an immunoglobulin promoter and leader exon stops somatic hypermutaion in a kappa transgene," Mol. Immunol., 34(5):359-366.
Xu and Davis (2000) "Diversity in the CDR3 Region of $V_H$ is Sufficient for Most Antibody Specificities," Immunity, 13:37-45.
Xu et al., (2008) "Combinatorial surrobody libraries," PNAS, 105(31):10756-10761.
Yeung et al., (2009) "Engineering Human IgG1 Affinity to Human Neonatal Fc Receptor: Impact of Affinity Improvement on Pharmacokinetics in Primates," J. Immunol. 182(12):7663-7671.
Zhou et al., (2009) "Developing tTA transgenic rats for inducible and reversible gene expression," International Journal of Biological Sciences, 5:171-181.
Chinese Search Report for related Chinese Application No. 201180013714.0, mailed May 15, 2013.
European Communication for Application No. 12 173 456.0 mailed Dec. 5, 2012.
European Examination for Application No. 11 703 799.4 mailed Oct. 9, 2012.
European Search Report for Application No. 12 173 456.0 dated Aug. 10, 2012.
Extended European Search Report with respect to EP Application No. 18158960.7, mailed Sep. 4, 2018.
International Search Report and Written Opinion for PCT Application No. PCT/US2011/023971 mailed Apr. 11, 2011.
International Search Report and Written Opinion for PCT Application No. PCT/US2012/034737 mailed Dec. 6, 2012.
International Search Report and Written Opinion for PCT Application No. PCT/US2012/049600 mailed Nov. 23, 2012.
International Search Report and Written Opinion for PCT Application No. PCT/US2013/029125 mailed Jun. 20, 2013.
International Search Report and Written Opinion for PCT Application No. PCT/US2013/044257 mailed Sep. 4, 2013 (9 pages).
International Search Report and Written Opinion for PCT Application No. PCT/US2013/031823 mailed Jul. 8, 2013.
International Search Report and Written Opinion for PCT Application No. PCT/US2013/031834 mailed Jul. 2, 2013.
International Search Report and Written Opinion for PCT Application No. PCT/US2013/032036 mailed Jul. 1, 2013.
International Search Report and Written Opinion for PCT Application No. PCT/US2014/025982 mailed Jul. 22, 2014 (13 pages).
International Search Report and Written Opinion for PCT Application No. PCT/US2014/026040 mailed Jul. 29, 2014, (14 pages).
International Search Report and Written Opinion for PCT Application No. PCT/US2014/056285 mailed Feb. 2, 2015.
Notice of Allowance with Respect to U.S. Appl. No. 13/832,309, Mailed Nov. 17, 2015.
Notice of Allowance with Respect to U.S. Appl. No. 13/832,247, Mailed Jan. 13, 2016.
Notice of Allowance with Respect to U.S. Appl. No. 14/705,916, Mailed Jan. 7, 2016.
Declaration 1.132 by Inventor Babb, Submitted with Respect to U.S. Appl. No. 13/832,309 on Oct. 13, 2015.
Declaration of Professor Dr. Roland Kontermann, Ph.D. for EP2505654 B1, 4 pages (May 19, 2017).
Declaration of Professor Michel Cogné, 26 pages (Jul. 17, 2017).
Notice of Opposition in EP2505654, 39 pages (May 24, 2017).
Opponent Reply to Patentee Submissions in EP2501817, 5 pages (Mar. 17, 2017).
Patent Oppositions—Decision in for AU2009263082, 53 pages (May 5, 2017).
Response to Opposition in EP2701499, 22 pages (Apr. 28, 2017).
Statement of Grounds of Appeal for Patent No. 2147594, 82 pages (2017).
Summons to Opposition in EP2501817, 12 pages (May 17, 2017).

(56) References Cited

OTHER PUBLICATIONS

Statement of Relatedness with Respect to U.S. Application No. to be assigned under MPEP 2001.06 dated Dec. 8, 2021.

* cited by examiner

| | Stop | SEQ ID NO. | Hydrophilic | SEQ ID NO. | Hydrophobic | SEQ ID NO. |
|---|---|---|---|---|---|---|
| D1-1 | VQLER | 8 | YNWND | 45 | GTTGT | 88 |
| HD1-1 | VPLAR | 9 | YHWHD | 46 | GTTGT | 88 |
| D1-7 | V*LEL | - | YNWNY | 47 | GITGT | 89 |
| HD1-7 | VSLAL | 10 | YHWHY | 48 | GITGT | 89 |
| D1-20 | V*LER | - | YNWND | 45 | GITGT | 89 |
| HD1-20 | VSLAR | 11 | YHWHD | 46 | GITGT | 89 |
| D1-26 | V*WELL | 12 | YSGSYY | 49 | GIVGAT | 90 |
| HD1-26 | VSWEPL | 13 | YHGSHY | 50 | GIMGAT | 91 |
| D2-2*02 | RIL**YQLLY | 14 | GYCSSTSCYT | 51 | DIVVVPAAI | 92 |
| HD2-2*02 | RTL*SYQLPY | 15 | GHCSHTSCHT | 52 | DIVVIPAAI | 93 |
| D2-8*01 | RILY*WCMLY | 16, 17 | GYCTNGVCYT | 53 | DIVLMVYAI | 94 |
| HD2-8*01 | RTLYSWCMPY | 18 | GHCTHGVCHT | 54 | DIVLMVYAI | 94 |
| D2-15 | RIL*WW*LLL | - | GYCSGGSCYS | 55 | DIVVVVAAT | 95 |
| HD2-15 | RTL*SW*LPL | - | GHCSHGSCHS | 56 | DIVVMVAAT | 96 |
| D2-21*02 | SILWW*LLF | 19 | AYCGGDCYS | 57 | HIVVVTAI | 97 |
| HD2-21*02 | STLWWSLPF | 20 | AHCGGHCHS | 58 | HIVVVTAI | 97 |
| D3-3*01 | VLRFLEWLLY | 21 | YYDFWSGYYT | 59 | ITIFGVVII | 98 |
| HD3-3*01 | VSPFLEWSLY | 22 | YHHFWSGHYT | 60 | ITIFGVVII | 98 |
| D3-9 | VLRYFDWLL* | 23 | YYDILTGYYN | 61 | ITIF*LVII | 99, 100 |
| HD3-9 | VSPYFDWSL* | 24 | YHHILTGHYN | 62 | ITIF*LVII | 99, 100 |
| D3-10*01 | VLLWFGELL* | 25 | YYYGSGSYYN | 63 | ITMVRGVII | 101 |
| HD3-10*01 | VSPWFGESL* | 26 | YHHGSGSHYN | 64 | ITMVRGVII | 101 |
| D3-16*02 | VL*LRLGELSLY | 27 | YYDYVWGSYRYT | 65 | IMITFGGVIVI | 102 |
| HD3-16*02 | VS*SRLGESSLY | 28 | YHDHVWGSHRYT | 66 | IMITFGGVIVI | 102 |
| D3-22 | VLL***WLLL | 29 | YYYDSSGYYY | 67 | ITMIVVVIT | 103 |
| HD3-22 | VSLS**WSLL | 30, 31 | YHYHSSGHYY | 68 | ITIVVVIT | 104 |
| D4-4 | *LQ*L | - | DYSNY | 69 | TTVT | 105 |
| HD4-4 | *PQSL | 32 | DHSHY | 70 | TTVT | 105 |
| D4-11p | *LQ*L | - | DYSNY | 69 | TTVT | 105 |

FIG. 1A

| | Stop | SEQ ID NO. | Hydrophilic | SEQ ID NO. | Hydrophobic | SEQ ID NO. |
|---|---|---|---|---|---|---|
| **HD4-11p** | *PQSL | 32 | DHSHY | 70 | TTVT | 105 |
| **D4-17** | *LR*L | - | DYGDY | 71 | TTVT | 105 |
| **HD4-17** | *PRSL | 33 | DHGHY | 72 | TTVT | 105 |
| **D4-23p** | *LRW*L | - | DYGGNS | 73 | TTVVT | 106 |
| **HD4-23p** | *PRWSL | 34 | DHGGHS | 74 | TTVVT | 106 |
| **D5-5** | WIQLWL | 35 | GYSYGY | 75 | VDTAMV | 107 |
| **HD5-5** | WTQPWL | 36 | GHSHGY | 76 | VDTAMV | 107 |
| **D5-12** | WI*WLRL | 37 | GYSGYDY | 77 | VDIVATI | 108 |
| **HD5-12** | WT*WPPL | 38 | GHSGHHY | 78 | VDIVATI | 108 |
| **D5-18** | WIQLWL | 35 | GYSYGY | 75 | VDTAMV | 107 |
| **HD5-18** | WTQPWL | 36 | GHSHGY | 76 | VDTAMV | 107 |
| **D5-24p** | *RWLQL | 39 | RDGYNY | 79 | VEMATI | 109 |
| **HD5-24p** | *TWPPL | 40 | RHGHHY | 80 | VDMATI | 110 |
| **D6-6** | V*QLV | - | EYSSSS | 81 | SIAAR | 111 |
| **HD6-6** | A*PLV | - | EHSHSS | 82 | SIATR | 112 |
| **D6-13** | V*QQLV | 41 | GYSSSWY | 83 | GIAAAG | 113 |
| **HD6-13** | A*PQLV | 42 | GHSHSWY | 84 | GIATAG | 114 |
| **D6-19** | V*QWLV | 43 | GYSSGWY | 85 | GIAVAG | 115 |
| **HD6-19** | A*PWLV | 44 | GHSHGWY | 86 | GIAMAG | 116 |
| **D6-25** | V*QRL | - | GYSSGY | 87 | GIAAA | 117 |
| **HD6-25** | A*PRL | - | GHSHGY | 76 | GIATA | 118 |

FIG. 1B

| Probes for MAID 6011 (deletion of hIgH DH segments in MAID1460 ) | | | | | | |
|---|---|---|---|---|---|---|
| **Name** | **Forward Primer** | **Probe** | **Reverse Primer** | **Type** | **Label** | **Location** |
| **hIgH DH-1** | CGGGTCACTGCCATTTCTG (SEQ ID NO: 119) | TCTGCATTCGCTCCCAGCGC (SEQ ID NO: 120) | TCTGCGGCATGAACCCAAT (SEQ ID NO: 121) | LOA | FAM-BHQ 1 | hIgH D segments |
| **hIgH DH-2** | GTGCAGGGAGGACCTTCTG (SEQ ID NO: 122) | AGTCACCAAGCACAGAGCCCTGAC (SEQ ID NO: 123) | GCCAGGGAGTTGCCTAGTG (SEQ ID NO: 124) | LOA | FAM-BHQ 1 | hIgH D segments |
| **hIgH DH-3** | GTGGCCCACTTCCCTTCCT (SEQ ID NO: 125) | CAGCTGGAACCCACCATGACCT (SEQ ID NO: 126) | GACCTGCCTCGGATGACA (SEQ ID NO: 127) | LOA | FAM-BHQ 1 | hIgH D segments |
| **hIgH DH-4** | TGGCCAGAACTGACCCTAC (SEQ ID NO: 128) | ACCGACAAGAGTCCCTCAGG (SEQ ID NO: 129) | GGAGTCGGCTCTGGATGTG (SEQ ID NO: 130) | LOA | BHQ-plus | hIgH D segments |
| **hyg** | TGCGGCCGATCTTAGCC (SEQ ID NO: 131) | ACGAGCGGGTTCGGCCCATTC (SEQ ID NO: 132) | TTGACCGATTCCTTGCGG (SEQ ID NO: 133) | GOA | FA-BHQ 1 | |
| **hIgH1** | CAGTCCCGTTGATCCAGCC (SEQ ID NO: 134) | CCCATCAGGGATTTTGTATCTCTGTGGACG (SEQ ID NO: 135) | GGATATGCAGCACTGTGCCAC (SEQ ID NO: 136) | AR | | hIgH |
| **hIgH9** | TCCTCCAACGACAGGTCCC (SEQ ID NO: 137) | TCCCTGGAACTCTGCCCCGACACA (SEQ ID NO: 138) | GATGAACTGACGGGCACAGG (SEQ ID NO: 139) | AR | | hIgH |
| **hIgH31** | ATCACACTCATCCCATCCCC (SEQ ID NO: 140) | CCCTTCCCTAAGTACCACAGAGTGGGCTC (SEQ ID NO: 141) | CACAGGGAAGCAGGAACTGC (SEQ ID NO: 142) | AR | | hIgH |

FIG. 6

| Probes for MAID 6012 (insertion of HD, His-substituted hIgH DH segments) | | | | | | |
|---|---|---|---|---|---|---|
| **Name** | **Forward Primer** | **Probe** | **Reverse Primer** | **Type** | **Label** | **Location** |
| **hyg** | TGCGGCCGATCTTAGCC (SEQ ID NO: 131) | ACGAGCGGGTTCGGCCCATTC (SEQ ID NO: 132) | TTGACCGATTCCTTGCGG (SEQ ID NO: 133) | LOA | FAM-BHQ1 | |
| **HD jxn-1** | GGAGCCAGGCAGGACACA (SEQ ID NO: 143) | TGGGCTCGTAGTTTGACGT (SEQ ID NO: 144) | GGGACTTTCTTACCCACACTTCA (SEQ ID NO: 145) | GOA | MGB | Synthetic linker-1 in HD segments |
| **HD jxn-2** | GGTCCCGAGCACTCTTAATTAAAC (SEQ ID NO: 146) | CCTCGAATGGAACTAC (SEQ ID NO: 147) | GGGAGAGCAACCATTCGTTGT (SEQ ID NO: 148) | GOA | MGB | Synthetic linker-2 in HD segments |
| **HD jxn-3** | CCGAGCACCGATGCATCTA (SEQ ID NO: 149) | CGCAGTCATGTAATGC (SEQ ID NO: 150) | GGGAGGCGAACTGACTGTCA (SEQ ID NO: 151) | GOA | MGB | Synthetic linker-3 in HD segments |
| **hIgH DH-1** | CGGGTCACTGCCATTTCTG (SEQ ID NO: 119) | TCTGCATTCGCTCCCAGCGC (SEQ ID NO: 120) | TCTGCGGCATGAACCCAAT (SEQ ID NO: 121) | GOA | FAM-BHQ1 | hIgH D segments |
| **hIgH DH-2** | GTGCAGGGAGGACCTTCTG (SEQ ID NO: 122) | AGTCACCAAGCACAGAGCCCTGAC (SEQ ID NO: 123) | GCCAGGGAGTTGCCTAGTG (SEQ ID NO: 124) | GOA | FAM-BHQ1 | hIgH D segments |
| **hIgH DH-3** | GTGGCCCACTTCCCTTCCT (SEQ ID NO: 125) | CAGCTGGAACCCACCATGACCT (SEQ ID NO: 126) | GACCTGCCTCGGATGACA (SEQ ID NO: 127) | GOA | FAM-BHQ1 | hIgH D segments |
| **hIgH DH-4** | TGGCCAGAACTGACCCTAC (SEQ ID NO: 128) | ACCGACAAGAGTCCCTCAGG (SEQ ID NO: 129) | GGAGTCGGCTCTGGATGTG (SEQ ID NO: 130) | GOA | BHQ-plus | hIgH D segments |
| **neo** | GGTGGAGAGGCTATTCGGC (SEQ ID NO: 152) | TGGGCACAACAGACAATCGGCTG (SEQ ID NO: 153) | GAACACGGCGGCATCAG (SEQ ID NO: 154) | GOA | FAM-BHQ1 | |
| **hIgH1** | CAGTCCCGTTGATCCAGCC (SEQ ID NO: 134) | CCCATCAGGGATTTTGTATCTCTGTGGACG (SEQ ID NO: 135) | GGATATGCAGCACTGTGCCAC (SEQ ID NO: 136) | AR | | hIgH |
| **hIgH9** | TCCTCCAACGACAGGTCCC (SEQ ID NO: 137) | TCCCTGGAACTCTGCCCCGACACA (SEQ ID NO: 138) | GATGAACTGACGGGCACAGG (SEQ ID NO: 139) | AR | | hIgH |
| **hIgH31** | ATCACACTCATCCCATCCCC (SEQ ID NO: 140) | CCCTTCCCTAAGTACCACAGAGTGGGCTC (SEQ ID NO: 141) | CACAGGGAAGCAGGAACTGC (SEQ ID NO: 142) | AR | | hIgH |

FIG. 8

| Human D Gene Segment | | Direct 5'- 3' Orientation | SEQ ID NO. | Inverted Orientation | SEQ ID NO. |
|---|---|---|---|---|---|
| IGHD1-1 | X97051, IGHD1-1*01 | ggtacaactggaacgac<br>G T T G T<br>V Q L E R<br>Y N W N D | 155<br>88<br>8<br>45 | gtcgttccagttgtacc<br>V V P V V<br>S F Q L Y<br>R S S C T | 206<br>207<br>208<br>209 |
| IGHD1-7 | X13972, IGHD1-7*01 | ggtataactggaactac<br>G I T G T<br>V * L E L<br>Y N W N Y | 156<br>89<br>-<br>47 | gtagttccagttatacc<br>V V P V I<br>* F Q L Y<br>S S S Y T | 210<br>211<br>212<br>213 |
| IGHD 1-20 | X13972, IGHD1-14*01 | ggtataaccggaaccac<br>G I T G T<br>V * P E P<br>Y N R N H | 157<br>89<br>-<br>158 | gtggttccggttatacc<br>V V P V I<br>W F R L Y<br>G S G Y T | 214<br>211<br>215<br>216 |
| IGHD 1-20 | X97501, IGHD1-20*01 | ggtataactggaacgac<br>G I T G T<br>V * L E R<br>Y N W N D | 159<br>89<br>-<br>45 | gtcgttccagttatacc<br>V V P V I<br>S F Q L Y<br>R S S Y T | 217<br>211<br>208<br>218 |
| IGHD1-26 | X97501, IGHD1-26*01 | ggtatagtgggagctactac<br>G I V G A T<br>V * W E L L<br>Y S G S Y Y | 160<br>90<br>12<br>49 | gtagtagctcccactatacc<br>V V A P T I<br>* * L P L Y<br>S S S H Y T | 219<br>220<br>221<br>222 |
| IGHD2-2 | J00232, IGHD2-2*01 | aggatattgtagtagtaccagctgctatgcc<br>R I L * * Y Q L L C<br>G Y C S S T S C Y A<br>D I V V V P A A M | 161<br>162<br>163<br>164 | ggcatagcagctggtactactacaatatcct<br>G I A A G T T T I S<br>A * Q L V L L Q Y P<br>H S S W Y Y Y N I | 223<br>224<br>225<br>226 |

FIG. 10A

| Human D Gene Segment | | Direct 5'- 3' Orientation | SEQ ID NO. | Inverted Orientation | SEQ ID NO. |
|---|---|---|---|---|---|
| | X97051, IGHD2-2*02 | aggatattgtagtagtaccagctgctatacc<br>R I L * * Y Q L L Y<br>G Y C S S T S C Y T<br>D I V V V P A A I | 165<br>14<br>51<br>92 | ggtatagcagctggtactactacaatatcct<br>G I A A G T T T I S<br>V * Q L V L L Q Y P<br>Y S S W Y Y Y N I | 227<br>224<br>225<br>226 |
| | M35648, IGHD2-2*03 | tggatattgtagtagtaccagctgctatgcc<br>W I L * * Y Q L L C<br>G Y C S S T S C Y A<br>D I V V V P A A M | 166<br>167<br>168<br>169 | ggcatagcagctggtactactacaatatcca<br>G I A A G T T T I S<br>A * Q L V L L Q Y P<br>H S S W Y Y Y N I | 228<br>224<br>225<br>226 |
| IGHD2-8 | X13972, IGHD2-8*01 | aggatattgtactaatggtgtatgctatacc<br>R I L Y * W C M L Y<br>G Y C T N G V C Y T<br>D I V L M V Y A I | 170<br>16, 17<br>53<br>94 | ggtatagcatacaccattagtacaatatcct<br>G I A Y T I S T I S<br>V * H T P L V Q Y P<br>Y S I H H * Y N I | 229<br>230<br>231<br>232 |
| | J000233, IGHD2-8*02 | aagatattgtactggtggtgtatgctatacc<br>R I L Y W W C M L Y<br>G Y C T G G V C Y T<br>D I V L V V Y A I | 171<br>172<br>173<br>174 | ggtatagcatacaccaccagtacaatatctt<br>G I A Y T T S T I S<br>V * H T P P V Q Y L<br>Y S I H H Q Y N I | 233<br>234<br>235<br>236 |
| IGHD2-15 | J00234, IGHD2-15*01 | aggatattgtagtggtggtagctgctactcc<br>R I L * W W * L L L<br>G Y C S G G S C Y S<br>D I V V V V A A T | 175<br>-<br>55<br>95 | ggagtagcagctaccaccactacaatatcct<br>G V A A T T T T I S<br>E * Q L P P L Q Y P<br>S S S Y H H Y N I | 237<br>238<br>239<br>240 |
| IGHD2-21 | J00235, IGHD2-21*01 | agcatattgtggtggtgattgctattcc<br>S I L W W * L L F<br>A Y C G G D C Y S<br>H I V V V I A I | 176<br>19<br>57<br>177 | ggaatagcaatcaccaccacaatatgct<br>G I A I T T T I C<br>E * Q S P P Q Y A<br>N S N H H H N M | 241<br>242<br>243<br>244 |
| | X97051, IGHD2-21*02 | agcatattgtggtggtgactgctattcc<br>S I L W W * L L F<br>A Y C G G D C Y S<br>H I V V V T A I | 178<br>19<br>57<br>97 | ggaatagcagtcaccaccacaatatgct<br>G I A V T T T I C<br>E * Q S P P Q Y A<br>N S S H H H N M | 245<br>246<br>247<br>248 |

FIG. 10B

| Human D Gene Segment | | Direct 5'- 3' Orientation | SEQ ID NO. | Inverted Orientation | SEQ ID NO. |
|---|---|---|---|---|---|
| IGHD3-3 | X13972, IGHD3-3*01 | gtattacgatttttggagtggttattatacc<br>V L R F L E W L L Y<br>Y Y D F W S G Y Y T<br>I T I F G V V I I | 179<br>21<br>59<br>98 | ggtataataaccactccaaaaatcgtaatac<br>G I I T T P K I V I<br>V * * P L Q K S * Y<br>Y N N H S K N R N | 249<br>250<br>251<br>252 |
| | X93618, IGHD3-3*02 | gtattagcatttttggagtggttattatacc<br>V L A F L E W L L Y<br>Y * H F W S G Y Y T<br>I S I F G V V I I | 180<br>181<br>182<br>183 | ggtataataaccactccaaaaatgctaatac<br>G I I T T P K M L I<br>V * * P L Q K C * Y<br>Y N N H S K N A N | 253<br>254<br>255<br>256 |
| IGHD3-9 | X13972, IGHD3-9*01 | gtattacgatattttgactggttattataac<br>V L R Y F D W L L *<br>Y Y D I L T G Y Y N<br>I T I F * L V I I | 184<br>23<br>61<br>99, 100 | gttataataaccagtcaaaatatcgtaatac<br>V I I T S Q N I V I<br>L * * P V K I S * Y<br>Y N N Q S K Y R N | 257<br>258<br>259<br>260 |
| IGHD3-10 | X13972, IGHD3-10*01 | gtattactatggttcggggagttattataac<br>V L L W F G E L L *<br>Y Y Y G S G S Y Y N<br>I T M V R G V I I | 185<br>25<br>63<br>101 | gttataataactccccgaaccatagtaatac<br>V I I T P R T I V I<br>L * * L P E P * * Y<br>Y N N S P N H S N | 261<br>262<br>263<br>264 |
| | X93615, IGHD3-10*02 | gtattactatgttcggggagttattataac<br>V L L C S G S Y Y N<br>Y Y Y V R G V I I<br>I T M F G R L L * | 186<br>187<br>188<br>189 | gttataataactccccgaacatagtaatac<br>V I I T P R T * * Y<br>L * * L P E H S N<br>Y N N S P N I V I | 265<br>266<br>267<br>268 |
| IGHD3-16 | X93614, IGHD3-16*01 | gtattatgattacgtttggggggagttatgcttatacc<br>V L * L R L G E L C L Y<br>Y Y D Y V W G S Y A Y T<br>I M I T F G G V M L I | 190<br>191<br>192<br>193 | ggtataagcataactccccccaaacgtaatcataatac<br>G I S I T P P N V I I I<br>V * A * L P Q T * S * Y<br>Y K H N S P K R N H N | 269<br>270<br>271<br>272 |
| IGHD3-22 | X93616, IGHD3-22*01 | gtattactatgatagtagtggttattactac<br>V L L * * * W L L L<br>Y Y Y D S S G Y Y Y<br>I T M I V V V I T | 194<br>29<br>67<br>103 | gtagtaataaccactactatcatagtaatac<br>V V I T T T I I V I<br>* * * P L L S * * Y<br>S N N H Y Y H S N | 273<br>274<br>275<br>276 |

FIG. 10C

| Human D Gene Segment | | Direct 5'- 3' Orientation | SEQ ID NO. | Inverted Orientation | SEQ ID NO. |
|---|---|---|---|---|---|
| **IGHD4-4** | X13972, IGHD4-4*01 | tgactacagtaactac<br>* L Q * L<br>D Y S N Y<br>T T V T | 195<br>-<br>69<br>105 | gtagttactgtagtca<br>V V T V V<br>* L L * S<br>S Y C S | 277<br>278<br>-<br>279 |
| **IGHD4-11** | X13972, IGHD4-11*01 | tgactacagtaactac<br>* L Q * L<br>D Y S N Y<br>T T V T | 195<br>-<br>69<br>105 | gtagttactgtagtca<br>V V T V V<br>* L L * S<br>S Y C S | 277<br>278<br>-<br>279 |
| **IGHD4-17** | X97501, IGHD4-17*01 | tgactacggtgactac<br>* L R * L<br>D Y G D Y<br>T T V T | 196<br>-<br>71<br>105 | gtagtcaccgtagtca<br>V V T V V<br>* S P * S<br>S H R S | 280<br>278<br>-<br>281 |
| **IGHD4-23** | X97051, IGHD4-23*01 | tgactacggtggtaactcc<br>* L R W * L<br>D Y G G N S<br>T T V V T | 197<br>-<br>73<br>106 | ggagttaccaccgtagtca<br>G V T T V V<br>E L P P * S<br>S Y H R S | 282<br>283<br>284<br>285 |
| **IGHD5-5** | X13972, IGHD5-5*01 | gtggatacagctatggttac<br>V D T A M V<br>W I Q L W L<br>G Y S Y G Y | 198<br>107<br>35<br>75 | gtaaccatagctgtatccac<br>V T I A V S<br>* P * L Y P<br>N H S C I H | 286<br>287<br>-<br>288 |
| **IGHD5-12** | X13972, IGHD5-12*01 | gtggatatagtggctacgattac<br>V D I V A T I<br>W I * W L R L<br>G Y S G Y D Y | 199<br>108<br>37<br>77 | gtaatcgtagccactatatccac<br>V I V A T I S<br>* S * P L Y P<br>N R S H Y I H | 289<br>290<br>291<br>292 |
| **IGHD5-18** | X97051, IGHD5-18*01 | gtggatacagctatggttac<br>V D T A M V<br>W I Q L W L<br>G Y S Y G Y | 198<br>107<br>35<br>75 | gtaaccatagctgtatccac<br>V T I A V S<br>* P * L Y P<br>N H S C I H | 286<br>287<br>-<br>288 |

FIG. 10D

| Human D Gene Segment | | Direct 5'- 3' Orientation | SEQ ID NO. | Inverted Orientation | SEQ ID NO. |
|---|---|---|---|---|---|
| IGHD5-24 | X97051, IGHD5-24*01 | gtagagatggctacaattac<br>V E M A T I<br>* R W L Q L<br>R D G Y N Y | 200<br>110<br>39<br>79 | gtaattgtagccatctctac<br>V I V A I S<br>* L * P S L<br>N C S H L Y | 293<br>294<br>-<br>295 |
| IGHD6-6 | X13972, IGHD6-6*01 | gagtatagcagctcgtcc<br>E Y S S S S<br>S I A A R<br>V * Q L V | 201<br>81<br>112<br>- | ggacgagctgctatactc<br>G R A A I L<br>D E L L Y<br>T S C Y T | 296<br>297<br>298<br>299 |
| IGHD6-13 | X13972, IGHD6-13*01 | gggtatagcagcagctggtac<br>G Y S S S W Y<br>G I A A A G<br>V * Q Q L V | 202<br>83<br>114<br>41 | gtaccagctgctgctataccc<br>V P A A A I P<br>Y Q L L L Y<br>T S C C Y T | 300<br>301<br>302<br>303 |
| IGHD6-19 | X97051, IGHD6-19*01 | gggtatagcagtggctggtac<br>G Y S S G W Y<br>G I A V A G<br>V * Q W L V | 203<br>85<br>116<br>44 | gtaccagccactgctataccc<br>V P A T A I P<br>Y Q P L L Y<br>T S H C Y T | 304<br>305<br>306<br>307 |
| IGHD6-25 | X97051, IGHD6-25*01 | gggtatagcagcggctac<br>G Y S S G Y<br>G I A A A<br>V * Q R L | 204<br>87<br>116<br>- | gtagccgctgctataccc<br>V A A A I P<br>* P L L Y<br>S R C Y T | 308<br>309<br>310<br>311 |
| IGHD7-27 | J00256, IGHD7-27*01 | ctaactgggga<br>L T G<br>* L G<br>N W G | 205<br>-<br>-<br>- | tccccagttag<br>S P V<br>P Q L<br>P S * | 312<br>-<br>-<br>- |

FIG. 10E

Antibody Sequence 1

```
                      <------------------------------------FWR1------------------------------------><-----------CDR1
lcl|Query_1_reversed   Q  V  Q  L  Q  Q  W  G  A  G  L  L  K  P  S  D  T  L  S  L  T  C  A  V  Y  G  G  S  F  S
IGHV4-34*01           CAGGTGCAGCTACAGCAGTGGGGCGCAGGACTGTTGAAGCCTTCGGATACCCTGTCCCTCACCTGCGCTGTCTATGGTGGGTCCTTCAGT
                      ...............................................G..........................................
                       Q  V  Q  L  Q  Q  W  G  A  G  L  L  K  P  S  E  T  L  S  L  T  C  A  V  Y  G  G  S  F  S

                      --------><-------------------------FWR2------------------------><-------CDR2-------><-------
lcl|Query_1_reversed   G  Y  Y  W  S  W  I  R  Q  P  P  G  K  G  L  E  W  I  G  E  I  N  H  S  G  S  T  N  Y  N
IGHV4-34*01           GGTTACTACTGGAGCTGGATCCGCCAGCCCCCAGGGAAGGGGCTGGAGTGGATTGGGGAAATCAATCATAGTGGAAGCACCAACTACAAC
                      ..........................................................................................
                       G  Y  Y  W  S  W  I  R  Q  P  P  G  K  G  L  E  W  I  G  E  I  N  H  S  G  S  T  N  Y  N

                      ------------------------------------------------FWR3-------------------------------------
lcl|Query_1_reversed   P  S  L  K  S  R  V  T  I  S  V  D  T  S  K  N  Q  F  S  L  K  L  S  S  V  T  A  A  D  T
IGHV4-34*01           CCGTCCCTCAAGAGTCGAGTCACCATATCAGTAGACACGTCCAAGAACCAGTTCTCCCTGAAGCTGAGCTCTGTGACCGCCGCGGACACG
                      ..........................................................................................
                       P  S  L  K  S  R  V  T  I  S  V  D  T  S  K  N  Q  F  S  L  K  L  S  S  V  T  A  A  D  T

                      --------------->
lcl|Query_1_reversed   A  V  Y  Y  C  A [G  H  S  H  G  W  Y] Y  Y  Y  Y  G  M  D  V  W  G  Q  G  T  T  V  T  V
IGHV4-34*01           GCTGTGTATTACTGTGCGGGCCATAGCCATGGCTGGTACTACTACTACTACGGTATGGACGTCTGGGGCCAAGGGACCACGGTCACCGTC
                      ..................------------------------------------------------------------------------
hIgHHD6-19.nucl        A  V  Y  Y  C  A (SEQ ID NO:314)
IGHJ6*02              ------------------.....................-------------------------------------------------
                      ------------------------------------...................................................

lcl|Query_1_reversed
IGHJ6*02               S  S         (SEQ ID NO:313)
                      TCCTCA    473 (SEQ ID NO:312)
                      ......    62
```

| D gene segment | Hydrophilic | SEQ ID NO. |
|---|---|---|
| **D6-19** | GYSSGWY | 85 |
| **HD6-19** | GHSHGWY | 86 |

FIG. 11

Antibody Sequence 2

```
                                <------------------------------FWR1-----------------------------><----------C
(SEQ ID NO:316)                  Q  V  Q  L  Q  E  S  G  P  G  L  V  K  P  S  Q  T  L  S  L  T  C  T  V  S  G  G  S  I  S
(SEQ ID NO:315)                 CAGGTGCAGCTGCAGGAGTCGGGCCCAGGACTGGTGAAGCCTTCACAGACCCTGTCCCTCACCTGCACTGTCTCTGGTGGCTCCATCAGC
lcl|Query_1_reversed            ..........................................................................................
IGHV4-39*01                      Q  V  Q  L  Q  E  S  G  P  G  L  V  K  P  S  Q  T  L  S  L  T  C  T  V  S  G  G  S  I  S

                                DR1----------><--------------------FWR2--------------------><--------CDR2-------><--
                                 S  G  G  Y  Y  W  S  W  I  R  Q  H  P  G  K  G  L  E  W  I  G  Y  I  Y  Y  S  G  S  T  Y
lcl|Query_1_reversed            AGTGGTGGTTACTACTGGAGCTGGATCCGCCAGCACCCAGGGAAGGGCCTGGAGTGGATTGGGTACATCTATTACAGTGGGAGCACCTAC
IGHV4-39*01                     ..........................................................................................
                                 S  G  G  Y  Y  W  S  W  I  R  Q  H  P  G  K  G  L  E  W  I  G  Y  I  Y  Y  S  G  S  T  Y

                                ---------------------------------------------------FWR3---------------------------------
lcl|Query_1_reversed             Y  N  P  S  L  K  S  R  V  T  I  S  V  D  T  S  K  N  Q  F  S  L  K  L  S  S  V  T  A  A
IGHV4-39*01                     TACAACCCGTCCCTCAAGAGTCGAGTTACCATATCAGTAGACACGTCTAAGAACCAGTTCTCCCTGAAGCTGAGCTCTGTGACTGCCGCG
                                ..........................................................................................
                                 Y  N  P  S  L  K  S  R  V  T  I  S  V  D  T  S  K  N  Q  F  S  L  K  L  S  S  V  T  A  A

lcl|Query_1_reversed            ------------------->
IGHV4-39*01                      D  T  A  V  Y  Y  C  A  R  G [D  H  G  H  Y] D  Y  W  G  Q  G  T  L  V  T  V  S  S
                                GACACGGCCGTGTATTACTGTGCGAGGGGGGACCACGGTCACTACGACTACTGGGGCCAGGGAACCCTGGTCACCGTCTCCTCAG   471
hIgHD6-13.nucl                  ..........................-----------------------------------------------------------   296
IGHJ5*02                         D  T  A  V  Y  Y  C  A  (SEQ ID NO:317)
                                ---------------------------------------..............--------------------------------   16
                                ----------------------------------------------.......................................   48
lcl|Query_1_reversed
IGHJ5*02
```

| D gene segment | Hydrophilic | SEQ ID NO. |
|---|---|---|
| **D4-17** | DYGDY | 71 |
| **HD4-17** | DHGHY | 72 |

FIG. 12

Antibody Sequence 3

```
                              <--------------------------------FWR1-------------------------------><----------C
                               Q  L  Q  L  Q  E  S  G  P  G  L  V  K  P  S  E  T  L  S  L  T  C  T  V  S  G  G  S  I  S
lcl|Query_1_reversed          CAGCTGCAGCTGCAGGAGTCGGGCCCAGGACTGGTGAAGCCTTCGGAGACCCTGTCCCTCACCTGCACTGTCTCTGGTGGCTCCATCAGC
IGHV4-39*01                   ..........................................................................................
                               Q  L  Q  L  Q  E  S  G  P  G  L  V  K  P  S  E  T  L  S  L  T  C  T  V  S  G  G  S  I  S

                              DR1---------><---------------------------FWR2----------------------><-------CDR2------><--
                               S  S  S  Y  Y  W  G  W  I  R  Q  P  P  G  K  G  L  E  W  I  G  S  I  Y  Y  S  G  S  T  Y
lcl|Query_1_reversed          AGTAGTAGTTACTACTGGGGCTGGATCCGCCAGCCCCCAGGGAAGGGGCTGGAGTGGATTGGGAGTATCTATTATAGTGGGAGCACCTAC
IGHV4-39*01                   ..........................................................................................
                               S  S  S  Y  Y  W  G  W  I  R  Q  P  P  G  K  G  L  E  W  I  G  S  I  Y  Y  S  G  S  T  Y

                              ------------------------------------------------FWR3---------------------------------------
                               Y  N  P  S  L  K  S  R  V  T  I  S  V  D  T  S  K  N  Q  F  S  L  K  L  S  S  V  T  A  A
lcl|Query_1_reversed          TACAACCCGTCCCTCAAGAGTCGAGTCACCATATCCGTAGACACGTCCAAGAACCAGTTCTCCCTGAAGCTGAGCTCTGTGACCGCCGCA
IGHV4-39*01                   ..........................................................................................
                               Y  N  P  S  L  K  S  R  V  T  I  S  V  D  T  S  K  N  Q  F  S  L  K  L  S  S  V  T  A  A

                              ------------------->
                               D  T  A  V  Y  Y  C  A  R  H  E [G  H  S  H] L  N  W  F  D  P  W  G  Q  G  G  T  L  V  T
lcl|Query_1_reversed          GACACGGCTGTGTATTACTGTGCGAGACATGAAGGGCATAGCCACCTTAACTGGTTCGACCCCTGGGGCCAGGGGGGAACCCTGGTCACC
IGHV4-39*01                   ...........................---------------------------------------------------------------
                               D  T  A  V  Y  Y  C  A  R  (SEQ ID NO:320)
hIgHHD6-13.nucl               -----------------------------------------...........--------------------------------------
IGHJ5*02                      ----------------------------------------------------..................--................

                               V  S  S              (SEQ ID NO:319)
lcl|Query_1_reversed          GTCTCCTCAG     471    (SEQ ID NO:318)
IGHJ5*02                      ..........     51
```

| D gene segment | Hydrophilic | SEQ ID NO. |
|---|---|---|
| **D6-13** | GYSSSWY | 83 |
| **HD6-13** | GHSHSWY | 84 |

FIG. 13

```
              |---------FR1-IMGT-------||CDR1||----FR2-IMGT---||C||-------
IGKV1-39*01   DIQMTQSPSSLSASVGDRVTITCRASQSISSYLNWYQQKPGKAPKLLIYAASSLQSGVPS
A             ....................F...T.H..................I....V...YT....
B             A..........................I..NF.................G.YN.......
C             ..........................HN.NN.....H.......N...............
D             ............................................................
E             .....................A.....T...N............................
F             ............................................N....D..........
G             A..L........................................N....D..........
H             A..........................N.N...H...............D...F......
I             A..L........................................................
J             A...........................................................
K             A..L...........................................M............

              -------FR3-IMGT------------||CDR3-|
IGKV1-39*01   RFSGSGSGTDFTLTISSLQPEDFATYYCQQSYST-P-------------   SEQ ID NO:325
A             ...A......................T.....NI..FTFGPGTKVDIKR
B             ........................I....H----.-LTFGGGTKVEIKR
C             ..........Y.....T.H....GN.........SMYTFGQGTQLEIKR
D             ..........................H......I..ITFGQGTRLEIKR
E             ............................H...I...ITFGQGTRLEIKR
F             ...............T..H............H....ITFGQGTRLEIKR
G             ...............T...............H....ITFGQGTRLEIKR
H             ..................................P.ITFGQGTRVEIKR
I             .....K...........................IH.ITFGQGTKLEIKR
J             ...............................H.IP.ITFGQGTRLEIK.
K             ....T..............R...........H..P.ITFGQGTKVEIKR
```

FIG. 15

| | | | | | | | | |
|---|---|---|---|---|---|---|---|---|
| | 105 | 106 | | 108 | | | 111 | |
| | Q | Q | S | Y | S | T | P | SEQ ID NO:327 |
| WT | CAG | CAG | AGC | TAC | AGC | ACC | CCC | SEQ ID NO:326 |
| | H | H | S | H | S | T | H | SEQ ID NO:329 |
| H105/106/108/111 | CAC | CAT | AGC | CAC | AGC | ACC | CAC | SEQ ID NO:328 |
| H105 | CAC | CAG | AGC | TAC | AGC | ACC | CCC | SEQ ID NO:330 |
| H106 | CAG | CAT | AGC | TAC | AGC | ACC | CCC | SEQ ID NO:332 |
| H108 | CAG | CAG | AGC | CAC | AGC | ACC | CCC | SEQ ID NO:334 |
| H111 | CAG | CAG | AGC | TAC | AGC | ACC | CAC | SEQ ID NO:336 |
| H105/106 | CAC | CAT | AGC | TAC | AGC | ACC | CCC | SEQ ID NO:338 |
| H105/108 | CAC | CAG | AGC | CAC | AGC | ACC | CCC | SEQ ID NO:340 |
| H105/111 | CAC | CAG | AGC | TAC | AGC | ACC | CAC | SEQ ID NO:342 |
| H106/108 | CAG | CAT | AGC | CAC | AGC | ACC | CCC | SEQ ID NO:344 |
| H106/111 | CAG | CAT | AGC | TAC | AGC | ACC | CAC | SEQ ID NO:346 |
| H108/111 | CAG | CAG | AGC | CAC | AGC | ACC | CAC | SEQ ID NO:348 |
| H105/106/108 | CAC | CAT | AGC | CAC | AGC | ACC | CCC | SEQ ID NO:350 |
| H105/106/111 | CAC | CAT | AGC | TAC | AGC | ACC | CAC | SEQ ID NO:352 |
| H105/108/111 | CAC | CAG | AGC | CAC | AGC | ACC | CAC | SEQ ID NO:354 |
| H106/108/111 | CAG | CAT | AGC | CAC | AGC | ACC | CAC | SEQ ID NO:356 |

FIG. 16

| | | Kinetics at pH 7.2 | | | | | | Kinetics at pH 5.75 | | | | | | low/neutral pH | | |
|---|---|---|---|---|---|---|---|---|---|---|---|---|---|---|---|---|
| HC | Vk mut | mAb capture level (RU) | 100nM Antigen bound (RU) | ka (1/Ms) | kd (1/s) | KD (M) | t½ (min) | mAb capture level (RU) | 100nM antigen bound (RU) | ka (1/Ms) | kd (1/s) | KD (M) | t½ (min) | ka | kd | KD |
| H4H6006 | H105 | 44 | 11 | 4.25E+05 | 1.18E-03 | 2.77E-09 | 10 | 32 | 5 | 1.27E+06 | 2.05E-03 | 1.61E-09 | 6 | 3.0 | 1.7 | 0.6 |
| | H106 | 46 | 12 | 4.42E+05 | 9.32E-04 | 2.11E-09 | 12 | 27 | 4 | 1.56E+06 | 1.72E-03 | 1.10E-09 | 7 | 3.5 | 1.8 | 0.5 |
| | H108 | 46 | 12 | 4.51E+05 | 9.02E-04 | 2.00E-09 | 13 | 33 | 5 | 1.15E+06 | 1.47E-03 | 1.28E-09 | 8 | 2.5 | 1.6 | 0.6 |
| | H111 | 47 | 13 | 3.86E+05 | 9.54E-04 | 2.47E-09 | 12 | 36 | 5 | 8.81E+05 | 1.52E-03 | 1.73E-09 | 8 | 2.3 | 1.6 | 0.7 |
| | H105 106 | 16 | 1 | NB | NB | NB | NB | 6 | -4 | NB | NB | NB | NB | | | |
| | H105 108 | 40 | 11 | 4.83E+05 | 8.73E-04 | 1.81E-09 | 13 | 30 | 4 | 1.54E+06 | 1.26E-03 | 8.20E-10 | 9 | 3.2 | 1.4 | 0.5 |
| | H105 111 | 22 | 4 | 3.81E+05 | 1.32E-03 | 3.45E-09 | 9 | 16 | -2 | NB | NB | NB | NB | | | |
| | H106 108 | 51 | 15 | 4.87E+05 | 7.60E-04 | 1.56E-09 | 15 | 40 | 8 | 1.16E+06 | 1.04E-03 | 8.96E-10 | 11 | 2.4 | 1.4 | 0.6 |
| | H106 111 | 38 | 9 | 3.94E+05 | 9.00E-04 | 2.28E-09 | 13 | 29 | 2 | 1.55E+06 | 1.60E-03 | 1.03E-09 | 7 | 3.9 | 1.8 | 0.5 |
| | H108 111 | 51 | 14 | 3.98E+05 | 8.29E-04 | 2.08E-09 | 14 | 40 | 6 | 8.42E+05 | 1.19E-03 | 1.42E-09 | 10 | 2.1 | 1.4 | 0.7 |
| | H105 106 108 | 14 | 1 | NB | NB | NB | NB | 9 | -5 | NB | NB | NB | NB | | | |
| | H105 1061 111 | 15 | 1 | NB | NB | NB | NB | 10 | -5 | NB | NB | NB | NB | | | |
| | H105 108 111 | 17 | 2 | 4.38E+05 | 9.60E-04 | 2.19E-09 | 12 | 12 | -5 | NB | NB | NB | NB | | | |
| | H10 108 111 | 40 | 10 | 3.72E+05 | 7.42E-04 | 2.00E-09 | 16 | 30 | 2 | NB | NB | NB | NB | | | |
| | H105 106 108 111 | 15 | 1 | NB | NB | NB | NB | 9 | -6 | NB | NB | NB | NB | | | |
| | 1-39 ULC | 72 | 22 | 3.90E+05 | 1.18E-03 | 3.03E-09 | 10 | 56 | 11 | 7.69E+05 | 1.84E-03 | 2.39E-09 | 6 | 2.0 | 1.6 | 0.8 |

FIG. 19A

| | | Kinetics at pH 7.2 | | | | | | Kinetics at pH 5.75 | | | | | | low/neutral pH | | |
|---|---|---|---|---|---|---|---|---|---|---|---|---|---|---|---|---|
| HC | Vk mut | mAb capture level (RU) | 100nM Antigen bound (RU) | ka (1/Ms) | kd (1/s) | KD (M) | t½ (min) | mAb capture level (RU) | 100nM antigen bound (RU) | ka (1/Ms) | kd (1/s) | KD (M) | t½ (min) | ka | kd | KD |
| H4H6008 | H105 | 79 | 21 | 3.47E+05 | 1.09E-03 | 3.15E-09 | 11 | 62 | 8 | 5.15E+05 | 3.54E-03 | 6.87E-09 | 3 | 1.5 | 3.2 | 2.2 |
| | H106 | 60 | 13 | 3.19E+05 | 1.92E-03 | 6.02E-09 | 6 | 48 | 2 | 1.92E+06 | 2.48E-02 | 1.29E-08 | 0 | 6.0 | 12.9 | 2.1 |
| | H108 | 84 | 20 | 2.89E+05 | 2.66E-03 | 9.17E-09 | 4 | 1 | -5 | NB | NB | NB | NB | | | |
| | H111 | 77 | 19 | 3.28E+05 | 1.54E-03 | 4.69E-09 | 8 | 60 | 5 | 4.96E+05 | 7.85E-03 | 1.58E-08 | 1 | 1.5 | 5.1 | 3.4 |
| | H105 106 | 30 | 4 | 3.39E+05 | 9.91E-04 | 2.92E-09 | 12 | -1 | -7 | NB | NB | NB | NB | | | |
| | H105 108 | 77 | 20 | 3.16E+05 | 1.40E-03 | 4.45E-09 | 8 | 62 | 6 | 4.76E+05 | 5.41E-03 | 1.14E-08 | 2 | 1.5 | 3.9 | 2.6 |
| | H105 111 | 44 | 11 | 3.51E+05 | 4.10E-04 | 1.17E-09 | 28 | 34 | 0 | NB | NB | NB | NB | | | |
| | H106 108 | 81 | 18 | 2.99E+05 | 2.20E-03 | 7.34E-09 | 5 | 66 | 4 | 3.87E+05 | 1.16E-02 | 3.01E-08 | 1 | 1.3 | 5.3 | 4.1 |
| | H106 111 | 87 | 19 | 3.05E+05 | 1.64E-03 | 5.38E-09 | 7 | 73 | 5 | 4.34E+05 | 6.96E-03 | 1.60E-08 | 2 | 1.4 | 4.2 | 3.0 |
| | H108 111 | 85 | 22 | 3.42E+05 | 1.63E-03 | 4.76E-09 | 7 | 70 | 5 | 3.94E+05 | 8.00E-03 | 2.03E-08 | 1 | 1.2 | 4.9 | 4.3 |
| | H105 106 108 | 29 | 4 | 3.53E+05 | 9.63E-04 | 2.73E-09 | 12 | 24 | -5 | NB | NB | NB | NB | | | |
| | H105 106 111 | 32 | 5 | 2.87E+05 | 9.83E-04 | 3.43E-09 | 12 | 26 | -5 | NB | NB | NB | NB | | | |
| | H105 108 111 | 39 | 9 | 3.47E+05 | 3.26E-04 | 9.38E-10 | 35 | 32 | -2 | NB | NB | NB | NB | | | |
| | H106 108 111 | 57 | 11 | 2.72E+05 | 1.63E-03 | 5.99E-09 | 7 | 46 | -1 | NB | NB | NB | NB | | | |
| | H105 106 108 111 | 36 | 6 | 2.93E+05 | 1.05E-03 | 3.58E-09 | 11 | 29 | -5 | NB | NB | NB | NB | | | |
| | 1-39 ULC | 128 | 33 | 3.02E+05 | 1.86E-03 | 6.15E-09 | 6 | 103 | 13 | 3.24E+05 | 5.67E-03 | 1.75E-08 | 2 | 1.1 | 3.1 | 2.8 |

FIG. 19B

| HC | Vk mut | Kinetics at pH 7.2 | | | | | | Kinetics at pH 5.75 | | | | | | low/neutral pH | | |
|---|---|---|---|---|---|---|---|---|---|---|---|---|---|---|---|---|
| | | mAb capture level (RU) | 100nM Antigen bound (RU) | ka (1/Ms) | kd (1/s) | KD (M) | t½ (min) | mAb capture level (RU) | 100nM antigen bound (RU) | ka (1/Ms) | kd (1/s) | KD (M) | t½ (min) | ka | kd | KD |
| H4H3046 | H105 | 73 | 0 | NB | NB | NB | NB | 62 | -8 | NB | NB | NB | NB | | | |
| | H106 | 64 | 0 | NB | NB | NB | NB | 54 | -9 | NB | NB | NB | NB | | | |
| | H108 | 75 | 1 | NB | NB | NB | NB | 64 | -8 | NB | NB | NB | NB | | | |
| | H111 | 73 | 0 | NB | NB | NB | NB | 62 | -9 | NB | NB | NB | NB | | | |
| | H105 106 | 45 | 0 | NB | NB | NB | NB | 38 | -9 | NB | NB | NB | NB | | | |
| | H105 108 | 65 | 0 | NB | NB | NB | NB | 56 | -9 | NB | NB | NB | NB | | | |
| | H105 111 | 34 | 0 | NB | NB | NB | NB | 27 | -9 | NB | NB | NB | NB | | | |
| | H106 108 | 77 | 0 | NB | NB | NB | NB | 67 | -9 | NB | NB | NB | NB | | | |
| | H106 111 | 75 | 0 | NB | NB | NB | NB | 67 | -9 | NB | NB | NB | NB | | | |
| | H108 111 | 66 | 0 | NB | NB | NB | NB | 56 | -9 | NB | NB | NB | NB | | | |
| | H105 106 108 | 54 | 0 | NB | NB | NB | NB | 46 | -9 | NB | NB | NB | NB | | | |
| | H105 106 111 | 47 | 0 | NB | NB | NB | NB | 41 | -9 | NB | NB | NB | NB | | | |
| | H105 108 111 | 37 | 0 | NB | NB | NB | NB | 31 | -9 | NB | NB | NB | NB | | | |
| | H106 108 111 | 69 | 0 | NB | NB | NB | NB | 59 | -9 | NB | NB | NB | NB | | | |
| | H105 106 108 111 | 54 | 0 | NB | NB | NB | NB | 49 | -9 | NB | NB | NB | NB | | | |
| | 1-39 ULC | 97 | 0 | NB | NB | NB | NB | 88 | -9 | NB | NB | NB | NB | | | |

FIG. 19C

| HC | Vk mut | Kinetics at pH 7.2 mAb capture level (RU) | 100nM Antigen bound (RU) | ka (1/Ms) | kd (1/s) | KD (M) | t½ (min) | Kinetics at pH 5.75 mAb capture level (RU) | 100nM antigen bound (RU) | ka (1/Ms) | kd (1/s) | KD (M) | t½ (min) | low/neutral pH ka | kd | KD |
|---|---|---|---|---|---|---|---|---|---|---|---|---|---|---|---|---|
| H4H2964 | H105 | 327 | 23 | 1.43E+05 | 8.40E-03 | 5.89E-08 | 1 | 318 | 2 | IC | IC | IC | IC | | | |
| | H106 | 303 | 26 | 9.67E+04 | 3.40E-03 | 3.52E-08 | 3 | 289 | 11 | 9.46E+04 | 2.08E-02 | 2.20E-07 | 1 | 1.0 | 6.1 | 6.3 |
| | H108 | 287 | 29 | 1.37E+05 | 2.46E-03 | 1.80E-08 | 5 | 268 | 12 | 7.69E+04 | 1.32E-02 | 1.71E-07 | 1 | 0.6 | 5.4 | 9.5 |
| | H111 | 311 | 21 | 1.31E+05 | 6.83E-03 | 5.20E-08 | 2 | 292 | 0 | NB | NB | NB | NB | | | |
| | H105 106 | 285 | 17 | 9.65E+04 | 6.20E-03 | 6.43E-08 | 2 | 262 | -3 | NB | NB | NB | NB | | | |
| | H105 108 | 271 | 21 | 1.23E+05 | 9.82E-03 | 7.99E-08 | 1 | 262 | -3 | NB | NB | NB | NB | | | |
| | H105 111 | 221 | 11 | 2.37E+05 | 2.11E-02 | 8.88E-08 | 1 | 216 | -6 | NB | NB | NB | NB | | | |
| | H106 108 | 344 | 28 | 1.04E+05 | 6.66E-03 | 6.38E-08 | 2 | 316 | 3 | IC | IC | IC | IC | | | |
| | H106 111 | 341 | 25 | 1.16E+05 | 9.09E-03 | 7.81E-08 | 1 | 321 | 2 | IC | IC | IC | IC | | | |
| | H108 111 | 300 | 20 | 9.64E+04 | 1.01E-02 | 1.05E-07 | 1 | 274 | -4 | NB | NB | NB | NB | | | |
| | H105 106 108 | 269 | 10 | 1.31E+05 | 2.52E-02 | 1.93E-07 | 0 | 243 | -8 | NB | NB | NB | NB | | | |
| | H105 106 111 | 286 | 5 | 6.34E+04 | 5.06E-02 | 7.99E-07 | 0 | 265 | -9 | NB | NB | NB | NB | | | |
| | H105 108 111 | 309 | 13 | 3.26E+05 | 3.47E-02 | 1.06E-07 | 0 | 279 | -8 | NB | NB | NB | NB | | | |
| | H106 108 111 | 315 | 9 | 1.55E+05 | 5.89E-02 | 3.81E-07 | 0 | 279 | -8 | NB | NB | NB | NB | | | |
| | H105 106 108 111 | 260 | 0 | NB | NB | NB | NB | 238 | -10 | NB | NB | NB | NB | | | |
| | 1-39 ULC | 386 | 32 | 1.30E+05 | 2.05E-03 | 1.58E-08 | 6 | 362 | 17 | 7.58E+04 | 7.97E-03 | 1.05E-07 | 1 | 0.6 | 3.9 | 6.6 |

FIG. 19D

| HC | Vk mut | Kinetics at pH 7.2 | | | | | | Kinetics at pH 5.75 | | | | | | low/neutral pH | | |
|---|---|---|---|---|---|---|---|---|---|---|---|---|---|---|---|---|
| | | mAb capture level (RU) | 100nM Antigen bound (RU) | ka (1/Ms) | kd (1/s) | KD (M) | t½ (min) | mAb capture level (RU) | 100nM antigen bound (RU) | ka (1/Ms) | kd (1/s) | KD (M) | t½ (min) | ka | kd | KD |
| H4H3010 | H105 | 52 | 8 | 1.06E+05 | 7.43E-04 | 7.04E-09 | 16 | 43 | -1 | NB | NB | NB | NB | | | |
| | H106 | 50 | 9 | 1.26E+05 | 3.54E-04 | 2.82E-09 | 33 | 40 | 0 | NB | NB | NB | NB | | | |
| | H108 | 50 | 8 | 9.29E+04 | 2.43E-04 | 2.62E-09 | 48 | 42 | -1 | NB | NB | NB | NB | | | |
| | H111 | 55 | 11 | 1.53E+05 | 1.66E-04 | 1.09E-09 | 69 | 48 | 2 | IC | IC | IC | IC | | | |
| | H105 106 | 55 | 10 | 1.31E+05 | 5.18E-04 | 3.94E-09 | 22 | 45 | 1 | NB | NB | NB | NB | | | |
| | H105 108 | 48 | 8 | 8.96E+04 | 4.58E-04 | 5.12E-09 | 25 | 41 | -1 | NB | NB | NB | NB | | | |
| | H105 111 | 38 | 6 | 8.85E+04 | 1.64E-04 | 1.85E-09 | 70 | 32 | -3 | NB | NB | NB | NB | | | |
| | H106 108 | 59 | 11 | 1.06E+05 | 1.61E-04 | 1.52E-09 | 72 | 52 | 2 | 4.79E+05 | 1.00E-06 | 2.09E-12 | 11550 | 4.5 | 0.0 | 0.0 |
| | H106 111 | 76 | 7 | 6.81E+04 | 5.23E-04 | 7.68E-09 | 22 | 72 | 0 | NB | NB | NB | NB | | | |
| | H108 111 | 58 | 11 | 1.17E+05 | 9.26E-05 | 7.92E-10 | 125 | 52 | 2 | IC | IC | IC | IC | | | |
| | H105 106 108 | 67 | 13 | 1.11E+05 | 3.17E-04 | 2.86E-09 | 36 | 58 | 4 | IC | IC | IC | IC | | | |
| | H105 106 111 | 70 | 8 | 6.45E+04 | 9.94E-04 | 1.54E-08 | 12 | 57 | -1 | NB | NB | NB | NB | | | |
| | H105 108 111 | 49 | 8 | 8.52E+04 | 1.10E-04 | 1.29E-09 | 105 | 44 | -1 | NB | NB | NB | NB | | | |
| | H106 108 111 | 54 | 3 | 1.02E+04 | 1.46E-03 | 1.44E-07 | 8 | 46 | -6 | NB | NB | NB | NB | | | |
| | H105 106 108 111 | 70 | 6 | 7.28E+04 | 5.55E-03 | 7.61E-08 | 2 | 62 | -6 | NB | NB | NB | NB | | | |
| | 1-39 ULC | 83 | 15 | 1.02E+05 | 1.79E-04 | 1.77E-09 | 64 | 77 | 7 | 2.11E+05 | 1.00E-06 | 4.74E-12 | 11550 | 2.1 | 0.0 | 0.0 |

FIG. 19E

| | | Kinetics at pH 7.2 | | | | | | Kinetics at pH 5.75 | | | | | | low/neutral pH | | |
|---|---|---|---|---|---|---|---|---|---|---|---|---|---|---|---|---|
| HC | Vk mut | mAb capture level (RU) | 100nM Antigen bound (RU) | ka (1/Ms) | kd (1/s) | KD (M) | t½ (min) | mAb capture level (RU) | 100nM antigen bound (RU) | ka (1/Ms) | kd (1/s) | KD (M) | t½ (min) | ka | kd | KD |
| H4H3029 | H105 | 71 | 8 | 1.41E+05 | 2.96E-04 | 2.10E-09 | 39 | 60 | -3 | NB | NB | NB | NB | | | |
| | H106 | 72 | 8 | 1.50E+05 | 2.39E-04 | 1.59E-09 | 48 | 64 | -2 | NB | NB | NB | NB | | | |
| | H108 | 68 | 7 | 1.19E+05 | 7.97E-05 | 6.70E-10 | 145 | 61 | -2 | NB | NB | NB | NB | | | |
| | H111 | 69 | 8 | 1.50E+05 | 1.78E-04 | 1.19E-09 | 65 | 63 | -2 | NB | NB | NB | NB | | | |
| | H105 106 | 88 | 10 | 1.60E+05 | 2.45E-04 | 1.53E-09 | 47 | 77 | 0 | NB | NB | NB | NB | | | |
| | H105 108 | 67 | 8 | 1.45E+05 | 1.14E-04 | 7.84E-10 | 102 | 59 | -3 | NB | NB | NB | NB | | | |
| | H105 111 | 13 | 0 | NB | NB | NB | NB | 14 | -11 | NB | NB | NB | NB | | | |
| | H106 108 | 92 | 10 | 1.34E+05 | 1.34E-04 | 9.98E-10 | 86 | 82 | 0 | NB | NB | NB | NB | | | |
| | H106 111 | 85 | 5 | 5.82E+04 | 1.10E-03 | 1.89E-08 | 10 | 78 | -4 | NB | NB | NB | NB | | | |
| | H108 111 | 62 | 7 | 1.48E+05 | 1.73E-04 | 1.17E-09 | 67 | 55 | -4 | NB | NB | NB | NB | | | |
| | H105 106 108 | 85 | 10 | 1.36E+05 | 1.97E-04 | 1.46E-09 | 59 | 75 | 0 | NB | NB | NB | NB | | | |
| | H105 106 111 | 78 | 6 | 1.35E+05 | 2.18E-03 | 1.61E-08 | 5 | 70 | -4 | NB | NB | NB | NB | | | |
| | H105 108 111 | 55 | 6 | 1.50E+05 | 2.48E-04 | 1.65E-09 | 47 | 48 | -5 | NB | NB | NB | NB | | | |
| | H106 108 111 | 73 | 4 | 8.60E+04 | 1.59E-03 | 1.85E-08 | 7 | 66 | -6 | NB | NB | NB | NB | | | |
| | H105 106 108 111 | 95 | 7 | 1.19E+05 | 6.71E-03 | 5.66E-08 | 2 | 86 | -6 | NB | NB | NB | NB | | | |
| | 1-39 ULC | 108 | 12 | 1.34E+05 | 1.65E-04 | 1.23E-09 | 70 | 98 | 2 | IC | IC | IC | IC | | | |

FIG. 19F

| | | Kinetics at pH 7.2 | | | | | | Kinetics at pH 5.75 | | | | | | low/neutral pH | | |
|---|---|---|---|---|---|---|---|---|---|---|---|---|---|---|---|---|
| HC | Vk mut | mAb capture level (RU) | 100nM Antigen bound (RU) | ka (1/Ms) | kd (1/s) | KD (M) | t½ (min) | mAb capture level (RU) | 100nM antigen bound (RU) | ka (1/Ms) | kd (1/s) | KD (M) | t½ (min) | ka | kd | KD |
| H4H5978 | H105 | 44 | 7 | 3.88E+05 | 5.73E-03 | 1.48E-08 | 2 | 41 | -5 | NB | NB | NB | NB | | | |
| | H106 | 36 | 7 | 3.15E+05 | 3.03E-03 | 9.62E-09 | 4 | 34 | -5 | NB | NB | NB | NB | | | |
| | H108 | 38 | 8 | 3.18E+05 | 9.61E-04 | 3.02E-09 | 12 | 32 | -4 | NB | NB | NB | NB | | | |
| | H111 | 43 | 8 | 3.13E+05 | 2.32E-03 | 7.40E-09 | 5 | 40 | -5 | NB | NB | NB | NB | | | |
| | H105 106 | 33 | 4 | 2.69E+05 | 5.41E-03 | 2.01E-08 | 2 | 29 | -9 | NB | NB | NB | NB | | | |
| | H105 108 | 34 | 7 | 2.13E+05 | 2.15E-03 | 1.01E-08 | 5 | 30 | -7 | NB | NB | NB | NB | | | |
| | H105 111 | 32 | 5 | 3.47E+05 | 6.27E-03 | 1.81E-08 | 2 | 30 | -8 | NB | NB | NB | NB | | | |
| | H106 108 | 50 | 10 | 3.67E+05 | 3.09E-03 | 8.42E-09 | 4 | 46 | -4 | NB | NB | NB | NB | | | |
| | H106 111 | 62 | 12 | 2.88E+05 | 4.47E-03 | 1.55E-08 | 3 | 56 | -2 | NB | NB | NB | NB | | | |
| | H108 111 | 45 | 9 | 3.22E+05 | 2.05E-03 | 6.37E-09 | 6 | 43 | -4 | NB | NB | NB | NB | | | |
| | H105 106 108 | 36 | 5 | 3.57E+05 | 7.48E-03 | 2.10E-08 | 2 | 35 | -8 | NB | NB | NB | NB | | | |
| | H105 106 111 | 39 | 7 | 3.37E+05 | 8.35E-03 | 2.48E-08 | 1 | 35 | -6 | NB | NB | NB | NB | | | |
| | H105 108 111 | 29 | 4 | 2.94E+05 | 4.52E-03 | 1.54E-08 | 3 | 28 | -8 | NB | NB | NB | NB | | | |
| | H106 108 111 | 41 | 7 | 3.12E+05 | 6.37E-03 | 2.04E-08 | 2 | 39 | -6 | NB | NB | NB | NB | | | |
| | H105 106 108 111 | 50 | 9 | 2.97E+05 | 6.83E-03 | 2.30E-08 | 2 | 45 | -5 | NB | NB | NB | NB | | | |
| | 1-39 ULC | 74 | 16 | 2.92E+05 | 1.73E-03 | 5.91E-09 | 7 | 67 | 3 | 1.20E+06 | 9.67E-03 | 8.05E-09 | 1 | 4.1 | 5.6 | 1.4 |

FIG. 19G

| HC | Vk mut | Kinetics at pH 7.2: mAb capture level (RU) | Kinetics at pH 7.2: 100nM Antigen bound (RU) | Kinetics at pH 7.2: ka (1/Ms) | Kinetics at pH 7.2: kd (1/s) | Kinetics at pH 7.2: KD (M) | Kinetics at pH 7.2: t½ (min) | Kinetics at pH 5.75: mAb capture level (RU) | Kinetics at pH 5.75: 100nM antigen bound (RU) | Kinetics at pH 5.75: ka (1/Ms) | Kinetics at pH 5.75: kd (1/s) | Kinetics at pH 5.75: KD (M) | Kinetics at pH 5.75: t½ (min) | low/neutral pH: ka | low/neutral pH: kd | low/neutral pH: KD |
|---|---|---|---|---|---|---|---|---|---|---|---|---|---|---|---|---|
| H4H5981 | H105 | 121 | 24 | 3.04E+05 | 8.81E-03 | 2.90E-08 | 1 | 112 | 7 | 4.47E+05 | 6.21E-02 | 1.39E-07 | 0 | 1.5 | 7.1 | 4.8 |
| | H106 | 113 | 29 | 2.41E+05 | 2.99E-03 | 1.24E-08 | 4 | 103 | 10 | 6.84E+05 | 1.89E-02 | 2.76E-08 | 1 | 2.8 | 6.3 | 2.2 |
| | H108 | 114 | 31 | 3.09E+05 | 2.83E-03 | 9.16E-09 | 4 | 104 | 11 | 5.06E+05 | 1.33E-02 | 2.63E-08 | 1 | 1.6 | 4.7 | 2.9 |
| | H111 | 104 | 26 | 3.45E+05 | 3.98E-03 | 1.15E-08 | 3 | 96 | 4 | 4.54E+05 | 6.26E-02 | 1.38E-07 | 0 | 1.3 | 15.8 | 12.0 |
| | H105 106 | 109 | 26 | 2.39E+05 | 3.10E-03 | 1.29E-08 | 4 | 103 | 9 | 5.00E+05 | 1.77E-02 | 3.53E-08 | 1 | 2.1 | 5.7 | 2.7 |
| | H105 108 | 109 | 27 | 2.91E+05 | 4.48E-03 | 1.54E-08 | 3 | 97 | 7 | 1.00E+06 | 9.77E-02 | 9.76E-08 | 0 | 3.4 | 21.8 | 6.3 |
| | H105 111 | 85 | 16 | 2.62E+05 | 7.59E-03 | 2.90E-08 | 2 | 80 | -1 | NB | NB | NB | NB | | | |
| | H106 108 | 121 | 33 | 2.33E+05 | 2.71E-03 | 1.16E-08 | 4 | 115 | 14 | 3.88E+05 | 1.19E-02 | 3.07E-08 | 1 | 1.7 | 4.4 | 2.6 |
| | H106 111 | 117 | 32 | 2.29E+05 | 2.28E-03 | 9.97E-09 | 5 | 113 | 13 | 3.71E+05 | 8.88E-03 | 2.40E-08 | 1 | 1.6 | 3.9 | 2.4 |
| | H108 111 | 93 | 24 | 3.39E+05 | 4.04E-03 | 1.19E-08 | 3 | 87 | 3 | 4.54E+05 | 5.11E-02 | 1.12E-07 | 0 | 1.3 | 12.7 | 9.4 |
| | H105 106 108 | 94 | 25 | 2.24E+05 | 1.23E-03 | 5.47E-09 | 9 | 85 | 8 | 4.94E+05 | 3.02E-03 | 6.12E-09 | 4 | 2.2 | 2.5 | 1.1 |
| | H105 106 111 | 111 | 24 | 2.31E+05 | 4.65E-03 | 2.01E-08 | 2 | 100 | 4 | 1.94E+05 | 8.05E-02 | 4.15E-07 | 0 | 0.8 | 17.3 | 20.6 |
| | H105 108 111 | 83 | 21 | 2.60E+05 | 5.20E-03 | 2.00E-08 | 2 | 79 | 1 | NB | NB | NB | NB | | | |
| | H106 108 111 | 100 | 28 | 2.11E+05 | 2.23E-03 | 1.05E-08 | 5 | 93 | 6 | 4.26E+05 | 1.83E-02 | 4.29E-08 | 1 | 2.0 | 8.2 | 4.1 |
| | H105 106 108 111 | 104 | 24 | 2.46E+05 | 5.05E-03 | 2.05E-08 | 2 | 98 | 2 | IC | IC | IC | IC | | | |
| | 1-39 ULC | 133 | 34 | 2.80E+05 | 3.40E-03 | 1.22E-08 | 3 | 124 | 13 | 4.29E+05 | 1.42E-02 | 3.30E-08 | 1 | 1.5 | 4.2 | 2.7 |

FIG. 19H

| HC | Vk mut | Kinetics at pH 7.2 | | | | | | Kinetics at pH 5.75 | | | | | | low/neutral pH | | |
|---|---|---|---|---|---|---|---|---|---|---|---|---|---|---|---|---|
| | | mAb capture level (RU) | 100nM Antigen bound (RU) | ka (1/Ms) | kd (1/s) | KD (M) | t½ (min) | mAb capture level (RU) | 100nM antigen bound (RU) | ka (1/Ms) | kd (1/s) | KD (M) | t½ (min) | ka | kd | KD |
| H4H5999 | H105 | 87 | 8 | 5.04E+04 | 1.18E-03 | 2.34E-08 | 10 | 78 | -5 | NB | NB | NB | NB | | | |
| | H106 | 72 | 7 | 1.04E+05 | 6.40E-04 | 6.17E-09 | 18 | 66 | -7 | NB | NB | NB | NB | | | |
| | H108 | 77 | 6 | 3.47E+04 | 1.47E-03 | 4.23E-08 | 8 | 72 | -8 | NB | NB | NB | NB | | | |
| | H111 | 77 | 6 | 1.39E+05 | 4.59E-03 | 3.31E-08 | 3 | 71 | -8 | NB | NB | NB | NB | | | |
| | H105 106 | 85 | 8 | 9.95E+04 | 3.69E-04 | 3.71E-09 | 31 | 77 | -6 | NB | NB | NB | NB | | | |
| | H105 108 | 71 | 6 | 2.60E+03 | 8.63E-04 | 3.32E-07 | 13 | 63 | -7 | NB | NB | NB | NB | | | |
| | H105 111 | 51 | 3 | 9.81E+03 | 7.03E-03 | 7.16E-07 | 2 | 47 | -10 | NB | NB | NB | NB | | | |
| | H106 108 | 80 | 6 | 4.81E+04 | 4.78E-04 | 9.94E-09 | 24 | 71 | -10 | NB | NB | NB | NB | | | |
| | H106 111 | 91 | 9 | 3.28E+04 | 6.44E-04 | 1.96E-08 | 18 | 85 | -6 | NB | NB | NB | NB | | | |
| | H108 111 | 70 | 6 | 3.98E+04 | 2.01E-03 | 5.05E-08 | 6 | 65 | -9 | NB | NB | NB | NB | | | |
| | H105 106 108 | 79 | 5 | 4.95E+04 | 5.53E-04 | 1.12E-08 | 21 | 74 | -10 | NB | NB | NB | NB | | | |
| | H105 106 111 | 74 | 8 | 1.92E+04 | 4.59E-04 | 2.39E-08 | 25 | 68 | -6 | NB | NB | NB | NB | | | |
| | H105 108 111 | 56 | 4 | 1.03E+03 | 4.18E-03 | 4.04E-06 | 3 | 52 | -10 | NB | NB | NB | NB | | | |
| | H106 108 111 | 74 | 5 | 8.96E+03 | 1.66E-03 | 1.86E-07 | 7 | 66 | -9 | NB | NB | NB | NB | | | |
| | H105 106 108 111 | 79 | 7 | 1.73E+04 | 9.49E-04 | 5.50E-08 | 12 | 75 | -9 | NB | NB | NB | NB | | | |
| | 1-39 ULC | 110 | 10 | 5.01E+05 | 4.02E-03 | 8.02E-09 | 3 | 100 | -5 | NB | NB | NB | NB | | | |

FIG. 19I

| | | Kinetics at pH 7.2 | | | | | | Kinetics at pH 5.75 | | | | | | low/neutral pH | | |
|---|---|---|---|---|---|---|---|---|---|---|---|---|---|---|---|---|
| HC | Vk mut | mAb capture level (RU) | 100nM Antigen bound (RU) | ka (1/Ms) | kd (1/s) | KD (M) | t½ (min) | mAb capture level (RU) | 100nM antigen bound (RU) | ka (1/Ms) | kd (1/s) | KD (M) | t½ (min) | ka | kd | KD |
| H4H6011 | H105 | 150 | 22 | 1.15E+05 | 3.17E-04 | 2.77E-09 | 36 | 147 | 6 | 7.61E+04 | 1.00E-06 | 1.31E-11 | 11550 | 0.7 | 0.0 | 0.0 |
| | H106 | 127 | 17 | 8.73E+04 | 3.46E-04 | 3.96E-09 | 33 | 119 | 2 | 4.89E+04 | 1.00E-06 | 2.05E-11 | 11550 | 0.6 | 0.0 | 0.0 |
| | H108 | 124 | 15 | 7.56E+04 | 5.90E-04 | 7.80E-09 | 20 | 112 | -4 | NB | NB | NB | NB | | | |
| | H111 | 135 | 17 | 1.08E+05 | 5.59E-04 | 5.19E-09 | 21 | 128 | 0 | NB | NB | NB | NB | | | |
| | H105 106 | 130 | 18 | 1.03E+05 | 3.91E-04 | 3.81E-09 | 30 | 123 | 3 | 1.89E+05 | 2.33E-04 | 1.23E-09 | 49 | 1.8 | 0.6 | 0.3 |
| | H105 108 | 117 | 16 | 9.29E+04 | 5.24E-04 | 5.64E-09 | 22 | 110 | -2 | NB | NB | NB | NB | | | |
| | H105 111 | 109 | 16 | 1.06E+05 | 4.39E-04 | 4.15E-09 | 26 | 105 | 0 | NB | NB | NB | NB | | | |
| | H106 108 | 105 | 8 | 6.95E+04 | 4.86E-04 | 7.00E-09 | 24 | 100 | -8 | NB | NB | NB | NB | | | |
| | H106 111 | 171 | 16 | 3.07E+05 | 1.44E-03 | 4.69E-09 | 8 | 163 | 0 | NB | NB | NB | NB | | | |
| | H108 111 | 133 | 16 | 9.17E+04 | 6.20E-04 | 6.76E-09 | 19 | 126 | -3 | NB | NB | NB | NB | | | |
| | H105 106 108 | 135 | 10 | 6.11E+04 | 6.93E-04 | 1.13E-08 | 17 | 132 | -8 | NB | NB | NB | NB | | | |
| | H105 106 111 | 117 | 12 | 6.52E+04 | 8.99E-04 | 1.38E-08 | 13 | 111 | -3 | NB | NB | NB | NB | | | |
| | H105 108 111 | 129 | 16 | 9.95E+04 | 5.82E-04 | 5.85E-09 | 20 | 121 | -3 | NB | NB | NB | NB | | | |
| | H106 108 111 | 124 | 11 | 2.36E+04 | 8.53E-04 | 3.62E-08 | 14 | 118 | -6 | NB | NB | NB | NB | | | |
| | H105 106 108 111 | 144 | 14 | 3.65E+04 | 9.51E-04 | 2.60E-08 | 12 | 140 | -6 | NB | NB | NB | NB | | | |
| | 1-39 ULC | 198 | 25 | 1.13E+05 | 4.36E-04 | 3.85E-09 | 27 | 181 | 6 | 6.02E+04 | 2.02E-04 | 3.36E-09 | 57 | 0.5 | 0.5 | 0.9 |
| | Buffer | 2 | 1 | NB | NB | NB | NB | -2 | -11 | NB | NB | NB | NB | | | |
| | Buffer | 3 | 1 | NB | NB | NB | NB | 0 | -10 | NB | NB | NB | NB | | | |

FIG. 19J

| | | Kinetics at pH 7.4 | | | | | | Kinetics at pH 5.75 | | | | | | Ratio of low pH / neutral pH | | |
|---|---|---|---|---|---|---|---|---|---|---|---|---|---|---|---|---|
| Heavy Chain | Light Chain Mutant | mAb captured (RU) | 50nM Antigen Bindng (RU) | ka (1/Ms) | kd (1/s) | KD (M) | t½ (min) | mAb captured (RU) | 50nM Antigen Bindng (RU) | ka (1/Ms) | kd (1/s) | KD (M) | t½ (min) | ka | kd | KD |
| 1 | H105 | 488 | **47.2** | 3.52E+05 | 9.30E-03 | 2.64E-08 | 1.2 | 378 | **37.8** | 4.24E+05 | 1.38E-02 | 3.24E-08 | 0.8 | 1.2 | 1.5 | 1.2 |
| | H106 | 620 | **73.7** | 3.22E+05 | 3.67E-03 | 1.14E-08 | 3.1 | 505 | **65.4** | 3.66E+05 | 4.86E-03 | 1.33E-08 | 2.4 | 1.1 | 1.3 | 1.2 |
| | H108 | 648 | **99.0** | 3.17E+05 | 2.07E-03 | 6.54E-09 | 5.6 | 496 | **80.7** | 3.59E+05 | 3.02E-03 | 8.41E-09 | 3.8 | 1.1 | 1.5 | 1.3 |
| | H111 | 669 | **81.0** | 3.01E+05 | 3.81E-03 | 1.27E-08 | 3.0 | 536 | **62.8** | 3.32E+05 | 5.41E-03 | 1.63E-08 | 2.1 | 1.1 | 1.4 | 1.3 |
| | H105/106 | 492 | **55.6** | 3.74E+05 | 6.44E-03 | 1.72E-08 | 1.8 | 404 | **45.7** | 4.30E+05 | 1.01E-02 | 2.34E-08 | 1.1 | 1.2 | 1.6 | 1.4 |
| | H105/108 | 538 | **75.2** | 3.28E+05 | 4.17E-03 | 1.27E-08 | 2.8 | 416 | **56.3** | 3.87E+05 | 7.43E-03 | 1.92E-08 | 1.6 | 1.2 | 1.8 | 1.5 |
| | H105/111 | 501 | **44.6** | 3.44E+05 | 9.77E-03 | 2.84E-08 | 1.2 | 402 | **31.9** | 4.06E+05 | 1.70E-02 | 4.19E-08 | 0.7 | 1.2 | 1.7 | 1.5 |
| | H106/108 | 494 | **64.9** | 3.36E+05 | 4.14E-03 | 1.23E-08 | 2.8 | 407 | **43.0** | 4.07E+05 | 1.17E-02 | 2.86E-08 | 1.0 | 1.2 | 2.8 | 2.3 |
| | H106/111 | 536 | **78.2** | 3.09E+05 | 3.10E-03 | 1.00E-08 | 3.7 | 423 | **61.4** | 3.62E+05 | 4.68E-03 | 1.29E-08 | 2.5 | 1.2 | 1.5 | 1.3 |
| | H108/111 | 584 | **78.5** | 3.11E+05 | 3.80E-03 | 1.22E-08 | 3.0 | 473 | **59.0** | 3.50E+05 | 6.13E-03 | 1.75E-08 | 1.9 | 1.1 | 1.6 | 1.4 |
| | H105/106/108 | 442 | **51.2** | 3.72E+05 | 6.38E-03 | 1.71E-08 | 1.8 | 370 | **28.4** | 4.26E+05 | 2.13E-02 | 5.00E-08 | 0.5 | 1.1 | 3.3 | 2.9 |
| | H105/106/111 | 473 | **62.8** | 3.40E+05 | 4.55E-03 | 1.34E-08 | 2.5 | 378 | **47.6** | 4.07E+05 | 7.42E-03 | 1.82E-08 | 1.6 | 1.2 | 1.6 | 1.4 |
| | H105/108/111 | 433 | **49.5** | 3.57E+05 | 7.42E-03 | 2.08E-08 | 1.6 | 354 | **31.3** | 4.09E+05 | 1.73E-02 | 4.23E-08 | 0.7 | 1.1 | 2.3 | 2.0 |
| | H106/108/111 | 491 | **66.6** | 3.44E+05 | 3.82E-03 | 1.11E-08 | 3.0 | 415 | **43.3** | 3.91E+05 | 1.06E-02 | 2.72E-08 | 1.1 | 1.1 | 2.8 | 2.5 |
| | H105/106/108/111 | 454 | **57.9** | 3.51E+05 | 5.77E-03 | 1.64E-08 | 2.0 | 368 | **36.8** | 4.06E+05 | 1.35E-02 | 3.32E-08 | 0.9 | 1.2 | 2.3 | 2.0 |
| | ULC + Heavy | 586 | **76.0** | 3.16E+05 | 3.85E-03 | 1.22E-08 | 3.0 | 483 | **66.5** | 3.45E+05 | 4.58E-03 | 1.33E-08 | 2.5 | 1.1 | 1.2 | 1.1 |
| | Heavy only | 141 | **-1.3** | NB | NB | NB | NB | 107 | **-6.7** | NB | NB | NB | NB | Negative Control | | |
| | No DNA | 60 | **-1.5** | NB | NB | NB | NB | 26 | **-7.2** | NB | NB | NB | NB | | | |

FIG. 20A

| Heavy Chain | Light Chain Mutant | Kinetics at pH 7.4 | | | | | | Kinetics at pH 5.75 | | | | | | Ratio of low pH / neutral pH | | |
|---|---|---|---|---|---|---|---|---|---|---|---|---|---|---|---|---|
| | | mAb captured (RU) | 50nM Antigen Bindng (RU) | ka (1/Ms) | kd (1/s) | KD (M) | t½ (min) | mAb captured (RU) | 50nM Antigen Bindng (RU) | ka (1/Ms) | kd (1/s) | KD (M) | t½ (min) | ka | kd | KD |
| 2 | **H105** | 720 | **33.7** | 1.02E+05 | 9.10E-04 | 8.89E-09 | 12.7 | 595 | **0.3** | NB | NB | NB | NB | No binding at Low pH | | |
| | **H106** | 735 | **32.9** | 9.11E+04 | 4.47E-04 | 4.91E-09 | 25.8 | 623 | **4.3** | 2.27E+04 | 6.41E-03 | 2.82E-07 | 1.8 | 0.2 | 14.3 | 57.4 |
| | **H108** | 728 | **32.2** | 8.48E+04 | 2.67E-04 | 3.14E-09 | 43.3 | 598 | **3.6** | 1.16E+03 | 3.41E-03 | 2.93E-06 | 3.4 | 0.0 | 12.8 | 933.1 |
| | **H111** | 802 | **42.4** | 1.17E+05 | 1.15E-04 | 9.88E-10 | 100.3 | 670 | **14.1** | 3.01E+04 | 7.08E-04 | 2.35E-08 | 16.3 | 0.3 | 6.1 | 23.8 |
| | **H105/106** | 570 | **24.9** | 8.51E+04 | 2.92E-04 | 3.43E-09 | 39.5 | 484 | **2.4** | 1.14E+04 | 6.47E-03 | 5.69E-07 | 1.8 | 0.1 | 22.1 | 165.9 |
| | **H105/108** | 723 | **28.4** | 8.73E+04 | 1.30E-03 | 1.49E-08 | 8.9 | 603 | **-2.6** | NB | NB | NB | NB | No binding at Low pH | | |
| | **H105/111** | 627 | **28.5** | 8.82E+04 | 3.60E-04 | 4.08E-09 | 32.1 | 519 | **2.3** | 1.02E+04 | 1.30E-02 | 1.27E-06 | 0.9 | 0.1 | 36.2 | 311.3 |
| | **H106/108** | 550 | **21.1** | 6.75E+04 | 9.12E-04 | 1.35E-08 | 12.7 | 470 | **-1.9** | NB | NB | NB | NB | No binding at Low pH | | |
| | **H106/111** | 808 | **32.7** | 9.01E+04 | 6.78E-04 | 7.52E-09 | 17.0 | 678 | **0.9** | NB | NB | NB | NB | No binding at Low pH | | |
| | **H108/111** | 801 | **40.5** | 1.17E+05 | 9.80E-05 | 8.40E-10 | 117.8 | 676 | **10.6** | 1.87E+04 | 5.84E-04 | 3.12E-08 | 19.8 | 0.2 | 6.0 | 37.1 |
| | **H105/106/108** | 409 | **13.0** | 8.21E+04 | 4.29E-04 | 5.22E-09 | 26.9 | 345 | **-4.4** | NB | NB | NB | NB | No binding at Low pH | | |
| | **H105/106/111** | 767 | **9.3** | 4.84E+04 | 1.25E-03 | 2.58E-08 | 9.3 | 645 | **-6.1** | NB | NB | NB | NB | No binding at Low pH | | |
| | **H105/108/111** | 578 | **24.5** | 8.99E+04 | 2.87E-04 | 3.19E-09 | 40.2 | 479 | **-0.7** | NB | NB | NB | NB | No binding at Low pH | | |
| | **H106/108/111** | 765 | **15.1** | 5.04E+04 | 1.65E-03 | 3.27E-08 | 7.0 | 661 | **-5.9** | NB | NB | NB | NB | No binding at Low pH | | |
| | **H105/106/108/111** | 723 | **0.3** | NB | NB | NB | NB | 611 | **-7.0** | NB | NB | NB | NB | No binding at either pH tested | | |
| | **ULC + Heavy** | 781 | **39.8** | 1.13E+05 | 1.78E-04 | 1.57E-09 | 64.9 | 665 | **11.7** | 2.04E+04 | 1.22E-03 | 6.00E-08 | 9.4 | 0.2 | 6.9 | 38.2 |
| | **Heavy only** | 143 | **-1.8** | NB | NB | NB | NB | 115 | **-6.1** | NB | NB | NB | NB | Negative Control | | |
| | **No DNA** | 63 | **-2.1** | NB | NB | NB | NB | 35 | **-6.4** | NB | NB | NB | NB | | | |

FIG. 20B

| | | Kinetics at pH 7.4 | | | | | | Kinetics at pH 5.75 | | | | | | Ratio of low pH / neutral pH | | |
|---|---|---|---|---|---|---|---|---|---|---|---|---|---|---|---|---|
| Heavy Chain | Light Chain Mutant | mAb captured (RU) | 50nM Antigen Bindng (RU) | ka (1/Ms) | kd (1/s) | KD (M) | t½ (min) | mAb captured (RU) | 50nM Antigen Bindng (RU) | ka (1/Ms) | kd (1/s) | KD (M) | t½ (min) | ka | kd | KD |
| 3 | H105 | 574 | **12.4** | 5.64E+04 | 1.21E-03 | 2.15E-08 | 9.5 | 496 | **0.1** | NB | NB | NB | NB | No binding at Low pH | | |
| | H106 | 662 | **16.1** | 7.37E+04 | 5.36E-04 | 7.27E-09 | 21.5 | 584 | **3.0** | 3.00E+04 | 4.79E-03 | 1.58E-07 | 2.4 | 0.4 | 8.9 | 21.7 |
| | H108 | 518 | **12.3** | 4.82E+04 | 2.15E-04 | 4.46E-09 | 53.7 | 440 | **2.2** | 3.70E+04 | 1.25E-03 | 3.40E-08 | 9.3 | 0.8 | 5.8 | 7.6 |
| | H111 | 480 | **9.1** | 1.82E+04 | 4.16E-04 | 2.28E-08 | 27.7 | 406 | **0.4** | NB | NB | NB | NB | No binding at Low pH | | |
| | H105/106 | 487 | **7.4** | 1.82E+04 | 7.45E-03 | 4.10E-07 | 1.6 | 423 | **-4.1** | NB | NB | NB | NB | Poor binding at Neutral, No binding at Low pH | | |
| | H105/108 | 548 | **11.8** | 3.25E+04 | 5.25E-04 | 1.62E-08 | 22.0 | 468 | **0.0** | NB | NB | NB | NB | No binding at Low pH | | |
| | H105/111 | 504 | **7.9** | 1.06E+04 | 1.66E-03 | 1.57E-07 | 7.0 | 430 | **-1.6** | NB | NB | NB | NB | Poor binding at Neutral, No binding at Low pH | | |
| | H106/108 | 487 | **10.7** | 6.64E+04 | 2.91E-04 | 4.38E-09 | 39.7 | 424 | **-4.2** | NB | NB | NB | NB | No binding at Low pH | | |
| | H106/111 | 563 | **10.5** | 2.75E+04 | 3.71E-04 | 1.35E-08 | 31.2 | 482 | **-1.9** | NB | NB | NB | NB | No binding at Low pH | | |
| | H108/111 | 528 | **10.1** | 1.10E+04 | 8.01E-05 | 7.27E-09 | 144.2 | 449 | **-0.5** | NB | NB | NB | NB | No binding at Low pH | | |
| | H105/106/108 | 470 | **6.4** | 2.64E+04 | 5.40E-03 | 2.04E-07 | 2.1 | 412 | **-5.3** | NB | NB | NB | NB | Poor binding at Neutral, No binding at Low pH | | |
| | H105/106/111 | 539 | **0.8** | NB | NB | NB | NB | 462 | **-5.6** | NB | NB | NB | NB | No binding at either pH tested | | |
| | H105/108/111 | 419 | **6.5** | 1.76E+04 | 4.01E-04 | 2.27E-08 | 28.8 | 354 | **-3.8** | NB | NB | NB | NB | No binding at Low pH | | |
| | H106/108/111 | 509 | **3.3** | 5.47E+04 | 9.07E-04 | 1.66E-08 | 12.7 | 443 | **-5.9** | NB | NB | NB | NB | Poor binding at Neutral, No binding at Low pH | | |
| | H105/106/108/111 | 450 | **-1.1** | NB | NB | NB | NB | 382 | **-6.4** | NB | NB | NB | NB | No binding at either pH tested | | |
| | ULC + Heavy | 688 | **16.9** | 3.54E+04 | 3.57E-04 | 1.01E-08 | 32.3 | 598 | **5.0** | 1.16E+04 | 1.76E-03 | 1.52E-07 | 6.6 | 0.3 | 4.9 | 15.0 |
| | Heavy only | 152 | **-1.6** | NB | NB | NB | NB | 127 | **-5.4** | NB | NB | NB | NB | Negative Control | | |
| | No DNA | 54 | **-1.7** | NB | NB | NB | NB | 30 | **-5.6** | NB | NB | NB | NB | | | |

FIG. 20C

| | | Kinetics at pH 7.4 | | | | | | Kinetics at pH 5.75 | | | | | | Ratio of low pH / neutral pH | | |
|---|---|---|---|---|---|---|---|---|---|---|---|---|---|---|---|---|
| Heavy Chain | Light Chain Mutant | mAb captured (RU) | 50nM Antigen Bindng (RU) | ka (1/Ms) | kd (1/s) | KD (M) | t½ (min) | mAb captured (RU) | 50nM Antigen Bindng (RU) | ka (1/Ms) | kd (1/s) | KD (M) | t½ (min) | ka | kd | KD |
| 4 | **H105** | 598 | **4.9** | 2.80E+04 | 1.38E-03 | 4.91E-08 | 8.4 | 512 | **-0.2** | NB | NB | NB | NB | Poor binding at Neutral, No binding at Low pH | | |
| | **H106** | 569 | **7.1** | 1.49E+04 | 9.67E-04 | 6.49E-08 | 11.9 | 494 | **1.2** | NB | NB | NB | NB | Poor binding at Neutral, No binding at Low pH | | |
| | **H108** | 587 | **6.3** | 2.25E+04 | 2.02E-03 | 8.96E-08 | 5.7 | 500 | **-0.9** | NB | NB | NB | NB | Poor binding at Neutral, No binding at Low pH | | |
| | **H111** | 606 | **5.6** | 3.46E+04 | 2.19E-03 | 6.33E-08 | 5.3 | 521 | **-0.9** | NB | NB | NB | NB | Poor binding at Neutral, No binding at Low pH | | |
| | **H105/106** | 517 | **3.1** | 2.00E+04 | 2.05E-03 | 1.03E-07 | 5.6 | 460 | **-1.1** | NB | NB | NB | NB | Poor binding at Neutral, No binding at Low pH | | |
| | **H105/108** | 581 | **2.5** | 1.61E+05 | 2.30E-03 | 1.43E-08 | 5.0 | 506 | **-2.7** | NB | NB | NB | NB | Poor binding at Neutral, No binding at Low pH | | |
| | **H105/111** | 575 | **3.8** | 1.01E+04 | 1.70E-03 | 1.68E-07 | 6.8 | 504 | **-2.0** | NB | NB | NB | NB | Poor binding at Neutral, No binding at Low pH | | |
| | **H106/108** | 498 | **2.5** | 4.01E+04 | 6.07E-04 | 1.51E-08 | 19.0 | 447 | **-3.9** | NB | NB | NB | NB | Poor binding at Neutral, No binding at Low pH | | |
| | **H106/111** | 587 | **3.0** | 7.85E+04 | 9.20E-04 | 1.17E-08 | 12.6 | 509 | **-2.6** | NB | NB | NB | NB | Poor binding at Neutral, No binding at Low pH | | |
| | **H108/111** | 599 | **4.0** | 9.68E+04 | 2.02E-03 | 2.09E-08 | 5.7 | 528 | **-2.6** | NB | NB | NB | NB | Poor binding at Neutral, No binding at Low pH | | |
| | **H105/106/108** | 64 | **-1.7** | NB | NB | NB | NB | 46 | **-5.4** | NB | NB | NB | NB | No binding at either pH tested | | |
| | **H105/106/111** | 561 | **1.1** | NB | NB | NB | NB | 493 | **-2.8** | NB | NB | NB | NB | No binding at either pH tested | | |
| | **H105/108/111** | 521 | **2.7** | 7.66E+04 | 1.29E-03 | 1.68E-08 | 9.0 | 461 | **-3.2** | NB | NB | NB | NB | Poor binding at Neutral, No binding at Low pH | | |
| | **H106/108/111** | 577 | **1.3** | NB | NB | NB | NB | 514 | **-4.2** | NB | NB | NB | NB | No binding at either pH tested | | |
| | **H105/106/108/111** | 554 | **0.6** | NB | NB | NB | NB | 495 | **-4.8** | NB | NB | NB | NB | No binding at either pH tested | | |
| | **ULC + Heavy** | 585 | **7.4** | 5.69E+04 | 2.01E-03 | 3.53E-08 | 5.7 | 527 | **1.9** | NB | NB | NB | NB | No binding at Low pH | | |
| | **Heavy only** | 187 | **-2.4** | NB | NB | NB | NB | 161 | **-5.4** | NB | NB | NB | NB | Negative Control | | |
| | **No DNA** | 49 | **-2.6** | NB | NB | NB | NB | 25 | **-5.6** | NB | NB | NB | NB | | | |

FIG. 20D

| Heavy Chain | Light Chain Mutant | Kinetics at pH 7.4: mAb captured (RU) | 50nM Antigen Bindng (RU) | ka (1/Ms) | kd (1/s) | KD (M) | t½ (min) | Kinetics at pH 5.75: mAb captured (RU) | 50nM Antigen Bindng (RU) | ka (1/Ms) | kd (1/s) | KD (M) | t½ (min) | Ratio of low pH / neutral pH: ka | kd | KD |
|---|---|---|---|---|---|---|---|---|---|---|---|---|---|---|---|---|
| 5 | H105 | 522 | 3.2 | 5.05E+04 | 9.48E-03 | 1.88E-07 | 1.2 | 463 | -4.3 | NB | NB | NB | NB | Poor binding at Neutral, No binding at Low pH | | |
| | H106 | 496 | 0.3 | NB | NB | NB | NB | 437 | -5.2 | NB | NB | NB | NB | No binding at either pH tested | | |
| | H108 | 475 | -0.1 | NB | NB | NB | NB | 415 | -5.7 | NB | NB | NB | NB | No binding at either pH tested | | |
| | H111 | 523 | 1.6 | NB | NB | NB | NB | 463 | -4.7 | NB | NB | NB | NB | No binding at either pH tested | | |
| | H105/106 | 534 | -0.6 | NB | NB | NB | NB | 472 | -5.5 | NB | NB | NB | NB | No binding at either pH tested | | |
| | H105/108 | 499 | 2.0 | 5.80E+04 | 1.16E-02 | 1.99E-07 | 1.0 | 433 | -5.5 | NB | NB | NB | NB | Poor binding at Neutral, No binding at Low pH | | |
| | H105/111 | 489 | 0.1 | NB | NB | NB | NB | 426 | -4.7 | NB | NB | NB | NB | No binding at either pH tested | | |
| | H106/108 | 441 | -0.5 | NB | NB | NB | NB | 386 | -4.2 | NB | NB | NB | NB | No binding at either pH tested | | |
| | H106/111 | 529 | -0.8 | NB | NB | NB | NB | 461 | -6.3 | NB | NB | NB | NB | No binding at either pH tested | | |
| | H108/111 | 495 | 4.1 | 1.73E+05 | 1.06E-02 | 6.11E-08 | 1.1 | 435 | -4.0 | NB | NB | NB | NB | Poor binding at Neutral, No binding at Low pH | | |
| | H105/106/108 | 505 | -1.1 | NB | NB | NB | NB | 444 | -5.5 | NB | NB | NB | NB | No binding at either pH tested | | |
| | H105/106/111 | 499 | -1.7 | NB | NB | NB | NB | 438 | -5.8 | NB | NB | NB | NB | No binding at either pH tested | | |
| | H105/108/111 | 436 | 0.8 | NB | NB | NB | NB | 388 | -3.7 | NB | NB | NB | NB | No binding at either pH tested | | |
| | H106/108/111 | 539 | -1.4 | NB | NB | NB | NB | 477 | -4.0 | NB | NB | NB | NB | No binding at either pH tested | | |
| | H105/106/108/111 | 556 | -1.6 | NB | NB | NB | NB | 490 | -4.4 | NB | NB | NB | NB | No binding at either pH tested | | |
| | ULC + Heavy | 516 | 0.6 | NB | NB | NB | NB | 451 | -5.0 | NB | NB | NB | NB | No binding at either pH tested | | |
| | Heavy only | 144 | -1.3 | NB | NB | NB | NB | 122 | -5.7 | NB | NB | NB | NB | Negative Control | | |
| | No DNA | 47 | -1.4 | NB | NB | NB | NB | 25 | -5.8 | NB | NB | NB | NB | Negative Control | | |

FIG. 20E

| $V_H$ | $V_K$ | $K_D$ at pH7.4 (nM) | $K_D$ at pH5.75 (nM) | $T_{1/2}$ at pH7.4 (min) | $T_{1/2}$ at pH5.75 (min) |
|---|---|---|---|---|---|
| 2 | Parental ULC | 1.6 | 60 | 65 | 9.4 |
| 2 | ULC (His105,106) | 3.4 | 570 | 39 | 1.8 |
| 2 | ULC (His105,111) | 4.1 | 1270 | 32 | 0.9 |
| 2 | ULC (His105,108,111) | 3.2 | NB | 40 | NB |
| 2 | ULC (His105,106,108) | 5.2 | NB | 27 | NB |
| 3 | Parental ULC | 10.1 | 152 | 32 | 6.6 |
| 3 | ULC (His106,108) | 4.4 | NB | 40 | NB |
| 3 | ULC (His108,111) | 7.3 | NB | 144 | NB |
| 6 | Parental ULC | 3.0 | 2.4 | 10 | 6 |
| 6 | ULC (His105,111) | 3.5 | NB | 9 | NB |
| 6 | ULC (His106, 108,111) | 2.0 | NB | 16 | NB |

FIG. 21

Site-directed mutagenesis primers for Histidine substitutions in CDR3 of Universal Light Chain of hVK1-39JK5

| Primer name | Sequence | %GC | N | %mismatch | Tm |
|---|---|---|---|---|---|
| GERMLINE hVH1-39/JK5 | CAACTTACTACTGTCAACAGAGTTACAGTACCCCTCCGATCACCTTCGGC | | | | |
| 1633-H106/108/111 F | CTTACTACTGTCAACA**T**AGT**C**ACAGTACCC**A**TCCGATCACCTTCG | 47.0 | 45 | 6.7 | 79.0 |
| 1633-H105/106/108/111 F | CAACTTACTACTGTCA**C**CA**T**AGT**C**ACAGTACCC**A**TCCGATCACCTTCGGC | 50.0 | 50 | 8.0 | 80.5 |
| 1633-H106/108/111 R | CGAAGGTGATCGGA**T**GGGTACTGT**G**ACT**A**TGTTGACAGTAGTAAG | 47.0 | 45 | 6.7 | 79.0 |
| 1633-H105/106/108/111 R | GCCGAAGGTGATCGGA**T**GGGTACTGT**G**ACT**A**TG**G**TGACAGTAGTAAGTTG | 50.0 | 50 | 8.0 | 80.5 |

| Primer | SEQ ID NO |
|---|---|
| GERMLINE hVK1-39/JK5 | 405 |
| 1633-H106/108/111 F | 358 |
| 1633-H105/106/108/111 F | 359 |
| 1633-H106/108/111 R | 360 |
| 1633-H105/106/108/111 R | 361 |

FIG. 22

| | 105 | 106 | 107 | 108 | 109 | 110 | 111 | |
|---|---|---|---|---|---|---|---|---|
| WT | Q | Q | Y | G | S | S | P | SEQ ID NO:399 |
| | CAG | CAG | TAT | GGT | AGC | TCA | CCT | SEQ ID NO:398 |
| H105/106/107/109 | **H** | **H** | **H** | G | **H** | S | P | SEQ ID NO:401 |
| | CA**T** | CA**C** | **C**AT | GGT | **CA**C | TCA | CCT | SEQ ID NO:400 |
| H105/106/109 | **H** | **H** | Y | G | **H** | S | P | SEQ ID NO:403 |
| | CA**T** | CA**C** | TAT | GGT | **CA**C | TCA | CCT | SEQ ID NO:402 |

FIG. 27

Site-directed mutagenesis primers for Histidine substitutions in CDR3 of VK3-20JK1 ULC plasmid

| Primer name | Sequence | %GC | N | mismatches | Tm |
|---|---|---|---|---|---|
| GERMLINE hVK3-20 | GATTTTGCAGTGTATTACTGTCA*GC*A*GT*ATGGT*AG*CTCACCTTGGACGTTCGGC | | | | |
| hVK3-20 (H105/106/107/109) F | GATTTTGCAGTGTATTACTGTCA**T**CA**CC**ATGGT**CA**CTCACCTTGGACGTTCGGC | 48 | 54 | 5 | 79.5 |
| hVK3-20 (H105/106/107/109) R | GCCGAACGTCCAAGGTGAG**TG**ACCAT**GG**TG**A**TGACAGTAATACACTGCAAAATC | 48 | 54 | 5 | 79.5 |
| hVK3-20 (H105/106/109) F | GCAGTGTATTACTGTCA**T**CA**C**TATGGT**CA**CTCACCTTGGACGTTCGG | 49 | 47 | 4 | 78.7 |
| hVK3-20 (H105/106/109) R | CCGAACGTCCAAGGTGAG**TG**ACCATA**G**TG**A**TGACAGTAATACACTGC | 49 | 47 | 4 | 79.7 |

| Primer | SEQ ID NO |
|---|---|
| GERMLINE hVK3-20/JK1 | 384 |
| hVK3-20 H105/106/107/109 F | 385 |
| hVK3-20 H105/106/107/109 R | 386 |
| hVK3-20 H105/106/109 F | 387 |
| hVK3-20 H105/106/109 R | 388 |

FIG. 28

SEQUENCE LISTING

```
<160> NUMBER OF SEQ ID NOS: 405

<210> SEQ ID NO 1
<211> LENGTH: 9586
<212> TYPE: DNA
<213> ORGANISM: Homo sapiens
<220> FEATURE:
```

<221> NAME/KEY: misc_feature
<222> LOCATION: (1)..(9586)
<223> OTHER INFORMATION: HD 1.1-6.6

<400> SEQUENCE: 1
tccccgttga agctgacctg cccagagggg cctgggccca ccccacacac cggggcggaa 60
tgtgtacagg ccccggtctc tgtgggtgtt ccgctaactg gggctcccag tgctcacccc 120
acaactaaag cgagccccag cctccagagc cccgaagga gatgccgccc acaagcccag 180
cccccatcca ggaggcccca gagctcaggg cgccggggca gattctgaac agccccgagt 240
cacggtgggt accactggca cgaccaccgt gagaaaaact gtgtccaaaa ctgtctcctg 300
gcccctgctg gaggccgcgc cagagagggg agcagccgcc ccgaacctag gtcctgctca 360
gctcacacga cccccagcac ccagagcaca acggagtccc cattgaatgg tgaggacggg 420
gaccagggct ccagggggtc atggaagggg ctggacccca tcctactgct atggtcccag 480
tgctcctggc cagaactgac cctaccaccg acaagagtcc ctcagggaaa cgggggtcac 540
tggcacctcc cagcatcaac cccaggcagc acaggcataa accccacatc cagagccgac 600
tccaggagca gagacacccc agtaccctgg gggacaccga ccctgatgac tccccactgg 660
aatccacccc agagtccacc aggaccaaag accccgcccc tgtctctgtc cctcactcag 720
gacctgctgc ggggcgggcc atgagaccag actcgggctt agggaacacc actgtggccc 780
caacctcgac caggccacag gcccttcctt cctgccctgc ggcagcacag actttggggt 840
ctgtgcagag aggaatcaca gaggccccag gctgaggtgg tgggggtgga agacccccag 900
gaggtggccc acttcccttc ctcccagctg gaacccacca tgaccttctt aagatagggg 960
tgtcatccga ggcaggtcct ccatggagct cccttcaggc tcctccccgg tcctcactag 1020
gcctcagtcc cggctgcggg aatgcagcca ccacaggcac accaggcagc ccagacccag 1080
ccagcctgca gtgcccaagc ccacattctg gagcagagca ggctgtgtct gggagagtct 1140
gggctcccca ccgccccccc gcacacccca cccacccctg tccaggccct atgcaggagg 1200
gtcagagccc cccatggggt atggacttag ggtctcactc acgtggctcc cctcctgggt 1260
gaaggggtct catgcccaga tccccacagc agagctggtc aaaggtggag gcagtggccc 1320
cagggccacc ctgacctgga ccctcaggct cctctagccc tggctgccct gctgtccctg 1380
ggaggcctgg actccaccag accacaggtc cagggcaccg cccataggtg ctgcccacac 1440
tcagttcaca ggaagaagat aagctccaga cccccaagac tgggacctgc cttcctgcca 1500
ccgcttgtag ctccagacct ccgtgcctcc cccgaccact tacacacggg ccagggagct 1560
gttccacaaa gatcaacccc aaaccgggac cgcctggcac tcgggccgct gccacttccc 1620
tctccatttg ttcccagcac ctctgtgctc cctccctcct ccctccttca ggggaacagc 1680
ctgtgcagcc cctccctgca ccccacaccc tggggaggcc caaccctgcc tccagccctt 1740
tctcccccgc tgctcttcct gcccatccag acaaccctgg ggtcccatcc ctgcagccta 1800
caccctggtc tccacccaga cccctgtctc tccctccaga caccccctccc aggccaaccc 1860 tgcacatgca ggccctcccc ttttctgctg ccagagcctc agtttctacc ctctgtgcct 1920 acccccctgcc tcctcctgcc cacaactcga gctcttcctc tcctggggcc cctgagccat 1980
ggcactgacc gtgcactccc acccccacac tgcccatgcc ctcaccttcc tcctggacac 2040
tctgaccccg ctcccctctt ggacccagcc ctggtatttc caggacaaag gctcacccaa 2100
gtcttcccca tgcaggccct tgccctcact gcccggttac acggcagcct cctgtgcaca 2160
gaagcaggga gctcagccct tccacaggca gaaggcactg aaagaaatcg gcctccagca 2220
ccctgatgca cgtccgcctg tgtctctcac tgcccgcacc tgcagggagg ctcggcactc 2280
cctgtaaaga cgagggatcc aggcagcaac atcatgggag aatgcagggc tcccagacag 2340
cccagccctc tcgcaggcct ctcctgggaa gagacctgca gccaccactg aacagccacg 2400
gagcccgctg gatagtaact gagtcagtga ccgacctgga gggcagggga gcagtgaacc 2460
ggagcccaga ccatagggac agagaccagc cgctgacatc ccgagcccct cactggcggc 2520
cccagaacac cgcgtggaaa cagaacagac ccacattccc acctggaaca gggcagacac 2580
tgctgagccc ccagcaccag ccctgagaaa caccaggcaa cggcatcaga gggggctcct 2640
gagaaagaaa ggaggggagg tctccttcac cagcaagtac ttcccttgac caaaaacagg 2700
gtccacgcaa ctcccccagg acaaaggagg agccccctgt acagcactgg gctcagagtc 2760
ctctcccaca caccctgagt ttcagacaaa aaccccctgg aaatcatagt atcagcagga 2820
gaactagcca gagacagcaa gaggggactc agtgactccc gcggggacag gaggattttg 2880
tgggggctcg tgtcactgtg aggacattgt agtcatacca gctgccatac ccacagtgac 2940
acagccccat tcccaaagcc ctgctgtaaa cgcttccact tctggagctg aggggctggg 3000
gggagcgtct gggaagtagg gcctaggggt ggccatcaat gcccaaaacg caccagactc 3060
ccccccagac atcaccccac tggccagtga gcagagtaaa cagaaaatga gaagcagctg 3120
ggaagcttgc acaggcccca aggaaagagc tttggcgggt gtgcaagagg ggatgcgggc 3180
agagcctgag cagggccttt tgctgtttct gctttcctgt gcagatagtt ccataaactg 3240
gtgttcaaga tcgatggctg ggagtgagcc caggaggaca gtgtgggaag ggcacaggga 3300
aggagaagca gccgctatcc tacactgtca tctttcaaga gtttgccctg tgcccacaat 3360
gctgcatcat gggatgctta acagctgatg tagacacagc taaagagaga atcagtgaaa 3420
tggatttgca gcacagatct gaataaattc tccagaatgt ggagccacac agaagcaagc 3480
acaaggaaag tgcctgatgc aagggcaaag tacagtgtgt accttcaggc tgggcacaga 3540
cactctgaaa agccttggca ggaactccct gcaacaaagc agagccctgc aggcaatgcc 3600
agctccagag ccctccctga gagcctcatg ggcaaagatg tgcacaacag gtgtttctca 3660
tagccccaaa ctgagaatga agcaaacagc catctgaagg aaaacaggca aataaacgat 3720
ggcaggttca tgaaatgcaa acccagacag ccagaaggac aacagtgagg gttacaggtg 3780
actctgtggt tgagttcatg acaatgctga gtaattggag taacaaagga aagtccaaaa 3840
aatactttca atgtgatttc ttctaaataa aatttacagc cggcaaaatg aactatcttc 3900
ttaagggata aactttccac taggaaaact ataaggaaaa tcaagaaaag gatgatcaca 3960
taaacacagt ggtcgttact tctactgggg aaggaagagg gtatgaactg agacacacag 4020
ggttggcaag tctcctaaca agaacagaac aaatacatta cagtaccttg aaaacagcag 4080
ttaaaattct aaattgcaag aagaggaaaa tgcacacagc tgtgtttaga aaattctcag 4140
tccagcactg ttcataatag caaagacatt aacccaggtt ggataaataa acgatgacac 4200
aggcaattgc acaatgatac agacatacat tcagtatatg agacattgat gatgtatccc 4260
caaagaaatg actttaaaga gaaaaggcct gatatgtggt ggcactcacc tccctgggca 4320
tccccggaca ggctgcaggc acactgtgtg gcagggcagg ctggtacctg ctggcagctc 4380
ctggggcctg atgtggagca ggcacagagc cgtatccccc cgaggacata tacccccaag 4440
gacggcacag ttggtacatt ccggagacaa gcaactcagc cacactccca ggccagagcc 4500
cgagagggac gcccatgcac agggaggcag agcccagctc ctccacagcc agcagcaccc 4560
gtgcaggggc cgccatctgg caggcacaga gcatgggctg ggaggagggg cagggacacc 4620
aggcagggtt ggcaccaact gaaaattaca gaagtctcat acatctacct cagccttgcc 4680
tgacctgggc ctcacctgac ctggacctca cctggcctgg acctcacctg gcctagacct 4740
cacctctggg cttcacctga gctcggcctc acctgacttg gaccttgcct gtcctgagct 4800
cacatgatct gggcctcacc tgacctgggt ttcacctgac ctgggcttca cctgacctgg 4860
gcctcatctg acctgggcct cactggcctg gacctcacct ggcctgggct tcacctggcc 4920
tcaggcctca tctgcacctg ctccaggtct tgctggaacc tcagtagcac tgaggctgca 4980
ggggctcatc cagggttgca gaatgactct agaacctccc acatctcagc tttctgggtg 5040
gaggcacctg gtggcccagg gaatataaaa agcctgaatg atgcctgcgt gatttggggg 5100
caatttataa acccaaaagg acatggccat gcagcgggta gggacaatac agacagatat 5160
cagcctgaaa tggagcctca gggcacaggt gggcacggac actgtccacc taagccaggg 5220
gcagacccga gtgtccccgc agtagacctg agagcgctgg gcccacagcc tcccctcggt 5280
gccctgctac ctcctcaggt cagccctgga catcccgggt ttccccaggc ctggcggtag 5340
gtttggggtg aggtctgtgt cactgtggta tcaccatttt tggagtggtc attataccca 5400
cagtgtcaca gagtccatca aaaacccatc cctgggaacc ttctgccaca gccctccctg 5460
tggggcaccg ccgcgtgcca tgttaggatt ttgactgagg acacagcacc atgggtatgg 5520
tggctaccgc agcagtgcag cccgtgaccc aaacacacag ggcagcaggc acaacagaca 5580
agcccacaag tgaccaccct gagctcctgc ctgccagccc tggagaccat gaaacagatg 5640
gccaggatta tcccataggt cagccagacc tcagtccaac aggtctgcat cgctgctgcc 5700
ctccaatacc agtccggatg gggacagggc tggcccacat taccatttgc tgccatccgg 5760
ccaacagtcc cagaagcccc tccctcaagg ctgggccaca tgtgtggacc ctgagagccc 5820
cccatgtctg agtaggggca ccaggaaggt ggggctggcc ctgtgcactg tccctgcccc 5880
tgtggtccct ggcctgcctg gccctgacac ctgggcctct cctgggtcat ttccaagaca 5940
gaagacattc ccaggacagc tggagctggg agtccatcat cctgcctggc cgtcctgagt 6000
cctgcgcctt tccaaacctc acccgggaag ccaacagagg aatcacctcc cacaggcaga 6060
gacaaagacc ttccagaaat ctctgtctct ctccccagtg ggcaccctct tccagggcag 6120
tcctcagtga tatcacagtg ggaacccaca tctggatcgg gactgccccc agaacacaag 6180
atggcccaca gggacagccc cacagcccag ccccttcccag accccctaaaa ggcgtcccac 6240
cccctgcatc tgccccaggg ctcaaactcc aggaggactg actcctgcac accctcctgc 6300
cagacatcac ctcagcccct cctggaaggg acaggagcgc gcaagggtga gtcagaccct 6360
cctgccctcg atggcaggcg gagaagattc agaaaggtct gagatcccca ggacgcagca 6420
ccactgtcaa tgggggcccc agacgcctgg accagggcct gcgtgggaaa ggcctctggg 6480
cacactcagg ggctttttgt gaagggtcct cctactgtgt gaccacagtc actaccacag 6540
tgatgaaccc agcagcaaaa actgaccgga ctcccaaggt ttatgcacac ttctccgctc 6600
agagctctcc aggatcagaa gagccgggcc caagggtttc tgcccagacc ctcggcctct 6660
agggacatct tggccatgac agcccatggg ctggtgcccc acacatcgtc tgccttcaaa 6720
caagggcttc agagggctct gaggtgacct cactgatgac cacaggtgcc ctggcccctt 6780
ccccaccagc tgcaccagac cccgtcatga cagatgcccc gattccaaca gccaattcct 6840
ggggccagga atcgctgtag acaccagcct ccttccaaca cctcctgcca attgcctgga 6900
ttcccatccc ggttggaatc aagaggacag catcccccag gctcccaaca ggcaggactc 6960

```
ccacaccctc ctctgagagg ccgctgtgtt ccgtagggcc aggctgcaga cagtccccct   7020
cacctgccac tagacaaatg cctgctgtag atgtccccac ctggaaaata ccactcatgg   7080
agcccccagc cccaggtaca gctgtagaga gagtctctga ggcccctaag aagtagccat   7140
gcccagttct gccgggaccc tcggccaggc tgacaggagt ggacgctgga gctgggccca   7200
tactgggcca cataggagct caccagtgag ggcaggagag cacatgccgg ggagcaccca   7260
gcctcctgct gaccagaggc ccgtcccaga gcccaggagg ctgcagaggc ctctccaggg   7320
ggacactgtg catgtctggt ccctgagcag ccccccacgt ccccagtcct gggggcccct   7380
ggcacagctg tctggaccct ctctattccc tgggaagctc ctcctgacag ccccgcctcc   7440
agttccaggt gtggttattg tcaggggggtg tcagactgtg gtggacacag ccatggttac   7500
cacagtggtg ctgcccatag cagcaaccag gccaagtaga caggcccctg ctgtgcagcc   7560
ccaggcctcc agctcacctg cttctcctgg ggctctcaag gctgctgttt tctgcactct   7620
cccctctgtg gggagggttc cctcagtggg agatctgttc tcaacatccc acggcctcat   7680
tcctgcaagg aaggccaatg gatgggcaac ctcacatgcc gcggctaaga tagggtgggc   7740
agcctggcgg ggacaggaca tcctgctggg gtatctgtca ctgtgcctag tggggcactg   7800
gctcccaaac aacgcagtcc ttgccaaaat ccccacggcc tcccccgcta ggggctggcc   7860
tgatctcctg cagtcctagg aggctgctga cctccagaat ggctccgtcc ccagttccag   7920
ggcgagagca gatcccaggc cggctgcaga ctgggaggcc acccccctcct tcccagggtt   7980
cactgcaggt gaccagggca ggaaatggcc tgaacacagg gataaccggg ccatccccca   8040
acagagtcca ccccctcctg ctctgtaccc cgcacccccc aggccagccc atgacatccg   8100
acaaccccac accagagtca ctgcccggtg ctgccctagg gaggacccct cagcccccac   8160
cctgtctaga ggactgggga ggacaggaca cgccctctcc ttatggttcc cccacctggc   8220
tctggctggg acccttgggg tgtggacaga aaggacgctt gcctgattgg cccccaggag   8280
cccagaactt ctctccaggg accccagccc gagcaccccc ttacccagga cccagccctg   8340
cccctcctcc cctctgctct cctctcatca ccccatggga atccagaatc cccaggaagc   8400
catcaggaag ggctgaggga ggaagtgggg ccactgcacc accaggcagg aggctctgtc   8460
tttgtgaacc cagggaggtg ccagcctcct agagggtatg gtccaccctg cctatggctc   8520
ccacagtggc aggctgcagg gaaggaccag ggacggtgtg ggggagggct cagggccccg   8580
cgggtgctcc atcttggatg agcctatctc tctcacccac ggactcgccc acctcctctt   8640
caccctggcc acacgtcgtc cacaccatcc taagtcccac ctacaccaga gccggcacag   8700
ccagtgcaga cagaggctgg ggtgcagggg ggccgactgg gcagcttcgg ggagggagga   8760
atggaggaag gggagttcag tgaagaggcc cccctcccct gggtccagga tcctcctctg   8820
ggacccccgg atcccatccc ctccaggctc tgggaggaga agcaggatgg gagaatctgt   8880
gcgggaccct ctcacagtgg aatacctcca cagcggctca ggccagatac aaaagcccct   8940
cagtgagccc tccactgcag tgctgggcct gggggcagcc gctcccacac aggatgaacc   9000
cagcaccccg aggatgtcct gccaggggga gctcagagcc atgaaggagc aggatatggg   9060
acccccgata caggcacaga cctcagctcc attcaggact gccacgtcct gccctgggag   9120
gaacccctt  ctctagtccc tgcaggccag gaggcagctg actcctgact tggacgccta   9180
ttccagacac cagacagagg ggcaggcccc ccagaaccag ggatgaggac gccccgtcaa   9240
ggccagaaaa gaccaagttg cgctgagccc agcaagggaa ggtccccaaa caaaccagga   9300
```

agtttctgaa ggtgtctgtg tcacagtgga gcatagccac tcgtcccaca gtgacactcg 9360
ccaggccaga aaccccatcc caagtcagcg gaatgcagag agagcaggga ggacatgttt 9420
aggatctgag gccgcacctg acacccaggc cagcagacgt ctcctgtcca cggcaccctg 9480
ccatgtcctg catttctgga agaacaaggg caggctgaag gggtccagg accaggagat 9540 gggtccgctc tacccagaga aggagccagg caggacacaa gccccc 9586

<210> SEQ ID NO 2
<211> LENGTH: 9268
<212> TYPE: DNA
<213> ORGANISM: Homo sapiens
<220> FEATURE:
<221> NAME/KEY: misc_feature
<222> LOCATION: (1)..(9268)
<223> OTHER INFORMATION: HD 1.7-6.13

<400> SEQUENCE: 2
tccccattga ggctgacctg cccagagggt cctgggccca cccaacacac cggggcggaa 60
tgtgtgcagg cctcggtctc tgtgggtgtt ccgctagctg gggctcacag tgctcacccc 120
acacctaaaa cgagccacag cctccggagc ccctgaagga gaccccgccc acaagcccag 180
cccccaccca ggaggcccca gagcacaggg cgccccgtcg gattctgaac agccccgagt 240
cacagtgggt atcactggca ctaccactgt gagaaaagct tcgtccaaaa cggtctcctg 300
gccacagtcg gaggccccgc cagagagggg agcagccacc ccaaacccat gttctgccgg 360
ctcccatgac cccgtgcacc tggagcccca cggtgtcccc actggatggg aggacaaggg 420
ccgggggctc cggcgggtcg gggcaggggc ttgatggctt ccttctgccg tggccccatt 480
gcccctggct ggagttgacc cttctgacaa gtgtcctcag agagtcaggg atcagtggca 540
cctcccaaca tcaaccccac gcagcccagg cacaaacccc acatccaggg ccaactccag 600
gaacagagac accccaatac cctgggggac cccgaccctg atgactcccg tcccatctct 660
gtccctcact tggggcctgc tgcggggcga gcacttggga gcaaactcag gcttagggga 720
caccactgtg ggcctgacct cgagcaggcc acagaccctt ccctcctgcc ctggtgcagc 780
acagactttg ggtctgggc agggaggaac ttctggcagg tcaccaagca cagagccccc 840
aggctgaggt ggccccaggg ggaaccccag caggtggccc actacccttc ctcccagctg 900
gaccccatgt cttccccaag ataggggtgc catccaaggc aggtcctcca tggagccccc 960
ttcaggctcc tctccagacc ccactgggcc tcagtcccca ctctaggaat gcagccacca 1020
cgggcacacc aggcagccca ggcccagcca ccctgcagtg cccaagccca caccctggag 1080
gagagcaggg tgcgtctggg aggggctggg ctccccaccc ccaccccac ctgcacaccc 1140 cacccaccct tgcccgggcc ccctgcagga gggtcagagc ccccatggga tatggactta 1200
gggtctcact cacgcacctc ccctcctggg agaaggggtc tcatgcccag atccccccag 1260
cagcgctggt cacaggtaga ggcagtggcc ccagggccac cctgacctgg cccctcaggc 1320
tcctctagcc ctggctgccc tgctgtccct gggaggcctg ggctccacca gaccacaggt 1380
ctagggcacc gcccacactg gggccgccca cacacagctc acaggaagaa gataagctcc 1440
agacccccag gcccgggacc tgccttgctg ctacgacttc ctgccccaga cctcgttgcc 1500
ctcccccgtc cacttacaca caggccagga agctgttccc acacagacca accccagacg 1560
gggaccacct ggcactcagg tcactgccat ttccttctcc attcacttcc aatgcctctg 1620
tgcttcctcc ctcctccttc cttcgggggga gcaccctgtg cagctcctcc ctgcagtcca 1680
caccctgggg agacccgacc ctgcagccca caccctgggg agacctgacc ctcctccagc 1740
cctttctccc ccgctgctct tgccacccac caagacagcc ctggggtcct gtccctacag 1800
cccccaccca gttctctacc tagacccgtc ttcctccctc taaacacctc tcccaggcca 1860
accctacacc tgcaggccct cccctccact gccaaagacc ctcagtttct cctgcctgtg 1920
cccacccccg tgctcctcct gcccacagct cgagctcttc ctctcctagg gcccctgagg 1980
gatggcattg accgtgccct cgcacccaca cactgcccat gccctcacat tcctcctggc 2040
cactccagcc ccactcccct ctcaggcctg gctctggtat ttctgggaca aagccttacc 2100
caagtctttc ccatgcaggc ctgggccctt accctcactg cccggttaca gggcagcctc 2160
ctgtgcacag aagcagggag ctcagccctt ccacaggcag aaggcactga aagaaatcgg 2220
cctccagcgc cttgacacac gtctgcctgt gtctctcact gcccgcacct gcagggaggc 2280
tcggcactcc ctctaaagac gagggatcca ggcagcagca tcacaggaga atgcagggct 2340
accagacatc ccagtcctct cacaggcctc tcctgggaag agacctgaag acgcccagtc 2400
aacggagtct aacaccaaac ctccctggag gccgatgggt agtaacggag tcattgccag 2460
acctggaggc aggggagcag tgagcccgag cccacaccat agggccagag gacagccact 2520
gacatcccaa gccactcact ggtggtccca caacacccca tggaaagagg acagacccac 2580
agtcccacct ggaccagggc agagactgct gagacccagc accagaacca accaagaaac 2640
accaggcaac agcatcagag ggggctctgg cagaacagag gaggggaggt ctccttcacc 2700
agcaggcgct tcccttgacc gaagacagga tccatgcaac tcccccagga caaaggagga 2760
gccccttgtt cagcactggg ctcagagtcc tctccaagac acccagagtt tcagacaaaa 2820
accccctgga atgcacagtc tcagcaggag agccagccag agccagcaag atggggctca 2880
gtgacacccg cagggacagg aggattttgt gggggctcgt gtcactgtga ggacattgta 2940
ctcatggtgt atgccatacc cacagtgaca cagccccatt cccaaagccc tactgcaaac 3000
gcattccact tctggggctg aggggctggg ggagcgtctg ggaaataggg ctcaggggtg 3060
tccatcaatg cccaaaacgc accagactcc cctccataca tcacacccac cagccagcga 3120
gcagagtaaa cagaaaatga gaagcaagct ggggaagctt gcacaggccc caaggaaaga 3180
gctttggcgg gtgtgtaaga ggggatgcgg gcagagcctg agcagggcct tttgctgttt 3240
ctgctttcct gtgcagagag ttccataaac tggtgttcga gatcaatggc tgggagtgag 3300
cccaggagga cagcgtggga agagcacagg gaaggaggag cagccgctat cctacactgt 3360
catctttcga aagtttgcct tgtgcccaca ctgctgcatc atgggatgct taacagctga 3420
tgtagacaca gctaaagaga gaatcagtga gatggatttg cagcacagat ctgaataaat 3480
tctccagaat gtggagcagc acagaagcaa gcacacagaa agtgcctgat gcaaggacaa 3540
agttcagtgg gcaccttcag gcattgctgc tgggcacaga cactctgaaa agccctggca 3600
ggaactccct gtgacaaagc agaaccctca ggcaatgcca gccccagagc cctccctgag 3660
agcctcatgg gcaaagatgt gcacaacagg tgtttctcat agccccaaac tgagagcaaa 3720
gcaaacgtcc atctgaagga gaacaggcaa ataaacgatg gcaggttcat gaaatgcaaa 3780
cccagacagc cacaagcaca aaagtacagg gttataagcg actctggttg agttcatgac 3840
aatgctgagt aattggagta acaaagtaaa ctccaaaaaa tactttcaat gtgatttctt 3900
ctaaataaaa tttacaccct gcaaaatgaa ctgtcttctt aagggataca tttcccagtt 3960
agaaaaccat aaagaaaacc aagaaaagga tgatcacata aacacagtgg tggttacttc 4020
tgctggggaa ggaagagggt atgaactgag atacacaggg tgggcaagtc tcctaacaag 4080
aacagaacga atacattaca gtaccttgaa aacagcagtt aaacttctaa attgcaagaa 4140
gaggaaaatg cacacagttg tgtttagaaa attctcagtc cagcactgtt cataatagca 4200
aagacattaa cccaggtcgg ataaataagc gatgacacag gcaattgcac aatgatacag 4260
acatatattt agtatatgag acatcgatga tgtatcccca aataaacgac tttaaagaga 4320
taaagggctg atgtgtggtg gcattcacct ccctgggatc cccggacagg ttgcaggctc 4380
actgtgcagc agggcaggcg ggtacctgct ggcagttcct ggggcctgat gtggagcaag 4440
cgcagggcca tatatcccgg aggacggcac agtcagtgaa ttccagagag aagcaactca 4500
gccacactcc ccaggcagag cccgagaggg acgcccacgc acagggaggc agagcccagc 4560
acctccgcag ccagcaccac ctgcgcacgg gccaccacct tgcaggcaca gagtgggtgc 4620
tgagaggagg ggcagggaca ccaggcaggg tgagcaccca gagaaaactg cagacgcctc 4680
acacatccac ctcagcctcc cctgacctgg acctcactgg cctgggcctc acttaacctg 4740
ggcttcacct gaccttggcc tcacctgact tggacctcgc ctgtcccaag ctttacctga 4800
cctgggcctc aactcacctg aacgtctcct gacctgggtt taacctgtcc tggaactcac 4860
ctggccttgg cttcccctga cctggacctc atctggcctg ggcttcacct ggcctgggcc 4920
tcacctgacc tggacctcat ctggcctgga cctcacctgg cctggacttc acctggcctg 4980
ggcttcacct gacctggacc tcacctggcc tcgggcctca cctgcacctg ctccaggtct 5040
tgctggagcc tgagtagcac tgagggtgca gaagctcatc cagggttggg gaatgactct 5100
agaagtctcc cacatctgac ctttctgggt ggaggcagct ggtggccctg ggaatataaa 5160
aatctccaga atgatgactc tgtgatttgt gggcaactta tgaacccgaa aggacatggc 5220
catggggtgg gtagggacat agggacagat gccagcctga ggtggagcct caggacacag 5280
gtgggcacgg acactatcca cataagcgag ggatagaccc gagtgtcccc acagcagacc 5340
tgagagcgct gggcccacag cctcccctca gagccctgct gcctcctccg gtcagccctg 5400
gacatcccag gtttccccag gcctggcggt aggtttagaa tgaggtctgt gtcactgtgg 5460
tatcaccata ttttgactgg tcattataac cacagtgtca cagagtccat caaaaaccca 5520
tgcctggaag cttcccgcca cagccctccc catggggccc tgctgcctcc tcaggtcagc 5580
cccggacatc ccgggtttcc ccaggctggg cggtaggttt ggggtgaggt ctgtgtcact 5640
gtggtatcac catggttcgg ggagtcatta taaccacagt gtcacagagt ccatcaaaaa 5700
cccatccctg ggagcctccc gccacagccc tccctgcagg ggaccggtac gtgccatgtt 5760
aggattttga tcgaggagac agcaccatgg gtatggtggc taccacagca gtgcagcctg 5820
tgacccaaac ccgcagggca gcaggcacga tggacaggcc cgtgactgac cacgctgggc 5880
tccagcctgc cagccctgga gatcatgaaa cagatggcca aggtcaccct acaggtcatc 5940
cagatctggc tccgaggggt ctgcatcgct gctgccctcc caacgccagt ccaaatggga 6000
cagggacggc ctcacagcac catctgctgc catcaggcca gcgatcccag aagcccctcc 6060
ctcaaggctg ggcacatgtg tggacactga gagccctcat atctgagtag gggcaccagg 6120
agggaggggc tggccctgtg cactgtccct gcccctgtgg tccctggcct gcctggccct 6180
gacacctgag cctctcctgg gtcatttcca agacagaaga cattcctggg gacagccgga 6240
gctgggcgtc gctcatcctg cccggccgtc ctgagtcctg ctcatttcca gacctcaccg 6300
gggaagccaa cagaggactc gcctcccaca ttcagagaca aagaaccttc cagaaatccc 6360
tgcctctctc cccagtggac accctcttcc aggacagtcc tcagtggcat cacagcggcc 6420
tgagatcccc aggacgcagc accgctgtca ataggggccc caaatgcctg gaccagggcc 6480
tgcgtgggaa aggcctctgg ccacactcgg gctttttgtg aagggccctc ctgctgtgtg 6540
accacagtca ctaccatagt gatgaaccca gtggcaaaaa ctggctggaa acccaggggc 6600
tgtgtgcacg cctcagcttg gagctctcca ggagcacaag agccgggccc aaggatttgt 6660
gcccagaccc tcagcctcta gggacacctg ggtcatctca gcctgggctg gtgccctgca 6720
caccatcttc ctccaaatag gggcttcaga gggctctgag gtgacctcac tcatgaccac 6780
aggtgacctg gcccttccct gccagctata ccagaccctg tcttgacaga tgccccgatt 6840
ccaacagcca attcctggga ccctgaatag ctgtagacac cagcctcatt ccagtacctc 6900
ctgccaattg cctggattcc catcctggct ggaatcaaga aggcagcatc cgccaggctc 6960
ccaacaggca ggactcccgc acaccctcct ctgagaggcc gctgtgttcc gcagggccag 7020
gccctggaca gttcccctca cctgccacta gagaaacacc tgccattgtc gtccccacct 7080
ggaaaagacc actcgtggag cccccagccc caggtacagc tgtagagaca gtcctcgagg 7140
cccctaagaa ggagccatgc ccagttctgc cgggaccctc ggccaggccg acaggagtgg 7200
acgctggagc tgggcccaca ctgggccaca taggagctca ccagtgaggg caggagagca 7260
catgccgggg agcacccagc ctcctgctga ccagaggccc gtcccagagc ccaggaggct 7320
gcagaggcct ctccagggag acactgtgca tgtctggtac ctaagcagcc ccccacgtcc 7380
ccagtcctgg gggcccctgg ctcagctgtc tgggccctcc ctgctccctg ggaagctcct 7440
cctgacagcc ccgcctccag ttccaggtgt ggttattgtc aggcgatgtc agactgtggt 7500
ggacatagtg gccaccatta ccacagtggt gccgcccata gcagcaacca ggccaagtag 7560
acaggcccct gctgcgcagc cccaggcatc cacttcacct gcttctcctg ggctctcaa 7620
ggctgctgtc tgtcctctgg ccctctgtgg ggagggttcc ctcagtggga ggtctgtgct 7680
ccagggcagg gatgattgag atagaaatca aaggctggca gggaaaggca gcttcccgcc 7740
ctgagaggtg caggcagcac cacggagcca cggagtcaca gagccacgga gcccccattg 7800
tgggcatttg agagtgctgt gcccccggca ggcccagccc tgatggggaa gcctgtccca 7860
tcccacagcc cgggtcccac gggcagcggg cacagaagct gccaggttgt cctctatgat 7920
cctcatccct ccagcagcat cccctccaca gtggggaaac tgaggcttgg agcaccaccc 7980
ggccccctgg aaatgaggct gtgagcccag acagtgggcc cagagcactg tgagtacccc 8040
ggcagtacct ggctgcaggg atcagccaga gatgccaaac cctgagtgac cagcctacag 8100
gaggatccgg ccccacccag gccactcgat taatgctcaa ccccctgccc tggagacctc 8160
ttccagtacc accagcagct cagcttctca gggcctcatc cctgcaagga aggtcaaggg 8220
ctgggcctgc cagaaacaca gcaccctccc tagccctggc taagacaggg tgggcagacg 8280
gctgtggacg ggacatattg ctggggcatt tctcactgtc acttctgggt ggtagctctg 8340
acaaaaacgc agaccctgcc aaaatcccca ctgcctcccg ctaggggctg gcctggaatc 8400
ctgctgtcct aggaggctgc tgacctccag gatggctccg tccccagttc cagggcgaga 8460
gcagatccca ggcaggctgt aggctgggag gccacccctg cccttgccgg ggttgaatgc 8520
aggtgcccaa ggcaggaaat ggcatgagca cagggatgac cgggacatgc cccaccagag 8580
tgcgcccctt cctgctctgc accctgcacc ccccaggcca gcccacgacg tccaacaact 8640
gggcctgggt ggcagcccca cccagacagg acagacccag caccctgagg aggtcctgcc 8700
agggggagct aagagccatg aaggagcaag atatggggcc cccgatacag gcacagatgt 8760
cagctccatc caggaccacc cagcccacac cctgagagga acgtctgtct ccagcctctg 8820
caggtcggga ggcagctgac ccctgacttg gacccctatt ccagacacca gacagaggcg 8880
caggcccccc agaaccaggg ttgagggacg ccccgtcaaa gccagacaaa accaaggggt 8940
gttgagccca gcaagggaag gcccccaaac agaccaggag gtttctgaag gtgtctgtgt 9000
cacagtgggg catagccaca gctggtacca cagtgacact cacccagcca gaaaccccat 9060
tccaagtcag cggaagcaga gagagcaggg aggacacgtt taggatctga gactgcacct 9120
gacacccagg ccagcagacg tctcccctcc agggcacccc accctgtcct gcatttctgc 9180
aagatcaggg gcggcctgag ggggggtcta gggtgaggag atgggtcccc tgtacaccaa 9240
ggaggagtta ggcaggtccc gagcactc 9268

<210> SEQ ID NO 3
<211> LENGTH: 9441
<212> TYPE: DNA
<213> ORGANISM: Homo sapiens
<220> FEATURE:
<221> NAME/KEY: misc_feature
<222> LOCATION: (1)..(9441)
<223> OTHER INFORMATION: HD 1.14-6.19

<400> SEQUENCE: 3
tccccattga ggctgacctg cccagagagt cctgggccca ccccacacac cggggcggaa 60
tgtgtgcagg cctcggtctc tgtgggtgtt ccgctagctg gggctcacag tgctcacccc 120
acacctaaaa tgagccacag cctccggagc ccccgcagga gaccccgccc acaagcccag 180
cccccaccca ggaggcccca gagctcaggg cgccccgtcg gattccgaac agccccgagt 240
cacagcgggt ataaccggaa ccaccactgt cagaatagct acgtcaaaaa ctgtccagtg 300
gccactgccg gaggccccgc cagagagggc agcagccact ctgatcccat gtcctgccgg 360
ctcccatgac cccagcacg cggagcccca cagtgtcccc actggatggg aggacaagag 420
ctggggattc cggcgggtcg gggcagggc ttgatcgcat ccttctgccg tggctccagt 480
gcccctggct ggagttgacc cttctgacaa gtgtcctcag agagacaggc atcaccggcg 540
cctcccaaca tcaaccccag gcagcacagg cacaaacccc acatccagag ccaactccag 600
gagcagagac accccaatac cctgggggac cccgaccctg atgacttccc actggaattc 660
gccgtagagt ccaccaggac caaagaccct gcctctgcct ctgtccctca ctcaggacct 720
gctgccgggc gaggccttgg gagcagactt gggcttaggg gacaccagtg tgaccccgac 780
cttgaccagg acgcagacct ttccttcctt tcctggggca gcacagactt tggggtctgg 840
gccaggagga acttctggca ggtcgccaag cacagaggcc acaggctgag gtggccctgg 900
aaagacctcc aggaggtggc cactcccctt cctcccagct ggaccccatg tcctccccaa 960
gataagggtg ccatccaagg caggtgctcc ttggagcccc attcagactc ctccctggac 1020
cccactgggc ctcagtccca gctctgggga tgaagccacc acaagcacac caggcagccc 1080
aggcccagcc accctgcagt gcccaagcac acactctgga gcagagcagg gtgcctctgg 1140
gaggggctga gctccccacc ccaccccac ctgcacaccc cacccacccc tgcccagcgg 1200
ctctgcagga gggtcagagc cccacatggg gtatggactt agggtctcac tcacgtggct 1260
cccatcatga gtgaaggggc ctcaagccca ggttcccaca gcagcgcctg tcgcaagtgg 1320
aggcagaggc ccgagggcca ccctgacctg gtccctgagg ttcctgcagc ccaggctgcc 1380
ctgctgtccc tgggaggcct gggctccacc agaccacagg tccagggcac cgggtgcagg 1440
agccacccac acacagctca caggaagaag ataagctcca gacccccagg gccagaacct 1500
gccttcctgc tactgcttcc tgccccagac ctgggcgccc tcccccgtcc acttacacac 1560

```
aggccaggaa gctgttccca cacagaacaa ccccaaacca ggaccgcctg gcactcaggt   1620
ggctgccatt tccttctcca tttgctccca gcgcctctgt cctccctggt tcctccttcg   1680
ggggaacagc ctgtgcagcc agtccctgca gcccacaccc tggggagacc caaccctgcc   1740
tggggccctt ccaaccctgc tgctcttact gcccacccag aaaactctgg ggtcctgtcc   1800
ctgcagtccc taccctggtc tccacccaga cccctgtgta tcactccaga cacccctccc   1860
aggcaaaccc tgcacctgca ggccctgtcc tcttctgtcg ctagagcctc agtttctccc   1920
ccctgtgccc acaccctacc tcctcctgcc cacaactcta actcttcttc tcctggagcc   1980
cctgagccat ggcattgacc ctgccctccc accacccaca gcccatgccc tcaccttcct   2040
cctggccact ccgaccccgc cccctctcag gccaagccct ggtatttcca ggacaaaggc   2100
tcacccaagt ctttcccagg caggcctggg ctcttgccct cacttcccgg ttacacggga   2160
gcctcctgtg cacagaagca gggagctcag cccttccaca ggcagaaggc actgaaagaa   2220
atcggcctcc agcaccttga cacacgtccg cccgtgtctc tcactgcccg cacctgcagg   2280
gaggctccgc actccctcta aagacaaggg atccaggcag cagcatcacg ggagaatgca   2340
gggctcccag acatcccagt cctctcacag gcctctcctg ggaagagacc tgcagccacc   2400
accaaacagc cacagaggct gctggatagt aactgagtca atgaccgacc tggagggcag   2460
gggagcagtg agccggagcc cataccatag ggacagagac cagccgctga catcccgagc   2520
tcctcaatgg tggccccata acacacctag gaaacataac acacccacag ccccacctgg   2580
aacagggcag agactgctga gcccccagca ccagccccaa gaaacaccag gcaacagtat   2640
cagagggggc tcccgagaaa gagaggaggg gagatctcct tcaccatcaa atgcttccct   2700
tgaccaaaaa cagggtccac gcaactcccc caggacaaag gaggagcccc ctatacagca   2760
ctgggctcag agtcctctct gagacaccct gagtttcaga caacaacccg ctggaatgca   2820
cagtctcagc aggagaacag accaaagcca gcaaaaggga cctcggtgac accagtaggg   2880
acaggaggat tttgtggggg ctcgtgtcac tgtgaggaca ttgtagtcat ggtagctgcc   2940
actcccacag tgacacagac ccattcccaa agccctactg caaacacacc cactcctggg   3000
gctgaggggc tgggggagcg tctgggaagt agggtccagg ggtgtctatc aatgtccaaa   3060
atgcaccaga ctccccgcca aacaccaccc caccagccag cgagcagggt aaacagaaaa   3120
tgagaggctc tgggaagctt gcacaggccc caaggaaaga gctttggcgg gtgtgcaaga   3180
ggggatgcag gcagagcctg agcagggcct tttgctgttt ctgctttcct gtgcagagag   3240
ttccataaac tggtgttcaa gatcagtggc tgggaatgag cccaggaggg cagtctgtgg   3300
gaagagcaca gggaaggagg agcagccgct atcctacact gtcatctttc aaaagtttgc   3360
cttgtgacca cactattgca tcatgggatg cttaagagct gatgtagaca cagctaaaga   3420
gagaatcagt gagatgaatt tgcagcatag atctgaataa actctccaga atgtggagca   3480
gtacagaagc aaacacacag aaagtgcctg atgcaaggac aaagttcagt gggcaccttc   3540
aggcattgct gctgggcaca gacactctga aaagccttgg caggatctcc ctgcgacaaa   3600
gcagaaccct caggcaatgc cagccccaga gccctccctg agagcgtcat ggggaaagat   3660
gtgcagaaca gctgattatc atagactcaa actgagaaca gagcaaacgt ccatctgaag   3720
aacagtcaaa taagcaatgg taggttcatg caatgcaaac ccagacagcc aggggacaac   3780
agtagagggc tacaggcggc tttgcggttg agttcatgac aatgctgagt aattggagta   3840
acagaggaaa gcccaaaaaa tacttttaat gtgatttctt ctaaataaaa tttacaccag   3900
```

gcaaaatgaa ctgtcttctt aagggataaa ctttcccctg gaaaaactac aaggaaaatt 3960
aagaaaacga tgatcacata aacacagttg tggttacttc tactggggaa ggaagagggt 4020
atgagctgag acacacagag tcggcaagtc tccaagcaag cacagaacga atacattaca 4080
gtaccttgaa tacagcagtt aaacttctaa atcgcaagaa caggaaaatg cacacagctg 4140
tgtttagaaa attctcagtc cagcactatt cataatagca aagacattaa cccaggttgg 4200
ataaataaat gatgacacag gcaattgcac aatgatacag acatacattt agtacatgag 4260
acatcgatga tgtatcccca aagaaatgac tttaaagaga aaaggcctga tgtgtggtgg 4320
cactcacctc cctgggatcc ccggacaggt tgcaggcaca ctgtgtggca gggcaggctg 4380
gtacatgctg gcagctcctg gggcctgatg tggagcaagc gcagggctgt ataccccccaa 4440
ggatggcaca gtcagtgaat tccagagaga agcagctcag ccacactgcc caggcagagc 4500
ccgagaggga cgcccacgta cagggaggca gagcccagct cctccacagc caccaccacc 4560
tgtgcacggg ccaccacctt gcaggcacag agtgggtgct gagaggaggg gcagggacac 4620
caggcagggt gagcacccag agaaaactgc agaagcctca cacatccacc tcagcctccc 4680
ctgacctgga cctcacctgg tctggacctc acctggcctg ggcctcacct gacctggacc 4740
tcacctggcc tgggcttcac ctgacctgga cctcacctgg cctccggcct cacctgcacc 4800
tgctccaggt cttgctggaa cctgagtagc actgaggctg cagaagctca tccagggttg 4860
gggaatgact ctggaactct cccacatctg acctttctgg gtggaggcat ctggtggccc 4920
tgggaatata aaaagcccca gaatggtgcc tgcgtgattt gggggcaatt tatgaacccg 4980
aaaggacatg gccatggggt gggtagggac atagggacag atgccagcct gaggtggagc 5040
ctcaggacac agttggacgc ggacactatc cacataagcg agggacagac ccgagtgttc 5100
ctgcagtaga cctgagagcg ctgggcccac agcctcccct cggtgccctg ctgcctcctc 5160
aggtcagccc tggacatccc gggtttcccc aggccagatg gtaggtttga agtgaggtct 5220
gtgtcactgt ggtatcatga tcacgtttgg gggagtcatc gttataccca cagcatcaca 5280
cggtccatca gaaacccatg ccacagccct ccccgcaggg gaccgccgcg tgccatgtta 5340
cgattttgat cgaggacaca gcgccatggg tatggtggct accacagcag tgcagcccat 5400
gacccaaaca cacagggcag caggcacaat ggacaggcct gtgagtgacc atgctgggct 5460
ccagcccgcc agccccggag accatgaaac agatggccaa ggtcacccca cagttcagcc 5520
agacatggct ccgtggggtc tgcatcgctg ctgccctcta acaccagccc agatggggac 5580
aaggccaacc ccacattacc atctcctgct gtccacccag tggtcccaga agcccctccc 5640
tcatggctga gccacatgtg tgaaccctga gagcacccca tgtcagagta ggggcagcag 5700
aagggcgggg ctggccctgt gcactgtccc tgcacccatg gtccctcgcc tgcctggccc 5760
tgacacctga gcctcttctg agtcatttct aagatagaag acattcccgg ggacagccgg 5820
agctgggcgt cgctcatccc gcccggccgt cctgagtcct gcttgtttcc agacctcacc 5880
agggaagcca acagaggact cacctcacac agtcagagac aaagaacctt ccagaaatcc 5940
ctgtctcact ccccagtggg caccttcttc caggacattc ctcggtcgca tcacagcagg 6000
cacccacatc tggatcagga cggcccccag aacacaagat ggcccatggg gacagcccca 6060
caacccaggc cttcccagac ccctaaaagg cgtcccaccc cctgcacctg ccccagggct 6120
aaaaatccag gaggcttgac tcccgcatac cctccagcca gacatcacct cagccccctc 6180
ctggagggga caggagcccg ggagggtgag tcagacccac ctgccctcga tggcaggcgg 6240
ggaagattca gaaaggcctg agatccccag gacgcagcac cactgtcaat gggggcccca 6300
gacgcctgga ccagggcctg cgtgggaaag gccgctgggc acactcaggg gctttttgtg 6360
aaggcccctc ctactgtgtg accacggtca ctaccacagt gatgaaacta gcagcaaaaa 6420
ctggccggac acccagggac catgcacact tctcagcttg gagctctcca ggaccagaag 6480
agtcaggtct gagggtttgt agccagaccc tcggcctcta gggacaccct ggccatcaca 6540
gcggatgggc tggtgcccca catgccatct gctccaaaca ggggcttcag agggctctga 6600
ggtgacttca ctcatgacca caggtgccct ggccccttcc ccgccagcta caccgaaccc 6660
tgtcccaaca gctgccccag ttccaacagc caattcctgg ggcccagaat tgctgtagac 6720
accagcctcg ttccagcacc tcctgccaat tgcctggatt cacatcctgg ctggaatcaa 6780
gagggcagca tccgccaggc tcccaacagg caggactccc gcacaccctc ctctgagagg 6840
ccgctgtgtt ccgcagggcc aggccctgga cagttcccct cacctgccac tagagaaaca 6900
cctgccattg tcgtccccac ctggaaaaga ccactcgtgg agcccccagc cccaggtaca 6960
gctgtagaga gactccccga gggatctaag aaggagccat gcgcagttct gccgggaccc 7020
tcggccaggc cgacaggagt ggacactgga gctgggccca cactgggcca cataggagct 7080
caccagtgag ggcaggagag cacatgccgg ggagcaccca gcctcctgct gaccagaggc 7140
ccgtcccaga gcccaggagg ctgcagaggc ctctccaggg ggacactgtg catgtctggt 7200
ccctgagcag ccccccacgt ccccagtcct gggggcccct ggcacagctg tctggaccct 7260
ccctgttccc tgggaagctc ctcctgacag ccccgcctcc agttccaggt gtggttattg 7320
tcaggggggtg tcagactgtg gtggacacag ccatggttac cacagtggtg ctgcccatag 7380
cagcaaccag gccaagtaga caggcccctg ctgtgcagcc ccaggcctcc acttcacctg 7440
cttctcctgg ggctctcaag gtcactgttg tctgtactct gccctctgtg gggagggttc 7500
cctcagtggg aggtctgttc tcaacatccc agggcctcat gtctgcacgg aaggccaatg 7560
gatgggcaac ctcacatgcc gcggctaaga tagggtgggc agcctggcgg gggacagtac 7620
atactgctgg ggtgtctgtc actgtgccta gtggggcact ggctcccaaa caacgcagtc 7680
ctcgccaaaa tccccacagc ctcccctgct aggggctggc ctgatctcct gcagtcctag 7740
gaggctgctg acctccagaa tgtctccgtc cccagttcca gggcgagagc agatcccagg 7800
ccggctgcag actgggaggc cacccccctcc ttcccagggt tcactggagg tgaccaaggt 7860
aggaaatggc cttaacacag ggatgactgc gccatccccc aacagagtca gccccctcct 7920
gctctgtacc ccgcaccccc caggccagtc cacgaaaacc agggccccac atcagagtca 7980
ctgcctggcc cggccctggg gcggacccct cagcccccac cctgtctaga ggacttgggg 8040
ggacaggaca caggccctct ccttatggtt cccccacctg cctccggccg ggacccttgg 8100
ggtgtggaca gaaaggacac ctgcctaatt ggcccccagg aacccagaac ttctctccag 8160
ggaccccagc ccgagcaccc ccttacccag gacccagccc tgcccctcct cccctctgct 8220
ctcctctcat caccccatgg gaatccggta tccccaggaa gccatcagga agggctgaag 8280
gaggaagcgg ggccgtgcac caccgggcag gaggctccgt cttcgtgaac ccagggaagt 8340
gccagcctcc tagagggtat ggtccaccct gcctggggct cccaccgtgg caggctgcgg 8400
ggaaggacca gggacggtgt gggggagggc tcagggccct gcgggtgctc ctccatcttc 8460
ggtgagcctc cccccttcacc caccgtcccg cccacctcct ctccaccctg gctgcacgtc 8520
ttccacacca tcctgagtcc tacctacacc agagccagca aagccagtgc agacaaaggc 8580
tggggtgcag gggggctgcc agggcagctt cggggaggga aggatggagg gaggggaggt 8640

```
cagtgaagag gccccccttcc cctgggtcca ggatcctcct ctgggacccc cggatcccat   8700

cccctcctgg ctctgggagg agaagcagga tgggagaatc tgtgcgggac cctctcacag   8760

tggaatatcc ccacagcggc tcaggccaga cccaaaagcc cctcagtgag ccctccactg   8820

cagtcctggg cctgggtagc agcccctccc acagaggaca gacccagcac cccgaagaag   8880

tcctgccagg gggagctcag agccatgaaa gagcaggata tggggtcccc gatacaggca   8940

cagacctcag ctccatccag gcccaccggg acccaccatg ggaggaacac ctgtctccgg   9000

gttgtgaggt agctggcctc tgtctcggac cccactccag acaccagaca gaggggcagg   9060

ccccccaaaa ccagggttga gggatgatcc gtcaaggcag acaagaccaa ggggcactga   9120

ccccagcaag ggaaggctcc caaacagacg aggaggtttc tgaagctgtc tgtatcacag   9180

tggggcatag ccatggctgg taccacagtg acactcgcca ggccagaaac cccgtcccaa   9240

gtcagcggaa gcagagagag cagggaggac acgtttagga tctgaggccg cacctgacac   9300

ccagggcagc agacgtctcc cctccagggc accctccacc gtcctgcgtt tcttcaagaa   9360

taggggcggc ctgagggggt ccagggccag gcgataggtc ccctctaccc caaggaggag   9420

ccaggcagga cccgagcacc g                                              9441
```

<210> SEQ ID NO 4
<211> LENGTH: 11592
<212> TYPE: DNA
<213> ORGANISM: Homo sapiens
<220> FEATURE:
<221> NAME/KEY: misc_feature
<222> LOCATION: (1)..(11592)
<223> OTHER INFORMATION: HD 1.20-6.25, 1.26

<400> SEQUENCE: 4

```
tccccattga ggctgacctg cccagacggg cctgggccca ccccacacac cggggcggaa     60

tgtgtgcagg ccccagtctc tgtgggtgtt ccgctagctg gggcccccag tgctcacccc    120

acacctaaag cgagccccag cctccagagc cccctaagca ttccccgccc agcagcccag    180

cccctgcccc cacccaggag gccccagagc tcagggcgcc tggtcggatt ctgaacagcc    240

ccgagtcaca gtgggtatca ctggcacgac caccgtgaga aaaactgtgt ccaaaactga    300

ctcctggcag cagtcggagg ccccgccaga gaggggagca gccggcctga acccatgtcc    360

tgccggttcc catgaccccc agcacccaga gccccacggt gtccccgttg gataatgagg    420

acaagggctg gggctccgg tggtttgcgg cagggacttg atcacatcct tctgctgtgg    480

ccccattgcc tctggctgga gttgaccctt ctgacaagtg tcctcagaaa gacagggatc    540

accggcacct cccaatatca accccaggca gcacagacac aaaccccaca tccagagcca    600

actccaggag cagagacacc ccaacactct gggggacccc aaccgtgata actccccact    660

ggaatccgcc ccagagtcta ccaggaccaa aggccctgcc ctgtctctgt ccctcactca    720

gggcctcctg cagggcgagc gcttgggagc agactcggtc ttaggggaca ccactgtggg    780

ccccaacttt gatgaggcca ctgacccttc cttcctttcc tggggcagca cagactttgg    840

ggtctgggca gggaagaact actggctggt ggccaatcac agagccccca ggccgaggtg    900

gccccaagaa ggccctcagg aggtggccac tccacttcct cccagctgga ccccaggtcc    960

tccccaagat aggggtgcca tccaaggcag gtcctccatg gagcccccctt cagactcctc   1020

ccgggacccc actggacctc agtccctgct ctgggaatgc agccaccaca agcacaccag   1080

gaagcccagg cccagccacc ctgcagtggg caagcccaca ctctggagca gagcagggtg   1140

cgtctgggag gggctaacct ccccaccccc cacccccat ctgcacacag ccacctacca   1200
```

-continued ctgcccagac cctctgcagg agggccaagc caccatgggg tatggactta gggtctcact 1260
cacgtgcctc ccctcctggg agaaggggcc tcatgcccag atccctgcag cactagacac 1320
agctggaggc agtggcccca gggccaccct gacctggcat ctaaggctgc tccagcccag 1380
acagcactgc cgttcctggg aagcctgggc tccaccagac cacaggtcca gggcacagcc 1440
cacaggagcc acccacacac agctcacagg aagaagataa gctccagacc ccagggcggg 1500
acctgccttc ctgccaccac ttacacacag gccagggagc tgttcccaca cagatcaacc 1560
ccaaaccggg actgcctggc actagggtca ctgccatttc cctctccatt ccctcccagt 1620
gcctctgtgc tccctccttc tggggaacac cctgtgcagc ccctccctgc agcccacacg 1680
ctggggagac cccaccctgc ctcgggcctt ttctacctgc tgcacttgcc gcccacccaa 1740
acaaccctgg gtacgtgacc ctgcagtcct caccctgatc tgcaaccaga cccctgtccc 1800
tccctctaaa cacccctccc aggccaactc tgcacctgca ggccctccgc tcttctgcca 1860
caagagcctc aggttttcct acctgtgccc accccctaac ccctcctgcc cacaacttga 1920
gttcttcctc tcctggagcc cttgagccat ggcactgacc ctacactccc acccacacac 1980
tgcccatgcc atcaccttcc tcctggacac tctgaccccg ctcccctccc tctcagaccc 2040
ggccctggta tttccaggac aaaggctcac ccaagtcttc cccatgcagg cccttgccct 2100
cactgcctgg ttacacggga gcctcctgtg cgcagaagca gggagctcag ctcttccaca 2160
ggcagaaggc actgaaagaa atcagcctcc agtgccttga cacacgtccg cctgtgtctc 2220
tcactgcctg cacctgcagg gaggctccgc actccctcta aagatgaggg atccaggcag 2280
caacatcacg ggagaatgca gggctcccag acagcccagc cctctcgcag gcctctcctg 2340
ggaagagacc tgcagccacc actgaacagc cacggaggtc gctggatagt aaccgagtca 2400
gtgaccgacc tggagggcag gggagcagtg aaccggagcc cataccatag ggacagagac 2460
cagccgctaa catcccgagc ccctcactgg cggccccaga acaccccgtg gaaagagaac 2520
agacccacag tcccacctgg aacagggcag acactgctga gcccccagca ccagccccaa 2580
gaaacactag gcaacagcat cagagggggc tcctgagaaa gagaggaggg gaggtctcct 2640
tcaccatcaa atgcttccct tgaccaaaaa cagggtccac gcaactcccc caggacaaag 2700
gaggagcccc ctgtacagca ctgggctcag agtcctctct gagacaggct cagtttcaga 2760
caacaacccg ctggaatgca cagtctcagc aggagagcca ggccagagcc agcaagagga 2820
gactcggtga caccagtctc ctgtagggac aggaggattt tgtgggggtt cgtgtcactg 2880
tgagcacatt gtggtggtca ctgccattcc cacagtgaca caaccccatt cctaaagccc 2940
tactgcaaac gcacccactc ctgggactga ggggctgggg gagcgtctgg gaagtatggc 3000
ctaggggtgt ccatcaatgc ccaaaatgca ccagactctc cccaagacat caccccacca 3060
gccagtgagc agagtaaaca gaaaatgaga agcagctggg aagcttgcac aggccccaag 3120
gaaagagctt tggcaggtgt gcaagagggg atgtgggcag agcctcagca gggccttttg 3180
ctgtttctgc tttcctgtgc agagagttcc ataaactggt attcaagatc aatggctggg 3240
agtgagccca ggaggacagt gtgggaagag cacagggaag gaggagcagc cgctatccta 3300
cactgtcatc ttttgaaagt ttgccctgtg cccacaatgc tgcatcatgg gatgcttaac 3360
agctgatgta gacacagcta aagagagaat cagtgaaatg gatttgcagc acagatctga 3420
ataaatcctc cagaatgtgg agcagcacag aagcaagcac acagaaagtg cctgatgcca 3480
aggcaaagtt cagtgggcac cttcaggcat tgctgctggg cacagacact ctgaaaagca 3540

-continued

```
ctggcaggaa ctgcctgtga caaagcagaa ccctcaggca atgccagccc tagagccctt   3600
cctgagaacc tcatgggcaa agatgtgcag aacagctgtt tgtcatagcc ccaaactatg   3660
gggctggaca aagcaaacgt ccatctgaag gagaacagac aaataaacga tggcaggttc   3720
atgaaatgca aactaggaca gccagaggac aacagtagag agctacaggc ggctttgcgg   3780
ttgagttcat gacaatgctg agtaattgga gtaacagagg aaagcccaaa aaatactttt   3840
aatgtgattt cttctaaata aaatttacac ccggcaaaat gaactatctt cttaagggat   3900
aaactttccc ctggaaaaac tataaggaaa atcaagaaaa cgatgatcac ataaacacag   3960
tggtggttac ttctactggg gaaggaagag ggtatgagct gagacacaca gagtcggcaa   4020
gtctcctaac aagaacagaa caaatacatt acagtacctt gaaaacagca gttaaacttc   4080
taaatcgcaa gaagaggaaa atgcacacac ctgtgtttag aaaattctca gtccagcact   4140
gttcataata gcaaagacat taacccaggt tggataaata agcgatgaca caggcaattg   4200
cacaatgata cagacataca ttcagtatat gagacatcga tgatgtatcc ccaaagaaat   4260
gactttaaag agaaaaggcc tgatgtgtgg tggcaatcac ctccctgggc atccccggac   4320
aggctgcagg ctcactgtgt ggcagggcag gcaggcacct gctggcagct cctggggcct   4380
gatgtggagc aggcacagag ctgtatatcc ccaaggaagg tacagtcagt gcattccaga   4440
gagaagcaac tcagccacac tccctggcca gaacccaaga tgcacaccca tgcacaggga   4500
ggcagagccc agcacctccg cagccaccac cacctgcgca cgggccacca ccttgcaggc   4560
acagagtggg tgctgagagg aggggcaggg acaccaggca gggtgagcac ccagagaaaa   4620
ctgcagaagc ctcacacatc cctcacctgg cctgggcttc acctgacctg gacctcacct   4680
ggcctcgggc ctcacctgca cctgctccag gtcttgctgg agcctgagta gcactgaggc   4740
tgtagggact catccagggt tggggaatga ctctgcaact ctcccacatc tgacctttct   4800
gggtggaggc acctggtggc ccagggaata taaaaagccc cagaatgatg cctgtgtgat   4860
ttgggggcaa tttatgaacc cgaaaggaca tggccatggg gtgggtaggg acagtaggga   4920
cagatgtcag cctgaggtga agcctcagga cacaggtggg catggacagt gtccacctaa   4980
gcgagggaca gacccgagtg tccctgcagt agacctgaga gcgctgggcc cacagcctcc   5040
cctcggggcc ctgctgcctc ctcaggtcag ccctggacat cccgggtttc cccaggcctg   5100
gcggtaggtt tgaagtgagg tctgtgtcac tgtggtatca ctatcatagt agtggtcatt   5160
actaccacag tgtcacagag tccatcaaaa actcatgcct gggagcctcc caccacagcc   5220
ctccctgcgg gggaccgctg catgccgtgt taggattttg atcgaggaca cggcgccatg   5280
ggtatggtgg ctaccacagc agtgcagccc atgacccaaa cacacggggc agcagaaaca   5340
atggacaggc ccacaagtga ccatgatggg ctccagccca ccagccccag agaccatgaa   5400
acagatggcc aaggtcaccc tacaggtcat ccagatctgg ctccaagggg tctgcatcgc   5460
tgctgccctc ccaacgccaa accagatgga gacagggccg gccccatagc accatctgct   5520
gccgtccacc cagcagtccc ggaagcccct ccctgaacgc tgggccacgt gtgtgaaccc   5580
tgcgagcccc ccatgtcaga gtaggggcag caggagggcg gggctggccc tgtgcactgt   5640
cactgcccct gtggtccctg gcctgcctgg ccctgacacc tgagcctctc ctgggtcatt   5700
tccaagacat tcccagggac agccggagct gggagtcgct catcctgcct ggctgtcctg   5760
agtcctgctc atttccagac ctcaccaggg aagccaacag aggactcacc tcacacagtc   5820
agagacaacg aaccttccag aaatccctgt ttctctcccc agtgagagaa accctcttcc   5880
agggtttctc ttctctccca ccctcttcca ggacagtcct cagcagcatc acagcgggaa   5940
```

cgcacatctg gatcaggacg gcccccagaa cacgcgatgg cccatgggga cagcccagcc 6000
cttcccagac ccctaaaagg tatccccacc ttgcacctgc cccagggctc aaactccagg 6060
aggcctgact cctgcacacc ctcctgccag atatcacctc agccccctcc tggaggggac 6120
aggagcccgg gagggtgagt cagacccacc tgccctcaat ggcaggcggg gaagattcag 6180
aaaggcctga gatccccagg acgcagcacc actgtcaatg gggcccccag acgcctggac 6240
cagggcctgt gtgggaaagg cctctggcca cactcagggg ctttttgtga agggccctcc 6300
tgctgtgtga ccacggtggt cactcccaca gtgatgaaac cagcagcaaa aactgaccgg 6360
actcgcaggg tttatgcaca cttctcggct cggagctctc caggagcaca agagccaggc 6420
ccgagggttt gtgcccagac cctcggcctc tagggacacc cgggccatct tagccgatgg 6480
gctgatgccc tgcacaccgt gtgctgccaa acaggggctt cagagggctc tgaggtgact 6540
tcactcatga ccacaggtgc cctggtccct tcactgccag ctgcaccaga ccctgttccg 6600
agagatgccc cagttccaaa agccaattcc tggggccggg aattactgta gacaccagcc 6660
tcattccagt acctcctgcc aattgcctgg attcccatcc tggctggaat caagagggca 6720
gcatccgcca ggctcccaac aggcaggact cccacacacc ctcctctgag aggccgctgt 6780
gttccgcagg gccaggccgc agacagttcc cctcacctgc ccatgtagaa acacctgcca 6840
ttgtcgtccc cacctggcaa agaccacttg tggagccccc agccccaggt acagctgtag 6900
agagagtcct cgaggcccct aagaaggagc catgcccagt tctgccggga ccctcggcca 6960
ggccgacagg agtggacgct ggagctgggc ccacactggg ccacatagga gctcaccagt 7020
gagggcagga gagcacatgc cggggagcac ccagcctcct gctgaccaga gacccgtccc 7080
agagcccagg aggctgcaga ggcctctcca gggggacaca gtgcatgtct ggtccctgag 7140
cagcccccag gctctctagc actgggggcc cctggcacag ctgtctggac cctccctgtt 7200
ccctgggaag ctcctcctga cagccccgcc tccagttcca ggtgtggtta ttgtcagggg 7260
gtgccaggcc gtggtagaca tggccaccat taccacagtg gtgccgccca tagcagcaac 7320
caggccaagt agacagaccc ctgccacgca gccccaggcc tccagctcac ctgcttctcc 7380
tggggctctc aaggctgctg tctgccctct ggccctctgt ggggagggtt ccctcagtgg 7440
gaggtctgtg ctccagggca gggatgactg agatagaaat caaaggctgg cagggaaagg 7500
cagcttcccg ccctgagagg tgcaggcagc accacagagc catggagtca cagagccacg 7560
gagcccccag tgtgggcgtg tgagggtgct gggctcccgg caggcccagc cctgatgggg 7620
aagcctgccc cgtcccacag cccaggtccc caggggcagc aggcacagaa gctgccaagc 7680
tgtgctctac gatcctcatc cctccagcag catccactcc acagtgggga aactgagcct 7740
tggagaacca cccagccccc tggaaacaag gcggggagcc cagacagtgg gcccagagca 7800
ctgtgtgtat cctggcacta ggtgcaggga ccacccggag atccccatca ctgagtggcc 7860
agcctgcaga aggacccaac cccaaccagg ccgcttgatt aagctccatc cccctgtcct 7920
gggaacctct tcccagcgcc accaacagct cggcttccca ggccctcatc cctccaagga 7980
aggccaaagg ctgggcctgc caggggcaca gtaccctccc ttgccctggc taagacaggg 8040
tgggcagacg gctgcagata ggacatattg ctggggcatc ttgctctgtg actactgggt 8100
actggctctc aacgcagacc ctaccaaaat ccccactgcc tcccctgcta ggggctggcc 8160
tggtctcctc ctgctgtcct aggaggctgc tgacctccag gatggcttct gtccccagtt 8220
ctagggccag agcagatccc aggcaggctg taggctggga ggccacccct gtccttgccg 8280
aggttcagtg caggcaccca ggacaggaaa tggcctgaac acagggatga ctgtgccatg 8340
ccctacctaa gtccgcccct ttctactctg caacccccac tccccaggtc agcccatgac 8400
gaccaacaac ccaacaccag agtcactgcc tggccctgcc ctggggagga cccctcagcc 8460
cccaccctgt ctagaggagt tggggggaca ggacacaggc tctctcctta tggttccccc 8520
acctggctcc tgccgggacc cttggggtgt ggacagaaag gacgcctgcc taattggccc 8580
ccaggaaccc agaacttctc tccagggacc ccagcccgag caccccctta cccaggaccc 8640
agccctgccc ctcctcccct ctgctctcct ctcatcactc catgggaatc cagaatcccc 8700
aggaagccat caggaagggc tgaaggagga agcggggccg ctgcaccacc gggcaggagg 8760
ctccgtcttc gtgaacccag ggaagtgcca gcctcctaga gggtatggtc caccctgcct 8820
ggggctccca ccgtggcagg ctgcggggaa ggaccaggga cggtgtgggg gagggctcag 8880
ggccctgcag gtgctccatc ttggatgagc ccatccctct cacccaccga cccgcccacc 8940
tcctctccac cctggccaca cgtcgtccac accatcctga gtcccaccta caccagagcc 9000
agcagagcca gtgcagacag aggctggggt gcagggggc cgccagggca gctttgggga 9060
gggaggaatg gaggaagggg aggtcagtga agaggccccc ctcccctggg tctaggatcc 9120
acctttggga cccccggatc ccatcccctc caggctctgg gaggagaagc aggatgggag 9180
attctgtgca ggaccctctc acagtggaat acctccacag cggctcaggc cagatacaaa 9240
agcccctcag tgagccctcc actgcagtgc agggcctggg ggcagcccct cccacagagg 9300
acagacccag caccccgaag aagtcctgcc agggggagct cagagccatg aaggagcaag 9360
atatggggac cccaatactg gcacagacct cagctccatc caggcccacc aggacccacc 9420
atgggtggaa cacctgtctc cggcccctgc tggctgtgag gcagctggcc tctgtctcgg 9480
acccccattc cagacaccag acagagggac aggcccccca gaaccagtgt tgagggacac 9540
ccctgtccag ggcagccaag tccaagaggc gcgctgagcc cagcaaggga aggcccccaa 9600
acaaaccagg aggtttctga agctgtctgt gtcacagtcg ggcatagcca cggctaccac 9660
aatgacactg ggcaggacag aaaccccatc ccaagtcagc cgaaggcaga gagagcaggc 9720
aggacacatt taggatctga ggccacacct gacactcaag ccaacagatg tctcccctcc 9780
agggcgccct gccctgttca gtgttcctga gaaaacaggg gcagcctgag gggatccagg 9840
gccaggagat gggtcccctc taccccgagg aggagccagg cgggaatccc agccccctcc 9900
ccattgaggc catcctgccc agaggggccc ggacccaccc cacacaccca ggcagaatgt 9960
gtgcaggcct caggctctgt gggtgccgct agctggggct gccagtcctc accccacacc 10020
taaggtgagc cacagccgcc agagcctcca caggagaccc cacccagcag cccagcccct 10080
acccaggagg ccccagagct cagggcgcct gggtggattc tgaacagccc cgagtcacgg 10140
tgggtatcat gggagccact accactgtga gaaaagctat gtccaaaact gtctcccggc 10200
cactgctgga ggcccagcca gagaagggac cagccgcccg aacatacgac cttcccagac 10260
ctcatgaccc ccagcacttg gagctccaca gtgtccccat tggatggtga ggatgggggc 10320
cggggccatc tgcacctccc aacatcaccc ccaggcagca caggcacaaa ccccaaatcc 10380
agagccgaca ccaggaacac agacacccca ataccctggg ggaccctggc cctggtgact 10440
tcccactggg atccaccccc gtgtccacct ggatcaaaga ccccaccgct gtctctgtcc 10500
ctcactcagg gcctgctgag gggcgggtgc tttggagcag actcaggttt aggggccacc 10560
attgtggggc ccaacctcga ccaggacaca gatttttctt tcctgccctg gggcaacaca 10620
gactttgggg tctgtgcagg gaggaccttc tggaaagtca ccaagcacag agccctgact 10680
gaggtggtct caggaagacc cccaggaggg ggcttgtgcc ccttcctctc atgtggaccc 10740
catgcccccc aagataggg catcatgcag ggcaggtcct ccatgcagcc accactaggc 10800
aactccctgg cgccggtccc cactgcgcct ccatcccggc tctggggatg cagccaccat 10860
ggccacacca ggcagcccgg gtccagcaac cctgcagtgc ccaagccctt ggcaggattc 10920
ccagaggctg gagcccaccc ctcctcatcc ccccacacct gcacacacac acctaccccc 10980
tgcccagtcc ccctccagga gggttggagc cgcccatagg gtgggggctc caggtctcac 11040
tcactcgctt cccttcctgg gcaaaggagc ctcgtgcccc ggtcccccct gacggcgctg 11100
ggcacaggtg tgggtactgg gccccagggc tcctccagcc ccagctgccc tgctctccct 11160
gggaggcctg ggcaccacca gaccaccagt ccagggcaca gccccaggga gccgcccact 11220
gccagctcac aggaagaaga taagcttcag accctcaggg ccgggagctg ccttcctgcc 11280
accccttcct gccccagacc tccatgccct cccccaacca cttacacaca agccagggag 11340
ctgtttccac acagttcaac cccaaaccag gacggcctgg cactcgggtc actgccattt 11400
ctgtctgcat tcgctcccag cgcccctgtg ttccctccct cctccctcct tcctttcttc 11460
ctgcattggg ttcatgccgc agagtgccag gtgcaggtca gccctgagct tggggtcacc 11520
tcctcactga aggcagcctc agggtgccca ggggcaggca gggtgggggt gaggcttcca 11580
gctccaaccg ct 11592

<210> SEQ ID NO 5
<211> LENGTH: 689
<212> TYPE: DNA
<213> ORGANISM: Mus musculus
<220> FEATURE:
<221> NAME/KEY: misc_feature
<222> LOCATION: (1)..(689)
<223> OTHER INFORMATION: Mouse Ei (an intronic enhancer)

<400> SEQUENCE: 5
tctagagagg tctggtggag cctgcaaaag tccagctttc aaaggaacac agaagtatgt 60
gtatggaata ttagaagatg ttgcttttac tcttaagttg gttcctagga aaaatagtta 120
aatactgtga ctttaaaatg tgagagggtt ttcaagtact catttttta aatgtccaaa 180 attcttgtca atcagtttga ggtcttgttt gtgtagaact gatattactt aaagtttaac 240
cgaggaatgg gagtgaggct ctctcataac ctattcagaa ctgactttta acaataataa 300
attaagtttc aaatattttt aaatgaattg agcaatgttg agttggagtc aagatggccg 360
atcagaacca gaacacctgc agcagctggc aggaagcagg tcatgtggca aggctatttg 420
gggaagggaa aataaaacca ctaggtaaac ttgtagctgt ggtttgaaga agtggttttg 480
aaacactctg tccagcccca ccaaaccgaa agtccaggct gagcaaaaca ccacctgggt 540
aatttgcatt tctaaaataa gttgaggatt cagccgaaac tggagaggtc ctcttttaac 600
ttattgagtt caacctttta attttagctt gagtagttct agtttcccca aacttaagtt 660
tatcgacttc taaaatgtat ttagaattc 689

<210> SEQ ID NO 6
<211> LENGTH: 3518
<212> TYPE: DNA
<213> ORGANISM: Mus musculus
<220> FEATURE:
<221> NAME/KEY: misc_feature
<222> LOCATION: (1)..(3518)
<223> OTHER INFORMATION: Mouse Switch Region

<400> SEQUENCE: 6
acttatttca gttgaacatg ctggttggtg gttgagagga cactcagtca gtcagtgacg 60
tgaagggctt ctaagccagt ccacatgctc tgtgtgaact ccctctggcc ctgcttattg 120
ttgaatgggc caaaggtctg agaccaggct gctgctgggt aggcctggac tttgggtctc 180
ccacccagac ctgggaatgt atggttgtgg cttctgccac ccatccacct ggctgctcat 240
ggaccagcca gcctcggtgg ctttgaagga acaattccac acaaagactc tggacctctc 300
cgaaaccagg caccgcaaat ggtaagccag aggcagccac agctgtggct gctgctctta 360
aagcttgtaa actgtttctg cttaagaggg actgagtctt cagtcattgc tttaggggga 420
gaaagagaca tttgtgtgtc ttttgagtac cgttgtctgg gtcactcaca tttaactttc 480
cttgaaaaac tagtaaaaga aaaatgttgc ctgttaacca ataatcatag agctcatggt 540
actttgagga aatcttagaa agcgtgtata caattgtctg gaattatttc agttaagtgt 600
attagttgag gtactgatgc tgtctctact tcagttatac atgtgggttt gaattttgaa 660
tctattctgg ctcttcttaa gcagaaaatt tagataaaat ggatacctca gtggttttta 720
atggtgggtt taatatagaa ggaatttaaa ttggaagcta atttagaatc agtaaggagg 780
gacccaggct aagaaggcaa tcctgggatt ctggaagaaa agatgttttt agtttttata 840
gaaaacacta ctacattctt gatctacaac tcaatgtggt ttaatgaatt tgaagttgcc 900
agtaaatgta cttcctggtt gttaaagaat ggtatcaaag gacagtgctt agatccgagg 960
tgagtgtgag aggacagggg ctggggtatg gatacgcaga aggaaggcca cagctgtaca 1020
gaattgagaa agaatagaga cctgcagttg aggccagcag gtcggctgga ctaactctcc 1080
agccacagta atgacccaga cagagaaagc cagactcata aagcttgctg agcaaaatta 1140
agggaacaag gttgagagcc ctagtaagcg aggctctaaa aagcacagct gagctgagat 1200
gggtgggctt ctctgagtgc ttctaaaatg cgctaaactg aggtgattac tctgaggtaa 1260
gcaaagctgg gcttgagcca aaatgaagta gactgtaatg aactggaatg agctgggccg 1320
ctaagctaaa ctaggctggc ttaaccgaga tgagccaaac tggaatgaac ttcattaatc 1380
taggttgaat agagctaaac tctactgcct acactggact gttctgagct gagatgagct 1440
ggggtgagct cagctatgct acgctgtgtt ggggtgagct gatctgaaat gagatactct 1500
ggagtagctg agatggggtg agatggggtg agctgagctg ggctgagcta gactgagctg 1560
agctagggtg agctgagctg ggtgagctga gctaagctgg ggtgagctga gctgagcttg 1620
gctgagctag ggtgagctgg gctgagctgg ggtgagctga gctgagctgg ggtaagctgg 1680
gatgagctgg ggtgagctga gctgagctgg agtgagctga gctgggctga gctggggtga 1740
gctgggctga gctgggctga gctgggctga gctggggtga gctgagctgg ggtgagctga 1800
gctgagctgg ggtgagctga gctgagctgg ggtgagctgg ggtgagctga gctggggtga 1860
gctgagctga gctggggtga gctgagctgg ggtgagctga gctgagctgg ggtgagctga 1920
gctgagctga gctgagctga gctggggtga gctgagctga gctgagctgg ggtgagctgg 1980
ggtgagctga gctgagctgg agtgagctga gctgggctga gctggggtga gctgggctga 2040
gctggggtga gctgagctga gctgagctga gctggggtga gctgagctga gctggggtga 2100
gctgagctgg ggtgagctgg gctgagctga gctgagctga gctgagctga gctgagctga 2160
gctgagctga gctgagctga gctgagctga gctgagctga gctgagctgg ggtgagctga 2220
gctgagctgg gctgagctgg ggtgagctgg gctgagctgg gctgagctgg gctgagctgg 2280
ggtgagctga gctggggtga gctgagctga gctgggctga gctgagctga gctggggtga 2340
gctgagctga gctggggtga gctgagctga gctgagctgg ggtgagctga gctgagctgg 2400
gctgagcagg gctgagctgg ggtgagctga gctgagctgg ggtgagctgg gctgagctgg 2460
gctgagctga gctgagctgg gctgagctgg gctgagctgg gctgagctgg gctgagctgg 2520
gctgagctgg ggtgagctga gctggggtga gctggggtga gctgagctgg ggtgagctga 2580
gctggggtga gctgagctga gctggggtga gctgagctgg ggtgagctga gctgagctgg 2640
ggtgagctga gctgagctgg ggtgagctga gctagggtga actgggctgg gtgagctgga 2700
gtgagctgag ctgaggtgaa ctggggtgag ccgggatgtt ttgagttgag ctggggtaag 2760
atgagctgaa ctggggtaaa ctgggatgag ctgtggtgag cggagctgga ttgaactgag 2820
ctgtgtgagc tgagctgggg tcagctgagc aagagtgagt agagctggct ggccagaacc 2880
agaatcaatt aggctaagtg agccagattg tgctgggatc agctgtactc agatgagctg 2940
ggatgaggta ggctgggatg agctgggcta gctgacatgg attatgtgag gctgagctag 3000
catgggctgg cctagctgat gagctaagct tgaatgagcg gggctgagct ggactcagat 3060
gtgctagact gagctgtact ggatgatctg gtgtagggtg atctggactc aactgggctg 3120
gctgatggga tgcgccaggt tgaactaggc tcagataagt taggctgagt agggcctggt 3180
tgagatggtt cgggatgagc tgggaaaaga tggactcgga ccatgaactg ggctgagctg 3240
ggttgggaga ccatgaattg agctgaactg agtgcagctg ggataaactg ggttgagcta 3300
agaatagact acctgaattg tgccaaactc ggctgggatc aattggaaat tatcaggatt 3360
tagatgagcc ggactaaact atgctgagct ggactggttg gatgtgttga actggcctgc 3420
tgctgggctg gcatagctga gttgaactta aatgaggaag gctgagcaag gctagcctgc 3480
ttgcatagag ctgaacttta gcctagcctg agctggac 3518

<210> SEQ ID NO 7
<211> LENGTH: 315
<212> TYPE: DNA
<213> ORGANISM: Mus musculus
<220> FEATURE:
<221> NAME/KEY: misc_feature
<222> LOCATION: (1)..(315)
<223> OTHER INFORMATION: mouse IgM exon 1

<400> SEQUENCE: 7
agagtcagtc cttcccaaat gtcttccccc tcgtctcctg cgagagcccc ctgtctgata 60
agaatctggt ggccatgggc tgcctggccc gggacttcct gcccagcacc atttccttca 120
cctggaacta ccagaacaac actgaagtca tccagggtat cagaaccttc ccaacactga 180
ggacaggggg caagtaccta gccacctcgc aggtgttgct gtctcccaag agcatccttg 240
aaggttcaga tgaatacctg gtatgcaaaa tccactacgg aggcaaaaac aaagatctgc 300
atgtgcccat tccag 315

<210> SEQ ID NO 8
<211> LENGTH: 5
<212> TYPE: PRT
<213> ORGANISM: Homo sapiens

<400> SEQUENCE: 8

Val Gln Leu Glu Arg
1 5

<210> SEQ ID NO 9
<211> LENGTH: 5

<212> TYPE: PRT
<213> ORGANISM: Unknown
<220> FEATURE:
<223> OTHER INFORMATION: Mammal

<400> SEQUENCE: 9

Val Pro Leu Ala Arg
1               5

<210> SEQ ID NO 10
<211> LENGTH: 5
<212> TYPE: PRT
<213> ORGANISM: Unknown
<220> FEATURE:
<223> OTHER INFORMATION: Mammal

<400> SEQUENCE: 10

Val Ser Leu Ala Leu
1               5

<210> SEQ ID NO 11
<211> LENGTH: 5
<212> TYPE: PRT
<213> ORGANISM: Unknown
<220> FEATURE:
<223> OTHER INFORMATION: Mammal

<400> SEQUENCE: 11

Val Ser Leu Ala Arg
1               5

<210> SEQ ID NO 12
<211> LENGTH: 4
<212> TYPE: PRT
<213> ORGANISM: Homo sapiens

<400> SEQUENCE: 12

Trp Glu Leu Leu
1

<210> SEQ ID NO 13
<211> LENGTH: 6
<212> TYPE: PRT
<213> ORGANISM: Unknown
<220> FEATURE:
<223> OTHER INFORMATION: Mammal

<400> SEQUENCE: 13

Val Ser Trp Glu Pro Leu
1               5

<210> SEQ ID NO 14
<211> LENGTH: 5
<212> TYPE: PRT
<213> ORGANISM: Homo sapiens

<400> SEQUENCE: 14

Tyr Gln Leu Leu Tyr
1               5

<210> SEQ ID NO 15
<211> LENGTH: 6
<212> TYPE: PRT
<213> ORGANISM: Unknown
<220> FEATURE:
<223> OTHER INFORMATION: Mammal

<400> SEQUENCE: 15

Ser Tyr Gln Leu Pro Tyr
1 5

<210> SEQ ID NO 16
<211> LENGTH: 4
<212> TYPE: PRT
<213> ORGANISM: Homo sapiens

<400> SEQUENCE: 16

Arg Ile Leu Tyr
1

<210> SEQ ID NO 17
<211> LENGTH: 5
<212> TYPE: PRT
<213> ORGANISM: Homo sapiens

<400> SEQUENCE: 17

Trp Cys Met Leu Tyr
1 5

<210> SEQ ID NO 18
<211> LENGTH: 10
<212> TYPE: PRT
<213> ORGANISM: Unknown
<220> FEATURE:
<223> OTHER INFORMATION: Mammal

<400> SEQUENCE: 18

Arg Thr Leu Tyr Ser Trp Cys Met Pro Tyr
1 5 10

<210> SEQ ID NO 19
<211> LENGTH: 5
<212> TYPE: PRT
<213> ORGANISM: Homo sapiens

<400> SEQUENCE: 19

Ser Ile Leu Trp Trp
1 5

<210> SEQ ID NO 20
<211> LENGTH: 9
<212> TYPE: PRT
<213> ORGANISM: Unknown
<220> FEATURE:
<223> OTHER INFORMATION: Mammal

<400> SEQUENCE: 20

Ser Thr Leu Trp Trp Ser Leu Pro Phe
1 5

<210> SEQ ID NO 21
<211> LENGTH: 10
<212> TYPE: PRT
<213> ORGANISM: Homo sapiens

<400> SEQUENCE: 21

Val Leu Arg Phe Leu Glu Trp Leu Leu Tyr
1 5 10

<210> SEQ ID NO 22
<211> LENGTH: 10
<212> TYPE: PRT

<213> ORGANISM: Unknown
<220> FEATURE:
<223> OTHER INFORMATION: Mammal

<400> SEQUENCE: 22

Val Ser Pro Phe Leu Glu Trp Ser Leu Tyr
1               5                   10

<210> SEQ ID NO 23
<211> LENGTH: 9
<212> TYPE: PRT
<213> ORGANISM: Homo sapiens

<400> SEQUENCE: 23

Val Leu Arg Tyr Phe Asp Trp Leu Leu
1               5

<210> SEQ ID NO 24
<211> LENGTH: 9
<212> TYPE: PRT
<213> ORGANISM: Unknown
<220> FEATURE:
<223> OTHER INFORMATION: Mammal

<400> SEQUENCE: 24

Val Ser Pro Tyr Phe Asp Trp Ser Leu
1               5

<210> SEQ ID NO 25
<211> LENGTH: 9
<212> TYPE: PRT
<213> ORGANISM: Homo sapiens

<400> SEQUENCE: 25

Val Leu Leu Trp Phe Gly Glu Leu Leu
1               5

<210> SEQ ID NO 26
<211> LENGTH: 9
<212> TYPE: PRT
<213> ORGANISM: Unknown
<220> FEATURE:
<223> OTHER INFORMATION: Mammal

<400> SEQUENCE: 26

Val Ser Pro Trp Phe Gly Glu Ser Leu
1               5

<210> SEQ ID NO 27
<211> LENGTH: 9
<212> TYPE: PRT
<213> ORGANISM: Homo sapiens

<400> SEQUENCE: 27

Leu Arg Leu Gly Glu Leu Ser Leu Tyr
1               5

<210> SEQ ID NO 28
<211> LENGTH: 9
<212> TYPE: PRT
<213> ORGANISM: Unknown
<220> FEATURE:
<223> OTHER INFORMATION: Mammal

<400> SEQUENCE: 28

Ser Arg Leu Gly Glu Ser Ser Leu Tyr 1 5

<210> SEQ ID NO 29
<211> LENGTH: 4
<212> TYPE: PRT
<213> ORGANISM: Homo sapiens

<400> SEQUENCE: 29

Trp Leu Leu Leu
1

<210> SEQ ID NO 30
<211> LENGTH: 4
<212> TYPE: PRT
<213> ORGANISM: Unknown
<220> FEATURE:
<223> OTHER INFORMATION: Mammal

<400> SEQUENCE: 30

Val Ser Leu Ser
1

<210> SEQ ID NO 31
<211> LENGTH: 4
<212> TYPE: PRT
<213> ORGANISM: Unknown
<220> FEATURE:
<223> OTHER INFORMATION: Mammal

<400> SEQUENCE: 31

Trp Ser Leu Leu
1

<210> SEQ ID NO 32
<211> LENGTH: 4
<212> TYPE: PRT
<213> ORGANISM: Unknown
<220> FEATURE:
<223> OTHER INFORMATION: Mammal

<400> SEQUENCE: 32

Pro Gln Ser Leu
1

<210> SEQ ID NO 33
<211> LENGTH: 4
<212> TYPE: PRT
<213> ORGANISM: Unknown
<220> FEATURE:
<223> OTHER INFORMATION: Mammal

<400> SEQUENCE: 33

Pro Arg Ser Leu
1

<210> SEQ ID NO 34
<211> LENGTH: 5
<212> TYPE: PRT
<213> ORGANISM: Unknown
<220> FEATURE:
<223> OTHER INFORMATION: Mammal

<400> SEQUENCE: 34

Pro Arg Trp Ser Leu
1 5

<210> SEQ ID NO 35
<211> LENGTH: 6
<212> TYPE: PRT
<213> ORGANISM: Homo sapiens

<400> SEQUENCE: 35

Trp Ile Gln Leu Trp Leu
1               5

<210> SEQ ID NO 36
<211> LENGTH: 6
<212> TYPE: PRT
<213> ORGANISM: Unknown
<220> FEATURE:
<223> OTHER INFORMATION: Mammal

<400> SEQUENCE: 36

Trp Thr Gln Pro Trp Leu
1               5

<210> SEQ ID NO 37
<211> LENGTH: 4
<212> TYPE: PRT
<213> ORGANISM: Homo sapiens

<400> SEQUENCE: 37

Trp Leu Arg Leu
1

<210> SEQ ID NO 38
<211> LENGTH: 4
<212> TYPE: PRT
<213> ORGANISM: Unknown
<220> FEATURE:
<223> OTHER INFORMATION: Mammal

<400> SEQUENCE: 38

Trp Pro Pro Leu
1

<210> SEQ ID NO 39
<211> LENGTH: 5
<212> TYPE: PRT
<213> ORGANISM: Homo sapiens

<400> SEQUENCE: 39

Arg Trp Leu Gln Leu
1               5

<210> SEQ ID NO 40
<211> LENGTH: 5
<212> TYPE: PRT
<213> ORGANISM: Unknown
<220> FEATURE:
<223> OTHER INFORMATION: Mammal

<400> SEQUENCE: 40

Thr Trp Pro Pro Leu
1               5

<210> SEQ ID NO 41
<211> LENGTH: 4
<212> TYPE: PRT
<213> ORGANISM: Homo sapiens

<400> SEQUENCE: 41

Gln Gln Leu Val
1

<210> SEQ ID NO 42
<211> LENGTH: 4
<212> TYPE: PRT
<213> ORGANISM: Unknown
<220> FEATURE:
<223> OTHER INFORMATION: Mammal

<400> SEQUENCE: 42

Pro Gln Leu Val
1

<210> SEQ ID NO 43
<211> LENGTH: 4
<212> TYPE: PRT
<213> ORGANISM: Homo sapiens

<400> SEQUENCE: 43

Gln Trp Leu Val
1

<210> SEQ ID NO 44
<211> LENGTH: 4
<212> TYPE: PRT
<213> ORGANISM: Unknown
<220> FEATURE:
<223> OTHER INFORMATION: Mammal

<400> SEQUENCE: 44

Pro Trp Leu Val
1

<210> SEQ ID NO 45
<211> LENGTH: 5
<212> TYPE: PRT
<213> ORGANISM: Homo sapiens

<400> SEQUENCE: 45

Tyr Asn Trp Asn Asp
1               5

<210> SEQ ID NO 46
<211> LENGTH: 5
<212> TYPE: PRT
<213> ORGANISM: Unknown
<220> FEATURE:
<223> OTHER INFORMATION: Mammal

<400> SEQUENCE: 46

Tyr His Trp His Asp
1               5

<210> SEQ ID NO 47
<211> LENGTH: 5
<212> TYPE: PRT
<213> ORGANISM: Homo sapiens

<400> SEQUENCE: 47

Tyr Asn Trp Asn Tyr
1               5

<210> SEQ ID NO 48
<211> LENGTH: 5
<212> TYPE: PRT

<213> ORGANISM: Unknown
<220> FEATURE:
<223> OTHER INFORMATION: Mammal

<400> SEQUENCE: 48

Tyr His Trp His Tyr
1 5

<210> SEQ ID NO 49
<211> LENGTH: 6
<212> TYPE: PRT
<213> ORGANISM: Homo sapiens

<400> SEQUENCE: 49

Tyr Ser Gly Ser Tyr Tyr
1 5

<210> SEQ ID NO 50
<211> LENGTH: 6
<212> TYPE: PRT
<213> ORGANISM: Unknown
<220> FEATURE:
<223> OTHER INFORMATION: Mammal

<400> SEQUENCE: 50

Tyr His Gly Ser His Tyr
1 5

<210> SEQ ID NO 51
<211> LENGTH: 10
<212> TYPE: PRT
<213> ORGANISM: Homo sapiens

<400> SEQUENCE: 51

Gly Tyr Cys Ser Ser Thr Ser Cys Tyr Thr
1 5 10

<210> SEQ ID NO 52
<211> LENGTH: 10
<212> TYPE: PRT
<213> ORGANISM: Unknown
<220> FEATURE:
<223> OTHER INFORMATION: Mammal

<400> SEQUENCE: 52

Gly His Cys Ser His Thr Ser Cys His Thr
1 5 10

<210> SEQ ID NO 53
<211> LENGTH: 10
<212> TYPE: PRT
<213> ORGANISM: Homo sapiens

<400> SEQUENCE: 53

Gly Tyr Cys Thr Asn Gly Val Cys Tyr Thr
1 5 10

<210> SEQ ID NO 54
<211> LENGTH: 10
<212> TYPE: PRT
<213> ORGANISM: Unknown
<220> FEATURE:
<223> OTHER INFORMATION: Mammal

<400> SEQUENCE: 54

Gly His Cys Thr His Gly Val Cys His Thr 1 5 10

<210> SEQ ID NO 55
<211> LENGTH: 10
<212> TYPE: PRT
<213> ORGANISM: Homo sapiens

<400> SEQUENCE: 55

Gly Tyr Cys Ser Gly Gly Ser Cys Tyr Ser
1 5 10

<210> SEQ ID NO 56
<211> LENGTH: 10
<212> TYPE: PRT
<213> ORGANISM: Unknown
<220> FEATURE:
<223> OTHER INFORMATION: Mammal

<400> SEQUENCE: 56

Gly His Cys Ser His Gly Ser Cys His Ser
1 5 10

<210> SEQ ID NO 57
<211> LENGTH: 9
<212> TYPE: PRT
<213> ORGANISM: Homo sapiens

<400> SEQUENCE: 57

Ala Tyr Cys Gly Gly Asp Cys Tyr Ser
1 5

<210> SEQ ID NO 58
<211> LENGTH: 9
<212> TYPE: PRT
<213> ORGANISM: Unknown
<220> FEATURE:
<223> OTHER INFORMATION: Mammal

<400> SEQUENCE: 58

Ala His Cys Gly Gly His Cys His Ser
1 5

<210> SEQ ID NO 59
<211> LENGTH: 10
<212> TYPE: PRT
<213> ORGANISM: Homo sapiens

<400> SEQUENCE: 59

Tyr Tyr Asp Phe Trp Ser Gly Tyr Tyr Thr
1 5 10

<210> SEQ ID NO 60
<211> LENGTH: 10
<212> TYPE: PRT
<213> ORGANISM: Unknown
<220> FEATURE:
<223> OTHER INFORMATION: Mammal

<400> SEQUENCE: 60

Tyr His His Phe Trp Ser Gly His Tyr Thr
1 5 10

<210> SEQ ID NO 61
<211> LENGTH: 10
<212> TYPE: PRT
<213> ORGANISM: Homo sapiens

<400> SEQUENCE: 61

Tyr Tyr Asp Ile Leu Thr Gly Tyr Tyr Asn
1 5 10

<210> SEQ ID NO 62
<211> LENGTH: 10
<212> TYPE: PRT
<213> ORGANISM: Unknown
<220> FEATURE:
<223> OTHER INFORMATION: Mammal

<400> SEQUENCE: 62

Tyr His His Ile Leu Thr Gly His Tyr Asn
1 5 10

<210> SEQ ID NO 63
<211> LENGTH: 10
<212> TYPE: PRT
<213> ORGANISM: Homo sapiens

<400> SEQUENCE: 63

Tyr Tyr Tyr Gly Ser Gly Ser Tyr Tyr Asn
1 5 10

<210> SEQ ID NO 64
<211> LENGTH: 10
<212> TYPE: PRT
<213> ORGANISM: Unknown
<220> FEATURE:
<223> OTHER INFORMATION: Mammal

<400> SEQUENCE: 64

Tyr His His Gly Ser Gly Ser His Tyr Asn
1 5 10

<210> SEQ ID NO 65
<211> LENGTH: 12
<212> TYPE: PRT
<213> ORGANISM: Homo sapiens

<400> SEQUENCE: 65

Tyr Tyr Asp Tyr Val Trp Gly Ser Tyr Arg Tyr Thr
1 5 10

<210> SEQ ID NO 66
<211> LENGTH: 12
<212> TYPE: PRT
<213> ORGANISM: Unknown
<220> FEATURE:
<223> OTHER INFORMATION: Mammal

<400> SEQUENCE: 66

Tyr His Asp His Val Trp Gly Ser His Arg Tyr Thr
1 5 10

<210> SEQ ID NO 67
<211> LENGTH: 10
<212> TYPE: PRT
<213> ORGANISM: Homo sapiens

<400> SEQUENCE: 67

Tyr Tyr Tyr Asp Ser Ser Gly Tyr Tyr Tyr
1 5 10

<210> SEQ ID NO 68
<211> LENGTH: 10
<212> TYPE: PRT
<213> ORGANISM: Unknown
<220> FEATURE:
<223> OTHER INFORMATION: Mammal

<400> SEQUENCE: 68

Tyr His Tyr His Ser Ser Gly His Tyr Tyr
1               5                   10

<210> SEQ ID NO 69
<211> LENGTH: 5
<212> TYPE: PRT
<213> ORGANISM: Homo sapiens

<400> SEQUENCE: 69

Asp Tyr Ser Asn Tyr
1               5

<210> SEQ ID NO 70
<211> LENGTH: 4
<212> TYPE: PRT
<213> ORGANISM: Unknown
<220> FEATURE:
<223> OTHER INFORMATION: Mammal

<400> SEQUENCE: 70

Pro Gln Ser Leu
1

<210> SEQ ID NO 71
<211> LENGTH: 5
<212> TYPE: PRT
<213> ORGANISM: Homo sapiens

<400> SEQUENCE: 71

Asp Tyr Gly Asp Tyr
1               5

<210> SEQ ID NO 72
<211> LENGTH: 5
<212> TYPE: PRT
<213> ORGANISM: Unknown
<220> FEATURE:
<223> OTHER INFORMATION: Mammal

<400> SEQUENCE: 72

Asp His Gly His Tyr
1               5

<210> SEQ ID NO 73
<211> LENGTH: 6
<212> TYPE: PRT
<213> ORGANISM: Homo sapiens

<400> SEQUENCE: 73

Asp Tyr Gly Gly Asn Ser
1               5

<210> SEQ ID NO 74
<211> LENGTH: 6
<212> TYPE: PRT
<213> ORGANISM: Unknown
<220> FEATURE:
<223> OTHER INFORMATION: Mammal

<400> SEQUENCE: 74

Asp His Gly Gly His Ser
1 5

<210> SEQ ID NO 75
<211> LENGTH: 6
<212> TYPE: PRT
<213> ORGANISM: Homo sapiens

<400> SEQUENCE: 75

Gly Tyr Ser Tyr Gly Tyr
1 5

<210> SEQ ID NO 76
<211> LENGTH: 6
<212> TYPE: PRT
<213> ORGANISM: Unknown
<220> FEATURE:
<223> OTHER INFORMATION: Mammal

<400> SEQUENCE: 76

Gly His Ser His Gly Tyr
1 5

<210> SEQ ID NO 77
<211> LENGTH: 7
<212> TYPE: PRT
<213> ORGANISM: Homo sapiens

<400> SEQUENCE: 77

Gly Tyr Ser Gly Tyr Asp Tyr
1 5

<210> SEQ ID NO 78
<211> LENGTH: 7
<212> TYPE: PRT
<213> ORGANISM: Unknown
<220> FEATURE:
<223> OTHER INFORMATION: Mammal

<400> SEQUENCE: 78

Gly His Ser Gly His His Tyr
1 5

<210> SEQ ID NO 79
<211> LENGTH: 6
<212> TYPE: PRT
<213> ORGANISM: Homo sapiens

<400> SEQUENCE: 79

Arg Asp Gly Tyr Asn Tyr
1 5

<210> SEQ ID NO 80
<211> LENGTH: 6
<212> TYPE: PRT
<213> ORGANISM: Unknown
<220> FEATURE:
<223> OTHER INFORMATION: Mammal

<400> SEQUENCE: 80

Arg His Gly His His Tyr
1 5

<210> SEQ ID NO 81

<211> LENGTH: 6
<212> TYPE: PRT
<213> ORGANISM: Homo sapiens

<400> SEQUENCE: 81

Glu Tyr Ser Ser Ser Ser
1 5

<210> SEQ ID NO 82
<211> LENGTH: 6
<212> TYPE: PRT
<213> ORGANISM: Unknown
<220> FEATURE:
<223> OTHER INFORMATION: Mammal

<400> SEQUENCE: 82

Glu His Ser His Ser Ser
1 5

<210> SEQ ID NO 83
<211> LENGTH: 7
<212> TYPE: PRT
<213> ORGANISM: Homo sapiens

<400> SEQUENCE: 83

Gly Tyr Ser Ser Ser Trp Tyr
1 5

<210> SEQ ID NO 84
<211> LENGTH: 7
<212> TYPE: PRT
<213> ORGANISM: Unknown
<220> FEATURE:
<223> OTHER INFORMATION: Mammal

<400> SEQUENCE: 84

Gly His Ser His Ser Trp Tyr
1 5

<210> SEQ ID NO 85
<211> LENGTH: 7
<212> TYPE: PRT
<213> ORGANISM: Homo sapiens

<400> SEQUENCE: 85

Gly Tyr Ser Ser Gly Trp Tyr
1 5

<210> SEQ ID NO 86
<211> LENGTH: 7
<212> TYPE: PRT
<213> ORGANISM: Unknown
<220> FEATURE:
<223> OTHER INFORMATION: Mammal

<400> SEQUENCE: 86

Gly His Ser His Gly Trp Tyr
1 5

<210> SEQ ID NO 87
<211> LENGTH: 6
<212> TYPE: PRT
<213> ORGANISM: Homo sapiens

<400> SEQUENCE: 87

Gly Tyr Ser Ser Gly Tyr 1 5

<210> SEQ ID NO 88
<211> LENGTH: 5
<212> TYPE: PRT
<213> ORGANISM: Homo sapiens

<400> SEQUENCE: 88

Gly Thr Thr Gly Thr
1 5

<210> SEQ ID NO 89
<211> LENGTH: 5
<212> TYPE: PRT
<213> ORGANISM: Homo sapiens

<400> SEQUENCE: 89

Gly Ile Thr Gly Thr
1 5

<210> SEQ ID NO 90
<211> LENGTH: 6
<212> TYPE: PRT
<213> ORGANISM: Homo sapiens

<400> SEQUENCE: 90

Gly Ile Val Gly Ala Thr
1 5

<210> SEQ ID NO 91
<211> LENGTH: 6
<212> TYPE: PRT
<213> ORGANISM: Unknown
<220> FEATURE:
<223> OTHER INFORMATION: Mammal

<400> SEQUENCE: 91

Gly Ile Met Gly Ala Thr
1 5

<210> SEQ ID NO 92
<211> LENGTH: 9
<212> TYPE: PRT
<213> ORGANISM: Homo sapiens

<400> SEQUENCE: 92

Asp Ile Val Val Val Pro Ala Ala Ile
1 5

<210> SEQ ID NO 93
<211> LENGTH: 9
<212> TYPE: PRT
<213> ORGANISM: Unknown
<220> FEATURE:
<223> OTHER INFORMATION: Mammal

<400> SEQUENCE: 93

Asp Ile Val Val Ile Pro Ala Ala Ile
1 5

<210> SEQ ID NO 94
<211> LENGTH: 9
<212> TYPE: PRT
<213> ORGANISM: Homo sapiens

<400> SEQUENCE: 94

Asp Ile Val Leu Met Val Tyr Ala Ile
1 5

<210> SEQ ID NO 95
<211> LENGTH: 9
<212> TYPE: PRT
<213> ORGANISM: Homo sapiens

<400> SEQUENCE: 95

Asp Ile Val Val Val Val Ala Ala Thr
1 5

<210> SEQ ID NO 96
<211> LENGTH: 9
<212> TYPE: PRT
<213> ORGANISM: Unknown
<220> FEATURE:
<223> OTHER INFORMATION: Mammal

<400> SEQUENCE: 96

Asp Ile Val Val Met Val Ala Ala Thr
1 5

<210> SEQ ID NO 97
<211> LENGTH: 8
<212> TYPE: PRT
<213> ORGANISM: Homo sapiens

<400> SEQUENCE: 97

His Ile Val Val Val Thr Ala Ile
1 5

<210> SEQ ID NO 98
<211> LENGTH: 9
<212> TYPE: PRT
<213> ORGANISM: Homo sapiens

<400> SEQUENCE: 98

Ile Thr Ile Phe Gly Val Val Ile Ile
1 5

<210> SEQ ID NO 99
<211> LENGTH: 4
<212> TYPE: PRT
<213> ORGANISM: Homo sapiens

<400> SEQUENCE: 99

Ile Thr Ile Phe
1

<210> SEQ ID NO 100
<211> LENGTH: 4
<212> TYPE: PRT
<213> ORGANISM: Homo sapiens

<400> SEQUENCE: 100

Leu Val Ile Ile
1

<210> SEQ ID NO 101
<211> LENGTH: 9
<212> TYPE: PRT
<213> ORGANISM: Homo sapiens

<400> SEQUENCE: 101

```
Ile Thr Met Val Arg Gly Val Ile Ile
1               5


<210> SEQ ID NO 102
<211> LENGTH: 11
<212> TYPE: PRT
<213> ORGANISM: Homo sapiens

<400> SEQUENCE: 102

Ile Met Ile Thr Phe Gly Gly Val Ile Val Ile
1               5                   10


<210> SEQ ID NO 103
<211> LENGTH: 9
<212> TYPE: PRT
<213> ORGANISM: Homo sapiens

<400> SEQUENCE: 103

Ile Thr Met Ile Val Val Val Ile Thr
1               5


<210> SEQ ID NO 104
<211> LENGTH: 8
<212> TYPE: PRT
<213> ORGANISM: Unknown
<220> FEATURE:
<223> OTHER INFORMATION: Mammal

<400> SEQUENCE: 104

Ile Thr Ile Val Val Val Ile Thr
1               5


<210> SEQ ID NO 105
<211> LENGTH: 4
<212> TYPE: PRT
<213> ORGANISM: Homo sapiens

<400> SEQUENCE: 105

Thr Thr Val Thr
1


<210> SEQ ID NO 106
<211> LENGTH: 5
<212> TYPE: PRT
<213> ORGANISM: Homo sapiens

<400> SEQUENCE: 106

Thr Thr Val Val Thr
1               5


<210> SEQ ID NO 107
<211> LENGTH: 6
<212> TYPE: PRT
<213> ORGANISM: Homo sapiens

<400> SEQUENCE: 107

Val Asp Thr Ala Met Val
1               5


<210> SEQ ID NO 108
<211> LENGTH: 7
<212> TYPE: PRT
<213> ORGANISM: Homo sapiens

<400> SEQUENCE: 108
```

Val Asp Ile Val Ala Thr Ile
1 5

<210> SEQ ID NO 109
<211> LENGTH: 6
<212> TYPE: PRT
<213> ORGANISM: Homo sapiens

<400> SEQUENCE: 109

Val Glu Met Ala Thr Ile
1 5

<210> SEQ ID NO 110
<211> LENGTH: 6
<212> TYPE: PRT
<213> ORGANISM: Unknown
<220> FEATURE:
<223> OTHER INFORMATION: Mammal

<400> SEQUENCE: 110

Val Asp Met Ala Thr Ile
1 5

<210> SEQ ID NO 111
<211> LENGTH: 5
<212> TYPE: PRT
<213> ORGANISM: Homo sapiens

<400> SEQUENCE: 111

Ser Ile Ala Ala Arg
1 5

<210> SEQ ID NO 112
<211> LENGTH: 5
<212> TYPE: PRT
<213> ORGANISM: Unknown
<220> FEATURE:
<223> OTHER INFORMATION: Mammal

<400> SEQUENCE: 112

Ser Ile Ala Thr Arg
1 5

<210> SEQ ID NO 113
<211> LENGTH: 6
<212> TYPE: PRT
<213> ORGANISM: Homo sapiens

<400> SEQUENCE: 113

Gly Ile Ala Ala Ala Gly
1 5

<210> SEQ ID NO 114
<211> LENGTH: 6
<212> TYPE: PRT
<213> ORGANISM: Unknown
<220> FEATURE:
<223> OTHER INFORMATION: Mammal

<400> SEQUENCE: 114

Gly Ile Ala Thr Ala Gly
1 5

<210> SEQ ID NO 115
<211> LENGTH: 6

<212> TYPE: PRT
<213> ORGANISM: Homo sapiens

<400> SEQUENCE: 115

Gly Ile Ala Val Ala Gly
1               5

<210> SEQ ID NO 116
<211> LENGTH: 6
<212> TYPE: PRT
<213> ORGANISM: Unknown
<220> FEATURE:
<223> OTHER INFORMATION: Mammal

<400> SEQUENCE: 116

Gly Ile Ala Met Ala Gly
1               5

<210> SEQ ID NO 117
<211> LENGTH: 5
<212> TYPE: PRT
<213> ORGANISM: Homo sapiens

<400> SEQUENCE: 117

Gly Ile Ala Ala Ala
1               5

<210> SEQ ID NO 118
<211> LENGTH: 5
<212> TYPE: PRT
<213> ORGANISM: Unknown
<220> FEATURE:
<223> OTHER INFORMATION: Mammal

<400> SEQUENCE: 118

Gly Ile Ala Thr Ala
1               5

<210> SEQ ID NO 119
<211> LENGTH: 19
<212> TYPE: DNA
<213> ORGANISM: Unknown
<220> FEATURE:
<223> OTHER INFORMATION: Mammal

<400> SEQUENCE: 119
cgggtcactg ccatttctg 19

<210> SEQ ID NO 120
<211> LENGTH: 20
<212> TYPE: DNA
<213> ORGANISM: Unknown
<220> FEATURE:
<223> OTHER INFORMATION: Mammal

<400> SEQUENCE: 120
tctgcattcg ctcccagcgc 20

<210> SEQ ID NO 121
<211> LENGTH: 19
<212> TYPE: DNA
<213> ORGANISM: Unknown
<220> FEATURE:
<223> OTHER INFORMATION: Mammal

<400> SEQUENCE: 121
tctgcggcat gaacccaat 19

<210> SEQ ID NO 122
<211> LENGTH: 19
<212> TYPE: DNA
<213> ORGANISM: Unknown
<220> FEATURE:
<223> OTHER INFORMATION: Mammal

<400> SEQUENCE: 122
gtgcagggag gaccttctg 19

<210> SEQ ID NO 123
<211> LENGTH: 24
<212> TYPE: DNA
<213> ORGANISM: Unknown
<220> FEATURE:
<223> OTHER INFORMATION: Mammal

<400> SEQUENCE: 123
agtcaccaag cacagagccc tgac 24

<210> SEQ ID NO 124
<211> LENGTH: 19
<212> TYPE: DNA
<213> ORGANISM: Unknown
<220> FEATURE:
<223> OTHER INFORMATION: Mammal

<400> SEQUENCE: 124
gccagggagt tgcctagtg 19

<210> SEQ ID NO 125
<211> LENGTH: 19
<212> TYPE: DNA
<213> ORGANISM: Unknown
<220> FEATURE:
<223> OTHER INFORMATION: Mammal

<400> SEQUENCE: 125
gtggcccact tcccttcct 19

<210> SEQ ID NO 126
<211> LENGTH: 22
<212> TYPE: DNA
<213> ORGANISM: Unknown
<220> FEATURE:
<223> OTHER INFORMATION: Mammal

<400> SEQUENCE: 126
cagctggaac ccaccatgac ct 22

<210> SEQ ID NO 127
<211> LENGTH: 18
<212> TYPE: DNA
<213> ORGANISM: Unknown
<220> FEATURE:
<223> OTHER INFORMATION: Mammal

<400> SEQUENCE: 127
gacctgcctc ggatgaca 18

<210> SEQ ID NO 128
<211> LENGTH: 19
<212> TYPE: DNA
<213> ORGANISM: Unknown

<220> FEATURE:
<223> OTHER INFORMATION: Mammal

<400> SEQUENCE: 128
tggccagaac tgaccctac 19

<210> SEQ ID NO 129
<211> LENGTH: 20
<212> TYPE: DNA
<213> ORGANISM: Unknown
<220> FEATURE:
<223> OTHER INFORMATION: Mammal

<400> SEQUENCE: 129
accgacaaga gtccctcagg 20

<210> SEQ ID NO 130
<211> LENGTH: 19
<212> TYPE: DNA
<213> ORGANISM: Unknown
<220> FEATURE:
<223> OTHER INFORMATION: Mammal

<400> SEQUENCE: 130
ggagtcggct ctggatgtg 19

<210> SEQ ID NO 131
<211> LENGTH: 17
<212> TYPE: DNA
<213> ORGANISM: Unknown
<220> FEATURE:
<223> OTHER INFORMATION: Mammal

<400> SEQUENCE: 131
tgcggccgat cttagcc 17

<210> SEQ ID NO 132
<211> LENGTH: 21
<212> TYPE: DNA
<213> ORGANISM: Unknown
<220> FEATURE:
<223> OTHER INFORMATION: Mammal

<400> SEQUENCE: 132
acgagcgggt tcggcccatt c 21

<210> SEQ ID NO 133
<211> LENGTH: 18
<212> TYPE: DNA
<213> ORGANISM: Unknown
<220> FEATURE:
<223> OTHER INFORMATION: Mammal

<400> SEQUENCE: 133
ttgaccgatt ccttgcgg 18

<210> SEQ ID NO 134
<211> LENGTH: 19
<212> TYPE: DNA
<213> ORGANISM: Unknown
<220> FEATURE:
<223> OTHER INFORMATION: Mammal

<400> SEQUENCE: 134
cagtcccgtt gatccagcc 19

<210> SEQ ID NO 135
<211> LENGTH: 30
<212> TYPE: DNA
<213> ORGANISM: Unknown
<220> FEATURE:
<223> OTHER INFORMATION: Mammal

<400> SEQUENCE: 135
cccatcaggg attttgtatc tctgtggacg 30

<210> SEQ ID NO 136
<211> LENGTH: 21
<212> TYPE: DNA
<213> ORGANISM: Unknown
<220> FEATURE:
<223> OTHER INFORMATION: Mammal

<400> SEQUENCE: 136
ggatatgcag cactgtgcca c 21

<210> SEQ ID NO 137
<211> LENGTH: 19
<212> TYPE: DNA
<213> ORGANISM: Unknown
<220> FEATURE:
<223> OTHER INFORMATION: Mammal

<400> SEQUENCE: 137
tcctccaacg acaggtccc 19

<210> SEQ ID NO 138
<211> LENGTH: 24
<212> TYPE: DNA
<213> ORGANISM: Unknown
<220> FEATURE:
<223> OTHER INFORMATION: Mammal

<400> SEQUENCE: 138
tccctggaac tctgccccga caca 24

<210> SEQ ID NO 139
<211> LENGTH: 20
<212> TYPE: DNA
<213> ORGANISM: Unknown
<220> FEATURE:
<223> OTHER INFORMATION: Mammal

<400> SEQUENCE: 139
gatgaactga cgggcacagg 20

<210> SEQ ID NO 140
<211> LENGTH: 20
<212> TYPE: DNA
<213> ORGANISM: Unknown
<220> FEATURE:
<223> OTHER INFORMATION: Mammal

<400> SEQUENCE: 140
atcacactca tcccatcccc 20

<210> SEQ ID NO 141
<211> LENGTH: 29
<212> TYPE: DNA
<213> ORGANISM: Unknown
<220> FEATURE:
<223> OTHER INFORMATION: Mammal

<400> SEQUENCE: 141
cccttcccta agtaccacag agtgggctc 29

<210> SEQ ID NO 142
<211> LENGTH: 20
<212> TYPE: DNA
<213> ORGANISM: Unknown
<220> FEATURE:
<223> OTHER INFORMATION: Mammal

<400> SEQUENCE: 142
cacagggaag caggaactgc 20

<210> SEQ ID NO 143
<211> LENGTH: 18
<212> TYPE: DNA
<213> ORGANISM: Unknown
<220> FEATURE:
<223> OTHER INFORMATION: Mammal

<400> SEQUENCE: 143
ggagccaggc aggacaca 18

<210> SEQ ID NO 144
<211> LENGTH: 19
<212> TYPE: DNA
<213> ORGANISM: Unknown
<220> FEATURE:
<223> OTHER INFORMATION: Mammal

<400> SEQUENCE: 144
tgggctcgta gtttgacgt 19

<210> SEQ ID NO 145
<211> LENGTH: 23
<212> TYPE: DNA
<213> ORGANISM: Unknown
<220> FEATURE:
<223> OTHER INFORMATION: Mammal

<400> SEQUENCE: 145
gggactttct tacccacact tca 23

<210> SEQ ID NO 146
<211> LENGTH: 24
<212> TYPE: DNA
<213> ORGANISM: Unknown
<220> FEATURE:
<223> OTHER INFORMATION: Mammal

<400> SEQUENCE: 146
ggtcccgagc actcttaatt aaac 24

<210> SEQ ID NO 147
<211> LENGTH: 16
<212> TYPE: DNA
<213> ORGANISM: Unknown
<220> FEATURE:
<223> OTHER INFORMATION: Mammal

<400> SEQUENCE: 147
cctcgaatgg aactac 16

<210> SEQ ID NO 148

<211> LENGTH: 21
<212> TYPE: DNA
<213> ORGANISM: Unknown
<220> FEATURE:
<223> OTHER INFORMATION: Mammal

<400> SEQUENCE: 148
gggagagcaa ccattcgttg t 21

<210> SEQ ID NO 149
<211> LENGTH: 19
<212> TYPE: DNA
<213> ORGANISM: Unknown
<220> FEATURE:
<223> OTHER INFORMATION: Mammal

<400> SEQUENCE: 149
ccgagcaccg atgcatcta 19

<210> SEQ ID NO 150
<211> LENGTH: 16
<212> TYPE: DNA
<213> ORGANISM: Unknown
<220> FEATURE:
<223> OTHER INFORMATION: Mammal

<400> SEQUENCE: 150
cgcagtcatg taatgc 16

<210> SEQ ID NO 151
<211> LENGTH: 20
<212> TYPE: DNA
<213> ORGANISM: Unknown
<220> FEATURE:
<223> OTHER INFORMATION: Mammal

<400> SEQUENCE: 151
gggaggcgaa ctgactgtca 20

<210> SEQ ID NO 152
<211> LENGTH: 19
<212> TYPE: DNA
<213> ORGANISM: Unknown
<220> FEATURE:
<223> OTHER INFORMATION: Mammal

<400> SEQUENCE: 152
ggtggagagg ctattcggc 19

<210> SEQ ID NO 153
<211> LENGTH: 23
<212> TYPE: DNA
<213> ORGANISM: Unknown
<220> FEATURE:
<223> OTHER INFORMATION: Mammal

<400> SEQUENCE: 153
tgggcacaac agacaatcgg ctg 23

<210> SEQ ID NO 154
<211> LENGTH: 17
<212> TYPE: DNA
<213> ORGANISM: Unknown
<220> FEATURE:
<223> OTHER INFORMATION: Mammal

<400> SEQUENCE: 154
gaacacggcg gcatcag 17

<210> SEQ ID NO 155
<211> LENGTH: 17
<212> TYPE: DNA
<213> ORGANISM: Homo sapiens

<400> SEQUENCE: 155
ggtacaactg gaacgac 17

<210> SEQ ID NO 156
<211> LENGTH: 17
<212> TYPE: DNA
<213> ORGANISM: Homo sapiens

<400> SEQUENCE: 156
ggtataactg gaactac 17

<210> SEQ ID NO 157
<211> LENGTH: 17
<212> TYPE: DNA
<213> ORGANISM: Homo sapiens

<400> SEQUENCE: 157
ggtataaccg gaaccac 17

<210> SEQ ID NO 158
<211> LENGTH: 5
<212> TYPE: PRT
<213> ORGANISM: Homo sapiens

<400> SEQUENCE: 158

Tyr Asn Arg Asn His
1               5

<210> SEQ ID NO 159
<211> LENGTH: 17
<212> TYPE: DNA
<213> ORGANISM: Homo sapiens

<400> SEQUENCE: 159
ggtataactg gaacgac 17

<210> SEQ ID NO 160
<211> LENGTH: 20
<212> TYPE: DNA
<213> ORGANISM: Homo sapiens

<400> SEQUENCE: 160
ggtatagtgg gagctactac 20

<210> SEQ ID NO 161
<211> LENGTH: 31
<212> TYPE: DNA
<213> ORGANISM: Homo sapiens

<400> SEQUENCE: 161
aggatattgt agtagtacca gctgctatgc c 31

<210> SEQ ID NO 162
<211> LENGTH: 5
<212> TYPE: PRT
<213> ORGANISM: Homo sapiens

<400> SEQUENCE: 162

Tyr Gln Leu Leu Cys
1 5

<210> SEQ ID NO 163
<211> LENGTH: 10
<212> TYPE: PRT
<213> ORGANISM: Homo sapiens

<400> SEQUENCE: 163

Gly Tyr Cys Ser Ser Thr Ser Cys Tyr Ala
1 5 10

<210> SEQ ID NO 164
<211> LENGTH: 9
<212> TYPE: PRT
<213> ORGANISM: Homo sapiens

<400> SEQUENCE: 164

Asp Ile Val Val Val Pro Ala Ala Met
1 5

<210> SEQ ID NO 165
<211> LENGTH: 31
<212> TYPE: DNA
<213> ORGANISM: Homo sapiens

<400> SEQUENCE: 165
aggatattgt agtagtacca gctgctatac c 31

<210> SEQ ID NO 166
<211> LENGTH: 31
<212> TYPE: DNA
<213> ORGANISM: Homo sapiens

<400> SEQUENCE: 166
tggatattgt agtagtacca gctgctatgc c 31

<210> SEQ ID NO 167
<211> LENGTH: 5
<212> TYPE: PRT
<213> ORGANISM: Homo sapiens

<400> SEQUENCE: 167

Tyr Gln Leu Leu Cys
1 5

<210> SEQ ID NO 168
<211> LENGTH: 10
<212> TYPE: PRT
<213> ORGANISM: Homo sapiens

<400> SEQUENCE: 168

Gly Tyr Cys Ser Ser Thr Ser Cys Tyr Ala
1 5 10

<210> SEQ ID NO 169
<211> LENGTH: 9
<212> TYPE: PRT
<213> ORGANISM: Homo sapiens

<400> SEQUENCE: 169

Asp Ile Val Val Val Pro Ala Ala Met 1 5

<210> SEQ ID NO 170
<211> LENGTH: 31
<212> TYPE: DNA
<213> ORGANISM: Homo sapiens

<400> SEQUENCE: 170
aggatattgt actaatggtg tatgctatac c 31

<210> SEQ ID NO 171
<211> LENGTH: 31
<212> TYPE: DNA
<213> ORGANISM: Homo sapiens

<400> SEQUENCE: 171
aagatattgt actggtggtg tatgctatac c 31

<210> SEQ ID NO 172
<211> LENGTH: 10
<212> TYPE: PRT
<213> ORGANISM: Homo sapiens

<400> SEQUENCE: 172

Arg Ile Leu Tyr Trp Trp Cys Met Leu Tyr
1 5 10

<210> SEQ ID NO 173
<211> LENGTH: 10
<212> TYPE: PRT
<213> ORGANISM: Homo sapiens

<400> SEQUENCE: 173

Gly Tyr Cys Thr Gly Gly Val Cys Tyr Thr
1 5 10

<210> SEQ ID NO 174
<211> LENGTH: 9
<212> TYPE: PRT
<213> ORGANISM: Homo sapiens

<400> SEQUENCE: 174

Asp Ile Val Leu Val Val Tyr Ala Ile
1 5

<210> SEQ ID NO 175
<211> LENGTH: 31
<212> TYPE: DNA
<213> ORGANISM: Homo sapiens

<400> SEQUENCE: 175
aggatattgt agtggtggta gctgctactc c 31

<210> SEQ ID NO 176
<211> LENGTH: 28
<212> TYPE: DNA
<213> ORGANISM: Homo sapiens

<400> SEQUENCE: 176
agcatattgt ggtggtgatt gctattcc 28

<210> SEQ ID NO 177
<211> LENGTH: 8
<212> TYPE: PRT

<213> ORGANISM: Homo sapiens

<400> SEQUENCE: 177

His Ile Val Val Val Ile Ala Ile
1 5

<210> SEQ ID NO 178
<211> LENGTH: 28
<212> TYPE: DNA
<213> ORGANISM: Homo sapiens

<400> SEQUENCE: 178
agcatattgt ggtggtgact gctattcc 28

<210> SEQ ID NO 179
<211> LENGTH: 31
<212> TYPE: DNA
<213> ORGANISM: Homo sapiens

<400> SEQUENCE: 179
gtattacgat ttttggagtg gttattatac c 31

<210> SEQ ID NO 180
<211> LENGTH: 31
<212> TYPE: DNA
<213> ORGANISM: Homo sapiens

<400> SEQUENCE: 180
gtattagcat ttttggagtg gttattatac c 31

<210> SEQ ID NO 181
<211> LENGTH: 10
<212> TYPE: PRT
<213> ORGANISM: Unknown
<220> FEATURE:
<223> OTHER INFORMATION: Mammal

<400> SEQUENCE: 181

Val Leu Ala Phe Leu Glu Trp Leu Leu Tyr
1 5 10

<210> SEQ ID NO 182
<211> LENGTH: 8
<212> TYPE: PRT
<213> ORGANISM: Homo sapiens

<400> SEQUENCE: 182

His Phe Trp Ser Gly Tyr Tyr Thr
1 5

<210> SEQ ID NO 183
<211> LENGTH: 9
<212> TYPE: PRT
<213> ORGANISM: Homo sapiens

<400> SEQUENCE: 183

Ile Ser Ile Phe Gly Val Val Ile Ile
1 5

<210> SEQ ID NO 184
<211> LENGTH: 31
<212> TYPE: DNA
<213> ORGANISM: Homo sapiens

<400> SEQUENCE: 184
gtattacgat attttgactg gttattataa c 31

<210> SEQ ID NO 185
<211> LENGTH: 31
<212> TYPE: DNA
<213> ORGANISM: Homo sapiens

<400> SEQUENCE: 185
gtattactat ggttcgggga gttattataa c 31

<210> SEQ ID NO 186
<211> LENGTH: 30
<212> TYPE: DNA
<213> ORGANISM: Homo sapiens

<400> SEQUENCE: 186
gtattactat gttcggggag ttattataac 30

<210> SEQ ID NO 187
<211> LENGTH: 10
<212> TYPE: PRT
<213> ORGANISM: Homo sapiens

<400> SEQUENCE: 187

Val Leu Leu Cys Ser Gly Ser Tyr Tyr Asn
1 5 10

<210> SEQ ID NO 188
<211> LENGTH: 9
<212> TYPE: PRT
<213> ORGANISM: Homo sapiens

<400> SEQUENCE: 188

Tyr Tyr Tyr Val Arg Gly Val Ile Ile
1 5

<210> SEQ ID NO 189
<211> LENGTH: 8
<212> TYPE: PRT
<213> ORGANISM: Homo sapiens

<400> SEQUENCE: 189

Ile Thr Met Phe Gly Arg Leu Leu
1 5

<210> SEQ ID NO 190
<211> LENGTH: 37
<212> TYPE: DNA
<213> ORGANISM: Homo sapiens

<400> SEQUENCE: 190
gtattatgat tacgtttggg ggagttatgc ttatacc 37

<210> SEQ ID NO 191
<211> LENGTH: 9
<212> TYPE: PRT
<213> ORGANISM: Homo sapiens

<400> SEQUENCE: 191

Leu Arg Leu Gly Glu Leu Cys Leu Tyr
1 5

<210> SEQ ID NO 192

<211> LENGTH: 12
<212> TYPE: PRT
<213> ORGANISM: Homo sapiens

<400> SEQUENCE: 192

Tyr Tyr Asp Tyr Val Trp Gly Ser Tyr Ala Tyr Thr
1 5 10

<210> SEQ ID NO 193
<211> LENGTH: 11
<212> TYPE: PRT
<213> ORGANISM: Homo sapiens

<400> SEQUENCE: 193

Ile Met Ile Thr Phe Gly Gly Val Met Leu Ile
1 5 10

<210> SEQ ID NO 194
<211> LENGTH: 31
<212> TYPE: DNA
<213> ORGANISM: Homo sapiens

<400> SEQUENCE: 194
gtattactat gatagtagtg gttattacta c 31

<210> SEQ ID NO 195
<211> LENGTH: 16
<212> TYPE: DNA
<213> ORGANISM: Homo sapiens

<400> SEQUENCE: 195
tgactacagt aactac 16

<210> SEQ ID NO 196
<211> LENGTH: 16
<212> TYPE: DNA
<213> ORGANISM: Homo sapiens

<400> SEQUENCE: 196
tgactacggt gactac 16

<210> SEQ ID NO 197
<211> LENGTH: 19
<212> TYPE: DNA
<213> ORGANISM: Homo sapiens

<400> SEQUENCE: 197
tgactacggt ggtaactcc 19

<210> SEQ ID NO 198
<211> LENGTH: 20
<212> TYPE: DNA
<213> ORGANISM: Homo sapiens

<400> SEQUENCE: 198
gtggatacag ctatggttac 20

<210> SEQ ID NO 199
<211> LENGTH: 23
<212> TYPE: DNA
<213> ORGANISM: Homo sapiens

<400> SEQUENCE: 199
gtggatatag tggctacgat tac 23

<210> SEQ ID NO 200
<211> LENGTH: 20
<212> TYPE: DNA
<213> ORGANISM: Homo sapiens

<400> SEQUENCE: 200
gtagagatgg ctacaattac 20

<210> SEQ ID NO 201
<211> LENGTH: 18
<212> TYPE: DNA
<213> ORGANISM: Homo sapiens

<400> SEQUENCE: 201
gagtatagca gctcgtcc 18

<210> SEQ ID NO 202
<211> LENGTH: 21
<212> TYPE: DNA
<213> ORGANISM: Homo sapiens

<400> SEQUENCE: 202
gggtatagca gcagctggta c 21

<210> SEQ ID NO 203
<211> LENGTH: 21
<212> TYPE: DNA
<213> ORGANISM: Homo sapiens

<400> SEQUENCE: 203
gggtatagca gtggctggta c 21

<210> SEQ ID NO 204
<211> LENGTH: 18
<212> TYPE: DNA
<213> ORGANISM: Homo sapiens

<400> SEQUENCE: 204
gggtatagca gcggctac 18

<210> SEQ ID NO 205
<211> LENGTH: 11
<212> TYPE: DNA
<213> ORGANISM: Homo sapiens

<400> SEQUENCE: 205
ctaactgggg a 11

<210> SEQ ID NO 206
<211> LENGTH: 17
<212> TYPE: DNA
<213> ORGANISM: Unknown
<220> FEATURE:
<223> OTHER INFORMATION: Mammal

<400> SEQUENCE: 206
gtcgttccag ttgtacc 17

<210> SEQ ID NO 207
<211> LENGTH: 5
<212> TYPE: PRT
<213> ORGANISM: Unknown
<220> FEATURE:

<223> OTHER INFORMATION: Mammal

<400> SEQUENCE: 207

Val Val Pro Val Val
1 5

<210> SEQ ID NO 208
<211> LENGTH: 5
<212> TYPE: PRT
<213> ORGANISM: Unknown
<220> FEATURE:
<223> OTHER INFORMATION: Mammal

<400> SEQUENCE: 208

Ser Phe Gln Leu Tyr
1 5

<210> SEQ ID NO 209
<211> LENGTH: 5
<212> TYPE: PRT
<213> ORGANISM: Unknown
<220> FEATURE:
<223> OTHER INFORMATION: Mammal

<400> SEQUENCE: 209

Arg Ser Ser Cys Thr
1 5

<210> SEQ ID NO 210
<211> LENGTH: 17
<212> TYPE: DNA
<213> ORGANISM: Unknown
<220> FEATURE:
<223> OTHER INFORMATION: Mammal

<400> SEQUENCE: 210
gtagttccag ttatacc 17

<210> SEQ ID NO 211
<211> LENGTH: 5
<212> TYPE: PRT
<213> ORGANISM: Unknown
<220> FEATURE:
<223> OTHER INFORMATION: Mammal

<400> SEQUENCE: 211

Val Val Pro Val Ile
1 5

<210> SEQ ID NO 212
<211> LENGTH: 4
<212> TYPE: PRT
<213> ORGANISM: Unknown
<220> FEATURE:
<223> OTHER INFORMATION: Mammal

<400> SEQUENCE: 212

Phe Gln Leu Tyr
1

<210> SEQ ID NO 213
<211> LENGTH: 5
<212> TYPE: PRT
<213> ORGANISM: Unknown
<220> FEATURE:
<223> OTHER INFORMATION: Mammal

<400> SEQUENCE: 213

Ser Ser Ser Tyr Thr
1 5

<210> SEQ ID NO 214
<211> LENGTH: 17
<212> TYPE: DNA
<213> ORGANISM: Unknown
<220> FEATURE:
<223> OTHER INFORMATION: Mammal

<400> SEQUENCE: 214
gtggttccgg ttatacc 17

<210> SEQ ID NO 215
<211> LENGTH: 5
<212> TYPE: PRT
<213> ORGANISM: Unknown
<220> FEATURE:
<223> OTHER INFORMATION: Mammal

<400> SEQUENCE: 215

Trp Phe Arg Leu Tyr
1 5

<210> SEQ ID NO 216
<211> LENGTH: 5
<212> TYPE: PRT
<213> ORGANISM: Unknown
<220> FEATURE:
<223> OTHER INFORMATION: Mammal

<400> SEQUENCE: 216

Gly Ser Gly Tyr Thr
1 5

<210> SEQ ID NO 217
<211> LENGTH: 17
<212> TYPE: DNA
<213> ORGANISM: Unknown
<220> FEATURE:
<223> OTHER INFORMATION: Mammal

<400> SEQUENCE: 217
gtcgttccag ttatacc 17

<210> SEQ ID NO 218
<211> LENGTH: 5
<212> TYPE: PRT
<213> ORGANISM: Unknown
<220> FEATURE:
<223> OTHER INFORMATION: Mammal

<400> SEQUENCE: 218

Arg Ser Ser Tyr Thr
1 5

<210> SEQ ID NO 219
<211> LENGTH: 20
<212> TYPE: DNA
<213> ORGANISM: Unknown
<220> FEATURE:
<223> OTHER INFORMATION: Mammal

<400> SEQUENCE: 219
gtagtagctc ccactatacc 20

<210> SEQ ID NO 220
<211> LENGTH: 6
<212> TYPE: PRT
<213> ORGANISM: Unknown
<220> FEATURE:
<223> OTHER INFORMATION: Mammal

<400> SEQUENCE: 220

Val Val Ala Pro Thr Ile
1 5

<210> SEQ ID NO 221
<211> LENGTH: 4
<212> TYPE: PRT
<213> ORGANISM: Unknown
<220> FEATURE:
<223> OTHER INFORMATION: Mammal

<400> SEQUENCE: 221

Leu Pro Leu Tyr
1

<210> SEQ ID NO 222
<211> LENGTH: 6
<212> TYPE: PRT
<213> ORGANISM: Unknown
<220> FEATURE:
<223> OTHER INFORMATION: Mammal

<400> SEQUENCE: 222

Ser Ser Ser His Tyr Thr
1 5

<210> SEQ ID NO 223
<211> LENGTH: 31
<212> TYPE: DNA
<213> ORGANISM: Unknown
<220> FEATURE:
<223> OTHER INFORMATION: Mammal

<400> SEQUENCE: 223
ggcatagcag ctggtactac tacaatatcc t 31

<210> SEQ ID NO 224
<211> LENGTH: 10
<212> TYPE: PRT
<213> ORGANISM: Unknown
<220> FEATURE:
<223> OTHER INFORMATION: Mammal

<400> SEQUENCE: 224

Gly Ile Ala Ala Gly Thr Thr Thr Ile Ser
1 5 10

<210> SEQ ID NO 225
<211> LENGTH: 8
<212> TYPE: PRT
<213> ORGANISM: Unknown
<220> FEATURE:
<223> OTHER INFORMATION: Mammal

<400> SEQUENCE: 225

Gln Leu Val Leu Leu Gln Tyr Pro
1 5

<210> SEQ ID NO 226
<211> LENGTH: 9
<212> TYPE: PRT
<213> ORGANISM: Unknown
<220> FEATURE:
<223> OTHER INFORMATION: Mammal

<400> SEQUENCE: 226

His Ser Ser Trp Tyr Tyr Tyr Asn Ile
1 5

<210> SEQ ID NO 227
<211> LENGTH: 31
<212> TYPE: DNA
<213> ORGANISM: Unknown
<220> FEATURE:
<223> OTHER INFORMATION: Mammal

<400> SEQUENCE: 227
ggtatagcag ctggtactac tacaatatcc t 31

<210> SEQ ID NO 228
<211> LENGTH: 31
<212> TYPE: DNA
<213> ORGANISM: Unknown
<220> FEATURE:
<223> OTHER INFORMATION: Mammal

<400> SEQUENCE: 228
ggcatagcag ctggtactac tacaatatcc a 31

<210> SEQ ID NO 229
<211> LENGTH: 31
<212> TYPE: DNA
<213> ORGANISM: Unknown
<220> FEATURE:
<223> OTHER INFORMATION: Mammal

<400> SEQUENCE: 229
ggtatagcat acaccattag tacaatatcc t 31

<210> SEQ ID NO 230
<211> LENGTH: 10
<212> TYPE: PRT
<213> ORGANISM: Unknown
<220> FEATURE:
<223> OTHER INFORMATION: Mammal

<400> SEQUENCE: 230

Gly Ile Ala Tyr Thr Ile Ser Thr Ile Ser
1 5 10

<210> SEQ ID NO 231
<211> LENGTH: 8
<212> TYPE: PRT
<213> ORGANISM: Unknown
<220> FEATURE:
<223> OTHER INFORMATION: Mammal

<400> SEQUENCE: 231

His Thr Pro Leu Val Gln Tyr Pro
1 5

<210> SEQ ID NO 232
<211> LENGTH: 5
<212> TYPE: PRT
<213> ORGANISM: Unknown

<220> FEATURE:
<223> OTHER INFORMATION: Mammal

<400> SEQUENCE: 232

Tyr Ser Ile His His
1 5

<210> SEQ ID NO 233
<211> LENGTH: 31
<212> TYPE: DNA
<213> ORGANISM: Unknown
<220> FEATURE:
<223> OTHER INFORMATION: Mammal

<400> SEQUENCE: 233
ggtatagcat acaccaccag tacaatatct t 31

<210> SEQ ID NO 234
<211> LENGTH: 10
<212> TYPE: PRT
<213> ORGANISM: Unknown
<220> FEATURE:
<223> OTHER INFORMATION: Mammal

<400> SEQUENCE: 234

Gly Ile Ala Tyr Thr Thr Ser Thr Ile Ser
1 5 10

<210> SEQ ID NO 235
<211> LENGTH: 8
<212> TYPE: PRT
<213> ORGANISM: Unknown
<220> FEATURE:
<223> OTHER INFORMATION: Mammal

<400> SEQUENCE: 235

His Thr Pro Pro Val Gln Tyr Leu
1 5

<210> SEQ ID NO 236
<211> LENGTH: 9
<212> TYPE: PRT
<213> ORGANISM: Unknown
<220> FEATURE:
<223> OTHER INFORMATION: Mammal

<400> SEQUENCE: 236

Tyr Ser Ile His His Gln Tyr Asn Ile
1 5

<210> SEQ ID NO 237
<211> LENGTH: 31
<212> TYPE: DNA
<213> ORGANISM: Unknown
<220> FEATURE:
<223> OTHER INFORMATION: Mammal

<400> SEQUENCE: 237
ggagtagcag ctaccaccac tacaatatcc t 31

<210> SEQ ID NO 238
<211> LENGTH: 10
<212> TYPE: PRT
<213> ORGANISM: Unknown
<220> FEATURE:
<223> OTHER INFORMATION: Mammal

<400> SEQUENCE: 238

Gly Val Ala Ala Thr Thr Thr Thr Ile Ser
1 5 10

<210> SEQ ID NO 239
<211> LENGTH: 8
<212> TYPE: PRT
<213> ORGANISM: Unknown
<220> FEATURE:
<223> OTHER INFORMATION: Mammal

<400> SEQUENCE: 239

Gln Leu Pro Pro Leu Gln Tyr Pro
1 5

<210> SEQ ID NO 240
<211> LENGTH: 9
<212> TYPE: PRT
<213> ORGANISM: Unknown
<220> FEATURE:
<223> OTHER INFORMATION: Mammal

<400> SEQUENCE: 240

Ser Ser Ser Tyr His His Tyr Asn Ile
1 5

<210> SEQ ID NO 241
<211> LENGTH: 28
<212> TYPE: DNA
<213> ORGANISM: Unknown
<220> FEATURE:
<223> OTHER INFORMATION: Mammal

<400> SEQUENCE: 241
ggaatagcaa tcaccaccac aatatgct 28

<210> SEQ ID NO 242
<211> LENGTH: 9
<212> TYPE: PRT
<213> ORGANISM: Unknown
<220> FEATURE:
<223> OTHER INFORMATION: Mammal

<400> SEQUENCE: 242

Gly Ile Ala Ile Thr Thr Thr Ile Cys
1 5

<210> SEQ ID NO 243
<211> LENGTH: 7
<212> TYPE: PRT
<213> ORGANISM: Unknown
<220> FEATURE:
<223> OTHER INFORMATION: Mammal

<400> SEQUENCE: 243

Gln Ser Pro Pro Gln Tyr Ala
1 5

<210> SEQ ID NO 244
<211> LENGTH: 8
<212> TYPE: PRT
<213> ORGANISM: Unknown
<220> FEATURE:
<223> OTHER INFORMATION: Mammal

<400> SEQUENCE: 244

Asn Ser Asn His His His Asn Met
1               5

<210> SEQ ID NO 245
<211> LENGTH: 28
<212> TYPE: DNA
<213> ORGANISM: Unknown
<220> FEATURE:
<223> OTHER INFORMATION: Mammal

<400> SEQUENCE: 245
ggaatagcag tcaccaccac aatatgct 28

<210> SEQ ID NO 246
<211> LENGTH: 9
<212> TYPE: PRT
<213> ORGANISM: Unknown
<220> FEATURE:
<223> OTHER INFORMATION: Mammal

<400> SEQUENCE: 246

Gly Ile Ala Val Thr Thr Thr Ile Cys
1               5

<210> SEQ ID NO 247
<211> LENGTH: 7
<212> TYPE: PRT
<213> ORGANISM: Unknown
<220> FEATURE:
<223> OTHER INFORMATION: Mammal

<400> SEQUENCE: 247

Gln Ser Pro Pro Gln Tyr Ala
1               5

<210> SEQ ID NO 248
<211> LENGTH: 8
<212> TYPE: PRT
<213> ORGANISM: Unknown
<220> FEATURE:
<223> OTHER INFORMATION: Mammal

<400> SEQUENCE: 248

Asn Ser Ser His His His Asn Met
1               5

<210> SEQ ID NO 249
<211> LENGTH: 31
<212> TYPE: DNA
<213> ORGANISM: Unknown
<220> FEATURE:
<223> OTHER INFORMATION: Mammal

<400> SEQUENCE: 249
ggtataataa ccactccaaa aatcgtaata c 31

<210> SEQ ID NO 250
<211> LENGTH: 10
<212> TYPE: PRT
<213> ORGANISM: Unknown
<220> FEATURE:
<223> OTHER INFORMATION: Mammal

<400> SEQUENCE: 250

Gly Ile Ile Thr Thr Pro Lys Ile Val Ile
1               5                   10

<210> SEQ ID NO 251
<211> LENGTH: 5
<212> TYPE: PRT
<213> ORGANISM: Unknown
<220> FEATURE:
<223> OTHER INFORMATION: Mammal

<400> SEQUENCE: 251

Pro Leu Gln Lys Ser
1 5

<210> SEQ ID NO 252
<211> LENGTH: 9
<212> TYPE: PRT
<213> ORGANISM: Unknown
<220> FEATURE:
<223> OTHER INFORMATION: Mammal

<400> SEQUENCE: 252

Tyr Asn Asn His Ser Lys Asn Arg Asn
1 5

<210> SEQ ID NO 253
<211> LENGTH: 31
<212> TYPE: DNA
<213> ORGANISM: Unknown
<220> FEATURE:
<223> OTHER INFORMATION: Mammal

<400> SEQUENCE: 253
ggtataataa ccactccaaa aatgctaata c 31

<210> SEQ ID NO 254
<211> LENGTH: 10
<212> TYPE: PRT
<213> ORGANISM: Unknown
<220> FEATURE:
<223> OTHER INFORMATION: Mammal

<400> SEQUENCE: 254

Gly Ile Ile Thr Thr Pro Lys Met Leu Ile
1 5 10

<210> SEQ ID NO 255
<211> LENGTH: 5
<212> TYPE: PRT
<213> ORGANISM: Unknown
<220> FEATURE:
<223> OTHER INFORMATION: Mammal

<400> SEQUENCE: 255

Pro Leu Gln Lys Cys
1 5

<210> SEQ ID NO 256
<211> LENGTH: 9
<212> TYPE: PRT
<213> ORGANISM: Unknown
<220> FEATURE:
<223> OTHER INFORMATION: Mammal

<400> SEQUENCE: 256

Tyr Asn Asn His Ser Lys Asn Ala Asn
1 5

<210> SEQ ID NO 257

<211> LENGTH: 31
<212> TYPE: DNA
<213> ORGANISM: Unknown
<220> FEATURE:
<223> OTHER INFORMATION: Mammal

<400> SEQUENCE: 257
gttataataa ccagtcaaaa tatcgtaata c 31

<210> SEQ ID NO 258
<211> LENGTH: 10
<212> TYPE: PRT
<213> ORGANISM: Unknown
<220> FEATURE:
<223> OTHER INFORMATION: Mammal

<400> SEQUENCE: 258

Val Ile Ile Thr Ser Gln Asn Ile Val Ile
1 5 10

<210> SEQ ID NO 259
<211> LENGTH: 5
<212> TYPE: PRT
<213> ORGANISM: Unknown
<220> FEATURE:
<223> OTHER INFORMATION: Mammal

<400> SEQUENCE: 259

Pro Val Lys Ile Ser
1 5

<210> SEQ ID NO 260
<211> LENGTH: 9
<212> TYPE: PRT
<213> ORGANISM: Unknown
<220> FEATURE:
<223> OTHER INFORMATION: Mammal

<400> SEQUENCE: 260

Tyr Asn Asn Gln Ser Lys Tyr Arg Asn
1 5

<210> SEQ ID NO 261
<211> LENGTH: 31
<212> TYPE: DNA
<213> ORGANISM: Unknown
<220> FEATURE:
<223> OTHER INFORMATION: Mammal

<400> SEQUENCE: 261
gttataataa ctccccgaac catagtaata c 31

<210> SEQ ID NO 262
<211> LENGTH: 10
<212> TYPE: PRT
<213> ORGANISM: Unknown
<220> FEATURE:
<223> OTHER INFORMATION: Mammal

<400> SEQUENCE: 262

Val Ile Ile Thr Pro Arg Thr Ile Val Ile
1 5 10

<210> SEQ ID NO 263
<211> LENGTH: 4
<212> TYPE: PRT
<213> ORGANISM: Unknown

<220> FEATURE:
<223> OTHER INFORMATION: Mammal

<400> SEQUENCE: 263

Leu Pro Glu Pro
1

<210> SEQ ID NO 264
<211> LENGTH: 9
<212> TYPE: PRT
<213> ORGANISM: Unknown
<220> FEATURE:
<223> OTHER INFORMATION: Mammal

<400> SEQUENCE: 264

Tyr Asn Asn Ser Pro Asn His Ser Asn
1 5

<210> SEQ ID NO 265
<211> LENGTH: 30
<212> TYPE: DNA
<213> ORGANISM: Unknown
<220> FEATURE:
<223> OTHER INFORMATION: Mammal

<400> SEQUENCE: 265
gttataataa ctccccgaac atagtaatac 30

<210> SEQ ID NO 266
<211> LENGTH: 7
<212> TYPE: PRT
<213> ORGANISM: Unknown
<220> FEATURE:
<223> OTHER INFORMATION: Mammal

<400> SEQUENCE: 266

Val Ile Ile Thr Pro Arg Thr
1 5

<210> SEQ ID NO 267
<211> LENGTH: 6
<212> TYPE: PRT
<213> ORGANISM: Unknown
<220> FEATURE:
<223> OTHER INFORMATION: Mammal

<400> SEQUENCE: 267

Leu Pro Glu His Ser Asn
1 5

<210> SEQ ID NO 268
<211> LENGTH: 9
<212> TYPE: PRT
<213> ORGANISM: Unknown
<220> FEATURE:
<223> OTHER INFORMATION: Mammal

<400> SEQUENCE: 268

Tyr Asn Asn Ser Pro Asn Ile Val Ile
1 5

<210> SEQ ID NO 269
<211> LENGTH: 37
<212> TYPE: DNA
<213> ORGANISM: Unknown
<220> FEATURE:
<223> OTHER INFORMATION: Mammal

<400> SEQUENCE: 269
ggtataagca taactccccc aaacgtaatc ataatac 37

<210> SEQ ID NO 270
<211> LENGTH: 12
<212> TYPE: PRT
<213> ORGANISM: Unknown
<220> FEATURE:
<223> OTHER INFORMATION: Mammal

<400> SEQUENCE: 270

Gly Ile Ser Ile Thr Pro Pro Asn Val Ile Ile Ile
1 5 10

<210> SEQ ID NO 271
<211> LENGTH: 4
<212> TYPE: PRT
<213> ORGANISM: Unknown
<220> FEATURE:
<223> OTHER INFORMATION: Mammal

<400> SEQUENCE: 271

Leu Pro Gln Thr
1

<210> SEQ ID NO 272
<211> LENGTH: 11
<212> TYPE: PRT
<213> ORGANISM: Unknown
<220> FEATURE:
<223> OTHER INFORMATION: Mammal

<400> SEQUENCE: 272

Tyr Lys His Asn Ser Pro Lys Arg Asn His Asn
1 5 10

<210> SEQ ID NO 273
<211> LENGTH: 31
<212> TYPE: DNA
<213> ORGANISM: Unknown
<220> FEATURE:
<223> OTHER INFORMATION: Mammal

<400> SEQUENCE: 273
gtagtaataa ccactactat catagtaata c 31

<210> SEQ ID NO 274
<211> LENGTH: 10
<212> TYPE: PRT
<213> ORGANISM: Unknown
<220> FEATURE:
<223> OTHER INFORMATION: Mammal

<400> SEQUENCE: 274

Val Val Ile Thr Thr Thr Ile Ile Val Ile
1 5 10

<210> SEQ ID NO 275
<211> LENGTH: 4
<212> TYPE: PRT
<213> ORGANISM: Unknown
<220> FEATURE:
<223> OTHER INFORMATION: Mammal

<400> SEQUENCE: 275

Pro Leu Leu Ser
1

<210> SEQ ID NO 276
<211> LENGTH: 9
<212> TYPE: PRT
<213> ORGANISM: Unknown
<220> FEATURE:
<223> OTHER INFORMATION: Mammal

<400> SEQUENCE: 276

Ser Asn Asn His Tyr Tyr His Ser Asn
1 5

<210> SEQ ID NO 277
<211> LENGTH: 16
<212> TYPE: DNA
<213> ORGANISM: Unknown
<220> FEATURE:
<223> OTHER INFORMATION: Mammal

<400> SEQUENCE: 277
gtagttactg tagtca 16

<210> SEQ ID NO 278
<211> LENGTH: 5
<212> TYPE: PRT
<213> ORGANISM: Unknown
<220> FEATURE:
<223> OTHER INFORMATION: Mammal

<400> SEQUENCE: 278

Val Val Thr Val Val
1 5

<210> SEQ ID NO 279
<211> LENGTH: 4
<212> TYPE: PRT
<213> ORGANISM: Unknown
<220> FEATURE:
<223> OTHER INFORMATION: Mammal

<400> SEQUENCE: 279

Ser Tyr Cys Ser
1

<210> SEQ ID NO 280
<211> LENGTH: 16
<212> TYPE: DNA
<213> ORGANISM: Unknown
<220> FEATURE:
<223> OTHER INFORMATION: Mammal

<400> SEQUENCE: 280
gtagtcaccg tagtca 16

<210> SEQ ID NO 281
<211> LENGTH: 4
<212> TYPE: PRT
<213> ORGANISM: Unknown
<220> FEATURE:
<223> OTHER INFORMATION: Mammal

<400> SEQUENCE: 281

Ser His Arg Ser
1

<210> SEQ ID NO 282
<211> LENGTH: 19
<212> TYPE: DNA
<213> ORGANISM: Unknown
<220> FEATURE:
<223> OTHER INFORMATION: Mammal

<400> SEQUENCE: 282
ggagttacca ccgtagtca 19

<210> SEQ ID NO 283
<211> LENGTH: 6
<212> TYPE: PRT
<213> ORGANISM: Unknown
<220> FEATURE:
<223> OTHER INFORMATION: Mammal

<400> SEQUENCE: 283

Gly Val Thr Thr Val Val
1 5

<210> SEQ ID NO 284
<211> LENGTH: 4
<212> TYPE: PRT
<213> ORGANISM: Unknown
<220> FEATURE:
<223> OTHER INFORMATION: Mammal

<400> SEQUENCE: 284

Glu Leu Pro Pro
1

<210> SEQ ID NO 285
<211> LENGTH: 5
<212> TYPE: PRT
<213> ORGANISM: Unknown
<220> FEATURE:
<223> OTHER INFORMATION: Mammal

<400> SEQUENCE: 285

Ser Tyr His Arg Ser
1 5

<210> SEQ ID NO 286
<211> LENGTH: 20
<212> TYPE: DNA
<213> ORGANISM: Unknown
<220> FEATURE:
<223> OTHER INFORMATION: Mammal

<400> SEQUENCE: 286
gtaaccatag ctgtatccac 20

<210> SEQ ID NO 287
<211> LENGTH: 6
<212> TYPE: PRT
<213> ORGANISM: Unknown
<220> FEATURE:
<223> OTHER INFORMATION: Mammal

<400> SEQUENCE: 287

Val Thr Ile Ala Val Ser
1 5

<210> SEQ ID NO 288
<211> LENGTH: 6

<212> TYPE: PRT
<213> ORGANISM: Unknown
<220> FEATURE:
<223> OTHER INFORMATION: Mammal

<400> SEQUENCE: 288

Asn His Ser Cys Ile His
1 5

<210> SEQ ID NO 289
<211> LENGTH: 23
<212> TYPE: DNA
<213> ORGANISM: Unknown
<220> FEATURE:
<223> OTHER INFORMATION: Mammal

<400> SEQUENCE: 289
gtaatcgtag ccactatatc cac 23

<210> SEQ ID NO 290
<211> LENGTH: 7
<212> TYPE: PRT
<213> ORGANISM: Unknown
<220> FEATURE:
<223> OTHER INFORMATION: Mammal

<400> SEQUENCE: 290

Val Ile Val Ala Thr Ile Ser
1 5

<210> SEQ ID NO 291
<211> LENGTH: 4
<212> TYPE: PRT
<213> ORGANISM: Unknown
<220> FEATURE:
<223> OTHER INFORMATION: Mammal

<400> SEQUENCE: 291

Pro Leu Tyr Pro
1

<210> SEQ ID NO 292
<211> LENGTH: 7
<212> TYPE: PRT
<213> ORGANISM: Unknown
<220> FEATURE:
<223> OTHER INFORMATION: Mammal

<400> SEQUENCE: 292

Asn Arg Ser His Tyr Ile His
1 5

<210> SEQ ID NO 293
<211> LENGTH: 20
<212> TYPE: DNA
<213> ORGANISM: Unknown
<220> FEATURE:
<223> OTHER INFORMATION: Mammal

<400> SEQUENCE: 293
gtaattgtag ccatctctac 20

<210> SEQ ID NO 294
<211> LENGTH: 6
<212> TYPE: PRT
<213> ORGANISM: Unknown
<220> FEATURE:

<223> OTHER INFORMATION: Mammal

<400> SEQUENCE: 294

Val Ile Val Ala Ile Ser
1 5

<210> SEQ ID NO 295
<211> LENGTH: 6
<212> TYPE: PRT
<213> ORGANISM: Unknown
<220> FEATURE:
<223> OTHER INFORMATION: Mammal

<400> SEQUENCE: 295

Asn Cys Ser His Leu Tyr
1 5

<210> SEQ ID NO 296
<211> LENGTH: 18
<212> TYPE: DNA
<213> ORGANISM: Unknown
<220> FEATURE:
<223> OTHER INFORMATION: Mammal

<400> SEQUENCE: 296
ggacgagctg ctatactc 18

<210> SEQ ID NO 297
<211> LENGTH: 6
<212> TYPE: PRT
<213> ORGANISM: Unknown
<220> FEATURE:
<223> OTHER INFORMATION: Mammal

<400> SEQUENCE: 297

Gly Arg Ala Ala Ile Leu
1 5

<210> SEQ ID NO 298
<211> LENGTH: 5
<212> TYPE: PRT
<213> ORGANISM: Unknown
<220> FEATURE:
<223> OTHER INFORMATION: Mammal

<400> SEQUENCE: 298

Asp Glu Leu Leu Tyr
1 5

<210> SEQ ID NO 299
<211> LENGTH: 5
<212> TYPE: PRT
<213> ORGANISM: Unknown
<220> FEATURE:
<223> OTHER INFORMATION: Mammal

<400> SEQUENCE: 299

Thr Ser Cys Tyr Thr
1 5

<210> SEQ ID NO 300
<211> LENGTH: 21
<212> TYPE: DNA
<213> ORGANISM: Unknown
<220> FEATURE:
<223> OTHER INFORMATION: Mammal

<400> SEQUENCE: 300
gtaccagctg ctgctatacc c 21

<210> SEQ ID NO 301
<211> LENGTH: 7
<212> TYPE: PRT
<213> ORGANISM: Unknown
<220> FEATURE:
<223> OTHER INFORMATION: Mammal

<400> SEQUENCE: 301

Val Pro Ala Ala Ala Ile Pro
1 5

<210> SEQ ID NO 302
<211> LENGTH: 6
<212> TYPE: PRT
<213> ORGANISM: Unknown
<220> FEATURE:
<223> OTHER INFORMATION: Mammal

<400> SEQUENCE: 302

Tyr Gln Leu Leu Leu Tyr
1 5

<210> SEQ ID NO 303
<211> LENGTH: 6
<212> TYPE: PRT
<213> ORGANISM: Unknown
<220> FEATURE:
<223> OTHER INFORMATION: Mammal

<400> SEQUENCE: 303

Thr Ser Cys Cys Tyr Thr
1 5

<210> SEQ ID NO 304
<211> LENGTH: 21
<212> TYPE: DNA
<213> ORGANISM: Unknown
<220> FEATURE:
<223> OTHER INFORMATION: Mammal

<400> SEQUENCE: 304
gtaccagcca ctgctatacc c 21

<210> SEQ ID NO 305
<211> LENGTH: 7
<212> TYPE: PRT
<213> ORGANISM: Unknown
<220> FEATURE:
<223> OTHER INFORMATION: Mammal'

<400> SEQUENCE: 305

Val Pro Ala Thr Ala Ile Pro
1 5

<210> SEQ ID NO 306
<211> LENGTH: 6
<212> TYPE: PRT
<213> ORGANISM: Unknown
<220> FEATURE:
<223> OTHER INFORMATION: Mammal

<400> SEQUENCE: 306

Tyr Gln Pro Leu Leu Tyr 1 5

<210> SEQ ID NO 307
<211> LENGTH: 6
<212> TYPE: PRT
<213> ORGANISM: Unknown
<220> FEATURE:
<223> OTHER INFORMATION: Mammal

<400> SEQUENCE: 307

Thr Ser His Cys Tyr Thr
1 5

<210> SEQ ID NO 308
<211> LENGTH: 18
<212> TYPE: DNA
<213> ORGANISM: Unknown
<220> FEATURE:
<223> OTHER INFORMATION: Mammal

<400> SEQUENCE: 308
gtagccgctg ctataccc 18

<210> SEQ ID NO 309
<211> LENGTH: 6
<212> TYPE: PRT
<213> ORGANISM: Unknown
<220> FEATURE:
<223> OTHER INFORMATION: Mammal

<400> SEQUENCE: 309

Val Ala Ala Ala Ile Pro
1 5

<210> SEQ ID NO 310
<211> LENGTH: 4
<212> TYPE: PRT
<213> ORGANISM: Unknown
<220> FEATURE:
<223> OTHER INFORMATION: Mammal

<400> SEQUENCE: 310

Pro Leu Leu Tyr
1

<210> SEQ ID NO 311
<211> LENGTH: 5
<212> TYPE: PRT
<213> ORGANISM: Unknown
<220> FEATURE:
<223> OTHER INFORMATION: Mammal

<400> SEQUENCE: 311

Ser Arg Cys Tyr Thr
1 5

<210> SEQ ID NO 312
<211> LENGTH: 366
<212> TYPE: DNA
<213> ORGANISM: Homo sapiens

<400> SEQUENCE: 312
caggtgcagc tacagcagtg gggcgcagga ctgttgaagc cttcggatac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180

```
ccgtccctca agagtcgagt caccatatca gtagacacgt ccaagaacca gttctccctg    240

aagctgagct ctgtgaccgc cgcggacacg gctgtgtatt actgtgcggg gcatagccat    300

ggctggtact actactacta cggtatggac gtctggggcc aagggaccac ggtcaccgtc    360

tcctca                                                               366
```

<210> SEQ ID NO 313
<211> LENGTH: 122
<212> TYPE: PRT
<213> ORGANISM: Homo sapiens

<400> SEQUENCE: 313

```
Gln Val Gln Leu Gln Gln Trp Gly Ala Gly Leu Leu Lys Pro Ser Asp
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly His Ser His Gly Trp Tyr Tyr Tyr Tyr Tyr Gly Met Asp Val Trp
            100                 105                 110

Gly Gln Gly Thr Thr Val Thr Val Ser Ser
        115                 120
```

<210> SEQ ID NO 314
<211> LENGTH: 96
<212> TYPE: PRT
<213> ORGANISM: Homo sapiens

<400> SEQUENCE: 314

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

<210> SEQ ID NO 315
<211> LENGTH: 355
<212> TYPE: DNA
<213> ORGANISM: Homo sapiens

<400> SEQUENCE: 315

```
caggtgcagc tgcaggagtc gggcccagga ctggtgaagc cttcacagac cctgtccctc     60

acctgcactg tctctggtgg ctccatcagc agtggtggtt actactggag ctggatccgc    120
```

cagcacccag ggaagggcct ggagtggatt gggtacatct attacagtgg gagcacctac 180
tacaacccgt ccctcaagag tcgagttacc atatcagtag acacgtctaa gaaccagttc 240
tccctgaagc tgagctctgt gactgccgcg gacacggccg tgtattactg tgcgaggggg 300
gaccacggtc actacgacta ctggggccag ggaaccctgg tcaccgtctc ctcag 355

<210> SEQ ID NO 316
<211> LENGTH: 118
<212> TYPE: PRT
<213> ORGANISM: Homo sapiens

<400> SEQUENCE: 316

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

Trp Ile Gly Tyr Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Gly Asp His Gly His Tyr Asp Tyr Trp Gly Gln Gly Thr
100 105 110

Leu Val Thr Val Ser Ser
115

<210> SEQ ID NO 317
<211> LENGTH: 98
<212> TYPE: PRT
<213> ORGANISM: Homo sapiens

<400> SEQUENCE: 317

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

Trp Ile Gly Tyr Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala

<210> SEQ ID NO 318
<211> LENGTH: 370
<212> TYPE: DNA
<213> ORGANISM: Homo sapiens

<400> SEQUENCE: 318
cagctgcagc tgcaggagtc gggcccagga ctggtgaagc cttcggagac cctgtccctc 60
acctgcactg tctctggtgg ctccatcagc agtagtagtt actactgggg ctggatccgc 120
cagcccccag ggaaggggct ggagtggatt gggagtatct attatagtgg gagcacctac 180
tacaacccgt ccctcaagag tcgagtcacc atatccgtag acacgtccaa gaaccagttc 240
tccctgaagc tgagctctgt gaccgccgca gacacggctg tgtattactg tgcgagacat 300
gaagggcata gccaccttaa ctggttcgac ccctggggcc agggggggaac cctggtcacc 360 gtctcctcag 370

<210> SEQ ID NO 319
<211> LENGTH: 123
<212> TYPE: PRT
<213> ORGANISM: Homo sapiens

<400> SEQUENCE: 319

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His Glu Gly His Ser His Leu Asn Trp Phe Asp Pro Trp
100 105 110

Gly Gln Gly Gly Thr Leu Val Thr Val Ser Ser
115 120

<210> SEQ ID NO 320
<211> LENGTH: 99
<212> TYPE: PRT
<213> ORGANISM: Homo sapiens

<400> SEQUENCE: 320

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg

<210> SEQ ID NO 321
<211> LENGTH: 22
<212> TYPE: DNA
<213> ORGANISM: Unknown
<220> FEATURE:
<223> OTHER INFORMATION: Mammal

<400> SEQUENCE: 321
tcttatcaga cagggggctc tc 22

<210> SEQ ID NO 322
<211> LENGTH: 22
<212> TYPE: DNA
<213> ORGANISM: Unknown
<220> FEATURE:
<223> OTHER INFORMATION: Mammal

<400> SEQUENCE: 322
ggaagacatt tgggaaggac tg 22

<210> SEQ ID NO 323
<211> LENGTH: 4
<212> TYPE: PRT
<213> ORGANISM: Unknown
<220> FEATURE:
<223> OTHER INFORMATION: Mammal
<220> FEATURE:
<221> NAME/KEY: MISC_FEATURE
<222> LOCATION: (3)..(3)
<223> OTHER INFORMATION: wherin the “Xaa” represents any amino acid

<400> SEQUENCE: 323

Phe Gly Xaa Gly
1

<210> SEQ ID NO 324
<211> LENGTH: 4
<212> TYPE: PRT
<213> ORGANISM: Unknown
<220> FEATURE:
<223> OTHER INFORMATION: Mammal
<220> FEATURE:
<221> NAME/KEY: MISC_FEATURE
<222> LOCATION: (3)..(3)
<223> OTHER INFORMATION: wherein the “Xaa” represents any amino acid

<400> SEQUENCE: 324

Trp Gly Xaa Gly
1

<210> SEQ ID NO 325
<211> LENGTH: 95
<212> TYPE: PRT
<213> ORGANISM: Artificial
<220> FEATURE:
<223> OTHER INFORMATION: Synthetic

<400> SEQUENCE: 325

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro
85 90 95

<210> SEQ ID NO 326
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 326

```
cag cag agc tac agc acc ccc                                  21
Gln Gln Ser Tyr Ser Thr Pro
1               5
```

<210> SEQ ID NO 327
<211> LENGTH: 7
<212> TYPE: PRT
<213> ORGANISM: Artificial
<220> FEATURE:
<223> OTHER INFORMATION: Synthetic Construct

<400> SEQUENCE: 327

```
Gln Gln Ser Tyr Ser Thr Pro
1               5
```

<210> SEQ ID NO 328
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 328

```
cac cat agc cac agc acc cac                                  21
His His Ser His Ser Thr His
1               5
```

<210> SEQ ID NO 329
<211> LENGTH: 7
<212> TYPE: PRT
<213> ORGANISM: Artificial
<220> FEATURE:
<223> OTHER INFORMATION: Synthetic Construct

<400> SEQUENCE: 329

```
His His Ser His Ser Thr His
1               5
```

<210> SEQ ID NO 330
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 330

```
cac cag agc tac agc acc ccc                                  21
His Gln Ser Tyr Ser Thr Pro
1               5
```

<210> SEQ ID NO 331
<211> LENGTH: 7

<212> TYPE: PRT
<213> ORGANISM: Artificial
<220> FEATURE:
<223> OTHER INFORMATION: Synthetic Construct

<400> SEQUENCE: 331

His Gln Ser Tyr Ser Thr Pro
1               5

<210> SEQ ID NO 332
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 332 cag cat agc tac agc acc ccc 21
Gln His Ser Tyr Ser Thr Pro
1               5

<210> SEQ ID NO 333
<211> LENGTH: 7
<212> TYPE: PRT
<213> ORGANISM: Artificial
<220> FEATURE:
<223> OTHER INFORMATION: Synthetic Construct

<400> SEQUENCE: 333

Gln His Ser Tyr Ser Thr Pro
1               5

<210> SEQ ID NO 334
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 334 cag cag agc cac agc acc ccc 21
Gln Gln Ser His Ser Thr Pro
1               5

<210> SEQ ID NO 335
<211> LENGTH: 7
<212> TYPE: PRT
<213> ORGANISM: Artificial
<220> FEATURE:
<223> OTHER INFORMATION: Synthetic Construct

<400> SEQUENCE: 335

Gln Gln Ser His Ser Thr Pro
1               5

<210> SEQ ID NO 336
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS

<222> LOCATION: (1)..(21)

<400> SEQUENCE: 336 cag cag agc tac agc acc cac 21
Gln Gln Ser Tyr Ser Thr His
1 5

<210> SEQ ID NO 337
<211> LENGTH: 7
<212> TYPE: PRT
<213> ORGANISM: Artificial
<220> FEATURE:
<223> OTHER INFORMATION: Synthetic Construct

<400> SEQUENCE: 337

Gln Gln Ser Tyr Ser Thr His
1 5

<210> SEQ ID NO 338
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 338 cac cat agc tac agc acc ccc 21
His His Ser Tyr Ser Thr Pro
1 5

<210> SEQ ID NO 339
<211> LENGTH: 7
<212> TYPE: PRT
<213> ORGANISM: Artificial
<220> FEATURE:
<223> OTHER INFORMATION: Synthetic Construct

<400> SEQUENCE: 339

His His Ser Tyr Ser Thr Pro
1 5

<210> SEQ ID NO 340
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 340 cac cag agc cac agc acc ccc 21
His Gln Ser His Ser Thr Pro
1 5

<210> SEQ ID NO 341
<211> LENGTH: 7
<212> TYPE: PRT
<213> ORGANISM: Artificial
<220> FEATURE:
<223> OTHER INFORMATION: Synthetic Construct

<400> SEQUENCE: 341

His Gln Ser His Ser Thr Pro

```
1               5


<210> SEQ ID NO 342
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 342

cac cag agc tac agc acc cac                                           21
His Gln Ser Tyr Ser Thr His
1               5


<210> SEQ ID NO 343
<211> LENGTH: 7
<212> TYPE: PRT
<213> ORGANISM: Artificial
<220> FEATURE:
<223> OTHER INFORMATION: Synthetic Construct

<400> SEQUENCE: 343

His Gln Ser Tyr Ser Thr His
1               5


<210> SEQ ID NO 344
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 344

cag cat agc cac agc acc ccc                                           21
Gln His Ser His Ser Thr Pro
1               5


<210> SEQ ID NO 345
<211> LENGTH: 7
<212> TYPE: PRT
<213> ORGANISM: Artificial
<220> FEATURE:
<223> OTHER INFORMATION: Synthetic Construct

<400> SEQUENCE: 345

Gln His Ser His Ser Thr Pro
1               5


<210> SEQ ID NO 346
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 346

cag cat agc tac agc acc cac                                           21
Gln His Ser Tyr Ser Thr His
1               5
```

<210> SEQ ID NO 347
<211> LENGTH: 7
<212> TYPE: PRT
<213> ORGANISM: Artificial
<220> FEATURE:
<223> OTHER INFORMATION: Synthetic Construct

<400> SEQUENCE: 347

Gln His Ser Tyr Ser Thr His
1               5

<210> SEQ ID NO 348
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 348 cag cag agc cac agc acc cac 21
Gln Gln Ser His Ser Thr His
1               5

<210> SEQ ID NO 349
<211> LENGTH: 7
<212> TYPE: PRT
<213> ORGANISM: Artificial
<220> FEATURE:
<223> OTHER INFORMATION: Synthetic Construct

<400> SEQUENCE: 349

Gln Gln Ser His Ser Thr His
1               5

<210> SEQ ID NO 350
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 350 cac cat agc cac agc acc ccc 21
His His Ser His Ser Thr Pro
1               5

<210> SEQ ID NO 351
<211> LENGTH: 7
<212> TYPE: PRT
<213> ORGANISM: Artificial
<220> FEATURE:
<223> OTHER INFORMATION: Synthetic Construct

<400> SEQUENCE: 351

His His Ser His Ser Thr Pro
1               5

<210> SEQ ID NO 352
<211> LENGTH: 21
<212> TYPE: DNA
<213> ORGANISM: Artificial
<220> FEATURE:

<223> OTHER INFORMATION: Synthetic
<220> FEATURE:
<221> NAME/KEY: CDS
<222> LOCATION: (1)..(21)

<400> SEQUENCE: 352 cac cat agc tac agc acc cac 21
His His Ser Tyr Ser Thr His
1 5

<210> SEQ ID NO 353
<211> LENGTH: 7
<212> TYPE: PRT
<213> ORGANISM: Artificial
<220> FEATURE:
<223> OTHER INFORMATION: Synthetic Construct

<400> SEQUENCE: 353

His His Ser Tyr Ser Thr His
1 5

<210> SEQ ID NO 354
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 354 cac cag agc cac agc acc cac 21
His Gln Ser His Ser Thr His
1 5

<210> SEQ ID NO 355
<211> LENGTH: 7
<212> TYPE: PRT
<213> ORGANISM: Artificial
<220> FEATURE:
<223> OTHER INFORMATION: Synthetic Construct

<400> SEQUENCE: 355

His Gln Ser His Ser Thr His
1 5

<210> SEQ ID NO 356
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 356 cag cat agc cac agc acc cac 21
Gln His Ser His Ser Thr His
1 5

<210> SEQ ID NO 357
<211> LENGTH: 7
<212> TYPE: PRT
<213> ORGANISM: Artificial
<220> FEATURE:
<223> OTHER INFORMATION: Synthetic Construct

<400> SEQUENCE: 357

Gln His Ser His Ser Thr His
1 5

<210> SEQ ID NO 358
<211> LENGTH: 45
<212> TYPE: DNA
<213> ORGANISM: Artificial
<220> FEATURE:
<223> OTHER INFORMATION: Synthetic

<400> SEQUENCE: 358
cttactactg tcaacatagt cacagtaccc atccgatcac cttcg 45

<210> SEQ ID NO 359
<211> LENGTH: 50
<212> TYPE: DNA
<213> ORGANISM: Artificial
<220> FEATURE:
<223> OTHER INFORMATION: Synthetic

<400> SEQUENCE: 359
caacttacta ctgtcaccat agtcacagta cccatccgat caccttcggc 50

<210> SEQ ID NO 360
<211> LENGTH: 45
<212> TYPE: DNA
<213> ORGANISM: Artificial
<220> FEATURE:
<223> OTHER INFORMATION: Synthetic

<400> SEQUENCE: 360
cgaaggtgat cggatgggta ctgtgactat gttgacagta gtaag 45

<210> SEQ ID NO 361
<211> LENGTH: 50
<212> TYPE: DNA
<213> ORGANISM: Artificial
<220> FEATURE:
<223> OTHER INFORMATION: Synthetic

<400> SEQUENCE: 361
gccgaaggtg atcggatggg tactgtgact atggtgacag tagtaagttg 50

<210> SEQ ID NO 362
<211> LENGTH: 23
<212> TYPE: DNA
<213> ORGANISM: Artificial
<220> FEATURE:
<223> OTHER INFORMATION: Synthetic

<400> SEQUENCE: 362
tgggcacaac agacaatcgg ctg 23

<210> SEQ ID NO 363
<211> LENGTH: 19
<212> TYPE: DNA
<213> ORGANISM: Artificial
<220> FEATURE:
<223> OTHER INFORMATION: Synthetic

<400> SEQUENCE: 363
ggtggagagg ctattcggc 19

<210> SEQ ID NO 364

<211> LENGTH: 17
<212> TYPE: DNA
<213> ORGANISM: Artificial
<220> FEATURE:
<223> OTHER INFORMATION: Synthetic

<400> SEQUENCE: 364
gaacacggcg gcatcag 17

<210> SEQ ID NO 365
<211> LENGTH: 29
<212> TYPE: DNA
<213> ORGANISM: Artificial
<220> FEATURE:
<223> OTHER INFORMATION: Synthetic

<400> SEQUENCE: 365
ccattatgat gctccatgcc tctctgttc 29

<210> SEQ ID NO 366
<211> LENGTH: 28
<212> TYPE: DNA
<213> ORGANISM: Artificial
<220> FEATURE:
<223> OTHER INFORMATION: Synthetic

<400> SEQUENCE: 366
aggtgagggt acagataagt gttatgag 28

<210> SEQ ID NO 367
<211> LENGTH: 27
<212> TYPE: DNA
<213> ORGANISM: Artificial
<220> FEATURE:
<223> OTHER INFORMATION: Synthetic

<400> SEQUENCE: 367
tgacaaatgc cctaattata gtgatca 27

<210> SEQ ID NO 368
<211> LENGTH: 26
<212> TYPE: DNA
<213> ORGANISM: Artificial
<220> FEATURE:
<223> OTHER INFORMATION: Synthetic

<400> SEQUENCE: 368
atcagcagaa accagggaaa gcccct 26

<210> SEQ ID NO 369
<211> LENGTH: 21
<212> TYPE: DNA
<213> ORGANISM: Artificial
<220> FEATURE:
<223> OTHER INFORMATION: Synthetic

<400> SEQUENCE: 369
gggcaagtca gagcattagc a 21

<210> SEQ ID NO 370
<211> LENGTH: 21
<212> TYPE: DNA
<213> ORGANISM: Artificial
<220> FEATURE:
<223> OTHER INFORMATION: Synthetic

<400> SEQUENCE: 370
tgcaaactgg atgcagcata g 21

<210> SEQ ID NO 371
<211> LENGTH: 19
<212> TYPE: DNA
<213> ORGANISM: Artificial
<220> FEATURE:
<223> OTHER INFORMATION: Synthetic

<400> SEQUENCE: 371
ggccacattc catgggttc 19

<210> SEQ ID NO 372
<211> LENGTH: 20
<212> TYPE: DNA
<213> ORGANISM: Artificial
<220> FEATURE:
<223> OTHER INFORMATION: Synthetic

<400> SEQUENCE: 372
gcaaacaaaa accactggcc 20

<210> SEQ ID NO 373
<211> LENGTH: 37
<212> TYPE: DNA
<213> ORGANISM: Artificial
<220> FEATURE:
<223> OTHER INFORMATION: Synthetic

<400> SEQUENCE: 373
ctgttcctct aaaactggac tccacagtaa atggaaa 37

<210> SEQ ID NO 374
<211> LENGTH: 22
<212> TYPE: DNA
<213> ORGANISM: Artificial
<220> FEATURE:
<223> OTHER INFORMATION: Synthetic

<400> SEQUENCE: 374
gggcactgga tacgatgtat gg 22

<210> SEQ ID NO 375
<211> LENGTH: 19
<212> TYPE: DNA
<213> ORGANISM: Artificial
<220> FEATURE:
<223> OTHER INFORMATION: Synthetic

<400> SEQUENCE: 375
cacagcttgt gcagcctcc 19

<210> SEQ ID NO 376
<211> LENGTH: 37
<212> TYPE: DNA
<213> ORGANISM: Artificial
<220> FEATURE:
<223> OTHER INFORMATION: Synthetic

<400> SEQUENCE: 376
agaagaagcc tgtactacag catccgtttt acagtca 37

<210> SEQ ID NO 377
<211> LENGTH: 19
<212> TYPE: DNA

<213> ORGANISM: Artificial
<220> FEATURE:
<223> OTHER INFORMATION: Synthetic

<400> SEQUENCE: 377
accatagtca cagtaccca 19

<210> SEQ ID NO 378
<211> LENGTH: 23
<212> TYPE: DNA
<213> ORGANISM: Artificial
<220> FEATURE:
<223> OTHER INFORMATION: Synthetic

<400> SEQUENCE: 378
agcagtctgc aacctgaaga ttt 23

<210> SEQ ID NO 379
<211> LENGTH: 18
<212> TYPE: DNA
<213> ORGANISM: Artificial
<220> FEATURE:
<223> OTHER INFORMATION: Synthetic

<400> SEQUENCE: 379
cccttggccg aaggtgat 18

<210> SEQ ID NO 380
<211> LENGTH: 19
<212> TYPE: DNA
<213> ORGANISM: Artificial
<220> FEATURE:
<223> OTHER INFORMATION: Synthetic

<400> SEQUENCE: 380
atagtcacag tacccatcc 19

<210> SEQ ID NO 381
<211> LENGTH: 23
<212> TYPE: DNA
<213> ORGANISM: Artificial
<220> FEATURE:
<223> OTHER INFORMATION: Synthetic

<400> SEQUENCE: 381
agtctgcaac ctgaagattt tgc 23

<210> SEQ ID NO 382
<211> LENGTH: 18
<212> TYPE: DNA
<213> ORGANISM: Artificial
<220> FEATURE:
<223> OTHER INFORMATION: Synthetic

<400> SEQUENCE: 382
cccttggccg aaggtgat 18

<210> SEQ ID NO 383
<211> LENGTH: 108
<212> TYPE: PRT
<213> ORGANISM: Artificial
<220> FEATURE:
<223> OTHER INFORMATION: Synthetic

<400> SEQUENCE: 383

Glu Ile Val Leu Thr Gln Ser Pro Gly Thr Leu Ser Leu Ser Pro Gly

```
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 384
<211> LENGTH: 54
<212> TYPE: DNA
<213> ORGANISM: Artificial
<220> FEATURE:
<223> OTHER INFORMATION: Synthetic

<400> SEQUENCE: 384
gattttgcag tgtattactg tcagcagtat ggtagctcac cttggacgtt cggc 54

<210> SEQ ID NO 385
<211> LENGTH: 54
<212> TYPE: DNA
<213> ORGANISM: Artificial
<220> FEATURE:
<223> OTHER INFORMATION: Synthetic

<400> SEQUENCE: 385
gattttgcag tgtattactg tcatcaccat ggtcactcac cttggacgtt cggc 54

<210> SEQ ID NO 386
<211> LENGTH: 54
<212> TYPE: DNA
<213> ORGANISM: Artificial
<220> FEATURE:
<223> OTHER INFORMATION: Synthetic

<400> SEQUENCE: 386
gccgaacgtc caaggtgagt gaccatggtg atgacagtaa tacactgcaa aatc 54

<210> SEQ ID NO 387
<211> LENGTH: 47
<212> TYPE: DNA
<213> ORGANISM: Artificial
<220> FEATURE:
<223> OTHER INFORMATION: Synthetic

<400> SEQUENCE: 387
gcagtgtatt actgtcatca ctatggtcac tcaccttgga cgttcgg 47

<210> SEQ ID NO 388
<211> LENGTH: 47
<212> TYPE: DNA
<213> ORGANISM: Artificial
<220> FEATURE:
<223> OTHER INFORMATION: Synthetic

<400> SEQUENCE: 388
ccgaacgtcc aaggtgagtg accatagtga tgacagtaat acactgc 47

<210> SEQ ID NO 389
<211> LENGTH: 24
<212> TYPE: DNA
<213> ORGANISM: Artificial
<220> FEATURE:
<223> OTHER INFORMATION: Synthetic

<400> SEQUENCE: 389
aaagagccac cctctcctgc aggg 24

<210> SEQ ID NO 390
<211> LENGTH: 19
<212> TYPE: DNA
<213> ORGANISM: Artificial
<220> FEATURE:
<223> OTHER INFORMATION: Synthetic

<400> SEQUENCE: 390
tccaggcacc ctgtctttg 19

<210> SEQ ID NO 391
<211> LENGTH: 26
<212> TYPE: DNA
<213> ORGANISM: Artificial
<220> FEATURE:
<223> OTHER INFORMATION: Synthetic

<400> SEQUENCE: 391
aagtagctgc tgctaacact ctgact 26

<210> SEQ ID NO 392
<211> LENGTH: 15
<212> TYPE: DNA
<213> ORGANISM: Artificial
<220> FEATURE:
<223> OTHER INFORMATION: Synthetic

<400> SEQUENCE: 392
ctgtcatcac catgg 15

<210> SEQ ID NO 393
<211> LENGTH: 23
<212> TYPE: DNA
<213> ORGANISM: Artificial
<220> FEATURE:
<223> OTHER INFORMATION: Synthetic

<400> SEQUENCE: 393
gcagactgga gcctgaagat ttt 23

<210> SEQ ID NO 394
<211> LENGTH: 20
<212> TYPE: DNA
<213> ORGANISM: Artificial
<220> FEATURE:
<223> OTHER INFORMATION: Synthetic

<400> SEQUENCE: 394
ccgaacgtcc aaggtgagtg 20

<210> SEQ ID NO 395
<211> LENGTH: 17
<212> TYPE: DNA
<213> ORGANISM: Artificial
<220> FEATURE:

<223> OTHER INFORMATION: Synthetic

<400> SEQUENCE: 395
tactgtcatc actatgg 17

<210> SEQ ID NO 396
<211> LENGTH: 22
<212> TYPE: DNA
<213> ORGANISM: Artificial
<220> FEATURE:
<223> OTHER INFORMATION: Synthetic

<400> SEQUENCE: 396
gcagactgga gcctgaagat tt 22

<210> SEQ ID NO 397
<211> LENGTH: 20
<212> TYPE: DNA
<213> ORGANISM: Artificial
<220> FEATURE:
<223> OTHER INFORMATION: Synthetic

<400> SEQUENCE: 397
ccgaacgtcc aaggtgagtg 20

<210> SEQ ID NO 398
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 398 cag cag tat ggt agc tca cct 21
Gln Gln Tyr Gly Ser Ser Pro
1 5

<210> SEQ ID NO 399
<211> LENGTH: 7
<212> TYPE: PRT
<213> ORGANISM: Artificial
<220> FEATURE:
<223> OTHER INFORMATION: Synthetic Construct

<400> SEQUENCE: 399

Gln Gln Tyr Gly Ser Ser Pro
1 5

<210> SEQ ID NO 400
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 400 cat cac cat ggt cac tca cct 21
His His His Gly His Ser Pro
1 5

<210> SEQ ID NO 401

<211> LENGTH: 7
<212> TYPE: PRT
<213> ORGANISM: Artificial
<220> FEATURE:
<223> OTHER INFORMATION: Synthetic Construct

<400> SEQUENCE: 401

His His His Gly His Ser Pro
1 5

<210> SEQ ID NO 402
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 402 cat cac tat ggt cac tca cct 21
His His Tyr Gly His Ser Pro
1 5

<210> SEQ ID NO 403
<211> LENGTH: 7
<212> TYPE: PRT
<213> ORGANISM: Artificial
<220> FEATURE:
<223> OTHER INFORMATION: Synthetic Construct

<400> SEQUENCE: 403

His His Tyr Gly His Ser Pro
1 5

<210> SEQ ID NO 404
<211> LENGTH: 108
<212> TYPE: PRT
<213> ORGANISM: Artificial
<220> FEATURE:
<223> OTHER INFORMATION: Synthetic

<400> SEQUENCE: 404

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Ile Thr Phe Gly Gln Gly Thr Arg Leu Glu Ile Lys
100 105

<210> SEQ ID NO 405
<211> LENGTH: 50
<212> TYPE: DNA
<213> ORGANISM: Artificial
<220> FEATURE:
<223> OTHER INFORMATION: Synthetic

<400> SEQUENCE: 405
caacttacta ctgtcaacag agttacagta cccctccgat caccttcggc 50

NON-HUMAN ANIMALS EXPRESSING pH-SENSITIVE IMMUNOGLOBULIN SEQUENCES

CROSS REFERENCE TO RELATED APPLICATIONS

This application is a continuation of U.S. application Ser. No. 15/703,490, filed Sep. 13, 2017, which is a continuation of U.S. application Ser. No. 13/834,129, filed Mar. 15, 2013, now U.S. Pat. No. 9,801,362, which claims the benefit of priority to U.S. Provisional Application No. 61/611,950, filed 16 Mar. 2012, U.S. Provisional Application No. 61/613,352, filed 20 Mar. 2012, and U.S. Provisional Application No. 61/736,930, filed 13 Dec. 2012, and U.S. Provisional Application 61/612,126, filed 16 Mar. 2012, the entire contents of each of the applications are incorporated herein by reference.

SEQUENCE LISTING

The present specification makes reference to a sequence listing submitted in electronic Form as an ASCII .txt file named "1900CON2-US_ST25" on Mar. 30, 2022. The .txt file was generated on Mar. 30, 2022, and is 131 KB in size. The same is incorporated herein by reference in its entirety.

FIELD OF THE INVENTION

A genetically modified non-human animal that expresses antibodies capable of binding to an antigen in a pH dependent manner. Genetically modified non-human animals that comprise immunoglobulin loci that are modified to contain at least one substitution or insertion of a codon encoding a protonatable amino acid. Genetically modified non-human animals that comprise immunoglobulin loci that are modified to contain at least one histidine substitution and/or at least one histidine insertion in an immunoglobulin heavy chain V, D, or J gene segment, or light chain V or J segment, or rearranged heavy chain VDJ region or rearranged light chain VJ region thereof. Genetically modified non-human animals that express immunoglobulins that exhibit pH sensitivity in antigen binding. Genetically modified animals that comprise B cell populations that are enriched with respect to immunoglobulin variable domains that comprise at least one histidine. Genetically modified non-human animals that comprise clusters of two or more histidines present as insertions and/or substitutions in an immunoglobulin heavy chain V, D, and/or J gene segment, and or a light chain V and/or J gene segment, and/or rearranged heavy chain VDJ sequences or rearranged light chain VJ sequences thereof.

Genetically modified immunoglobulin loci of non-human animals comprising an unrearranged human heavy chain variable region nucleotide sequence, wherein the unrearranged human heavy chain variable region nucleotide sequence comprises an addition of least one histidine codon or a substitution of at least one endogenous non-histidine codon with a histidine codon. Non-human animals, including rodents, e.g., mice and rats, comprising a genetically modified immunoglobulin locus in their genome an unrearranged human heavy chain variable region nucleotide sequence, wherein the unrearranged human heavy chain variable region nucleotide sequence comprises an addition of least one histidine codon or a substitution of at least one endogenous non-histidine codon with a histidine codon. Genetically engineered non-human animals capable of expressing an antigen-binding protein that is characterized by pH-dependent antigen binding, improved recyclability, and/or enhanced serum half-life.

BACKGROUND

Immunoglobulin binding domains find therapeutic use in a wide variety of formats, including the traditional antibody format of a homodimeric immunoglobulin heavy chain associated with a cognate light chain. Many of these formats, including the traditional format, exhibit pharmacokinetic features in vivo that are suboptimal, due to a wide variety of factors. In recent decades, disparate approaches have been tried to improve pharmacokinetics. These include, e.g., increasing hydrodynamic radius to reduce renal clearance by conjugation to polymers (e.g., PEG; reviewed in, e.g., Duncan, R. (2006) Polymer conjugates as anticancer nanomedicines, Nat. Rev. Cancer 6:688-701); sialylation of N-glycans (reviewed in, e.g., Stork, R. et al. N-glycosylation as novel strategy to improve pharmacokinetic properties of bispecific single-chain diabodies, J. Biol. Chem. 283(12): 7804-7812); Fc modifications for promoting neutral pH Fc-FcRn binding while promoting release at endosomal pH and association with serum albumin (see, e.g., Chuang et al. (2002) Pharmaceutical Strategies Utilizing Recombinant Serum Albumin, Pharm. Res. 19(5):569-577). In appropriate applications and for appropriate formats, each of these approaches may offer some benefits.

However, there remains a need in the art for improving therapeutic effects and modalities for biopharmaceuticals, including but not limited to manipulating immunoglobulin variable domain structures to engineer variable domains that exhibit pH-dependent binding. There is a need for variable domains for use in antigen-binding proteins of a variety of formats, wherein the variable domains (or antigen-binding fragments thereof) confer upon the antigen-binding protein pH sensitivity with respect to binding a target antigen or receptor. There is also a need in the art for systems and methods for generating pH-dependent immunoglobulin variable domains and antigen-binding fragments thereof. There is a need for biological systems that can generate a wide diversity of immunoglobulin variable domains, wherein the wide diversity is enriched with respect to titratable amino acids that may confer upon the variable domain pH sensitivity, e.g., the ability to bind a target antigen or epitope at one pH (e.g., a neutral, or high pH), yet release the target antigen or epitope at a second pH (e.g., a low, or endosomal, pH).

Immunoglobulin light chains in certain formats present unique challenges. Antibodies typically comprise a homodimeric heavy chain component, wherein each heavy chain monomer is associated with an identical light chain. Antibodies having a heterodimeric heavy chain component (e.g., bispecific antibodies) are desirable as therapeutic antibodies. But making bispecific antibodies having a suitable light chain component that can satisfactorily associate with each of the heavy chains of a bispecific antibody has proved problematic.

In one approach, a light chain might be selected by surveying usage statistics for all light chain variable domains, identifying the most frequently employed light chain in human antibodies, and pairing that light chain in vitro with the two heavy chains of differing specificity.

In another approach, a light chain might be selected by observing light chain sequences in a phage display library (e.g., a phage display library comprising human light chain variable region sequences, e.g., a human scFv library) and selecting the most commonly used light chain variable region from the library. The light chain can then be tested on the two different heavy chains of interest.

In another approach, a light chain might be selected by assaying a phage display library of light chain variable sequences using the heavy chain variable sequences of both heavy chains of interest as probes. A light chain that associates with both heavy chain variable sequences might be selected as a light chain for the heavy chains.

In another approach, a candidate light chain might be aligned with the heavy chains' cognate light chains, and modifications are made in the light chain to more closely match sequence characteristics common to the cognate light chains of both heavy chains. If the chances of immunogenicity need to be minimized, the modifications preferably result in sequences that are present in known human light chain sequences, such that proteolytic processing is unlikely to generate a T cell epitope based on parameters and methods known in the art for assessing the likelihood of immunogenicity (i.e., in silico as well as wet assays).

All of such approaches rely on in vitro methods that subsume a number of a priori restraints, e.g., sequence identity, ability to associate with specific pre-selected heavy chains, etc. There is a need in the art for compositions and methods that do not rely on manipulating in vitro conditions, but that instead employ more biologically sensible approaches to making human epitope-binding proteins that include a common light chain.

In addition, therapeutic antibodies, e.g., bispecific therapeutic antibodies, have some limitations in that they often require high doses to achieve desired efficacy. This is partly due to the fact that antibody-antigen complexes are internalized into the endosome, and are targeted for lysosomal degradation in a process called target-mediated clearance. Thus, there is a need in the art for methods and compositions that lead to more efficient antibody recycling, e.g., bispecific antibody recycling, and prevent degradation of the antibody by promoting dissociation of antibody-antigen complexes in the endosomal compartment without compromising the specificity and affinity of the antibody toward the antigen.

Drugs administered into the body, including therapeutic monoclonal antibodies, can be affected via various elimination mechanisms, including glomerular filtration (e.g., into urine), secretion (e.g., into the bile), and catabolism by cells. While small molecules are cleared from the body via renal filtration, the majority of secreted antibodies (e.g., IgG, which are too big to be filtered through glomeruli) are primarily removed from the body via cell-mediated catabolism, e.g., fluid-phase endocytosis (phagocytosis) or receptor-mediated endocytosis. For example, soluble molecules with several repeated epitopes are bound by a plurality of circulating antibodies, and the resulting large antigen-antibody complexes are phagocytosed rapidly into cells for degradation. On the other hand, cell surface target receptors, which are bound by antibodies (i.e., receptor-antibody complexes), undergo target-mediated endocytosis in a dose-dependent manner, which leads to formation of endosomes destined for lysosomal degradation inside cells. In some cases, the endocytosed receptor-antibody complexes bind neonatal Fc receptors (FcRn) inside the endosomes in a pH-dependent manner and are routed back to the cell surface for release into plasma or interstitial fluids upon exposure to a neutral extracellular pH (e.g., pH 7.0-7.4).

There is a need in the art for systems, e.g., non-human animals, cells, and genomic loci that generate antigen-binding proteins with titratable residues, e.g., genetically modified loci that rearrange immunoglobulin gene segments to generate heavy chain variable domains that respond to changes in pH, e.g., that donate or accept protons and, e.g., whose binding characteristics differ according to protonation state.

There is also a need in the art for methods and compositions that can further increase recycling efficiency of endocytosed antigen-binding proteins by promoting dissociation of antigen-binding proteins from receptor-antigen-binding protein complexes or by increasing the affinity of antigen-binding proteins toward FcRn in an acidic endosomal compartment without compromising the specificity and affinity of the antigen-binding protein toward an antigen of interest.

SUMMARY

Compositions and methods are provided for making genetically modified animals that make immunoglobulin variable domains that comprise at least one histidine residue encoded by a germline modification of the non-human animal, wherein the germline modification comprises at least one of the insertion of a histidine codon into a heavy chain V, D, or J segment, insertion of a histidine codon into a light chain V or J segment, insertion of a histidine codon into a rearranged light chain VJ gene, substitution of a non-histidine codon with a histidine codon in a heavy chain V, D, or J segment, substitution of a non-histidine codon with a histidine codon in a light chain V or J segment, substitution of a non-histidine codon with a histidine codon in a rearranged light chain VJ sequence.

Compositions and methods are also provided for introducing clusters of histidine codons in germline immmunoglobulin sequences of non-human animals.

Compositions and methods are also provided for introducing histidine insertions, or substitutions of non-histidine codons with histidine codons, in N-terminal-encoding regions of immunoglobulin genes, loop 4-encoding regions of immunoglobulin genes, CDR-encoding regions of immunoglobulin genes (e.g., rearranged V(D)J sequences or V, (D), J gene segments).

Compositions and methods for making non-human animal progeny that comprise insertions of histidine codons and/or substitutions of non-histidine codons with histidine codons in both immunoglobulin heavy chain loci and in immunoglobulin light chain loci.

In one aspect, a genetically modified non-human animal comprising in its germline an immunoglobulin locus comprising a substitution or an insertion in an immunoglobulin variable locus of at least one non-histidine codon with a histidine codon. In one embodiment, the variable locus (e.g., an unrearranged V(D)J segments locus) comprises at least a portion of a human variable (V(D)J segments) locus.

In one embodiment, the genetically modified non-human animal comprises in its germline a first variable locus (e.g., an unrearranged immunoglobulin heavy chain (V(D)J segments locus) and a second variable locus (e.g., an unrearranged immunoglobulin light chain (V, J segments locus; or a rearranged immunoglobulin light chain VJ sequence).

In one embodiment, the non-human animal comprises a first and a second variable locus, wherein at least the first or the second variable locus comprises an insertion of at least one histidine codon or a substitution of at least one non-histidine codon with a histidine codon.

In one embodiment, both the first and the second variable locus each comprise a substitution or insertion of at least one non-histidine codon with a histidine codon.

In one embodiment, the first variable locus comprises at least a functional portion of an unrearranged heavy chain variable locus (unrearranged V, D, J segments).

In one embodiment, the unrearranged heavy chain variable locus comprises at least a portion of a human locus (unrearranged V, D, J segments).

In one embodiment, the unrearranged heavy chain locus is a human locus comprising unrearranged V segments, a synthetic D segment that comprises a linker, and a human J segment. In one embodiment, the synthetic D segment comprises at least one histidine codon.

In one embodiment, the second variable locus comprises at least a functional portion of an unrearranged light chain locus (unrearranged V, J segments).

In one embodiment, the second variable locus comprises a rearranged immunoglobulin light chain variable gene sequence (rearranged VJ sequence).

In one embodiment, the substitution of an non-histidine codon with a histidine codon and/or the insertion of a histidine codon is in a nucleic acid sequence that encodes a variable domain and the histidine is in a region selected from an N-terminal region of an immunoglobulin chain, a loop 4 region of an immunoglobulin chain, a CDR1 of a heavy chain, a CDR2 of a heavy chain, a CDR3 of a heavy chain, a CDR1 of a light chain, a CDR2 of a light chain, a CDR3 of a light chain, and a combination thereof.

In one embodiment, at least one of the first variable locus or the second variable locus is operably linked to an endogenous non-human constant region nucleic acid sequence at an endogenous non-human immunoglobulin locus.

In one embodiment the first variable locus (unrearranged human V, D, J segments) is operably linked to an endogenous non-human immunoglobulin heavy chain constant region nucleic acid sequence.

In one embodiment, the first variable locus (unrearranged human V, D, J segments) is operably linked to the endogenous non-human immunoglobulin heavy chain constant region nucleic acid sequence at an endogenous non-human immunoglobulin locus.

In one embodiment, the second variable locus (unrearranged V, J segments) is operably linked to an endogenous non-human immunoglobulin light chain constant region sequence.

In one embodiment, the endogenous non-human immunoglobulin light chain constant region sequence is at an endogenous non-human immunoglobulin locus.

In one embodiment, the variable region sequence comprises a cluster of 2, 3, 4, or 5 histidines that are substitutions of non-histidine codons with histidine codons and/or insertions of histidine codons.

In one embodiment, the unrearranged heavy chain locus comprises D gene segments that are inverted with respect to the direction of orientation of the heavy chain locus. In one embodiment, the inverted D segments are in a hydrophilic reading frame.

In one aspect, a genetically modified non-human animal is provided, comprising at least a portion of a human unrearranged immunoglobulin heavy chain variable region nucleic acid sequence (unrearranged V, D, J segments) operably linked to a constant region gene sequence, wherein one or more of the V, D, and J gene segments comprise at least one substitution of a non-histidine codon for a histidine codon, or at least one histidine codon insertion; at least a portion of a human unrearranged immunoglobulin light chain variable region nucleic acid sequence (unrearranged V, J segments) operably linked to a constant region gene sequence, wherein one or more of the V and J gene segments comprise at least one substitution of a non-histidine codon for a histidine codon, or at least one histidine codon insertion; wherein the non-human animal expresses an immunoglobulin heavy chain variable domain and/or an immunoglobulin light chain variable domain that comprises a histidine derived from a histidine substitution or insertion in the germline of the mouse.

In one embodiment, the non-human animal is a mammal. In one embodiment, the mammal is a rodent. In one embodiment, the rodent is selected from the group consisting of a mouse, a rat, and a hamster.

In one embodiment, the human unrearranged immunoglobulin heavy chain variable region nucleic acid sequence is operably linked to a non-human constant region sequence.

In one embodiment, the non-human constant region nucleic acid sequence operably linked to the human unrearranged immunoglobulin heavy chain variable region nucleic acid sequence is at an endogenous non-human immunoglobulin locus in the germline of the non-human animal.

In one embodiment, the non-human constant region nucleic acid sequence operably linked to the human unrearranged immunoglobulin light chain variable region nucleic acid sequence is at an endogenous non-human immunoglobulin locus in the germline of the non-human animal.

In one aspect, a genetically modified non-human animal is provided, comprising at least a portion of a human unrearranged immunoglobulin heavy chain variable region nucleic acid sequence (unrearranged V, D, J segments) operably linked to a constant region gene sequence, wherein one or more of the unrearranged V, D, and J gene segments comprise at least one substitution of a non-histidine codon for a histidine codon, or at least one histidine codon insertion; a human rearranged immunoglobulin light chain variable region nucleic acid sequence (rearranged VJ sequence) operably linked to a light chain constant region gene sequence, wherein the rearranged VJ sequence comprises at least one substitution of a non-histidine codon for a histidine codon, or at least one histidine codon insertion; wherein the non-human animal expresses an immunoglobulin heavy chain variable domain and/or an immunoglobulin light chain variable domain that comprises a histidine derived from a histidine substitution or insertion in the germline of the mouse.

In one embodiment, the genetically modified non-human animal is a mammal. In one embodiment, the mammal is a rodent. In one embodiment, the rodent is selected from the group consisting of a mouse, a rat, and a hamster.

In one embodiment, the human unrearranged immunoglobulin heavy chain variable region nucleic acid sequence is operably linked to a non-human constant region sequence. In one embodiment, the non-human constant region sequence operably linked to the human unrearranged immunoglobulin heavy chain variable region nucleic acid sequence is at an endogenous non-human immunoglobulin locus in the germline of the non-human animal. In one embodiment, the non-human constant region sequence operably linked to the human rearranged immunoglobulin light chain variable region nucleic acid sequence is at an endogenous non-human immunoglobulin locus in the germline of the non-human animal.

In one aspect, a genetically modified non-human animal is provided, wherein the animal comprises a B cell population that is characterized by an enhanced presence of histidine residues in immunoglobulin heavy and light chains of the B cell population as compared with a wild-type non-human animal. In one embodiment, the enhancement is about 2-4 fold. In one embodiment, the enhancement is about 2-10 fold.

In one aspect, a genetically modified non-human animal is provided that expresses immunoglobulin light and heavy chains that comprise histidines encoded by substitutions and/or insertions in germline immunoglobulin sequences of the non-human animal.

In one aspect, a method is provided for making a non-human animal that makes antibody variable domains with histidines encoded by germline histidine codons, comprising: modifying the non-human animal in its germline to comprise at least one substitution of histidine codon for a non-histidine codon, or insertion of a histidine codon, in an unrearranged immunoglobulin heavy chain variable (unrearranged V, D, J segments) locus; and, modifying the non-human animal in its germline to comprise at least one substitution of a histidine codon for a non-histidine codon, or insertion of a histidine codon, in an unrearranged immunoglobulin light chain variable (unrearranged V, J segments) locus.

In one embodiment, the method comprises genetically modifying the germline of the mouse to comprise at least a portion of a human unrearranged immunoglobulin heavy chain variable (V, D, J segments) locus, and making the histidine substitution or insertion in the unrearranged immunoglobulin heavy chain variable (unrearranged V, D, J segments) human locus.

In one embodiment, the method comprises genetically modifying the germline of the mouse to comprise at least a portion of a human unrearranged immunoglobulin light chain (unrearranged V, J segments) locus, and making the histidine substitution or insertion in the unrearranged human immunoglobulin light chain locus.

In one embodiment of the method, the non-human animal is a rodent. In one embodiment, the rodent is selected from a mouse, a rat, and a hamster.

In one aspect, a method is provided for making a non-human animal that makes antibody variable domains with histidines encoded by germline histidine codons, comprising: modifying the non-human animal to comprise at least one substitution of histidine codon for a non-histidine codon, or insertion of a histidine codon, in an unrearranged immunoglobulin heavy chain variable (unrearranged V, D, J segments) locus; and, modifying the non-human animal to comprise at least one substitution of a histidine codon for a non-histidine codon, or insertion of a histidine codon, in a rearranged immunoglobulin light chain variable sequence (rearranged VJ sequence) in the germline.

In one embodiment of the method, the non-human animal is a rodent. In one embodiment, the rodent is selected from a mouse, a rat, and a hamster.

In various aspects and embodiments, the non-human animals are genetically modified by genetically modifying pluripotent or totipotent cells (e.g., embryonic stem (ES) cells), and employing the genetically modified cells as donor cells with a host embryo in a surrogate mother to gestate an animal derived from the genetically modified donor cells. In various aspects and embodiments, the non-human animals are genetically modified by any other method known in the art.

Methods and compositions for making antibody variable domains that exhibit a pH-dependent antigen binding are provided. Modified antigen-binding proteins are provided, as well as compositions and methods for making them, that bind target antigen with low affinity at a low (e.g., endosomal) pH and that bind the same target antigen with high affinity at a higher (e.g., extracellular), or neutral, pH.

In one aspect, a method for making an antibody that exhibits pH-dependent binding is provided, comprising modifying a sequence of a variable domain of the antibody to add a histidine residue, or to substitute an existing residue for a histidine residue, to form a histidine-modified variable domain. In one embodiment, the substitution is of a residue that is not critical for binding antigen (e.g., at a neutral or extracellular pH).

In one embodiment, two, three, four, five, or six or more residues are substituted to histidines. In one embodiment, the two, three, four, five, or six or more residues substituted to histidines are in a cluster. In one embodiment, the cluster comprises two or more consecutive histidine substitutions. In one embodiment, the cluster comprises two or more histidine substitutions separated by one or more non-histidine residues. In one embodiment, the cluster is 2, 3, 4, 5, 6, 7, 8, 9, or 10 residues in length, and all residues not critical for binding antigen (e.g., at a neutral or extracellular pH) are modified to histidine.

In one embodiment the variable domain is a light chain variable domain (e.g., κ or λ). In one embodiment, the variable domain is in a heavy chain variable domain. In one embodiment, the sequence of a light chain variable domain and a heavy chain variable domain are modified.

In one embodiment, the sequence of the variable domain is a CDR sequence. In one embodiment, the CDR sequence is a CDR sequence of a heavy chain. In one embodiment, the CDR sequence is a CDR sequence of a light chain. In one embodiment, the CDR sequence is a CDR sequence of a heavy chain and a CDR sequence of a light chain.

In one embodiment, the CDR sequence is a CDR3 sequence. In one embodiment, the CDR sequence is a CDR2 sequence. In one embodiment, the CDR sequence is a CDR3 sequence.

In one embodiment, the CDR sequence is a CDR1, a CDR2, and/or a CDR3 sequence of a light chain. In one embodiment, the CDR sequence is a CDR1, a CDR2, and/or a CDR3 sequence of a heavy chain.

In one embodiment, the sequence of the variable domain of the antibody is a loop 4 sequence. In one embodiment, the loop 4 sequence is a heavy chain loop 4 sequence. In one embodiment, the loop 4 sequence is a light chain loop 4 sequence.

In one embodiment, the sequence of the variable domain of the antibody is an N-terminal sequence. In one embodiment, the N-terminal sequence is a heavy chain N-terminal sequence. In one embodiment, the N-terminal sequence is a light chain N-terminal sequence.

In one embodiment, the sequence of the variable domain of the antibody is selected from a CDR sequence of a heavy chain, a CDR sequence of a light chain, a loop 4 sequence of a heavy chain, a loop 4 sequence of a light chain, an N-terminal sequence of a heavy chain, an N-terminal sequence of a light chain, and a combination thereof.

In one embodiment, the variable domain is from a heavy chain, and the sequence of the variable domain comprises a first CDR sequence and a sequence selected from an N-terminal sequence, a loop 4 sequence, a second CDR sequence, a third CDR sequence, and a combination thereof. In a specific embodiment, the first CDR sequence is a CDR3, and the sequence of the variable domain further comprises a sequence selected from an N-terminal sequence, a loop 4 sequence, a CDR2 sequence, a CDR1 sequence, and a combination thereof.

In one embodiment, the histidine-modified variable domain is from a heavy chain, and the histidine modification is in a loop 4 sequence and a sequence selected from a CDR1 or CDR2 or CDR3, an N-terminal sequence, and a combination thereof. In a specific embodiment, the histidine modification is in a loop 4 sequence and a CDR3 sequence. In a specific embodiment, the histidine modification is in a loop 4 sequence and a CDR3 sequence and an N-terminal sequence. In a specific embodiment, the histidine modification is in a loop 4 sequence and an N-terminal sequence.

In one aspect, a his-modified immunoglobulin variable domain as described herein is provided, wherein the his-modified immunoglobulin variable domain that does not bind an antigen of interest or that binds the antigen of interest at a first affinity at a pH of less than 6; and binds the same antigen of interest at a second affinity at a pH of about 7 or more. In one embodiment the first pH is less than 5.5, or less than 5. In one embodiment the first pH is 5.75. In one embodiment the second pH is about 7 or higher. In one embodiment, the second pH is an extracellular pH of a human. In one embodiment, the second pH is 7.2 to 7.4. In a specific embodiment, the second pH is 7.2.

In one embodiment, the his-modified variable domain comprises one, two, three, four, five, or six or more histidine substitutions in a sequence selected from a CDR, an N-terminal, a loop 4, and a combination thereof. In a specific embodiment, the his-modified variable domain comprises a modification in a CDR3. In one embodiment, the his-modified variable domain comprises a modification selected from a modification of a CDR3 in a heavy chain, a modification of a CDR3 in a light chain, and a combination thereof. In one embodiment, the his-modified variable domain comprises at least one substitution in a CDR (e.g., CDR3) and at least one substitution in a sequence selected from an N-terminal, a loop 4, and a combination thereof.

In one embodiment, the CDR is selected from the group consisting of a heavy chain CDR1, a heavy chain CDR2, a heavy chain CDR3, a light chain CDR1, a light chain CDR2, a light chain CDR3, and a combination thereof.

In one embodiment, the at least one CDR comprises a light chain CDR3. In one embodiment, the at least one CDR comprises a light chain CDR3 and a heavy chain CDR3.

In one embodiment, the his-modified immunoglobulin variable domain binds an antigen of interest at a neutral or basic pH (e.g., pH 7-7.4) with a $K_D$ of about $10^{-6}$ or less (e.g., $10^{-7}$, $10^{-8}$, $10^{-9}$, $10^{-10}$, $10^{-11}$, $10^{-12}$), wherein the his-modified immunoglobulin variable domain comprises: a CDR1 wherein all non-antigen-binding amino acid residues are substituted with histidine, or wherein the CDR1 comprises a cluster of histidine substitutions. In one embodiment the variable domain does not bind the antigen of interest, or binds the antigen of interest $10^2$-$10^6$-fold weaker at an acidic pH (e.g., pH 5-6, in one embodiment, pH 6).

In one embodiment, the his-modified immunoglobulin variable domain binds an antigen of interest at a neutral or basic pH (e.g., pH 7-7.4) with a $K_D$ of about $10^{-6}$ or less (e.g., $10^{-7}$, $10^{-8}$, $10^{-9}$, $10^{-10}$, $10^{-11}$, $10^{-12}$), wherein the his-modified immunoglobulin variable domain comprises a CDR2 wherein all non-antigen-binding amino acid residues are substituted with histidine, or wherein the CDR2 comprises a cluster of histidine substitutions. In one embodiment the variable domain does not bind the antigen of interest, or binds the antigen of interest $10^2$-$10^6$-fold weaker at an acidic pH (e.g., pH 5-6, in one embodiment, pH 6).

In one embodiment, the his-modified immunoglobulin variable domain binds an antigen of interest at a neutral or basic pH (e.g., pH 7-7.4) with a $K_D$ of about $10^{-6}$ or less (e.g., $10^{-7}$, $10^{-8}$, $10^{-9}$, $10^{-10}$, $10^{-11}$, $10^{-12}$), wherein the his-modified immunoglobulin variable domain comprises a CDR3 wherein all non-antigen-binding amino acid residues are substituted with histidine, or wherein the CDR3 comprises a cluster of histidine substitutions. In one embodiment the variable domain does not bind the antigen of interest, or binds the antigen of interest $10^2$-$10^6$-fold weaker at an acidic pH (e.g., pH 5-6, in one embodiment, pH 6).

In one aspect, a method is provided for making a human antigen-binding polypeptide comprising a his-modified domain, the method comprising modifying an immunoglobulin variable domain nucleotide sequence as described herein to encode one or more histidines to form a nucleic acid sequence encoding a his-modified domain, and fusing the nucleic acid sequence encoding the his-modified domain (directly or with a linker) to a human immunoglobulin sequence.

In one embodiment, the human immunoglobulin sequence is an immunoglobulin constant domain sequence. In a specific embodiment, the human immunoglobulin constant domain sequence encodes an amino acid sequence selected from the group consisting of a $C_H1$, a hinge, a $C_H2$, a $C_H3$, and a combination thereof.

In one aspect, a cell that expresses a his-modified variable domain is provided, wherein the his-modified variable domain is modified as described herein. In one embodiment, the cell is a mammalian cell. In one embodiment, the cell is selected from a HeLa cell, a DU145 cell, a Lncap cell, a MCF-7 cell, a MDA-MB-438 cell, a PC3 cell, a T47D cell, a THP-1 cell, a U87 cell, a SHSY5Y (human neuroblastoma) cell, a Saos-2 cell, a Vero cell, a CHO cell, a GH3 cell, a PC12 cell, a human retinal cell (e.g., a PERC.6™ cell) and a MC3T3 cell. In a specific embodiment, the cell is a CHO cell.

In one aspect, a his-modified immunoglobulin variable domain as described herein is provided, wherein the his-modified immunoglobulin variable domain does not bind an antigen of interest or binds the antigen of interest at a first affinity at a pH of 5-6 (e.g., 5.75) and binds the same antigen of interest at a second affinity at a pH of 7-7.4 (e.g., 7.2), wherein at least one CDR comprises two or more histidine substitutions, and at least one non-CDR sequence comprises one or more histidine substitutions wherein the at least one non-CDR sequence is selected from an N-terminal sequence, a loop 4 sequence, and a combination thereof.

In one embodiment, the first affinity is characterized by no binding, or a $K_D$ of $10^{-6}$ or higher (e.g., $10^{-3}$), and the second affinity is characterized as being at least 2-fold, at least 5-fold, at least 10-fold, at least $10^2$-fold, at least $10^3$-fold, at least $10^4$-fold, at least $10^5$-fold, or at least $10^6$-fold stronger than the first affinity.

In one embodiment, the non-CDR sequence is on the same polypeptide as the at least one CDR sequence. In one embodiment, the non-CDR sequence is on a different polypeptide as the at least one CDR sequence.

In one embodiment, the at least one CDR is a CDR 3 of a heavy and/or light chain, and the CDR3 comprises a substitution of at least half of the non-antigen-binding amino acid residues to histidine. In a specific embodiment, all of the non-antigen-binding amino acid residues of the CDR3 are substituted to histidine.

In one embodiment, the at least one CDR is a CDR3 of a heavy and/or light chain, and the CDR3 comprises a substitution of three or more non-antigen-binding amino acid residues to histidine. In one embodiment, four or more of the non-antigen-binding amino acid residues are substituted to histidine.

In one embodiment, the at least one CDR is a CDR3 of a heavy and/or light chain, and the CDR3 comprises a substitution of two or more contiguous non-antigen-binding amino acid residues to histidine. In one embodiment, the CDR3 comprises a substitution of three or more contiguous non-antigen-binding amino acids residues to histidine.

In one embodiment, the at least one CDR is a CDR3 of a light and/or a heavy chain, and further comprises a CDR selected from a light chain CDR1, a light chain CDR2, and a combination thereof.

In one embodiment, the at least one CDR is a CDR3 of a light and/or a heavy chain, and further comprises a CDR selected from a heavy chain CDR1, a heavy chain CDR2, and a combination thereof.

In one embodiment, the CDR is selected from the group consisting of a heavy chain CDR1, a heavy chain CDR2, a heavy chain CDR3, a light chain CDR1, a light chain CDR2, a light chain CDR3, and a combination thereof.

In one embodiment, the at least one CDR comprises a light chain CDR3. In one embodiment, the at least one CDR comprises a light chain CDR3 and a heavy chain CDR3.

In one embodiment, the at least one CDR is a CDR3 of light and/or a heavy chain, and the at least one non-CDR sequence is a loop 4 sequence, wherein the loop 4 sequence comprises one or more histidine substitutions.

In one embodiment, the at least one CDR is a CDR3 of light and/or a heavy chain, and the at least one non-CDR sequence is an N-terminal sequence, wherein the N-terminal sequence comprises one or more histidine substitutions.

In one embodiment, the at least one CDR is a CDR3 of a light chain, the at least one non-CDR sequence comprises an N-terminal sequence with one or more histidine substitutions and a loop 4 sequence with one or more histidine substitutions.

In one embodiment, the at least one CDR is a CDR3 of a heavy chain, the at least one non-CDR sequence comprises an N-terminal sequence with one or more histidine substitutions and a loop 4 sequence with one or more histidine substitutions.

In one embodiment, the his-modified immunoglobulin variable domain binds an antigen of interest at pH 7-7.4 (e.g., pH 7.2) with a $K_D$ of about $10^{-7}$ or less (e.g., $10^{-8}$, $10^{-9}$, $10^{-10}$, $10^{-11}$, $10^{-12}$), wherein the his-modified immunoglobulin variable domain comprises a CDR1 wherein all non-antigen-binding amino acid residues are substituted with histidine.

In one embodiment, the his-modified immunoglobulin variable domain binds an antigen of interest at pH 7-7.4 (e.g., pH 7.2) with a $K_D$ of about $10^{-7}$ or less (e.g., $10^{-8}$, $10^{-9}$, $10^{-10}$, $10^{-11}$, $10^{-12}$), wherein the his-modified immunoglobulin variable domain comprises a CDR2 wherein all non-antigen-binding amino acid residues are substituted with histidine.

In one embodiment, the his-modified immunoglobulin variable domain binds an antigen of interest at pH 7-7.4 (e.g., pH 7.2) with a $K_D$ of about $10^{-7}$ or less (e.g., $10^{-8}$, $10^{-9}$, $10^{-10}$, $10^{-11}$, $10^{-12}$), wherein the his-modified immunoglobulin variable domain comprises a CDR3 wherein all non-antigen-binding amino acid residues are substituted with histidine.

In one aspect, use of a method as described herein in the manufacture of a medicament for treating a human disease or disorder is provided. In one embodiment, the medicament is an antibody. In a specific embodiment, the antibody is a human antibody.

In one aspect, use of a his-modified variable domain as described herein in the manufacture of a medicament for treating a human disease or disorder is provided. In one embodiment, the medicament is an antibody. In a specific embodiment, the antibody is a human antibody.

In one aspect, use of a method or his-modified variable domain as described herein in the manufacture of a medicament for treating a human disease or disorder is provided, wherein the medicament comprises an antigen-binding protein selected from an antibody, a multi-specific antibody (e.g., a bi-specific antibody), an scFv, a bi-specific scFv, a diabody, a triabody, a tetrabody, a V-NAR, a VHH, a VL, a F(ab), a F(ab)2, a DVD (i.e., dual variable domain antigen-binding protein), an SVD (i.e., single variable domain antigen-binding protein), or a bispecific T-cell engager (i.e., a BiTE).

In one aspect, a method as described herein is employed to generate a heavy and a κ or a λ light chain variable region sequence for making a human antigen-binding protein, further comprising fusing heavy and/or light chain his-modified variable region sequences (directly or through a linker) to human heavy and light chain constant region sequences to form fused sequences, expressing the fused sequences in a cell, and recovering an expressed antigen-binding protein comprising the fused sequences. In various embodiments, the human heavy chain constant regions are selected from IgM, IgD, IgA, IgE and IgG. In various specific embodiments, the IgG is selected from an IgG1, an IgG2, an IgG3 and an IgG4. In various embodiments, the human heavy chain constant region is selected from a sequence comprising a $C_H1$, a hinge, a $C_H2$, a $C_H3$, a $C_H4$, and a combination thereof. In a specific embodiment the combination is a $C_H1$, a hinge, a $C_H2$, and a $C_H3$. In a specific embodiment the combination is a $C_H1$, a $C_H2$, and a $C_H3$. In a specific embodiment the combination is a hinge, a $C_H2$, and a $C_H3$. In a specific embodiment the combination is a hinge, a $C_H2$, and a $C_H3$.

In one aspect, a biological system is provided for generating an antibody or an antibody variable domain that binds a target antigen at a neutral pH but exhibits reduced binding of the same antigen at an acidic pH (e.g., pH 5.0-6.0). The biological system comprises a non-human animal, e.g., a rodent (e.g, a mouse or rat) that has a rearranged light chain sequence (e.g., a rearranged V-J) that comprises one or more histidine modifications. In various aspects, the one or more histidine modifications are in the light chain CDR3 codon. In various aspects, the non-human animal comprises a human or humanized heavy chain immunoglobulin locus. In various aspects, the non-human animal comprises a replacement of endogenous non-human heavy chain variable gene segments with one or more human heavy chain $V_H$, $D_H$, and $J_H$ segments, wherein the human segments are operably linked to a non-human immunoglobulin constant region. In various aspects, non-human animals with universal light chains comprising light chain variable domains with substitutions of non-histidine residues for histidine residues are provided. In various aspects these histidine-modified universal light chain non-human animals (e.g., rodents, e.g., mice) are referred to as histidine-universal light chain mice, histidine-ULC mice, or HULC mice.

Thus, in one aspect, provided herein is a genetically modified non-human animal that comprises in its germline an immunoglobulin light chain locus that comprises a single rearranged human immunoglobulin light chain variable region gene sequence comprising human $V_L$ and $J_L$ segment sequences, wherein the single rearranged human immunoglobulin light chain variable region sequence comprises a substitution of at least one non-histidine codon with a histidine codon. In one embodiment, the single rearranged human immunoglobulin variable region sequence is operably linked to an immunoglobulin light chain constant region gene sequence. In one embodiment, the immunoglobulin light chain constant region gene sequence is a non-human immunoglobulin light chain constant region gene sequence. In one embodiment, the non-human immunoglobulin light chain constant region gene sequence is an endogenous immunoglobulin light chain constant region gene sequence. In one embodiment, the non-human animal lacks a functional unrearranged immunoglobulin light chain variable region. In one embodiment, the immunoglobulin light chain locus is at an endogenous non-human immunoglobulin light chain locus.

In one embodiment, the animal further comprises in its germline an immunoglobulin heavy chain locus that comprises an unrearranged immunoglobulin heavy chain variable region gene sequence comprising human $V_H$, $D_H$, and $J_H$ segments operably linked to an immunoglobulin heavy chain constant region gene sequence. In one embodiment, the immunoglobulin heavy chain constant region gene sequence is a non-human heavy chain constant region gene sequence. In one embodiment, the non-human heavy chain constant region gene sequence is an endogenous immunoglobulin heavy chain constant region gene sequence. In one embodiment, the immunoglobulin heavy chain locus is at an endogenous immunoglobulin heavy chain locus.

In one embodiment, the substitution of at least one non-histidine codon with a histidine codon is in the nucleotide sequence encoding a complementary determining region (CDR). In one embodiment, the substitution of at least one non-histidine codon with a histidine codon is in the nucleotide sequence encoding a CDR3. In one embodiment, the substitution is of one, two, three, four, or more CDR3 codons. In one aspect, the single rearranged human immunoglobulin light chain variable region sequence comprised at the immunoglobulin light chain locus is derived from a human Vκ1-39 or Vκ3-20 gene segment. In one embodiment, the single rearranged human immunoglobulin light chain variable region is derived from a rearranged Vκ1-39/Jκ5 or Vκ3-20/Jκ1 gene sequence. In one embodiment, the single rearranged human immunoglobulin light chain variable region is derived from a rearranged Vκ1-39/Jκ5 gene sequence, and the Vκ1-39/Jκ5 gene sequence comprises a replacement of at least one non-histidine codon with a histidine codon designed to express a histidine at a position selected from 105, 106, 108, 111, and a combination thereof. In another embodiment, the single rearranged human immunoglobulin light chain variable region is derived from a rearranged Vκ3-20/Jκ1 gene sequence, and the Vκ3-20/Jκ1 gene sequence comprises a replacement of at least one non-histidine codon with a histidine codon designed to express a histidine at a position selected from 105, 106, 107, 109, and a combination thereof.

In one aspect, the non-human animal described herein comprises a population of B cells in response to an antigen of interest that is enriched for antibodies that exhibit a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, the decrease in $t_{1/2}$ at an acidic pH as compared to a neutral pH is about 30 fold or more.

In one embodiment, the animal expresses an antibody comprising a human immunoglobulin light chain variable domain with a substitution of at least one non-histidine residue with a histidine residue at an amino acid position encoded by the at least one codon substituted in the immunoglobulin light chain variable region gene sequence. In one embodiment, the animal expresses an antibody that retains a substitution of at least one non-histidine residue with a histidine residue in an expressed human immunoglobulin light chain variable domain, despite somatic hypermutations.

In one embodiment, the non-human animal is a mammal. In one embodiment, the mammal is a rodent, e.g., a rat or a mouse. In one embodiment, the non-human animal is a mouse. Thus, in one aspect, also provided herein is a genetically modified mouse comprising in its germline an immunoglobulin light chain locus that comprises a single rearranged human immunoglobulin light chain variable region gene sequence comprising human $V_L$ and $J_L$ segment sequences, wherein the single rearranged human immunoglobulin light chain variable region sequence comprises a substitution of at least one non-histidine codon with a histidine. In one embodiment, the mouse lacks a functional unrearranged immunoglobulin light chain variable region.

In one embodiment, the single rearranged immunoglobulin light chain variable region gene sequence in the germline of the mouse is operably linked to an immunoglobulin light chain constant region gene sequence. In one embodiment, the immunoglobulin light chain constant region gene sequence is selected from a rat or a mouse immunoglobulin light chain constant region gene sequence. In one embodiment, the immunoglobulin light chain constant region gene sequence is a mouse sequence. In one embodiment, the immunoglobulin light chain locus is at an endogenous mouse immunoglobulin light chain locus.

In a further embodiment, the mouse also comprises in its germline an immunoglobulin heavy chain locus that comprises an unrearranged immunoglobulin heavy chain variable region sequence comprising human $V_H$, $D_H$, and $J_H$ segments operably linked to an immunoglobulin heavy chain constant region gene sequence. In one aspect, the immunoglobulin heavy chain constant region gene sequence is a rat or a mouse heavy chain constant region gene sequence. In one embodiment, the immunoglobulin heavy chain constant region gene sequence is a mouse sequence. In one embodiment, the immunoglobulin heavy chain locus is at an endogenous mouse immunoglobulin heavy chain locus.

In one aspect, the mouse comprises a substitution of at least one non-histidine codon with a histidine codon wherein the substitution is in the nucleotide sequence encoding a CDR. In one embodiment, the substitution is in a CDR3 codon, e.g., in one, two, three, four, or more CDR3 codons. In one embodiment, the immunoglobulin light chain locus of the mouse comprises the single rearranged human immunoglobulin light chain variable region sequence derived from a human Vκ1-39 or Vκ3-20 gene segment, e.g., the single rearranged immunoglobulin light chain variable region sequence is derived from a rearranged Vκ1-39/Jκ5 or Vκ3-20/Jκ1 gene sequence. In one embodiment, the single rearranged immunoglobulin light chain variable region sequence is derived from a rearranged Vκ1-39/Jκ5 gene sequence and the Vκ1-39/Jκ5 sequence comprises a replacement of at least one non-histidine codon with a histidine codon designed to express a histidine at a position selected from 105, 106, 108, 111, and a combination thereof. In one embodiment, such replacement is designed to replace histidines at positions 105, 106, 108, and 111. In another embodiment, such replacement is designed to replace histidines at positions 106, 108, and 111.

In another embodiment, the single rearranged immunoglobulin light chain variable region sequence is derived from a rearranged Vκ3-20/Jκ1 gene sequence and the Vκ3-20/Jκ1 sequence comprises a replacement of at least one non-histidine codon with a histidine codon designed to express a histidine at a position selected from 105, 106, 107, 109, and a combination thereof. In one embodiment, such replacement is designed to replace histidines at positions 105, 106, 107, and 109. In another embodiment, such replacement is designed to replace histidines at positions 105, 106, and 109.

In one embodiment, the mouse described herein comprises a population of B cells in response to an antigen of interest that is enriched for antibodies that exhibit a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, the decrease in $t_{1/2}$ at an acidic pH as compared to a neutral pH is about 30 fold or more.

In one embodiment, the mouse described herein expresses a population of antigen-specific antibodies in response to an antigen of interest wherein all antibodies comprise (a) immunoglobulin light chain variable domains derived from the same single rearranged human light chain variable region gene sequence which comprises a substitution of at least one non-histidine codon with a histidine codon, and (b) immunoglobulin heavy chains comprising heavy chain variable domains derived from a repertoire of human heavy chain V, D, and J segments.

Also provided herein is a non-human locus, e.g., mouse locus, comprising a single rearranged human immunoglobulin light chain variable region gene sequence comprising human $V_L$ and $J_L$ segment sequences, wherein the single rearranged human immunoglobulin light chain variable region gene sequence comprises a substitution of at least one non-histidine codon with a histidine codon. In one embodiment, the locus is comprised in the germline of a non-human animal. In one embodiment, the locus comprises the single rearranged human immunoglobulin light chain variable region gene sequence derived from a human Vκ1-39 or Vκ3-20 gene segment, e.g., derived from a rearranged Vκ1-39/Jκ5 or Vκ3-20/Jκ1 gene sequence. In one embodiment, wherein the single rearranged human immunoglobulin light chain variable region gene sequence present in the locus is derived from the rearranged Vκ1-39/Jκ5 sequence, the substitution of at least one non-histidine codon with a histidine codon is designed to express a histidine at a position selected from 105, 106, 108, 111, and a combination thereof. In another embodiment, wherein the single rearranged human immunoglobulin light chain variable region gene sequence present in the locus is derived from the rearranged Vκ3-20/Jκ1 sequence, the substitution of at least one non-histidine codon with a histidine codon is designed to express a histidine at a position selected from 105, 106, 107, 109, and a combination thereof. In various embodiments, the non-human loci described herein may be generated using methods described below for making a genetically modified non-human animal.

In yet another aspect, provided herein is a method for making a non-human animal that comprises a genetically modified immunoglobulin light chain locus in its germline, wherein the method comprises modifying a genome of a non-human animal to delete or render non-functional endogenous immunoglobulin light chain V and J segments in an immunoglobulin light chain locus, and placing in the genome a single rearranged human light chain variable region gene sequence comprising a substitution of at least one non-histidine codon with a histidine codon. In one embodiment, such method results in a genetically modified non-human animal that comprises a population of B cells enriched for antibodies exhibiting pH-dependent binding to the antigen of interest. In one embodiment, the single rearranged human immunoglobulin light chain variable region sequence placed in the genome is derived from a human Vκ1-39 or Vκ3-20, e.g., a rearranged Vκ1-39/Jκ5 or Vκ3-20/Jκ1 gene sequence. Thus, in the embodiment wherein the single rearranged human immunoglobulin light chain variable region sequence is derived from a rearranged Vκ1-39/Jκ5, the substitution of at least one non-histidine codon with a histidine codon is designed to express a histidine at a position selected from 105, 106, 108, 111, and a combination thereof. In an embodiment wherein the single rearranged human immunoglobulin light chain variable region sequence is derived from a rearranged $V\kappa^3$-20/Jκ1, the substitution of at least one non-histidine codon with a histidine codon is designed to express a histidine at a position selected from 105, 106, 107, 109, and a combination thereof.

In another aspect, provided herein is a method of generating an antibody that exhibits pH-dependent binding to an antigen of interest comprising (a) generating a mouse described herein (e.g., a mouse that comprises in its germline an immunoglobulin light chain locus that comprises a single rearranged human immunoglobulin light chain variable region sequence comprising human $V_L$ and $J_L$ segment sequences and a substitution of at least one non-histidine codon with a histidine codon in its rearranged light chain variable region sequence), (b) immunizing the mouse with an antigen of interest, and (c) selecting an antibody that binds to the antigen of interest with a desired affinity at a neutral pH while displaying reduced binding to the antigen at an acidic pH. In one embodiment, the method results in a generation of an antibody that exhibits $t_{1/2}$ at acidic pH and 37° C. of about 2 minutes or less. In one embodiment, the method results in a generation of an antibody that displays a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold.

In other aspects, provided herein are additional methods of generating an antibody that exhibits pH-dependent binding to an antigen of interest. One such method comprises (a) selecting a first antibody that binds to an antigen of interest with a desired affinity, (b) modifying an immunoglobulin light chain nucleotide sequence of the first antibody to comprise a substitution of at least one non-histidine codon with a histidine codon, (c) expressing an immunoglobulin heavy chain of the first antibody and the modified immunoglobulin light chain in a cell, and (d) selecting a second antibody expressed in the cell that retains a desired affinity for the antigen of interest at neutral pH and displays reduced binding to the antigen of interest at an acidic pH. In one embodiment, the immunoglobulin light chain nucleotide sequence of the first antibody comprises a single rearranged human immunoglobulin light chain variable region sequence. In one embodiment, the first antibody is generated in a non-human animal, e.g., a mouse, comprising an immunoglobulin light chain sequence derived from a single rearranged human immunoglobulin light chain variable region sequence, and the modification of the immunoglobulin light chain is made in the single rearranged human immunoglobulin variable region sequence. In one embodiment, the first antibody is generated in a non-human animal, e.g., a mouse, further comprising an immunoglobulin heavy chain sequence derived from a repertoire of human $V_H$, $D_H$, and $J_H$ segments. In one embodiment, the single rearranged human immunoglobulin light chain variable region sequence is selected from Vκ1-39/Jκ5 and Vκ3-20/Jκ1 gene sequence. In an embodiment, wherein the single rearranged human immunoglobulin light chain variable region sequence is Vκ1-39/Jκ5, the modification in the immunoglobulin light chain nucleotide sequence of the first antibody is made in the CDR3 codon at a position selected from 105, 106, 108, 111, and a combination thereof. In an embodiment wherein the single rearranged human immunoglobulin light chain variable region sequence is Vκ3-20/Jκ1, the modification in the immunoglobulin light chain nucleotide sequence of the first antibody is made in the CDR3 codon at a position selected from 105, 106, 107, 109, and a combination thereof.

In one embodiment, the method of generating an antibody that exhibits pH-dependent binding to an antigen of interest described herein results in an antibody that displays a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, the method of generating the antibody results in an antibody that exhibits a $t_{1/2}$ at acidic pH and 37° C. of about 2 minutes or less.

Genetically modified immunoglobulin heavy chain loci in the germline genome of non-human animals are provided, wherein the immunoglobulin heavy chain loci comprise a genetically modified unrearranged heavy chain variable region nucleotide sequence (e.g., one or more genetically modified human $V_H$, D, and/or $J_H$ gene segment), wherein the unrearranged heavy chain variable region nucleotide sequence comprises an addition of at least one histidine codon or a substitution of at least one endogenous non-histidine codon with a histidine codon. In various embodiments, the genetically modified unrearranged heavy chain variable region nucleotide sequence comprises at least one histidine codon in at least one reading frame that encodes an immunoglobulin heavy chain variable domain. In various embodiments, the unrearranged heavy chain variable region nucleotide sequence comprising the at least one histidine codon is operably linked to a human or non-human heavy chain constant region nucleotide sequence (e.g., a heavy chain constant region nucleotide sequence that encodes an immunoglobulin isotype selected from IgM, IgD, IgA, IgE, and IgG).

Non-human animals (mammals, e.g., rodents such as mice, rats, or hamsters) are provided that are genetically engineered to contain immunoglobulin heavy chain genomic loci in their germline genome, wherein the genomic loci comprise an unrearranged heavy chain variable region nucleotide sequence (e.g., one or more genetically modified human $V_H$, D, and/or $J_H$ gene segments), wherein the unrearranged heavy chain variable region nucleotide sequence comprises an addition of at least one histidine codon or a substitution of at least one endogenous non-histidine codon with a histidine codon. In various embodiments, the genome of the non-human animals comprises a modification (i) that deletes or renders nonfunctional all, or substantially all, endogenous immunoglobulin $V_H$, D, and/or $J_H$ gene segments (e.g., via insertion of a nucleotide sequence, e.g., an exogenous nucleotide sequence, in the immunoglobulin locus or via non-functional rearrangement or inversion of endogenous $V_H$, D, and/or $J_H$ gene segments); and (ii) that introduces an unrearranged human heavy chain variable region nucleotide sequence (e.g., genetically modified human $V_H$, D, or $J_H$ gene segments), wherein the unrearranged heavy chain variable region nucleotide sequence comprises an addition of at least one histidine codon or a substitution of at least one endogenous non-histidine codon with a histidine codon. In various embodiments, the unrearranged heavy chain variable region nucleotide sequence is present at an endogenous locus (i.e., where the unrearranged heavy chain variable region nucleotide sequence is located in a wild-type non-human animal) or present ectopically (e.g., at a locus different from the endogenous immunoglobulin heavy chain locus in its genome) or within its endogenous locus (e.g., within an immunoglobulin variable locus, wherein the endogenous locus is placed or moved to a different location in the genome). In various embodiments, the immunoglobulin heavy chain variable region nucleotide sequence is operably linked to a human or non-human heavy chain constant region nucleotide sequence (e.g., a heavy chain constant region nucleotide sequence that encodes an immunoglobulin isotype selected from IgM, IgD, IgA, IgE, and IgG).

Genetically modified non-human animals are provided that are capable of expressing a genetically modified immunoglobulin heavy variable domain comprising one or more histidines, wherein the one or more histidines are not encoded by a germline gene segment of a corresponding wild-type non-human animal.

Genetically modified non-human animals are provided that comprise a B cell population that is characterized by rearranged immunoglobulin heavy chain variable genes that encode an immunoglobulin heavy chain variable domain with one or more histidines that are not encoded by a germline gene segment of a corresponding wild-type non-human animal.

Methods and compositions are provided for making non-human animals that comprise a genetically modified immunoglobulin heavy chain variable locus comprising an unrearranged human heavy chain variable region nucleotide sequence containing one or more histidine codons in at least one reading frame that encodes a heavy chain variable domain.

Methods and compositions are provided for non-human animals that make antigen-binding proteins that exhibit a pH-dependent binding of antigen. Methods and compositions are provided for making non-human animals that have B cell populations, or antibody populations, that are enriched (as compared with corresponding wild-type animals) with antigen-binding proteins that are pH-dependent, e.g., in particular, heavy chain variable domains, and/or antigen-binding fragments thereof.

In one aspect, a genetically modified immunoglobulin locus in a germline genome of a non-human animal is provided comprising an unrearranged human heavy chain variable region nucleotide sequence, wherein the unrearranged heavy chain variable region nucleotide sequence comprises an addition of least one histidine codon or a substitution of at least one endogenous non-histidine codon with a histidine codon.

In one embodiment, the non-human animal is a mammal, including a rodent, e.g., a mouse, a rat, or a hamster.

In one embodiment, the added or substituted histidine codon is present in an immunoglobulin heavy chain gene segment selected from a human $V_H$ gene segment, a human D gene segment, a human $J_H$ gene segment, and a combination thereof. In one embodiment, the immunoglobulin heavy chain gene segment is selected from a human germline $V_H$ gene segment, a human germline D gene segment, a human germline $J_H$ gene segment, and a combination thereof.

In one embodiment, the human V gene segment ($V_H$) is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a combination thereof.

In one embodiment, the human D gene segment is selected from the group consisting of D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, and a combination thereof.

In one embodiment, the human J gene segment is selected from the group consisting of $J_H$1, $J_H$2, $J_H$3, $J_H$4, $J_H$5, $J_H$6, and a combination thereof.

In one embodiment, the added or substituted histidine codon is present in the unrearranged heavy chain variable region nucleotide sequence that encodes an N-terminal region, a loop 4 region, a CDR1, a CDR2, a CDR3, or a combination thereof.

In one embodiment, the unrearranged heavy chain variable region nucleotide sequence comprises 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more, 26 or more, 27 or more, 28 or more, 29 or more, 30 or more, 31 or more, 32 or more, 33 or more, 34 or more 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of histidine codons.

In one embodiment, the unrearranged heavy chain variable region nucleotide sequence is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H$1, a hinge, a $C_H$2, a $C_H$3, and a combination thereof. In one embodiment, the heavy chain constant region nucleotide sequence comprises a $C_H$1, a hinge, a $C_H$2, and a $C_H$3 ($C_H$1-hinge-$C_H$2-$C_H$3).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H$2 or a $C_H$3, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H$2 amino acid sequence comprising at least one modification between amino acid residues at positions 252 and 257, wherein the modification increases the affinity of the human $C_H$2 amino acid sequence to FcRn in an acidic environment (e.g., in an endosome where pH ranges from about 5.5 to about 6.0).

In one embodiment, the heavy chain constant region nucleotide sequence encodes a human $C_H$2 amino acid sequence comprising at least one modification between amino acid residues at positions 307 and 311, wherein the modification increases the affinity of the $C_H$2 amino acid sequence to FcRn in an acidic environment (e.g., in an endosome where pH ranges from about 5.5 to about 6.0).

In one embodiment, the heavy chain constant region nucleotide sequence encodes a human $C_H$3 amino acid sequence, wherein the $C_H$3 amino acid sequence comprises at least one modification between amino acid residues at positions 433 and 436, wherein the modification increases the affinity of the $C_H$3 amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising one or more human $V_H$, D, and/or $J_H$ gene segments having one or more histidine codons, wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a human Adam6a gene. In one embodiment, the Adam6b gene is a non-human Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, the genetically modified immunoglobulin locus described herein comprises a B cell population that, upon stimulation with an antigen of interest, is capable of producing antigen-binding proteins, e.g., antibodies, comprising a heavy chain variable domain with one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification described herein.

In one aspect, a genetically modified immunoglobulin locus in a germline genome of a non-human animal is provided comprising an unrearranged human heavy chain variable region nucleotide sequence, wherein the human unrearranged heavy chain variable region nucleotide sequence comprises a substitution of at least one endogenous non-histidine codon with a histidine codon.

In one embodiment, the non-human animal is a mammal, including a rodent, e.g., a mouse, a rat, or a hamster.

In one embodiment, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of the endogenous non-histidine codons are replaced with histidine codons.

In one embodiment, the endogenous non-histone codon encodes the amino acid selected from Y, N, D, Q, S, W, and R.

In one embodiment, the endogenous non-histidine codon that is substituted by the histidine codon is present in an unrearranged heavy chain variable region nucleotide sequence that encodes an immunoglobulin variable domain selected from an N-terminal region, a loop 4 region, a CDR1, a CDR2, a CDR3, a combination thereof.

In one embodiment, the substituted histidine codon is present in an unrearranged heavy chain variable region nucleotide sequence that encodes a complementary determining region (CDR) selected from a CDR1, a CDR2, a CDR3, and a combination thereof.

In one embodiment, the substituted histidine codon is present in an unrearranged heavy chain variable region nucleotide sequence that encodes a frame region (FR) selected from FR1, FR2, FR3, FR4, and a combination thereof.

In one embodiment, the unrearranged heavy chain variable region nucleotide sequence comprises a genetically modified human $V_H$ gene segment, wherein one or more endogenous non-histidine codon in at least one reading frame of the human $V_H$ gene segment has been replaced with a histidine codon.

In one embodiment, the human unrearranged heavy chain variable region nucleotide sequence comprises a modification that replaces at least one endogenous non-histidine codon of a human $V_H$ gene segment with a histidine codon, wherein the human $V_H$ gene segment is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-$2^6$, $V_H$2-70, $V_H$3-7, $V_H$3-9, $V_H$3-11, $V_H$3-13, $V_H$3-15, $V_H$3-16, $V_H$3-20, $V_H$3-21, $V_H$3-$2^3$, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-$2^8$, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a combination thereof.

In one embodiment, the human unrearranged heavy chain variable region nucleotide sequence comprises a genetically modified human $J_H$ gene segment, wherein one or more endogenous non-histidine codon in at least one reading frame of the human $J_H$ gene segment has been replaced with a histidine codon.

In one embodiment, the human unrearranged heavy chain variable region nucleotide sequence comprises a modification that replaces at least one endogenous non-histidine codon of a human $J_H$ segment with a histidine codon, wherein the human $J_H$ gene segment is selected from the group consisting of $J_H1$, $J_H2$, $J_H3$, $J_H4$, $J_H5$, $J_H6$, and a combination thereof.

In one embodiment, the substituted histidine codon is present in a heavy chain variable region nucleotide sequence that encodes part of a CDR3. In one embodiment, the part of CDR3 comprises an amino acid sequence derived from a reading frame of a genetically modified human D gene segment comprising a modification that replaces at least one endogenous non-histidine codon in the reading frame with a histidine codon.

In one embodiment, the endogenous non-histidine codon that is substituted with a histidine codon encodes the amino acid selected from Y, N, D, Q, S, W, and R.

In one embodiment, the substituted histidine codon is present in at least one reading frame of the human D gene segment that is most frequently observed in VELOCIMMUNE® humanized immunoglobulin mice.

In one embodiment, the reading frame of the genetically modified human D gene segment that encodes part of CDR3 is selected from a hydrophobic frame, a stop frame, and a hydrophilic frame.

In one embodiment, the reading frame is a hydrophobic frame of a human D gene segment.

In one embodiment, the hydrophobic frame of the human D gene segment comprises a nucleotide sequence that encodes the amino acid sequence selected from the group consisting of D1-1 (GTTGT; SEQ ID NO: 88), D1-7 (GITGT; SEQ ID NO: 89), D1-20 (GITGT; SEQ ID NO: 89), and D1-26 (GIVGAT; SEQ ID NO: 90), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D2-2 (DIVVVPAAI; SEQ ID NO: 92), D2-8 (DIVLMVYAI; SEQ ID NO: 94), D2-15 (DIVVVVAAT; SEQ ID NO: 95), and D2-21 (HIVVVTAI; SEQ ID NO: 97), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D3-3 (ITIFGVVII; SEQ ID NO: 98), D3-9 (ITIF*LVII; SEQ ID NO: 99, SEQ ID NO:100), D3-10 (ITMVRGVII; SEQ ID NO:101), D3-16 (IMITFGGVIVI; SEQ ID NO:102), and D3-22 (ITMIVVVIT; SEQ ID NO:103), and the human D gene segment further comprises a modification that replaces at least one endogenous codon in the nucleotide sequence with a histidine codon.

In one embodiment, the hydrophobic frame of the human D gene segment comprises a nucleotide sequence that encodes the amino acid sequence selected from the group consisting of D4-4 (TTVT; SEQ ID NO: 105), D4-11 (TTVT; SEQ ID NO:105), D4-17 (TTVT; SEQ ID NO:105), D4-23 (TTVVT; SEQ ID NO: 106) and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D5-5 (VDTAMV; SEQ ID NO: 107), D5-12 (VDIVATI; SEQ ID NO: 108), D5-18 (VDTAMV; SEQ ID NO:107), and D5-24 (VEMATI; SEQ ID NO:109), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D6-6 (SIAAR; SEQ ID NO: 111), D6-13 (GIAAAG; SEQ ID NO: 113), and D6-19 (GIAVAG; SEQ ID NO:115), and the human D gene segment further comprises a modification that replaces at least one endogenous non-histidine codon in the nucleotide sequence with a histidine codon.

In one embodiment, the hydrophobic frame comprises a nucleotide sequence that encodes human D7-27 (LTG), and the human D gene segment further comprises a modification that replaces at least one endogenous non-histidine codon in the nucleotide sequence with a histidine codon.

In one embodiment, the reading frame is a stop reading frame of a human D gene segment.

In one embodiment, the stop reading frame of the human D gene segment comprises a nucleotide sequence that encodes the amino acid sequence selected from the group consisting of D1-1 (VQLER; SEQ ID NO:8), D1-7 (V*LEL), D1-20(V*LER), D1-26 (V*WELL; SEQ ID NO: 12), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D2-2 (RIL**YQLLY; SEQ ID NO:14), D2-8 (RILY*WCMLY; SEQ ID NO:16 and SEQ ID NO: 17), D2-15 (RIL*WW*LLL), and D2-21 (SILWW*LLF; SEQ ID NO:19), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D3-3 (VLRFLEWLLY; SEQ ID NO:21), D3-9 (VLRYFDWLL*; SEQ ID NO:23), D3-10 (VLL-WFGELL*; SEQ ID NO:25), D3-16 (VL*LRLGELSLY; SEQ ID NO:27), and D3-22 (VLL***WLLL; SEQ ID NO:29), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D4-4 (*LQ*L), D4-11 (*LQ*L), D4-17

(*LR*L), and D4-23 (*LRW*L), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D5-5 (WIQLWL; SEQ ID NO:35); D5-12 (WI*WLRL; SEQ ID NO:37), D5-18 (WIQLWL; SEQ ID NO:35), and D5-24 (*RWLQL; SEQ ID NO:39), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D6-6 (V*QLV), D6-13 (V*QQLV; SEQ ID NO:41), and D6-19 (V*QWLV; SEQ ID NO:43), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes D7-27 (*LG), and the human D gene segment further comprises a modification that replaces at least one endogenous codon of the human D gene segment in the nucleotide sequence with a histidine codon.

In one embodiment, the reading frame is a hydrophilic frame of a human D gene segment.

In one embodiment, the hydrophilic frame of the human D gene segment comprises a nucleotide sequence that encodes the amino acid sequence selected from the group consisting of D1-1 (YNWND; SEQ ID NO: 45), D1-7 (YNWNY; SEQ ID NO: 47), D1-20 (YNWND; SEQ ID NO: 45), and D1-26 (YSGSYY; SEQ ID NO:49), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 46, SEQ ID NO: 48, SEQ ID NO: 50, and a combination thereof.

In one embodiment, the hydrophilic frame of the human D gene segment comprises a nucleotide sequence that encodes the amino acid sequence selected from the group consisting of D2-2 (GYCSSTSCYT; SEQ ID NO:51), D2-8 (GYCTNGVCYT; SEQ ID NO: 53), D2-15 (GYCSGGSCYS; SEQ ID NO:55), and D2-21 (AYCGGDCYS; SEQ ID NO:57), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 52, SEQ ID NO: 54, SEQ ID NO: 56, SEQ ID NO: 58, and a combination thereof.

In one embodiment, the hydrophilic frame of the human D gene segment comprises a nucleotide sequence that encodes the amino acid sequence selected from the group consisting of D3-3 (YYDFWSGYYT; SEQ ID NO:59), D3-9 (YYDILTGYYN; SEQ ID NO:61), D3-10 (YYYGSGSYYN; SEQ ID NO:63), D3-16 (YYDYVWGSYRYT; SEQ ID NO:65), and D3-22 (YYYDSSGYYY; SEQ ID NO:67), and the human D gene segment further comprises a modification that replaces at least one endogenous codon in the nucleotide sequence with a histidine codon. In one embodiment, the hydrophilic frame comprises a nucleotide sequence encodes the amino acid sequence selected from the group consisting of SEQ ID NO: 60, SEQ ID NO: 62, SEQ ID NO: 64, SEQ ID NO: 66, SEQ ID NO: 68, and a combination thereof.

In one embodiment, the hydrophilic frame of the human D gene segment comprises a nucleotide sequence that encodes the amino acid sequence selected from the group consisting of D4-4 (DYSNY; SEQ ID NO:69), D4-11 (DYSNY; SEQ ID NO:69), D4-17 (DYGDY; SEQ ID NO:71), and D4-23 (DYGGNS; SEQ ID NO:73), and the human D gene segment comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 70, SEQ ID NO: 72, SEQ ID NO: 74, and a combination thereof.

In one embodiment, the hydrophilic frame of the human D gene segment comprises a nucleotide sequence that encodes the amino acid sequence selected from the group consisting of D5-5 (GYSYGY; SEQ ID NO:75), D5-12 (GYSGYDY; SEQ ID NO:77), D5-18 (GYSYGY; SEQ ID NO:75), and D5-24 (RDGYNY; SEQ ID NO:79), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 76, SEQ ID NO: 78, SEQ ID NO: 80, and a combination thereof.

In one embodiment, the hydrophilic frame of the human D gene segment comprises a nucleotide sequence that encodes the amino acid sequence selected from the group consisting of D6-6 (EYSSSS; SEQ ID NO: 81), D6-13 (GYSSSWY; SEQ ID NO:83), and D6-19 (GYSSGWY; SEQ ID NO:85), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 82, SEQ ID NO: 84, SEQ ID NO: 86, SEQ ID NO: 76, and a combination thereof.

In one embodiment, the hydrophilic frame of the human D gene segment comprises a nucleotide sequence that encodes D7-27 (NWG), and the human D gene segment further comprises a modification that replaces at least one endogenous codon in the nucleotide sequence a histidine codon.

In one embodiment, the hydrophilic frame of the human D gene segment comprises a nucleotide sequence that encodes the amino acid sequence selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, and a combination thereof.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ ($C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified locus comprises a modification that deletes or renders non-functional all or substantially all endogenous $V_H$, D, and $J_H$ gene segments; and the genomic locus comprises the genetically modified, unrearranged human heavy chain variable region nucleotide sequence comprising a substitution of at least one endogenous non-histidine codon with a histidine codon in at least one reading frame. In one embodiment, the genetically modified, unrearranged immunoglobulin heavy chain variable gene sequence is present at an endogenous location (i.e., where the nucleotide sequence is located in a wild-type non-human animal) or present ectopically (e.g., at a locus different from the endogenous immunoglobulin chain locus in its genome or within its endogenous locus, e.g., within an immunoglobulin variable locus, wherein the endogenous locus is placed or moved to a different location in the genome).

In one embodiment, the genetically modified locus comprises an endogenous Adam6a gene, Adam6b gene, or both, and the genetic modification does not affect the expression and/or function of the endogenous Adam6a gene, Adam6b gene, or both.

In one embodiment, the genetically modified locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification described herein.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a genetically modified immunoglobulin locus of a non-human animal comprising a human $V_H$, D, and $J_H$ gene segment is provided, wherein at least one of the human D gene segment has been inverted 5' to 3' with respect to a corresponding wild-type sequence, and wherein at least one reading frame of the inverted human D gene segment comprises a histidine codon.

In one embodiment, the non-human animal is a mammal, including a rodent, e.g., a mouse, a rat, or a hamster In one embodiment, the genetically modified immunoglobulin locus is present in a germline genome.

In one embodiment, the genetically modified immunoglobulin locus encodes an immunoglobulin heavy chain variable domain comprising one or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, or 34 or more of histidine residues.

In one embodiment, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, or all or substantially all of functional human D gene segments have inverted orientation with respect to corresponding wild type sequences.

In one embodiment, all or substantially all of endogenous immunoglobulin $V_H$, D, $J_H$ gene segments are deleted from the immunoglobulin heavy chain locus or rendered non-functional (e.g., via insertion of a nucleotide sequence, e.g., exogenous nucleotide sequence, in the immunoglobulin locus or via non-functional rearrangement or inversion of all, or substantially all, endogenous immunoglobulin $V_H$, D, $J_H$ segments), and the genetically modified immunoglobulin locus comprises a human $V_H$, D, and $J_H$ gene segments, wherein at least one of the human D gene segment is present in an inverted orientation with respect to a corresponding wild type sequence, and wherein at least one reading frame in the inverted human D gene segment comprises at least one histidine codon.

In one embodiment, the inverted human D gene segment is operably linked to a human $V_H$ gene segment, and/or human $J_H$ gene segment In one embodiment, the human D gene segment that is present in the inverted orientation relative to a corresponding wild type sequence is selected from the group consisting of D1-1, D1-7, D1-20, D1-26, D2-2, D2-8, D2-15, D2-21, D3-3, D3-9, D3-10, D3-16, D3-22, D4-4, D4-11, D4-17, D4-23, D5-5, D5-12, D5-18, D5-24, D6-6, D6-13, D6-19, D7-27, and a combination thereof.

In one embodiment, the human D gene segment that is present in the inverted orientation relative to a corresponding wild type sequence is a D1 gene segment selected from the group consisting of D1-1, D1-7, D1-20, D1-26, and a combination thereof.

In one embodiment, the human D gene segment that is present in the inverted orientation relative a corresponding wild type sequence is a D2 gene segment selected from the group consisting of D2-2, D2-8, D2-15, D2-21, and a combination thereof.

In one embodiment, the human D gene segment that is present in the inverted orientation relative to a corresponding wild type sequence is a D3 gene segment selected from the group consisting of D3-3, D3-9, D3-10, D3-16, D3-22, and a combination thereof.

In one embodiment, the human D gene segment that is present in the inverted orientation relative to a corresponding wild type sequence is a D4 gene segment selected from the group consisting of D4-4, D4-11, D4-17, D4-23, and a combination thereof.

In one embodiment, the human D gene segment that is present in the inverted orientation relative to a corresponding wild type sequence is a D5 gene segment selected from the group consisting of D5-5, D5-12, D5-18, D5-24, and a combination thereof.

In one embodiment, the human D gene segment that is present in the inverted orientation relative to a corresponding wild type sequence is a D6 gene segment selected from the group consisting of D6-6, D6-13, D6-19, and a combination thereof.

In one embodiment, the human D gene segment that is present in the inverted orientation relative to a corresponding wild type sequence is D7-27.

In one embodiment, the reading frame of the human D gene segment is selected from a stop reading frame, a hydrophilic reading frame, and a hydrophobic reading frame, and at least one reading frame of the inverted human D gene segment comprises a histidine codon.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H{}^1$, a hinge, a $C_H2$, a $C_H3$, and a combination thereof. In one embodiment, the heavy chain constant region nucleotide sequence comprises a $C_H1$, a hinge, a $C_H2$, and a $C_H3$ ($C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising at least one inverted human D gene segment as described herein wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a non-human animal is provided comprising in its germline genome a genetically modified immunoglobulin locus comprising an unrearranged human heavy chain variable region nucleotide sequence, wherein the unrearranged heavy chain variable region nucleotide sequence comprises an addition of least one histidine codon or a substitution of at least one endogenous non-histidine codon with a histidine codon.

In one embodiment, the non-human animal is a mammal, including a rodent, e.g., a mouse, a rat, or a hamster.

In one embodiment, the added or substituted histidine codon is present in an immunoglobulin heavy chain gene segment selected from a human $V_H$ gene segment, a human D gene segment, a human $J_H$ gene segment, and a combination thereof. In one embodiment, the immunoglobulin heavy chain gene segment is selected from a human germline $V_H$ gene segment, a human germline D gene segment, a human germline $J_H$ gene segment, and a combination thereof.

In one embodiment, the human $V_H$ gene segment is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a combination thereof.

In one embodiment, the human D gene segment is selected from the group consisting of D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, and a combination thereof.

In one embodiment, the human $J_H$ gene segment is selected from the group consisting of $J_H$1, $J_H$2, $J_H$3, $J_H$4, $J_H$5, $J_H$6, and a combination thereof.

In one embodiment, the added or substituted histidine codon is present in the unrearranged heavy chain variable region nucleotide sequence encoding an N-terminal region, a loop 4 region, a CDR1, a CDR2, a CDR3, or a combination thereof.

In one embodiment, the unrearranged heavy chain variable region nucleotide sequence comprises 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more, 26 or more, 27 or more, 28 or more, 29 or more, 30 or more, 31 or more, 32 or more, 33 or more, 34 or more 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of histidine codons.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H$1, a hinge, a $C_H$2, a $C_H$3, and a combination thereof. In one embodiment, the heavy chain constant region nucleotide sequence comprises a $C_H$1, a hinge, a $C_H$2, and a $C_H$3 ($C_H$1-hinge-$C_H$2-$C_H$3).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H$2 or a $C_H$3, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising one or more human $V_H$, D, and/or $J_H$ gene segments having one or more histidine codons, wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a human Adam6a gene. In one embodiment, the Adam6b gene is a non-human Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, the non-human animal is heterozygous for the genetically modified immunoglobulin heavy chain locus, and the non-human animal is capable of expressing a human immunoglobulin heavy chain variable domain comprising at least one histidine residue derived predominantly from the genetically modified immunoglobulin heavy chain locus as described herein.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a non-human animal comprising a genetically modified immunoglobulin locus is provided, wherein the genetically modified immunoglobulin locus comprises an unrearranged human heavy chain variable region nucleotide sequence, and wherein the human unrearranged heavy chain variable region nucleotide sequence comprises a substitution of at least one endogenous non-histidine codon with a histidine codon.

In one embodiment, the non-human animal is a mammal, including a rodent, e.g., a mouse, a rat, or a hamster.

In one embodiment, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of the endogenous non-histidine codons are replaced with histidine codons.

In one embodiment, the endogenous non-histone codon encodes the amino acid selected from Y, N, D, Q, S, W, and R.

In one embodiment, the substituted histidine codon is present in an unrearranged heavy chain variable region nucleotide sequence that encodes an immunoglobulin variable domain selected from an N-terminal region, a loop 4 region, a CDR1, a CDR2, a CDR3, a combination thereof.

In one embodiment, the substituted histidine codon is present in an unrearranged heavy chain variable region nucleotide sequence that encodes a complementary determining region (CDR) selected from a CDR1, a CDR2, a CDR3, and a combination thereof.

In one embodiment, the substituted histidine codon is present in an unrearranged heavy chain variable region nucleotide sequence that encodes a frame region (FR) selected from FR1, FR2, FR3, FR4, and a combination thereof.

In one embodiment, the unrearranged heavy chain variable region nucleotide sequence comprises a genetically modified human $V_H$ gene segment, wherein one or more endogenous non-histidine codon in at least one reading frame of the human $V_H$ gene segment has been replaced with a histidine codon.

In one embodiment, the human unrearranged heavy chain variable region nucleotide sequence comprises a modification that replaces at least one endogenous non-histidine codon of a human $V_H$ gene segment with a histidine codon, wherein the human $V_H$ gene segment is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-$2^6$, $V_H$2-70, $V_H$3-7, $V_H$3-9, $V_H$3-11, $V_H$3-13, $V_H$3-15, $V_H$3-16, $V_H$3-20, $V_H$3-21, $V_H$3-$2^3$, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-$2^8$, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a combination thereof.

In one embodiment, the human unrearranged heavy chain variable region nucleotide sequence comprises a genetically modified human $J_H$ gene segment, wherein one or more endogenous non-histidine codon in at least one reading frame of the human $J_H$ gene segment has been replaced with a histidine codon.

In one embodiment, the human unrearranged heavy chain variable region nucleotide sequence comprises a modification that replaces at least one endogenous non-histidine codon of a human $J_H$ segment with a histidine codon, wherein the human $J_H$ gene segment is selected from the group consisting of $J_H$1, $J_H$2, $J_H$3, $J_H$4, $J_H$5, $J_H$6, and a combination thereof.

In one embodiment, the substituted histidine codon is present in a heavy chain variable region nucleotide sequence that encodes part of a CDR3. In one embodiment, the part of CDR3 comprises an amino acid sequence derived from a reading frame of a genetically modified human D gene segment comprising a modification that replaces at least one endogenous non-histidine codon in the reading frame with a histidine codon.

In one embodiment, the endogenous non-histidine codon that is substituted with a histidine codon encodes the amino acid selected from Y, N, D, Q, S, W, and R.

In one embodiment, the substituted histidine codon is present in at least one reading frame of the human D gene segment that is most frequently observed in VELOCIMMUNE® humanized immunoglobulin mice.

In one embodiment, the reading frame of the genetically modified human D gene segment that encodes part of CDR3 is selected from a hydrophobic frame, a stop frame, and a hydrophilic frame.

In one embodiment, the reading frame is a hydrophobic frame of a human D gene segment.

In one embodiment, the hydrophobic frame of the human D gene segment comprises a nucleotide sequence that encodes the amino acid sequence selected from the group consisting of D1-1 (GTTGT; SEQ ID NO: 88), D1-7 (GITGT; SEQ ID NO: 89), D1-20 (GITGT; SEQ ID NO: 89), and D1-26 (GIVGAT; SEQ ID NO:90), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D2-2 (DIVVVPAAI; SEQ ID NO:92), D2-8 (DIVLMVYAI; SEQ ID NO: 94), D2-15 (DIVVVVAAT; SEQ ID NO:95), and D2-21 (HIVVVTAI; SEQ ID NO: 97), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D3-3 (ITIFGVVII; SEQ ID NO:98), D3-9 (ITIF*LVII; SEQ ID NO:99, SEQ ID NO:100), D3-10 (ITMVRGVII; SEQ ID NO:101), D3-16 (IMITFGGVIVI; SEQ ID NO:102), and D3-22 (ITMIVVVIT; SEQ ID NO:103), and the human D gene segment further comprises a modification that replaces at least one endogenous codon in the nucleotide sequence with a histidine codon.

In one embodiment, the hydrophobic frame of the human D gene segment comprises a nucleotide sequence that encodes the amino acid sequence selected from the group consisting of D4-4 (TTVT; SEQ ID NO:105), D4-11 (TTVT; SEQ ID NO:105), D4-17 (TTVT; SEQ ID NO:105), D4-23 (TTVVT; SEQ ID NO: 106) and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D5-5 (VDTAMV; SEQ ID NO: 107), D5-12 (VDIVATI; SEQ ID NO:108), D5-18 (VDTAMV; SEQ ID NO:107), and D5-24 (VEMATI; SEQ ID NO:109), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D6-6 (SIAAR; SEQ ID NO:111), D6-13 (GIAAAG; SEQ ID NO:113), and D6-19 (GIAVAG; SEQ ID NO: 115), and the human D gene segment further comprises a modification that replaces at least one endogenous non-histidine codon in the nucleotide sequence with a histidine codon.

In one embodiment, the hydrophobic frame comprises a nucleotide sequence that encodes human D7-27 (LTG), and the human D gene segment further comprises a modification that replaces at least one endogenous non-histidine codon in the nucleotide sequence with a histidine codon.

In one embodiment, the reading frame is a stop reading frame of a human D gene segment.

In one embodiment, the stop reading frame of the human D gene segment comprises a nucleotide sequence that encodes the amino acid sequence selected from the group consisting of D1-1 (VQLER; SEQ ID NO:8), D1-7 (V*LEL), D1-20(V*LER), D1-26 (V*WELL; SEQ ID NO:12), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D2-2 (RIL**YQLLY; SEQ ID NO:14), D2-8 (RILY*WCMLY; SEQ ID NO:16 and SEQ ID NO: 17), D2-15 (RIL*WW*LLL), and D2-21 (SILWW*LLF; SEQ ID NO:19), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D3-3 (VLRFLEWLLY; SEQ ID NO:21), D3-9 (VLRYFDWLL*; SEQ ID NO:23), D3-10 (VLLWFGELL*; SEQ ID NO:25), D3-16 (VL*LRLGELSLY; SEQ ID NO:27), and D3-22 (VLL***WLLL; SEQ ID NO:29), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D4-4 (*LQ*L), D4-11 (*LQ*L), D4-17 (*LR*L), and D4-23 (*LRW*L), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D5-5 (WIQLWL; SEQ ID NO:35); D5-12 (WI*WLRL; SEQ ID NO:37), D5-18 (WIQLWL; SEQ ID NO:35), and D5-24 (*RWLQL; SEQ ID NO:39), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D6-6 (V*QLV), D6-13 (V*QQLV; SEQ ID NO:41), and D6-19 (V*QWLV; SEQ ID NO:43), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes D7-27 (*LG), and the human D gene segment further comprises a modification that replaces at least one endogenous codon of the human D gene segment in the nucleotide sequence with a histidine codon.

In one embodiment, the reading frame is a hydrophilic frame of a human D gene segment.

In one embodiment, the hydrophilic frame of the human D gene segment comprises a nucleotide sequence that encodes the amino acid sequence selected from the group consisting of D1-1 (YNWND; SEQ ID NO: 45), D1-7 (YNWNY; SEQ ID NO: 47), D1-20 (YNWND; SEQ ID NO: 45), and D1-26 (YSGSYY; SEQ ID NO:49), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 46, SEQ ID NO: 48, SEQ ID NO: 50, and a combination thereof.

In one embodiment, the hydrophilic frame of the human D gene segment comprises a nucleotide sequence that encodes the amino acid sequence selected from the group consisting of D2-2 (GYCSSTSCYT; SEQ ID NO:51), D2-8 (GYCTNGVCYT; SEQ ID NO: 53), D2-15 (GYCSGGSCYS; SEQ ID NO:55), and D2-21 (AYCGGDCYS; SEQ ID NO:57), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 52, SEQ ID NO: 54, SEQ ID NO: 56, SEQ ID NO: 58, and a combination thereof.

In one embodiment, the hydrophilic frame of the human D gene segment comprises a nucleotide sequence that encodes the amino acid sequence selected from the group consisting of D3-3 (YYDFWSGYYT; SEQ ID NO:59), D3-9 (YYDILTGYYN; SEQ ID NO:61), D3-10 (YYYGSGSYYN; SEQ ID NO:63), D3-16 (YYDYVWGSYRYT; SEQ ID NO:65), and D3-22 (YYYDSSGYYY; SEQ ID NO:67), and the human D gene segment further comprises a modification that replaces at least one endogenous codon in the nucleotide sequence with a histidine codon. In one embodiment, the hydrophilic frame comprises a nucleotide sequence encodes the amino acid sequence selected from the group consisting of SEQ ID NO: 60, SEQ ID NO: 62, SEQ ID NO: 64, SEQ ID NO: 66, SEQ ID NO: 68, and a combination thereof.

In one embodiment, the hydrophilic frame of the human D gene segment comprises a nucleotide sequence that encodes the amino acid sequence selected from the group consisting of D4-4 (DYSNY; SEQ ID NO:69), D4-11 (DYSNY; SEQ ID NO:69), D4-17 (DYGDY; SEQ ID NO:71), and D4-23 (DYGGNS; SEQ ID NO:73), and the human D gene segment comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 70, SEQ ID NO: 72, SEQ ID NO: 74, and a combination thereof.

In one embodiment, the hydrophilic frame of the human D gene segment comprises a nucleotide sequence that encodes the amino acid sequence selected from the group consisting of D5-5 (GYSYGY; SEQ ID NO:75), D5-12 (GYSGYDY; SEQ ID NO:77), D5-18 (GYSYGY; SEQ ID NO:75), and D5-24 (RDGYNY; SEQ ID NO:79), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 76, SEQ ID NO: 78, SEQ ID NO: 80, and a combination thereof.

In one embodiment, the hydrophilic frame of the human D gene segment comprises a nucleotide sequence that encodes the amino acid sequence selected from the group consisting of D6-6 (EYSSSS; SEQ ID NO: 81), D6-13 (GYSSSWY; SEQ ID NO:83), and D6-19 (GYSSGWY; SEQ ID NO:85), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 82, SEQ ID NO: 84, SEQ ID NO: 86, SEQ ID NO: 76, and a combination thereof.

In one embodiment, the hydrophilic frame of the human D gene segment comprises a nucleotide sequence that encodes D7-27 (NWG), and the human D gene segment further comprises a modification that replaces at least one endogenous codon in the nucleotide sequence a histidine codon.

In one embodiment, the hydrophilic frame of the human D gene segment comprises a nucleotide sequence that encodes the amino acid sequence selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, and a combination thereof.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ ($C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., LIY/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified locus comprises a modification that deletes or renders non-functional all or substantially all endogenous $V_H$, D, and $J_H$ gene segments; and the genomic locus comprises the genetically modified, unrearranged human heavy chain variable region nucleotide sequence comprising a substitution of at least one endogenous non-histidine codon with a histidine codon in at least one reading frame. In one embodiment, the genetically modified, unrearranged immunoglobulin heavy chain variable gene sequence is present at an endogenous location (i.e., where the nucleotide sequence is located in a wild-type non-human animal) or present ectopically (e.g., at a locus different from the endogenous immunoglobulin chain locus in its genome or within its endogenous locus, e.g., within an immunoglobulin variable locus, wherein the endogenous locus is placed or moved to a different location in the genome).

In one embodiment, the genetically modified locus comprises an endogenous Adam6a gene, Adam6b gene, or both, and the genetic modification does not affect the expression and/or function of the endogenous Adam6a gene, Adam6b gene, or both.

In one embodiment, the genetically modified locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one embodiment, the non-human animal is heterozygous for the genetically modified immunoglobulin heavy chain locus, and the non-human animal is capable of expressing the human immunoglobulin heavy chain variable domain comprising at least one histidine residue derived predominantly from the genetically modified immunoglobulin heavy chain locus as described herein.

In one aspect, a non-human animal comprising a genetically modified immunoglobulin locus comprising a human $V_H$, D, and $J_H$ gene segment is provided, wherein at least one of the human D gene segment has been inverted 5' to 3' with respect to a corresponding wild-type sequence, and wherein at least one reading frame of the inverted human D gene segment comprises a histidine codon.

In one embodiment, the non-human animal is a mammal, including a rodent, e.g., a mouse, a rat, or a hamster In one embodiment, the genetically modified immunoglobulin locus is present in a germline genome.

In one embodiment, wherein the reading frame of the inverted human D gene segment comprises one or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, or 34 or more of histidine codons.

In one embodiment, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, or all or substantially all of functional human D gene segments have inverted orientation with respect to corresponding wild type sequences.

In one embodiment, all or substantially all of endogenous immunoglobulin $V_H$, D, $J_H$ gene segments are deleted from the immunoglobulin heavy chain locus or rendered nonfunctional (e.g., via insertion of a nucleotide sequence, e.g., exogenous nucleotide sequence, in the immunoglobulin locus or via non-functional rearrangement or inversion of all, or substantially all, endogenous immunoglobulin $V_H$, D, $J_H$ segments), and the genetically modified immunoglobulin locus comprises a human $V_H$, D, and $J_H$ gene segments, wherein at least one of the human D gene segment is present in an inverted orientation with respect to corresponding wild type sequences, and wherein at least one reading frame of the inverted human D gene segment comprises at least one histidine codon.

In one embodiment, the inverted human D gene segment is operably linked to a human $V_H$ gene segment, and/or human $J_H$ gene segment In one embodiment, the human D gene segment that is present in the inverted orientation relative to a corresponding wild type sequence is selected from the group consisting of D1-1, D1-7, D1-20, D1-26, D2-2, D2-8, D2-15, D2-21, D3-3, D3-9, D3-10, D3-16, D3-22, D4-4, D4-11, D4-17, D4-23, D5-5, D5-12, D5-18, D5-24, D6-6, D6-13, D6-19, D7-27, and a combination thereof.

In one embodiment, the human D gene segment that is present in the inverted orientation relative to a corresponding wild type sequence is a D1 gene segment selected from the group consisting of D1-1, D1-7, D1-20, D1-26, and a combination thereof.

In one embodiment, the human D gene segment that is present in the inverted orientation relative to a corresponding wild type sequences is a D2 gene segment selected from the group consisting of D2-2, D2-8, D2-15, D2-21, and a combination thereof.

In one embodiment, the human D gene segment that is present in the inverted orientation relative to a corresponding wild type sequence is a D3 gene segment selected from the group consisting of D3-3, D3-9, D3-10, D3-16, D3-22, and a combination thereof.

In one embodiment, the human D gene segment that is present in the inverted orientation relative to a corresponding wild type sequence is a D4 gene segment selected from the group consisting of D4-4, D4-11, D4-17, D4-23, and a combination thereof.

In one embodiment, the human D gene segment that is present in the inverted orientation relative to a corresponding wild type sequence is a D5 gene segment selected from the group consisting of D5-5, D5-12, D5-18, D5-24, and a combination thereof.

In one embodiment, the human D gene segment that is present in the inverted orientation relative to a corresponding wild type sequence is a D6 gene segment selected from the group consisting of D6-6, D6-13, D6-19, and a combination thereof.

In one embodiment, the human D gene segment that is present in the inverted orientation relative to a corresponding wild type sequence is D7-27.

In one embodiment, the reading frame of the human D gene segment is selected from a stop reading frame, a hydrophilic reading frame, a hydrophobic reading frame, and a combination thereof, wherein at least one reading frame of the inverted human D gene segment comprises a histidine codon.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ ($C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising at least one inverted human D gene segment as described herein wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, the non-human animal is heterozygous for the genetically modified immunoglobulin heavy chain locus, and the non-human animal is capable of expressing the human immunoglobulin heavy chain variable domain comprising at least one histidine residue derived predominantly from the genetically modified immunoglobulin heavy chain locus as described herein.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a non-human animal that is capable of expressing an antigen-binding protein with enhanced pH-dependent recyclability and/or enhanced serum half-life are provided, wherein the non-human animal comprises in its germline genome an unrearranged human immunoglobulin heavy chain variable region nucleotide sequence, wherein the unrearranged heavy chain variable region nucleotide sequence comprises an addition of least one histidine codon or a substitution of at least one endogenous non-histidine codon with a histidine codon as described herein.

In one embodiment, the antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, the antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a targeting construct is provided, comprising 5' and 3' targeting arms homologous to a genomic D region or genomic V and J region of a non-human animal, wherein at least one $V_H$, D, or $J_H$ gene segment comprises any of the modifications as described herein, e.g., an addition of at least one histidine codon, a substitution of at least one endogenous non-histidine codon into a histidine codon, and/or inversion of at least one functional D gene segment with respect to a corresponding wild type sequence.

In one aspect, a hybridoma or quadroma is provided that is derived from a cell of any of the non-human animal as described herein. In one embodiment, the non-human animal is a rodent, e.g., a mouse, a rat, or a hamster.

In one aspect, pluripotent, induced pluripotent, or totipotent stem cells derived form a non-human animal comprising the various genomic modifications of the described invention are provided. In a specific embodiment, the pluripotent, induced pluripotent, or totipotent stem cells are mouse or rat embryonic stem (ES) cells. In one embodiment, the pluripotent, induced pluripotent, or totipotent stem cells have an XX karyotype or an XY karyotype. In one embodiment, the pluripotent or induced pluripotent stem cells are hematopoietic stem cells.

In one aspect, cells that comprise a nucleus containing a genetic modification as described herein are also provided, e.g., a modification introduced into a cell by pronuclear injection. In one embodiment, the pluripotent, induced pluripotent, or totipotent stem cells comprise a genetically modified immunoglobulin genomic locus, wherein the genomic locus comprises, from 5' to 3', (1) an FRT recombination site, (2) human $V_H$ gene segments, (3) a mouse adam6 gene, (4) a loxP recombination site, (5) histidine-substituted human D gene segments, (6) human $J_H$ gene segments, followed by (7) a mouse $E_i$ (intronic enhancer), and (8) a mouse IgM constant region nucleotide sequence.

In one aspect, a lymphocyte isolated from a genetically modified non-human animal as described herein is provided. In one embodiment, the lymphocyte is a B cell, wherein the B cell comprises an immunoglobulin genomic locus comprising an unrearranged heavy chain variable region nucleotide sequence wherein the unrearranged heavy chain variable gene sequence comprises an addition of least one histidine codon or a substitution of at least one endogenous non-histidine codon with a histidine codon.

In one aspect, a lymphocyte isolated from a genetically modified non-human animal as described herein is provided. In one embodiment, the lymphocyte is a B cell, wherein the B cell comprises an immunoglobulin locus that comprises a human V, D, and J gene segment, wherein at least one of the human D gene segment has been inverted 5' to 3' with respect to wild-type sequences, and wherein at least one reading frame of the inverted human D gene segment encodes at least one histidine residue. In one embodiment, the B cell is capable of producing an antigen-binding protein comprising the genetically modified heavy chain variable domain as described herein. In one embodiment, the genetically modified heavy chain variable domain as described herein is operably linked to a heavy chain constant region amino acid sequence.

In one aspect, a B cell population is provided that are capable of expressing an antigen-binding protein wherein the antigen-binding protein comprises at least one histidine residue in a heavy chain variable domain, wherein the B cell population comprises any genetic modifications as described herein. In one embodiment, the at least one histidine residue is present in a heavy chain CDR. In one embodiment, the CDR is a selected from a CDR1, CDR2, CDR3, and a combination thereof. In one embodiment, the at least one histidine residue is present in CDR3.

In one aspect, a B cell population is provided that are capable of expressing an antigen-binding protein with enhanced serum half-life and/or enhanced pH-dependent recyclability, wherein the B cell population comprises any genetic modifications as described herein.

In one aspect, a method for making a non-human animal comprising a genetically modified immunoglobulin heavy chain variable locus is provided, comprising: (a) modifying a genome of a non-human animal to delete or render non-functional endogenous immunoglobulin heavy chain V, D, and J gene segments (e.g., via insertion of a nucleotide sequence, e.g., an exogenous nucleotide sequence, in the immunoglobulin locus or via non-functional rearrangement or inversion of endogenous $V_H$, D, $J_H$ segments); and (b) placing in the genome an unrearranged heavy chain variable region nucleotide sequence, wherein the unrearranged heavy chain variable region nucleotide sequence comprises an addition of least one histidine codon or a substitution of at least one endogenous non-histidine codon with a histidine codon as described herein.

In one embodiment, the non-human animal is a mammal, including a rodent, e.g., a mouse, a rat, or a hamster.

In one embodiment, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of the endogenous non-histidine codons are replaced with histidine codons.

In one embodiment, the endogenous non-histone codon encodes the amino acid selected from Y, N, D, Q, S, W, and R.

In one embodiment, the added or substituted histidine codon is present in an unrearranged heavy chain variable region nucleotide sequence that encodes an immunoglobulin variable domain selected from an N-terminal region, a loop 4 region, a CDR1, a CDR2, a CDR3, a combination thereof.

In one embodiment, the added substituted histidine codon histidine codon is present in an unrearranged heavy chain variable region nucleotide sequence that encodes a complementary determining region (CDR) selected from a CDR1, a CDR2, a CDR3, and a combination thereof.

In one embodiment, the added or substituted histidine codon is present in an unrearranged heavy chain variable region nucleotide sequence that encodes a frame region (FR) selected from FR1, FR2, FR3, FR4, and a combination thereof.

In one embodiment, the unrearranged heavy chain variable region nucleotide sequence comprises a genetically modified human $V_H$ gene segment, wherein one or more endogenous non-histidine codon in at least one reading frame of the human $V_H$ gene segment has been replaced with a histidine codon.

In one embodiment, the human unrearranged heavy chain variable region nucleotide sequence comprises a modification that replaces at least one endogenous non-histidine codon of a human $V_H$ gene segment with a histidine codon, wherein the human $V_H$ gene segment is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-2$^6$, $V_H$2-70, $V_H$3-7, $V_H$3-9, $V_H$3-11, $V_H$3-13, $V_H$3-15, $V_H$3-16, $V_H$3-20, $V_H$3-21, $V_H$3-2$^3$, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-2$^8$, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a combination thereof.

In one embodiment, the human unrearranged heavy chain variable region nucleotide sequence comprises a genetically modified human $J_H$ gene segment, wherein one or more endogenous non-histidine codon in at least one reading frame of the human $J_H$ gene segment has been replaced with a histidine codon.

In one embodiment, the human unrearranged heavy chain variable region nucleotide sequence comprises a modification that replaces at least one endogenous non-histidine codon of a human $J_H$ segment with a histidine codon, wherein the human $J_H$ gene segment is selected from the group consisting of $J_H$1, $J_H$2, $J_H$3, $J_H$4, $J_H$5, $J_H$6, and a combination thereof.

In one embodiment, the added or substituted histidine codon is present in a heavy chain variable region nucleotide sequence that encodes part of a CDR3. In one embodiment, the part of CDR3 comprises an amino acid sequence derived from a reading frame of a genetically modified human D gene segment comprising a modification that replaces at least one endogenous non-histidine codon in the reading frame with a histidine codon.

In one embodiment, the endogenous non-histidine codon that is substituted with a histidine codon encodes the amino acid selected from Y, N, D, Q, S, W, and R.

In one embodiment, the added or substituted histidine codon is present in at least one reading frame of the human D gene segment that is most frequently observed in VELOCIMMUNE® humanized immunoglobulin mice.

In one embodiment, the reading frame of the genetically modified human D gene segment that encodes part of CDR3 is selected from a hydrophobic frame, a stop frame, and a hydrophilic frame.

In one embodiment, the reading frame is a hydrophobic frame of a human D gene segment.

In one embodiment, the hydrophobic frame of the human D gene segment comprises a nucleotide sequence that encodes the amino acid sequence selected from the group consisting of D1-1 (GTTGT; SEQ ID NO: 88), D1-7 (GITGT; SEQ ID NO: 89), D1-20 (GITGT; SEQ ID NO: 89), and D1-26 (GIVGAT; SEQ ID NO:90), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D2-2 (DIVVVPAAI; SEQ ID NO:92), D2-8 (DIVLMVYAI; SEQ ID NO: 94), D2-15 (DIVVVVAAT; SEQ ID NO:95), and D2-21 (HIVVVTAI; SEQ ID NO: 97), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D3-3 (ITIFGVVII; SEQ ID NO:98), D3-9 (ITIF*LVII; SEQ ID NO:99, SEQ ID NO:100), D3-10 (ITMVRGVII; SEQ ID NO:101), D3-16 (IMITFGGVIVI; SEQ ID NO:102), and D3-22 (ITMIVVVIT; SEQ ID NO:103), and the human D gene segment further comprises a modification that replaces at least one endogenous codon in the nucleotide sequence with a histidine codon.

In one embodiment, the hydrophobic frame of the human D gene segment comprises a nucleotide sequence that encodes the amino acid sequence selected from the group consisting of D4-4 (TTVT; SEQ ID NO:105), D4-11 (TTVT; SEQ ID NO:105), D4-17 (TTVT; SEQ ID NO:105), D4-23 (TTVVT; SEQ ID NO: 106) and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D5-5 (VDTAMV; SEQ ID NO: 107), D5-12 (VDIVATI; SEQ ID NO:108), D5-18 (VDTAMV; SEQ ID NO:107), and D5-24 (VEMATI; SEQ ID NO:109), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D6-6 (SIAAR; SEQ ID NO:111), D6-13 (GIAAAG; SEQ ID NO:113), and D6-19 (GIAVAG; SEQ ID NO: 115), and the human D gene segment further comprises a modification that replaces at least one endogenous non-histidine codon in the nucleotide sequence with a histidine codon.

In one embodiment, the hydrophobic frame comprises a nucleotide sequence that encodes human D7-27 (LTG), and the human D gene segment further comprises a modification that replaces at least one endogenous non-histidine codon in the nucleotide sequence with a histidine codon.

In one embodiment, the reading frame is a stop reading frame of a human D gene segment.

In one embodiment, the stop reading frame of the human D gene segment comprises a nucleotide sequence that encodes the amino acid sequence selected from the group consisting of D1-1 (VQLER; SEQ ID NO:8), D1-7 (V*LEL), D1-20(V*LER), D1-26 (V*WELL; SEQ ID NO:12), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D2-2 (RIL**YQLLY; SEQ ID NO:14), D2-8 (RILY*WCMLY; SEQ ID NO:16 and SEQ ID NO: 17), D2-15 (RIL*WW*LLL), and D2-21 (SILWW*LLF; SEQ ID NO:19), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D3-3 (VLRFLEWLLY; SEQ ID NO:21), D3-9 (VLRYFDWLL*; SEQ ID NO:23), D3-10 (VLLWFGELL*; SEQ ID NO:25), D3-16 (VL*LRLGELSLY; SEQ ID NO:27), and D3-22 (VLL***WLLL; SEQ ID NO:29), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D4-4 (*LQ*L), D4-11 (*LQ*L), D4-17 (*LR*L), and D4-23 (*LRW*L), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D5-5 (WIQLWL; SEQ ID NO:35); D5-12 (WI*WLRL; SEQ ID NO:37), D5-18 (WIQLWL; SEQ ID NO:35), and D5-24 (*RWLQL; SEQ ID NO:39), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D6-6 (V*QLV), D6-13 (V*QQLV; SEQ ID NO:41), and D6-19 (V*QWLV; SEQ ID NO:43), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes D7-27 (*LG), and the human D gene segment further comprises a modification that replaces at least one endogenous codon of the human D gene segment in the nucleotide sequence with a histidine codon.

In one embodiment, the reading frame is a hydrophilic frame of a human D gene segment.

In one embodiment, the hydrophilic frame of the human D gene segment comprises a nucleotide sequence that encodes the amino acid sequence selected from the group consisting of D1-1 (YNWND; SEQ ID NO: 45), D1-7 (YNWNY; SEQ ID NO: 47), D1-20 (YNWND; SEQ ID NO: 45), and D1-26 (YSGSYY; SEQ ID NO:49), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 46, SEQ ID NO: 48, SEQ ID NO: 50, and a combination thereof.

In one embodiment, the hydrophilic frame of the human D gene segment comprises a nucleotide sequence that encodes the amino acid sequence selected from the group consisting of D2-2 (GYCSSTSCYT; SEQ ID NO:51), D2-8 (GYCTNGVCYT; SEQ ID NO: 53), D2-15 (GYCSGGSCYS; SEQ ID NO:55), and D2-21 (AYCGGDCYS; SEQ ID NO:57), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 52, SEQ ID NO: 54, SEQ ID NO: 56, SEQ ID NO: 58, and a combination thereof.

In one embodiment, the hydrophilic frame of the human D gene segment comprises a nucleotide sequence that encodes the amino acid sequence selected from the group consisting of D3-3 (YYDFWSGYYT; SEQ ID NO:59), D3-9 (YYDILTGYYN; SEQ ID NO:61), D3-10 (YYYGSGSYYN; SEQ ID NO:63), D3-16 (YYDYVWGSYRYT; SEQ ID NO:65), and D3-22 (YYYDSSGYYY; SEQ ID NO:67), and the human D gene segment further comprises a modification that replaces at least one endogenous codon in the nucleotide sequence with a histidine codon. In one embodiment, the hydrophilic frame comprises a nucleotide sequence encodes the amino acid sequence selected from the group consisting of SEQ ID NO: 60, SEQ ID NO: 62, SEQ ID NO: 64, SEQ ID NO: 66, SEQ ID NO: 68, and a combination thereof.

In one embodiment, the hydrophilic frame of the human D gene segment comprises a nucleotide sequence that encodes the amino acid sequence selected from the group consisting of D4-4 (DYSNY; SEQ ID NO:69), D4-11 (DYSNY; SEQ ID NO:69), D4-17 (DYGDY; SEQ ID NO:71), and D4-23 (DYGGNS; SEQ ID NO:73), and the human D gene segment comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 70, SEQ ID NO: 72, SEQ ID NO: 74, and a combination thereof.

In one embodiment, the hydrophilic frame of the human D gene segment comprises a nucleotide sequence that encodes the amino acid sequence selected from the group consisting of D5-5 (GYSYGY; SEQ ID NO:75), D5-12 (GYSGYDY; SEQ ID NO:77), D5-18 (GYSYGY; SEQ ID NO:75), and D5-24 (RDGYNY; SEQ ID NO:79), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 76, SEQ ID NO: 78, SEQ ID NO: 80, and a combination thereof.

In one embodiment, the hydrophilic frame of the human D gene segment comprises a nucleotide sequence that encodes the amino acid sequence selected from the group consisting of D6-6 (EYSSSS; SEQ ID NO: 81), D6-13 (GYSSSWY; SEQ ID NO:83), and D6-19 (GYSSGWY; SEQ ID NO:85), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 82, SEQ ID NO: 84, SEQ ID NO: 86, SEQ ID NO: 76, and a combination thereof.

In one embodiment, the hydrophilic frame of the human D gene segment comprises a nucleotide sequence that encodes D7-27 (NWG), and the human D gene segment further comprises a modification that replaces at least one endogenous codon in the nucleotide sequence a histidine codon.

In one embodiment, the hydrophilic frame of the human D gene segment comprises a nucleotide sequence that encodes the amino acid sequence selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, and a combination thereof.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ ($C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $C_H3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified locus comprises a modification that deletes or renders non-functional all or substantially all endogenous $V_H$, D, and $J_H$ gene segments; and the genomic locus comprises the genetically modified, unrearranged human heavy chain variable region nucleotide sequence comprising a substitution of at least one endogenous non-histidine codon with a histidine codon in at least one reading frame. In one embodiment, the genetically modified, unrearranged immunoglobulin heavy chain variable gene sequence is present at an endogenous location (i.e., where the nucleotide sequence is located in a wild-type non-human animal) or present ectopically (e.g., at a locus different from the endogenous immunoglobulin chain locus in its genome or within its endogenous locus, e.g., within an immunoglobulin variable locus, wherein the endogenous locus is placed or moved to a different location in the genome).

In one embodiment, the genetically modified locus comprises an endogenous Adam6a gene, Adam6b gene, or both, and the genetic modification does not affect the expression and/or function of the endogenous Adam6a gene, Adam6b gene, or both.

In one embodiment, the genetically modified locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a method for making a non-human animal comprising a genetically modified immunoglobulin heavy chain variable locus is provided, comprising: (a) modifying a genome of a non-human animal to delete or render non-functional endogenous immunoglobulin heavy chain V, D, and J gene segments (e.g., via insertion of a nucleotide sequence (e.g., an exogenous nucleotide sequence) in the immunoglobulin locus or via non-functional rearrangement or inversion of endogenous $V_H$, D, $J_H$ segments); and (b) placing in the genome a human $V_H$, D, and $J_H$ gene segment, wherein at least one of the human D gene segment has been inverted 5' to 3' with respect to a corresponding wild-type sequence, and wherein at least one reading frame of the inverted human D gene segment comprises a histidine codon.

In one embodiment, the non-human animal is a mammal, including a rodent, e.g., a mouse, a rat, or a hamster In one embodiment, the genetically modified immunoglobulin locus is present in a germline genome.

In one embodiment, the genetically modified immunoglobulin locus encodes an immunoglobulin heavy chain variable domain comprising one or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, or 34 or more of histidine residues.

In one embodiment, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, or all or substantially all of functional human D gene segments have inverted orientation with respect to corresponding wild type sequences.

In one embodiment, all or substantially all of endogenous immunoglobulin $V_H$, D, $J_H$ gene segments are deleted from the immunoglobulin heavy chain locus or rendered non-functional (e.g., via insertion of a nucleotide sequence, e.g., exogenous nucleotide sequence, in the immunoglobulin locus or via non-functional rearrangement or inversion of all, or substantially all, endogenous immunoglobulin $V_H$, D, $J_H$ segments), and the genetically modified immunoglobulin locus comprises a human $V_H$, D, and $J_H$ gene segments, wherein at least one of the human D gene segment is present in an inverted orientation with respect to a corresponding wild type sequence, and wherein at least one reading frame in the inverted human D gene segment comprises at least one histidine codon.

In one embodiment, the inverted human D gene segment is operably linked to a human $V_H$ gene segment, and/or human $J_H$ gene segment In one embodiment, the human D gene segment that is present in the inverted orientation relative to wild type sequences is selected from the group consisting of D1-1, D1-7, D1-20, D1-26, D2-2, D2-8, D2-15, D2-21, D3-3, D3-9, D3-10, D3-16, D3-22, D4-4, D4-11, D4-17, D4-23, D5-5, D5-12, D5-18, D5-24, D6-6, D6-13, D6-19, D7-27, and a combination thereof.

In one embodiment, the human D gene segment that is present in the inverted orientation relative to a corresponding wild type sequence is a D1 gene segment selected from the group consisting of D1-1, D1-7, D1-20, D1-26, and a combination thereof.

In one embodiment, the human D gene segment that is present in the inverted orientation relative to a corresponding wild type sequence is a D2 gene segment selected from the group consisting of D2-2, D2-8, D2-15, D2-21, and a combination thereof.

In one embodiment, the human D gene segment that is present in the inverted orientation relative to a corresponding wild type sequence is a D3 gene segment selected from the group consisting of D3-3, D3-9, D3-10, D3-16, D3-22, and a combination thereof.

In one embodiment, the human D gene segment that is present in the inverted orientation relative to a corresponding wild type sequence is a D4 gene segment selected from the group consisting of D4-4, D4-11, D4-17, D4-23, and a combination thereof.

In one embodiment, the human D gene segment that is present in the inverted orientation relative to a corresponding wild type sequence is a D5 gene segment selected from the group consisting of D5-5, D5-12, D5-18, D5-24, and a combination thereof.

In one embodiment, the human D gene segment that is present in the inverted orientation relative to a corresponding wild type sequence is a D6 gene segment selected from the group consisting of D6-6, D6-13, D6-19, and a combination thereof.

In one embodiment, the human D gene segment that is present in the inverted orientation relative to a corresponding wild type sequence is D7-27.

In one embodiment, the reading frame of the human D gene segment is selected from a stop reading frame, a hydrophilic reading frame, a hydrophobic reading frame, and a combination thereof.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ ($C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising at least one inverted human D gene segment as described herein wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises an enriched B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a method for making a non-human animal that is capable of producing an immunoglobulin heavy chain variable domain with enhanced serum half-life and/or enhanced pH-dependent recyclability is provided, comprising (a) modifying a genome of a non-human animal to delete or render non-functional endogenous immunoglobulin heavy chain V, D, and J gene segments (e.g., via insertion of a nucleotide sequence (e.g., an exogenous nucleotide sequence) in the immunoglobulin locus or via non-functional rearrangement or inversion of endogenous $V_H$, D, $J_H$ segments); and (b) placing in the genome an unrearranged human heavy chain variable region nucleotide sequence, wherein the unrearranged heavy chain variable region nucleotide sequence comprises an addition of least one histidine codon or a substitution of at least one endogenous non-histidine codon with a histidine codon, and wherein an antigen-binding protein comprising the immunoglobulin heavy chain variable domain produced by the non-human animal exhibits enhanced serum half-life and/or enhanced pH-dependent recyclability as compared to a wild-type immunoglobulin heavy chain domain.

In one embodiment, the non-human animal, upon contact with an antigen, can produce an enriched population of B cell repertoire that expresses an antigen-binding protein with enhanced serum half-life and/or enhanced pH-dependent recyclability, wherein the enriched B cell population comprises any genetic modifications as described herein.

In one embodiment, an antigen-binding protein produced by the genetically modified non-human animal is characterized by sufficient affinity to an antigen of interest at a neutral pH (e.g., pH of about 7.0 to about 7.4) and enhanced dissociation of the antibody from an antigen-antigen-binding protein complex at a pH less than the neutral pH (e.g., at an endosomal pH, e.g. pH of about 5.5 to 6.0).

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a an enriched B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one embodiment, the antigen-binding protein comprises an immunoglobulin heavy chain variable domain that is capable of specifically binding an antigen of interest with an affinity ($K_D$) lower than $10^{-6}$, $10^{-7}$, $10^{-8}$, $10^{-9}$, $10^{-10}$, $10^{-11}$, and $10^{-12}$ at a neutral pH (pH of about 7.0 to about 7.4).

In one aspect, a method for obtaining an antigen-binding protein with enhanced recyclability and/or improved serum half-life is provided, comprising: (a) immunizing a non-human animal having a genetically modified immunoglobulin locus as described herein wherein the non-human animal comprises an unrearranged human heavy chain variable region nucleotide sequence comprising an addition of least one histidine codon or a substitution of at least one endogenous non-histidine codon with a histidine codon; (b) allowing the non-human animal to mount an immune response; (c) harvesting a lymphocyte (e.g., a B cell) from the immunized non-human animal; (d) fusing the lymphocyte with a myeloma cell to form a hybridoma cell, and (e) obtaining an antigen-binding protein produced by the hybridoma cell, wherein the antigen-binding protein exhibits enhanced recyclability and/or serum stability.

In one aspect, a genetically modified immunoglobulin heavy chain locus obtainable by any of the methods as described herein is provided.

In one aspect, a genetically modified non-human animal obtainable by any of the methods as described herein is provided.

In various embodiments, the non-human animal is a mammal. In one embodiment, the mammal is a rodent, e.g., a mouse, a rat, or a hamster.

In various embodiments, the genetically modified immunoglobulin loci as described herein are present in the germline genome of a non-human animal, e.g., a mammal, e.g., a rodent, e.g., a mouse, a rat, or a hamster.

BRIEF DESCRIPTION OF THE DRAWINGS

FIGS. 1A and 1B illustrate the amino acid sequences encoded by the three reading frames (i.e., stop, hydrophilic, and hydrophobic reading frames) of human D gene segments (D) and the amino acid sequences encoded by the three reading frames of histidine-substituted human D gene segments (HD). Introduction of histidine codons (typed in bold) in the hydrophilic reading frame also changed many stop codons in the stop reading frame to Ser codons (typed in bold) but introduced few changes in the hydrophobic reading frame. The "*" symbol represents a stop codon, and the comma between the two SEQ ID NOs indicates that there are two amino acid sequences separated by the stop codon.

FIG. 6 shows a list of primers and probes used to confirm a loss of allele (LOA), a gain of allele (GOA), or a parental allele (Parental) in the screening assays for identifying MAID 6011.

FIG. 8 shows a list of primers and probes used to confirm a loss of allele (LOA), a gain of allele (GOA), or a parental allele (Parental) in the screening assay for identifying MAID 6012.

FIGS. 10A-10E illustrate human D gene segment nucleotide sequences with translations for each of the six reading frames, i.e., three reading frames for direct 5' to 3' orientation and three reading frames for inverted orientation (3' to 5' orientation). The "*" symbol represents a stop codon, and the comma between two SEQ ID NOs indicates that there are two amino acid sequences separated by the stop codon.

FIGS. 11-13 illustrate mRNA sequences and their encoded protein sequences expressed by 6013 F0 heterozygous mice, which comprise histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)) in the immunoglobulin heavy chain locus in their 129 strain-derived chromosome. The boxed sequences in each figure indicate the presence of histidine codons in the CDR3 sequences derived from the genetically modified immunoglobulin heavy chain locus comprising the histidine-substituted human D gene segments. FWR represents frame region and CDR represents complementarity determining region. In the alignment, the dot "." indicates a sequence identical to the query sequence, and the dash "-" indicates a gap in the sequence.

FIG. 15 illustrates an amino acid alignment of human Vκ1-39-derived light chains from various antigen-specific antibodies (A-K antibodies). Histidine (H) residues located within each light chain sequence are in bold. Various light chain regions (Framework and CDR) are indicated above the alignment.

FIG. 16 illustrates the combinations and locations of histidine residues engineered in the CDR3 region of human Vκ1-39-derived light chains by mutagenesis. Corresponding nucleic acid sequences are included. Histidine residues introduced through mutagenesis and corresponding nucleic acid residues are shown in bold. Amino acid positions (105, 106, etc.) are based on a unique numbering described in Lefranc et al. (2003) Dev. Comp. Immunol. 27:55-77, and can also be viewed on the website of the International Immunogenetics Information System (IMGT).

FIGS. 19A-19J shows the binding kinetics for selected heavy chains from antigen-specific antibodies paired with various histidine engineered light chains at a neutral (7.4) and acidic (5.5) pH.

FIGS. 20A-20E show the binding kinetics for selected heavy chains (1-5) from antigen-specific antibodies paired with various histidine engineered light chains at a neutral (7.4) and acidic (5.75) pH. Various kinetic parameters including $k_a$, $k_d$, $K_D$, and $t_{1/2}$ are shown. NB=no binding.

FIG. 21 shows kinetic parameters ($K_D$ and $t_{1/2}$) for antibodies comprising parental universal light chain or histidine-modified universal light chain paired with indicated heavy chains (2, 3, and 6). Histidine substitutions lead to strong pH dependence in several antibodies. Histidine substitutions were made in CDR3 to convert the sequence $_{105}$QQSYSTP$_{111}$ (SEQ ID NO:3) to $_{105}$HHSYSTH$_{111}$ (SEQ ID NO:329). Note that NB=no binding detected ($K_D$>10 micromolar).

FIG. 22 shows the sequence and properties (% GC content, N, % mismatch, Tm) of selected mutagenesis primers used to engineer histidine residues into CDR3 of a rearranged human Vκ1-39/Jκ5 light chain sequence. SEQ ID NOs for these primers used in the Sequence Listing are included in the Table below. F=forward primer, R=reverse primer.

FIGS. 23C-23D show introduction of the targeting vector for ULC-H105/106/108/111 substitutions into ES cells and generation of heterozygous mice from the same; while

FIG. 27 shows positions of histidine residues engineered in the CDR3 region of human Vκ3-20-derived light chains by mutagenesis. Histidine residues introduced through mutagenesis and corresponding nucleic acid residues are shown in bold. Amino acid positions (105, 106, etc.) are based on a unique numbering described in Lefranc et al. (2003) Dev. Comp. Immunol. 27:55-77, and can also be viewed on the website of the International Immunogenetics Information System (IMGT).

FIG. 28 shows the sequence and properties (% GC content, N, % mismatch, Tm) of selected mutagenesis primers used to engineer histidine residues into CDR3 of a rearranged human Vκ3-20/Jκ1 light chain sequence. SEQ ID NOs for these primers used in the Sequence Listing are included in the Table below. F=forward primer, R=reverse primer.

FIG. 29C shows introduction of the targeting vector for ULC-Q105H/Q106H/Y107H/S109H substitutions into ES cells and generation of heterozygous mice from the same; while

DETAILED DESCRIPTION

Figure 2:
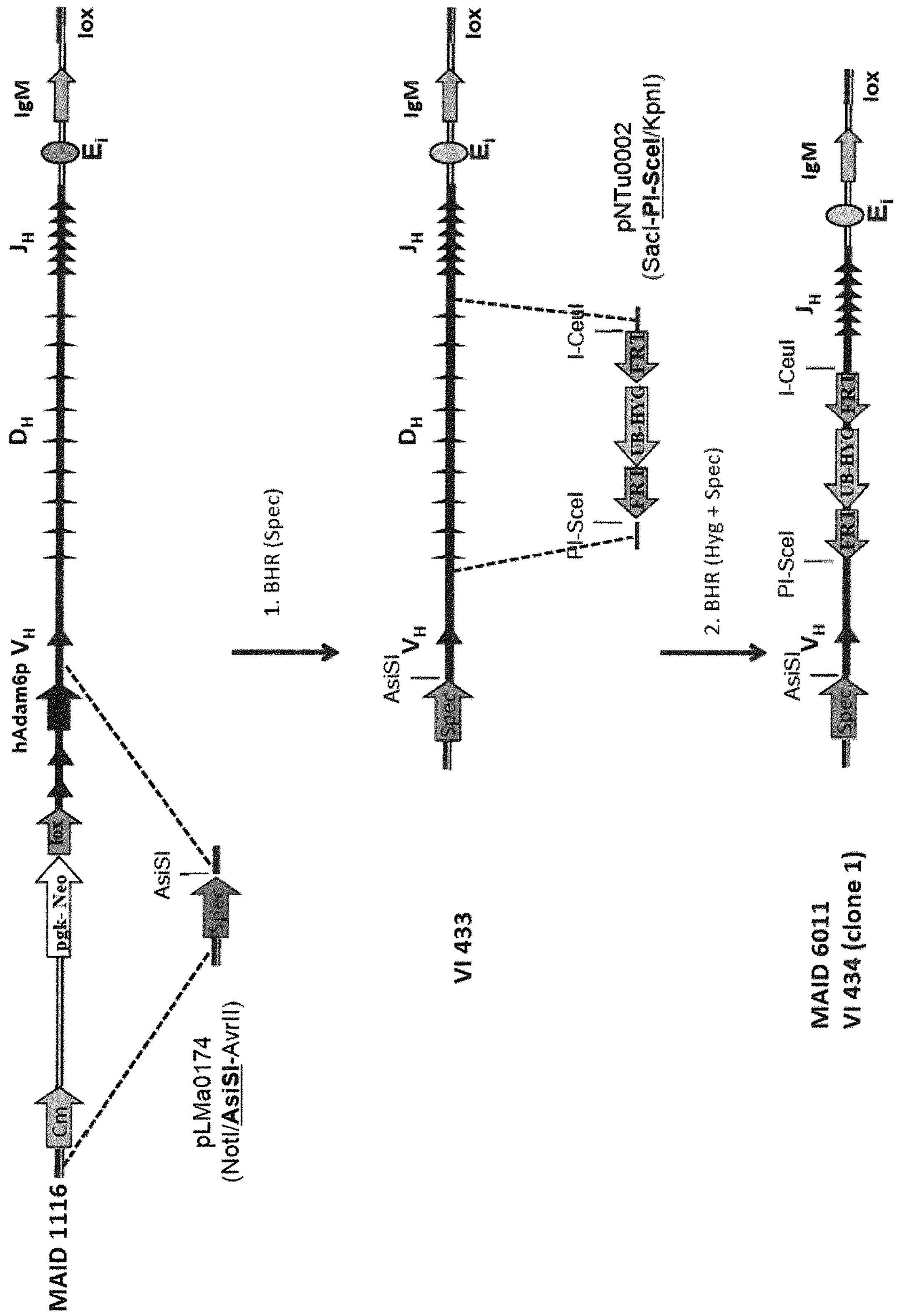
FIG. 2 illustrates schemes for targeting pLMa0174 containing a spectinomycin selection cassette into the 5' end of MAID 1116 (Step 1. BHR (Spec)). In Step 1, a chloramphenicol selection cassette, a neomycin selection cassette, a loxP site, two $V_H$ gene segments ($hV_H1$-3 and $hV_H1$-2), the human Adam6 gene, all of which are located upstream of $hV_H6$-1, were deleted from the clone and replaced by a spectinomycin cassette to yield the VI433 clone. In Step 2 (BHR (Hyg+Spec)), pNTu0002 containing a hygromycin cassette flanked by FRT sites was targeted into a region comprising human immunoglobulin D gene segments. Via Step 2, all human D gene segments were deleted from VI433 and replaced with the hygromycin cassette to yield MAID6011 VI 434 (clone 1).

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

Definitions

The term "antibody", as used herein, includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises three domains, $C_H1$, $C_H2$ and $C_H3$. Each light chain comprises a light chain variable domain and a light chain constant region ($C_L$). The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to an antibody that has a $K_D$ with respect to its target epitope about of $10^{-9}$ M or lower (e.g., about $1\times10^{-9}$ M, $1\times10^{-10}$ M, $1\times10^{-11}$ M, or about $1\times10^{-12}$ M). In one embodiment, $K_D$ is measured by surface plasmon resonance, e.g., BIACORE™; in another embodiment, $K_D$ is measured by ELISA.

The phrase "bispecific antibody" includes an antibody capable of selectively binding two or more epitopes. Bispecific antibodies generally comprise two nonidentical heavy chains, with each heavy chain specifically binding a different epitope—either on two different molecules (e.g., different epitopes on two different immunogens) or on the same molecule (e.g., different epitopes on the same immunogen). If a bispecific antibody is capable of selectively binding two different epitopes (a first epitope and a second epitope), the affinity of the first heavy chain for the first epitope will generally be at least one to two or three or four or more orders of magnitude lower than the affinity of the first heavy chain for the second epitope, and vice versa. Epitopes specifically bound by the bispecific antibody can be on the same or a different target (e.g., on the same or a different protein). Exemplary bispecific antibodies include those with a first heavy chain specific for a tumor antigen and a second heavy chain specific for a cytotoxic marker, e.g., an Fc receptor (e.g., FcγRI, FcγRII, FcγRIII, etc.) or a T cell marker (e.g., CD3, CD28, etc.). Further, the second heavy chain variable domain can be substituted with a heavy chain variable domain having a different desired specificity. For example, a bispecific antibody with a first heavy chain specific for a tumor antigen and a second heavy chain specific for a toxin can be paired so as to deliver a toxin (e.g., saporin, vinca alkaloid, etc.) to a tumor cell. Other exemplary bispecific antibodies include those with a first heavy chain specific for an activating receptor (e.g., B cell receptor, FcγRI, FcγRIIA, FcγRIIIA, FcαRI, T cell receptor, etc.) and a second heavy chain specific for an inhibitory receptor (e.g., FcγRIIB, CD5, CD22, CD72, CD300a, etc.). Such bispecific antibodies can be constructed for therapeutic conditions associated with cell activation (e.g. allergy and asthma). Bispecific antibodies can be made, for example, by combining heavy chains that recognize different epitopes of the same immunogen. For example, nucleic acid sequences encoding heavy chain variable sequences that recognize different epitopes of the same immunogen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a $C_H1$ domain, a hinge, a $C_H2$ domain, and a $C_H3$ domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding of one or both of the heavy chains to one or both epitopes.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

The term "complementary determining region" or "CDR," as used herein, includes an amino acid sequence encoded by a nucleic acid sequence of an organism's immunoglobulin genes that normally (i.e., in a wild type animal) appears between two framework regions in a variable region of a light or a heavy chain of an immunoglobulin molecule (e.g., an antibody or a T cell receptor). A CDR can be encoded by, for example, a germline sequence or a rearranged sequence, and, for example, by a naïve or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as a result of splicing or connecting the sequences (e.g., V-D-J recombination to form a heavy chain CDR3).

The term "conservative," when used to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a variable region to specifically bind a target epitope with a desired affinity. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

In some embodiments, residue positions in an immunoglobulin light chain or heavy chain differ by one or more conservative amino acid substitutions. In some embodiments, residue positions in an immunoglobulin light chain or functional fragment thereof (e.g., a fragment that allows expression and secretion from, e.g., a B cell) are not identical to a light chain whose amino acid sequence is listed herein, but differs by one or more conservative amino acid substitutions.

The term "dissociative half-life" or "$t_{1/2}$" as used herein refers to the value calculated by the following formula: $t_{1/2}$ (min)=(ln $2/k_d$)/60, wherein $k_d$ represents a dissociation rate constant.

The phrase "epitope-binding protein" includes a protein having at least one CDR and that is capable of selectively recognizing an epitope, e.g., is capable of binding an epitope with a $K_D$ that is at about one micromolar or lower (e.g., a $K_D$ that is about $1\times10^{-6}$ M, $1\times10^{-7}$ M, $1\times10^{-9}$ M, $1\times10^{-9}$ M, $1\times10^{-10}$ M, $1\times10^{-11}$ M, or about $1\times10^{-12}$ M). Therapeutic epitope-binding proteins (e.g., therapeutic antibodies) frequently require a $K_D$ that is in the nanomolar or the picomolar range.

The term "functional" as used herein, e.g., in reference to a functional polypeptide, includes a polypeptide that retains at least one biological activity normally associated with the native protein. In another instance, a functional immunoglobulin gene segment may include a variable gene segment that is capable of productive rearrangement to generate a rearranged immunoglobulin gene sequence.

The phrase "functional fragment" includes fragments of epitope-binding proteins that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The term "germline" as used herein, in reference to an immunoglobulin nucleic acid sequence, includes reference to nucleic acid sequences that can be passed to progeny.

The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H^3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. Heavy chain variable domains are encoded by variable region nucleotide sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found in IMGT database, which is accessible via the internet on the website of the International Immunogenetics Information System (IMGT).

The term "identity" when used in connection with sequence, includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008). The length of the sequences compared with respect to identity of sequences will depend upon the particular sequences, but in the case of a light chain constant domain, the length should contain sequence of sufficient length to fold into a light chain constant domain that is capable of self-association to form a canonical light chain constant domain, e.g., capable of forming two beta sheets comprising beta strands and capable of interacting with at least one $C_H1$ domain of a human or a mouse. In the case of a $C_H1$ domain, the length of sequence should contain sequence of sufficient length to fold into a $C_H1$ domain that is capable of forming two beta sheets comprising beta strands and capable of interacting with at least one light chain constant domain of a mouse or a human.

The phrase "immunoglobulin molecule" includes two immunoglobulin heavy chains and two immunoglobulin light chains. The heavy chains may be identical or different, and the light chains may be identical or different.

The phrase "light chain" includes an immunoglobulin light chain sequence from any organism, and unless otherwise specified includes human kappa (κ) and lambda (λ) light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region amino acid sequence. Light chain variable domains are encoded by the light chain variable region nucleotide sequence, which generally comprises light chain $V_L$ and light chain $J_L$ gene segments, derived from a repertoire of light chain V and J gene segments present in the germline. Sequences, locations and nomenclature for light chain V and J gene segments for various organisms can be found in IMGT database, which is accessible via the website of the International Immunogenetics Information System (IMGT). Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear. Light chains also include those that bind and recognize, or assist the heavy chain with binding and recognizing, one or more epitopes selectively bound by the epitope-binding protein in which they appear. Common or universal light chains include those derived from a human Vκ1-39Jκ5 gene or a human Vκ3-20Jκ1 gene, and include somatically mutated (e.g., affinity matured) versions of the same.

The phrase "micromolar range" is intended to mean 1-999 micromolar; the phrase "nanomolar range" is intended to mean 1-999 nanomolar; the phrase "picomolar range" is intended to mean 1-999 picomolar.

"Neutral pH" includes pH between about 7.0 and about 8.0, e.g., pH between about 7.0 and about 7.4, e.g., between about 7.2 and about 7.4, e.g., physiological pH in, e.g., a mouse or a human. "Acidic pH" includes pH of 6.0 or lower, e.g., pH between about 5.0 and about 6.0, pH between about 5.75 and about 6.0, e.g., pH of endosomal or lysosomal compartments.

The term "operably linked" refers to a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

The phrase "somatically mutated," as used herein, includes reference to a nucleic acid sequence from a B cell that has undergone class-switching, wherein the nucleic acid sequence of an immunoglobulin variable region, e.g., a heavy chain variable region (e.g., a heavy chain variable domain or including a heavy chain CDR or FR sequence) in the class-switched B cell is not identical to the nucleic acid sequence in the B cell prior to class-switching, such as, for example a difference in a CDR or a framework nucleic acid sequence between a B cell that has not undergone class-switching and a B cell that has undergone class-switching. The phrase "somatically mutated" includes reference to nucleic acid sequences from affinity-matured B cells that are not identical to corresponding immunoglobulin variable region nucleotide sequences in B cells that are not affinity-matured (i.e., sequences in the genome of germline cells). The phrase "somatically matured" also includes reference to an immunoglobulin variable region nucleic acid sequence from a B cell after exposure of the B cell to an epitope of interest, wherein the nucleic acid sequence differs from the corresponding nucleic acid sequence prior to exposure of the B cell to the epitope of interest. The term "somatically mutated" also refers to sequences from antibodies that have been generated in an animal, e.g., a mouse having human immunoglobulin variable region nucleic acid sequences, in response to an immunogen challenge, and that result from the selection processes inherently operative in such an animal.

The term "unrearranged," with reference to a nucleic acid sequence, includes nucleic acid sequences that exist in the germline of an animal cell.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4.

The phrase "operably linked" refers to a juxtaposition wherein the components so described are in a relationship permitting them to function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

The term "replacement" in reference to gene replacement refers to placing exogenous genetic material at an endogenous genetic locus, thereby replacing all or a portion of the endogenous gene with an orthologous or homologous nucleic acid sequence.

The term "functional" as used herein, e.g., in reference to a functional polypeptide, includes a polypeptide that retains at least one biological activity normally associated with the native protein. In another instance, a functional immunoglobulin gene segment may include a variable gene segment that is capable of productive rearrangement to generate a rearranged immunoglobulin gene sequence.

Variable Domains with Histidine Substitutions

The design of human immunoglobulin-based therapeutics is a well-studied phenomenon, yet certain unsolved problems persist in making such therapeutics with optimal characteristics, e.g., extending serum half-life of such therapeutics or otherwise improving their ability to bind more target per therapeutic molecule. Much work over the last couple of decades aimed at elucidating serum immunoglobulin turnover has focused on ways to increase serum half-life of therapeutically important antibodies, or immunoglobulin-based therapeutics, by modifying antibody structure. For the most part, this modification work has focused on the interaction of the constant domains of antibodies with the neonatal Fc receptor (FcRn). The neonatal Fc receptor on the extracellular surface binds circulating antibodies through their Fc regions to form an antibody-FcRn complex that is incorporated, or endocytosed, into the cell where the ligand and antibody part ways and the antibody-FcRn complex undergoes a cycling process that brings the antibody and the FcRn back to the cell's surface where the antibody is released and can re-bind a new target molecule. Cycling of the antibody-FcRn complex became an area of intense interest following the discovery of general mechanisms of receptor cycling.

Receptor cycling can proceed by a variety of mechanisms. Receptor-mediated endocytosis provides an endosomal pathway for a regulated recycling of cell surface receptors and (in some cases, e.g., FcRns) their ligands. (Pinocytosed molecules are otherwise typically shuttled through an endosomal pathway that ends in degradation.) The discovery of the mechanism of receptor-mediated endocytosis and the body of work concerning recycling of membrane receptors provided a framework for a detailed understanding of receptor-ligand turnover in general (for a review see, e.g., Brown, M. S., Anderson, R. G. W., and Goldstein, J. L. (1983) Recycling Receptors: The Round-Trip Itinerary of Migrant Membrane Proteins, Cell 32:663-667; see also, Goldstein, J. L. and Brown, M. S. (2009) The LDL Receptor, Arterioscler. Thromb. Vasc. Biol. 29:431-438; Basu, S. K. (1984) Receptor-mediated endocytosis: An overview of a dynamic process, J. Biosci. 6(4):535-542). Other work on endosomal sorting helped properly frame the question of the fate of circulating immunoglobulins and the phenomenon of immunoglobulin receptor recycling and pharmacokinetics of antibody drugs. This work revealed a complex antibody-FcRn complex cycling process that appears to be primarily responsible for the relatively long half-life of IgG molecules in serum. Indeed, even rather early work in this area established that endosomes are the most plentiful in vivo source of FcRn (see, Roberts, D. M. et al. (1990) Isolation and Characterization of the Fc Receptor from the Fetal Yolk Sac of the Rat, J. Cell. Biol. 111:1867-1876). And it had long been observed that receptor-positive endosomal fractions are in large part not headed for lysosomal degradation (see, e.g., Brown, M. S. et al. (1983) Recycling Receptors: The Round-Trip Itinerary of Migrant Membrane Proteins, Cell 32:663-667; see also, von Figura et al. (1984) Antibody to mannos 6-phosphate specific receptor induces receptor deficiency in human fibroblasts, EMBO J. 3(6):1281-1286), in the absence of aggregation (see, e.g., Dunn, K. W. et al. (1989) Iterative Fractionation of Recycling Receptors from Lysosomally Destined Ligands in an Early Sorting Endosome, J. Cell. Biol. 109(6):3303-3314). It is this endosomal system that participates in a cycling process that ensures that antibodies that bind FcRn well under acidic conditions (e.g., human IgG1 antibodies) persist for an extended period of time in serum.

According to some reports, the recycling mechanism of FcRn-containing endosomes is novel and unusual; it does not involve ubiquitin-dependent complete organelle merging but rather resembles incomplete merging mediated by tubular extensions more similar to a kiss-and-linger model (Gan, Z. et al. (2009) Analyses of the recycling receptor, FcRn, in live cells reveal novel pathways for lysosomal delivery, Traffic 10(5):600; see also, Tzaban, S. et al. (2009) The recycling and transcytotic pathways for IgG transport by FcRn are distinct and display an inherent polarity, J. Cell Biol. 185(4):673-684). Thus, the antibody-FcRn cycling model appears to be distinct from other endosomal pathways.

The antibody-FcRn endosomal cycling mechanism assures that antibodies that bind well to FcRn are able to sustain prolonged presence in serum through a more or less continuous FcRn-protective process that entails sequestering bound antibody in an endosomal compartment where the binding of antibody to FcRn is maintained, preventing lysosomal degradation of antibody bound to FcRn. Typically, circulating antibody molecules bind FcRn on the cell surface. Antibody-FcRn complexes appear in endosomes as the result of a continuous endocytosis process. FcRn-bound molecules (e.g., antibodies, or Fc fusion proteins) remain associated with FcRn in the acidic endosomal compartment through acid-stable Fc-FcRn interaction. Molecules not bound to the endosomal surface (through, e.g., FcRn or another receptor) are shuttled to the lysosomal pathway and degraded, whereas receptor-bound molecules are recycled to the plasma membrane when the endosome fuses with the plasma membrane. Upon fusion with the plasma membrane, the acid-stable Fc-FcRn interaction is exposed to a near neutral extracellular pH where the Fc readily dissociates from the FcRn. It is the pH binding differential of the Fc, coupled with a differential thermal stability of FcRn that varies with protonation state, that is believed to be primarily responsible for the ability of certain Fc's to sustain serum concentrations through binding FcRn. A key to the endosomal cycling mechanism is ligand release by receptors in the acidic endosomal compartment (reviewed, e.g., in Brown, M. S. et al. (1983)).

IgG1 Fc moieties bind FcRn with high affinity at pH 6.0 to about 6.5; binding at pH 7.0 to about pH 7.5 is about two orders of magnitude weaker, presumably due to titration of histidine residues near the region of the Fc that binds FcRn, residues 310-433, and an FcRn intramolecular thermal stability differential mediated by protonation state (Raghaven, M. et al. (1995) Analysis of the pH dependence of the neonatal Fc receptor/immunoglobulin G interaction using antibody and receptor variants, Biochemistry 34:14649-14657; Vaughn, D. E. and Bjorkman, P. J. (1998) Structural basis of pH-dependent antibody binding by the neonatal Fc receptor, Structure 6:63-73); it has been demonstrated that rat FcRn exhibits a better thermal stability profile at pH 6.0 than at pH 8.0 (Raghavan, M. et al. (1993) The class I MHC-related Fc receptor shows pH dependent stability differences correlating with immunoglobulin binding and release, Biochemistry 32:8654-8660).

Although nature gave rise to Fc structures that bind FcRn differentially, the science of Fc engineering arose to design Fc structures that would result in tighter binding to FcRn and—presumably—longer serum half-life. Many such structures were designed and tested, far too numerous to review here, with varying degrees of success. Mutating immunoglobulin constant region sequences to promote recycling of antibody by modifying FcRn binding characteristics has a long and varied history. To date, most if not all effort to identify mutations have focused on residues believed to be critical in binding or interacting with FcRn, i.e., residues whose modification affect affinity of the Fc for FcRn.

But binding of Fc to FcRn is itself a complex matter. Different types of therapeutic antibodies (humanized, chimeric, and mouse), and even within types (e.g., comparing different humanized antibodies to one another, comparing IgG1 isotype antibodies to one another, etc.), exhibit dissociation constants with respect to FcRn that vary as much as about two-fold (see, e.g., Suzuki, T. et al. (2010) Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR, J. Immunol. 184:1968-1976). This observation permits an inference that the primary structure of the constant region may not account for all pharmacokinetic behavior. Others have postulated that overall isoelectric point (pI) of an antibody, keeping the constant region primary structure fixed, is an important determinant of serum half-life—presumably through an unspecified non-FcRn-dependent mechanism (Igawa, T. et al. (2010) Reduced elimination of IgG antibodies by engineering the variable region, Protein Engineering, Design & Selection 23(5):385-392). Under this view, the lower the pI of the antibody, the tighter the binding to FcRn (Id.). For at least one IgG4 isotype antibody, a change in pI from 9.2 to 7.2 correlated with a 2.4-fold increase in half-life and a 4.4-fold reduction in clearance (Id.), consistent with an inference that a nonspecific lowering of pI by modifying residues in both the heavy and light chain variable regions together can significantly impact pharmacokinetic behavior. In that report, residue modification did not follow any particular pattern and no residue was substituted to histidine, although at least one residue in a light chain CDR2 was changed from a histidine residue to a glutamate residue (Id., at FIG. 5, p. 390). Further, an odd paradox may erupt when comparing in vitro FcRn binding and in vivo pharmacokinetics: for at least one clinically important IgG1 antibody with multiple substitutions in the Fc region that interacts with FcRn, in vitro FcRn binding did not correlate with in vivo pharmacokinetic behavior (see, Petkova, S. B. et al. (2006) Enhanced half-life of genetically engineered human IgG1 antibodies in a humanized FcRn mouse model: potential application in humorally mediated autoimmune disease, Int'l Immunol. 18(12):1759-1769). Finally, release of Fc ligand from FcRn upon fusion with the plasma membrane appears to occur in two phases—a rapid phase and an extended phase—of unknown mechanism (see, Ober R. J. et al. (2004) Exocytosis of IgG as mediated by the receptor FcRn: an analysis at the single-molecule level, Proc. Natl Acad. Sci. USA 101:11076-11081).

Finally, extending half-life of antibodies in serum is one way to enhance efficiency of antibody therapy. Improved efficacy, or improved availability of the same antibody or variable domain to bind and eliminate two or three or more target molecules are not necessarily addressed by improving FcRn binding and turnover that affects target antigen. Modifications that increase affinity of an Fc to FcRN are expected to increase turnover and thus improve pharmacokinetics of a therapeutic antibody. Antigen-antibody complexes bind FcRn tightly, resulting in the antigen-antibody complex cycling back into extracellular space rather than being degraded by a lysosomal pathway. In this scenario, however, the antigen, or target, may largely remain complexed to the antibody and recycled together with the antibody into the extracellular space. For therapeutic antibodies, this phenomenon can be very undesirable.

However, antibodies whose interaction with antigen are pH-dependent, i.e., antibodies engineered to bind antigen with lower affinity at an endosomal pH, would not recycle antigen in an FcRn-dependent manner due to instability of the antigen-antibody complex in the endosomal compartment. This is because in the acidic environment of the endosome, the antigen will disengage from the antibody-FcRn complex, and the antibody-bound FcRn will recycle to the surface of the cell, whereas disengaged free antigen will shuttle to a lysosomal degradation pathway. In this way, pH-dependent antigen binding can provide enhanced efficacy and/or pharmacokinetics within the context of FcRn-mediated cycling (but not directly depending on the Fc-FcRn interaction) by freeing cycled antibody to bind antigen, bind FcRn, cycle through endosomes, and re-enter the extracellular space to bind more antigen and shuttle more antigen to a lysosomal degradation pathway.

Capitalizing on the observation that ligands will frequently dissociate from their receptors at an endosomal pH, it had been suggested to search for antibodies that effectively release antigen at an endosomal pH in order to make certain specific multifunctional molecules that target specific cells in order to import toxins into the cells and release the toxins within endosomes (see, e.g., U.S. Pat. Nos. 5,599,908 and 5,603,931). But that does not address antigen-antibody cycling, in particular for human therapeutics.

To leverage antibody structure for shuttling endosomally disengaged antigen through a lysosomal pathway while maintaining FcRn-dependent cycling of antigen-FcRn complexes, certain approaches to pH-dependent antigen binding have been explored. Such approaches include a generalized histidine-scanning over the variable region to substitute residues with histidine and test to see whether the generalized approach of histidine replacement yields an antibody with desired pH-dependent antigen binding (see, e.g., Igawa, T. et al. (2010) Antibody recycling by engineered pH-dependent antigen binding improves the duration of antigen neutralization, Nature Biotech. 28(11):1203-1208; see also, U.S. Patent Application Publication No. 2011/0111406 A1)). A likely disadvantage of this approach is that modifying residues important for antigen binding are likely to disrupt binding at either an acidic or neutral pH, which can eliminate any leverage due to the pH differential between the endosomal compartment and the extracellular space.

In various aspects, compositions and methods are provided for making one or more histidine substitutions at a few judiciously-selected regions in an antibody variable region (heavy chain and/or light chain variable domain) provides a method for making antibody variable domains that bind a target antigen in a pH-dependent manner, e.g., variable domains that bind an antigen of interest with a first affinity at a neutral or basic or extracellular pH, yet bind the same antigen of interest with a second affinity at an acidic pH, wherein the first affinity is high and wherein the second affinity is low.

In various aspects, the one or more histidine substitutions are in a CDR1, a CDR2, a CDR3, an N-terminal, and/or a loop 4 sequence.

In some aspects the one or more histidine substitutions are in a CDR1, a CDR2, and/or a CDR3.

In some aspects, the one or more histidine substitutions are in a CDR3 and a loop 4 sequence. In a further embodiment, the substitutions are also in an N-terminal sequence.

In some aspects, the one or more histidine substitutions are in a CDR3 and an N-terminal sequence. In a further embodiment, the substitutions are also in a loop 4 sequence.

In some aspects, the one or more histidine substitutions are in a CDR2 sequence and a loop 4 sequence. In a further embodiment, the substitutions are also in an N-terminal sequence.

In some aspects, the loop 4 sequence is for a λ light chain variable domain residues 83-88; for a κ light chain variable domain residues 83-88; and for a heavy chain variable region 82-88 (IMGT numbering).

In some aspects, the N-terminal sequence for a light chain variable domain or a heavy chain variable domain are residues 1-26 (IMGT numbering). In one embodiment, the N-terminal sequence that comprises one or more (e.g., clustered) histidine substitutions is residues 1-5, in one embodiment residues 1-10, in one embodiment 1-15, in one embodiment 1-20, in one embodiment 1-25, in one embodiment 5-10, in one embodiment 10-15, in one embodiment 15-20, in one embodiment 20-25, in one embodiment 5-15, in one embodiment 10-20, in one embodiment 5-20. In one embodiment, the histidine substitutions are two or more (e.g., three, four, five, or six or more), and at least two or more of the histidine substitutions are made within a stretch of N-terminal sequence that is about 3 residues, 4 residues, five residues, or six residues or more. In one embodiment, a plurality of histidine substitutions are made in the N-terminal, and the histidine substitutions comprise clusters of at least two, at least three, or at least four histidine substitutions. In one embodiment, at least one cluster of histidine substitutions comprises histidine substitutions that are separated by one or more non-histidine substitutions.

In some aspects, the one or more histidine substitutions the CDR are two, three, four, five, or six substitutions within the CDR. In one embodiment, all residues in the CDR that are not critical for binding at a neutral pH are substituted with a histidine. In one embodiment, the two, three, four, five, or six substitutions are contiguous; in one embodiment, one or more of the two, three, four, five, or six substitutions are present in a cluster, wherein the cluster comprises at least one non-histidine residue; in one embodiment, the cluster comprises two non-histidine residues; in one embodiment, the cluster comprises three non-histidine residues; in one embodiment, the cluster comprises four non-histidine residues.

In some aspects, the one or more histidine substitutions in the N-terminal are one, two, three, four, five, or six substitutions. In one embodiment, all residues in the N-terminal that do not reduce antigen binding at a neutral pH (e.g., by more than 1%, 2%, 3%, 4%, or 5%), are substituted with a histidine. In one embodiment, the two, three, four, five, or six substitutions are contiguous; in one embodiment, one or more of the two, three, four, five, or six substitutions are present in a cluster, wherein the cluster comprises at least one non-histidine residue; in one embodiment, the cluster comprises two non-histidine residues; in one embodiment, the cluster comprises three non-histidine residues; in one embodiment, the cluster comprises four non-histidine residues.

In some aspects, the method comprises modifying a variable domain to comprise a cluster of histidine substitutions (e.g., as described herein, contiguous or interrupted with one or more non-histidine residues) in a region selected from a CDR1, a CDR2, a CDR3, an N-terminal, a loop 4, and a combination thereof. In some aspects, the cluster is a sequence bounded upstream by a first histidine residue, and downstream by a second histidine residue, and comprises one or more residues between the first and second histidine residues. In one embodiment, the one or more residues between the first and second histidine residues are 1, 2, 3, 4, 5, or 6 or more non-histidine residues. In one embodiment, the one or more residues between the first and second histidine residues are 1, 2, 3, 4, 5, or six histidine residues. In one embodiment, the cluster is 3 residues, in one embodiment 4 residues, in one embodiment 5 residues, in one embodiment 6 residues, in one embodiment 7 residues, in one embodiment 8 residues or more.

In various aspects, the method comprises identifying sequences in an antibody variable domain (heavy and/or light chain) that are critical for binding antigen (e.g., at a neutral pH, e.g., pH 7-7,4, e.g., pH 7.2, e.g., an extracellular pH), and substituting one or more residues within the sequence to histidine, wherein the substitution to histidine does not eliminate binding of the variable domain to a target antigen at a neutral pH. In various aspects, a cluster of two or more, three or more, four or more, or five or more residues that are not critical for binding at a neutral pH are substituted with histidine residues. In various aspects, the cluster of histidine residues is within a CDR, a loop 4, an N-terminal, or a combination thereof.

In various aspects, a residue that is critical for binding is identified as a residue that when substituted with a substitute amino acid at about a neutral (or extracellular) pH, reduces binding of the variable domain by in one embodiment at least 5%, in one embodiment at least 10%, in one embodiment at least 20%, in one embodiment at least 30%, in one embodiment at least 40%, in one embodiment at least 50%, in one embodiment at least 60%, in one embodiment at least 70%, in one embodiment at least 80%, in one embodiment at least 90%, in one embodiment results in no detectable binding. In one embodiment, the substitute amino acid is a histidine. In one embodiment, the substitute amino acid is an alanine.

In one aspect, a method is provided for making an antibody variable domain that binds and antigen weaker at an acidic pH than it binds the same antigen at a neutral or basic pH, wherein the method comprises substituting one or more amino acid residues of the variable region with one or more histidine residues. In one embodiment, the binding at the acidic pH is negligible or zero.

In one embodiment, the one or more amino acid residues substituted are in a light chain. In a specific embodiment, the one or more residues are in an N-terminal region of a light chain. In a specific embodiment, the N-terminal residues are selected from 1-26, 1-20, 1-15, 1-10, 1-6, or 1-5 (IMGT numbering). In one embodiment, the one or more residues are in loop 3. In a specific embodiment, the loop 4 residues are 83-88 in Vκ or Vλ, and 82-88 in $V_H$ (IMGT numbering).

In one embodiment, the one or more residues are in a heavy chain. In a specific embodiment, the one or more residues are in an N-terminal region of a heavy chain. In a specific embodiment, the N-terminal residues are selected from 1-26, 1-20, 1-15, 1-10, 1-6, or 1-5 (IMGT numbering). In one embodiment, the one or more residues are in loop 4. In a specific embodiment, the loop 3 residues are selected from (for Vκ and/or Vλ) 83, 84, 85, 86, 87, 88, and a combination thereof (IMGT numbering); or (for $V_H$) 82, 83, 84, 85, 86, 87, 88, and a combination thereof (IMGT numbering); and, a combination thereof.

In one embodiment, the one or more residues are in a CDR selected from a CDR1, a CDR2, and a CDR3; and the one or more residues when substituted (e.g., with alanine or with histidine) do not result in decreased binding of the target antigen at a neutral or a basic pH. In a specific embodiment, decreased binding of the target antigen at neutral or basic pH as the result of substitution (e.g., by alanine or histidine substitution) is no more than 5%, no more than 10%, no more than 15%, or no more than 20%, no more than 25%, or no more than 30% as compared with non-substituted variable domain.

In some aspects, the his-modified variable domain complexed with the target antigen exhibits a half-life of at least about 20 minutes at an elevated pH (e.g., an extracellular pH, or a pH from 7-7.4, e.g., pH 7.2) and exhibits a half-life of less than 5 minutes, less than 4 minutes, less than 3 minutes, less than 2 minutes, or less than a minute at an endosomal pH, or a pH from e.g., pH 5-6, e.g., pH 5.75. In one embodiment, the his-modified variable domain complexed with the target antigen exhibits a half-life of at least about 20 minutes at the elevated pH, and exhibits a half-life at an endosomal pH of less than 60 seconds, less than 30 seconds, less than 10 seconds, less than 5 seconds, less than 4 seconds, less than 3 seconds, or less than 2 seconds. In one embodiment, the his-modified variable domain complexed with the target antigen exhibits a half-life of at least about 20 minutes at the elevated pH (e.g., pH 7-7.4, e.g., pH 7.2), and exhibits a half-life at an endosomal pH of less than about a second, less than 0.5 second, less than 0.1 second, or less than 0.05 second. In one embodiment, half-life at an endosomal pH is measured using a BIACORE™ assay in which his-modified variable domain complexed with target antigen is equilibrated on the surface of a BIACORE™ chip at neutral or elevated pH, and buffer at an endosomal pH (or, e.g., a pH of 5-6, e.g., pH 5.75) is flowed over the complex.

In various aspects, a method for making an antibody variable domain that binds a target antigen with a first affinity at an extracellular pH, and that does not bind the target antigen or binds the target antigen with a second affinity at an endosomal pH, wherein the first affinity is about 10, $10^2$-, $10^3$-, $10^4$-, $10^5$-, $10^6$-, $10^7$-, $10^8$-, $10^9$, $10^{10}$-, $10^{11}$-, or $10^{12}$-fold (or higher-fold) than the second affinity. In some aspects, the first affinity is in the picomolar to nanomolar range (e.g., $K_D$ is $10^{-12}$ to $10^{-9}$), and the second affinity is in the micromolar or higher range (e.g., $K_D=10^{-6}$ or greater, e.g., $10^{-5}$, $10^{-4}$, $10^{-3}$, $10^{-2}$, $10^{-1}$, 1, or higher). In some aspects, the first affinity is in the range of about $K_D$ $10^{-9}$ to about $K_D$ $10^{-12}$, and the second affinity is in the range of about $K_D$ $10^{-3}$ to about 1 or larger. In one embodiment, the first affinity is in the range of about $K_D$ $10^{-9}$ to about $K_D$ $10^{-12}$, and the second affinity is characterized by a $K_D>1$; in a specific embodiment, the second affinity is characterized by a $K_D>>1$ (e.g., 10, $10^2$, $10^3$ or higher). In a specific embodiment, the first affinity is characterized by a $K_D$ from about $10^{-9}$ to about $10^{-12}$, and the second affinity is characterized by an inability to detect binding over background in a BIACORE™ binding assay.

Various aspects are illustrated by a particular case in which a human light chain variable sequence is modified to contain a one or more, including a cluster, of histidines in a light chain CDR3, and the light chain is expressed in a CHO cell with a cognate human heavy chain. The identity of the antigen to which the histidine-modified antibody binds is unimportant, as is the particular sequence of the light chain variable domain. The principles illustrated in the Examples are applicable to CDR3, CDR2, CDR1, the N-terminal region, or loop 4. For example, residues in the cited regions can be substituted for histidine, alone or in clusters of 2, 3, 4, or 5, e.g., and the resulting antibodies tested for pH-dependent antigen binding.

Methods for engineering antibodies that are capable of binding to an antigen in a pH dependent manner can be made by making modifications of an immunoglobulin light chain variable region at one or more positions along the sequence of the light chain as described (e.g., in a CDR3, CDR2, CDR1, loop 4, N-terminal). Histidines are tolerated in CDR regions; light chains, typically show somatic hypermutation along the variable region sequence, and, in some cases, such mutations can result in a substitution of histidine residues in CDRs (FIG. 15).

In the Examples, histidine substitutions have been identified at one to four positions in the light chain CDR3 region, at residues not critical for binding target antigen at a neutral pH, from which fifteen mutant constructs were made. The particular light chain shown—with a variety of different but cognate heavy chains—is derived from a single Vκ and a single Jκ segment (Vκ1-39/Jκ5). Such mutants when expressed confer upon the antibody (in conjunction with a cognate heavy chain) the property of pH-dependent antigen binding. The mutant constructs were made using antigen-specific antibody variable domains and tested for expression and antigen binding at approximately a neutral pH and release at low pH ("catch-and-release"). In certain examples shown the locations of the four identified residues (where mutation to histidine is not critical for binding at neutral pH) are Q105H, Q106H, Y108H and P111H. For an antibody that binds a different target antigen, or for an antibody comprising a different rearranged V-J sequence, his-mutatable residues for making a pH-dependent variable domain are found by identifying which residues are not critical for binding at neutral pH, then modifying one or more of those residues (e.g., in clusters) and expressing an antibody comprising the mutations, and testing for binding (and/or release time, e.g., $t_{1/2}$) at a neutral pH (e.g., an extracellular pH) and at an acidic pH (e.g., an endosomal pH). Although the data shown here are for a Vκ1-39/Jκ5 light chain, other light chains, including those derived from a Vκ3-20/Jκ1 rearrangement, are amenable to the approach described herein, as are heavy chains.

All of the histidine-engineered light chain constructs that were made in this experiment expressed well in conjunction with heavy chains. Further, binding of the antibodies to antigen in a pH-dependent manner was demonstrated from BIACORE™ assay data showing the binding of antigen at around a neutral pH and at an acidic pH for the 15 mutants with five different heavy chains that specifically recognize the same cell surface antigen (FIG. 19A-J).

The methods described, and those particular methods used for purposes of illustration in certain of the examples and figures herein, are useful to generate variable regions of antibodies that can be used to make, e.g., human therapeutic binding proteins that bind their targets by human immunoglobulin variable domains that comprise the histidines in a CDR3. The altered binding at a lower pH will in some circumstances allow faster turnover because the therapeutic will bind a target on a cell's surface, be internalized in an endosome, and more readily or more rapidly dissociate from the target in the endosome, so that the therapeutic can be recycled to bind yet another molecule of target (e.g., on another cell or the same cell). In various embodiments, this will result in the ability to dose the therapeutic at a lower dose, or dose the therapeutic less frequently. This is particularly useful where it is not desirable to dose frequently, or to administer above a certain dosage, for safety or toxicity reasons. For example, the half-life of an antibody therapeutic in the serum of a subject will be increased as a result.

Thus, in various embodiments codons in a gene encoding a rearranged human light chain can be made at positions 105, 106, 108, 111, or a combination thereof. For example, position 105 in conjunction with one or more of 106, 108, and 111; position 106 in conjunction with one or more of 105, 108, and 111; position 108 in conjunction with one or more of 105, 106, and 111; position 111 in conjunction with one or more of 105, 106, and 108. Corresponding positions in other light chains (i.e., derived from other V-J rearrangements) are included in various embodiments.

Non-Human Animals that Express Immunoglobulin Heavy Chain Variable Domain Comprising Histidine Residues The described invention provides genetically modified non-human animals that can produce antigen-binding proteins with pH-dependent antigen binding characteristics. In various embodiments, the antigen-binding proteins produced by the genetically modified non-human animals as described herein exhibit increased pH-dependent recycling efficiency and/or enhanced serum half-life. In particular, the described invention employs genetic modifications in the immunoglobulin heavy chain locus to introduce histidine codons into a human heavy chain variable region nucleotide sequence and, optionally, to introduce a mutation(s) in a constant region nucleotide sequence that encodes $C_H2$ and/or $C_H3$ domains that increases the binding of the antibody constant region to an FcRn receptor, which facilitates recycling of the antigen-binding protein. Antigen-binding proteins comprising the modification may more loosely bind its target in an acidic intracellular compartment (e.g., in an endosome where pH ranges from about 5.5 to about 6.0) than in an extracellular environment or at the surface of a cell (i.e., at a physiological pH, e.g., a pH ranging from about 7.0 to about 7.4) due to protonated histidine residues located in the antigen binding sites. Therefore, the antigen-binding proteins comprising the genetic modifications as described herein would be able to be recycled more rapidly or efficiently than wild-type antigen-binding proteins that do not comprise such genetic modifications following target-mediated endocytosis. Furthermore, since the modified histidine residues are protonated only in an acidic environment, but not at a neutral pH, it is expected that such modification would not affect binding affinity and/or specificity of the antigen-binding protein toward an antigen of interest at a physiological pH.

In various aspects, non-human animals are provided comprising immunoglobulin heavy chain loci that comprise an unrearranged human heavy chain variable region nucleotide sequence, wherein the unrearranged human heavy chain variable region nucleotide sequence comprises an addition of least one histidine codon or a substitution of at least one endogenous non-histidine codon with a histidine codon.

In various aspects, methods of making and using the non-human animals are also provided. When immunized with an antigen of interest, the genetically modified non-human animals are capable of generating B cell populations that produce antigen-binding proteins comprising heavy chain variable domains with histidine residues, wherein the antigen-binding proteins exhibit enhanced pH-dependent recycling and/or increased serum half-life. In various embodiments, the non-human animals generate B cell populations that express human heavy chain variable domains along with cognate human light chain variable domains. In various embodiments, the genetically modified immunoglobulin heavy chain loci are present in a germline genome of the non-human animal.

In various embodiments, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising one or more human $V_H$, D, and/or $J_H$ gene segments having one or more histidine codons, wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome). In one embodiment, e.g., about 80% or more, about 85% or more, about 90% or more, about 95% or more, about 96% or more, about 97% or more, about 98% or more, or about 99% or more of all endogenous heavy chain V, D, or J gene segments are deleted or rendered non-functional. In one embodiment, e.g., at least 95%, 96%, 97%, 98%, or 99% of endogenous functional heavy chain V, D, or J gene segments are deleted or rendered non-functional.

In one embodiment, the non-human animal is a mammal. Although embodiments directed to introducing histidine codons into an unrearranged human heavy chain variable gene sequence in a mouse are extensively discussed herein, other non-human animals are also provided that comprise a genetically modified immunoglobulin locus containing an unrearranged human heavy chain variable region nucleotide sequence comprising an addition of least one histidine codon or a substitution of at least one endogenous non-histidine codon with a histidine codon. Such non-human animals include any of those which can be genetically modified to express the histidine-containing heavy chain variable domain as disclosed herein, including, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo. Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a nucleotides sequence that encodes In one embodiment, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In one embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6N, C57BL/6NJ, C57BL/10, C57BL/10ScSn, C57BL/10Cr, and C57BL/Ola. In another embodiment, the mouse is a 129 strain. In one embodiment, the 129 strain is selected from the group consisting of 129P1, 129P2, 129P3, 129X1, 129S1 (e.g., 129S1/SV, 129S1/Svlm), 129S2, 129S4, 12955, 129S9/SvEvH, 129S6 (129/SvEvTac), 12957, 12958, 129T1, 129T2 (see, e.g., Festing et al. (1999) Revised nomenclature for strain 129 mice, Mammalian Genome 10:836, see also, Auerbach et al. (2000) Establishment and Chimera Analysis of 129/SvEv- and C57BL/6-Derived Mouse Embryonic Stem Cell Lines). In one embodiment, the genetically modified mouse is a mix of an aforementioned 129 strain and an aforementioned C57BL strain (e.g., a C57BL/6 strain). In another embodiment, the mouse is a mix of aforementioned 129 strains, or a mix of aforementioned C57BL/6 strains. In one embodiment, the 129 strain of the mix is a 129S6 (129/SvEvTac) strain. In another embodiment, the mouse is a mix of a 129/SvEv- and a C57BL/6-derived strain. In a specific embodiment, the mouse is a mix of a 129/SvEv- and a C57BL/6-derived strain as described in Auerbach et al. 2000 BioTechniques 29:1024-1032. In another embodiment, the mouse is a BALB strain, e.g., BALB/c strain. In another embodiment, the mouse is a mix of a BALB strain (e.g., BALB/c strain) and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more of a strain selected from the group consisting of Wistar, LEA, Sprague Dawley, Fischer, F344, F6, and Dark Agouti.

In one embodiment, the non-human animal is a mouse. In one embodiment, the mouse is a VELOCIMMUNE® humanized mouse.

VELOCIMMUNE® humanized mice (see, e.g., U.S. Pat. Nos. 6,596,541, 7,105,348, and US20120322108A1, which are incorporated herein by reference in their entireties), which contain a precise replacement of mouse immunoglobulin variable regions with human immunoglobulin variable regions at the endogenous mouse loci, display a surprising and remarkable similarity to wild-type mice with respect to B cell development. VELOCIMMUNE® humanized mice display an essentially normal, wild-type response to immunization that differed only in one significant respect from wild-type mice—the variable regions generated in response to immunization are fully human.

VELOCIMMUNE® humanized mice contain a precise, large-scale replacement of germline variable region nucleotide sequences of mouse immunoglobulin heavy chain (IgH) and immunoglobulin light chain (e.g., κ light chain, Igκ) with corresponding human immunoglobulin variable region nucleotide sequences, at the endogenous loci (see, e.g., U.S. Pat. Nos. 6,596,541, 7,105,348, US 20120322108A1, which are incorporated herein by reference in their entireties). In total, about six megabases of mouse loci are replaced with about 1.5 megabases of human genomic sequence. This precise replacement results in a mouse with hybrid immunoglobulin loci that make heavy and light chains that have a human variable regions and a mouse constant region. The precise replacement of mouse $V_H$-D-$J_H$ and Vκ-Jκ segments leave flanking mouse sequences intact and functional at the hybrid immunoglobulin loci. The humoral immune system of the mouse functions like that of a wild-type mouse. B cell development is unhindered in any significant respect and a rich diversity of human variable regions is generated in the mouse upon antigen challenge.

VELOCIMMUNE® humanized mice are possible because immunoglobulin gene segments for heavy and κ light chains rearrange similarly in humans and mice, which is not to say that their loci are the same or even nearly so—clearly they are not. However, the loci are similar enough that humanization of the heavy chain variable gene locus can be accomplished by replacing about three million base pairs of contiguous mouse sequence that contains all the $V_H$, D, and $J_H$ gene segments with about one million bases of contiguous human genomic sequence covering basically the equivalent sequence from a human immunoglobulin locus.

In some embodiments, further replacement of certain mouse constant region nucleotide sequences with human constant region nucleotide sequences (e.g., replacement of mouse heavy chain $C_H1$ nucleotide sequence with human heavy chain $C_H1$ nucleotide sequence, and replacement of mouse light chain constant region nucleotide sequence with human light chain constant region nucleotide sequence) results in mice with hybrid immunoglobulin loci that make antibodies that have human variable regions and partly human constant regions, suitable for, e.g., making fully human antibody fragments, e.g., fully human Fab's. Mice with hybrid immunoglobulin loci exhibit normal variable gene segment rearrangement, normal somatic hypermutation frequencies, and normal class switching. These mice exhibit a humoral immune system that is indistinguishable from wild type mice, and display normal cell populations at all stages of B cell development and normal lymphoid organ structures—even where the mice lack a full repertoire of human variable region nucleotide segments. Immunizing these mice results in robust humoral responses that display a wide diversity of variable gene segment usage.

The precise replacement of the mouse germline variable region nucleotide sequence allows for making mice that have partly human immunoglobulin loci. Because the partly human immunoglobulin loci rearrange, hypermutate, and class switch normally, the partly human immunoglobulin loci generate antibodies in a mouse that comprise human variable regions. Nucleotide sequences that encode the variable regions can be identified and cloned, then fused (e.g., in an in vitro system) with any sequences of choice, e.g., any immunoglobulin isotype suitable for a particular use, resulting in an antibody or antigen-binding protein derived wholly from human sequences.

In various embodiments, at least one histidine codon is present in an unrearranged heavy chain variable region nucleotide sequence that encodes an N-terminal region, a loop 4 region, a CDR1, a CDR2, a CDR3, or a combination thereof.

In various embodiments, at least one histidine codon is present in an unrearranged heavy chain variable region nucleotide sequence that encodes a framework region (FR) selected from the group consisting of FR1, FR2, FR3, and FR4.

In various aspects, the genetically modified immunoglobulin locus comprises a nucleotide sequence wherein at least one codon has been replaced with a histidine codon.

In various aspects, the genetically modified immunoglobulin locus comprises an unrearranged human heavy chain variable region nucleotide sequence comprising a substitution of at least one endogenous non-histidine codon with a histidine codon.

In one embodiment, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of the endogenous non-histidine codons are replaced with histidine codons.

Previous studies on reading frame usage of human immunoglobulin D gene segments have shown that, of the three reading frames (i.e., stop, hydrophobic, and hydrophilic), the stop frame is used very infrequently. Apparently, some stop frames are chewed back and result in expression. However, stop reading frames are used at such a low frequency that for the purposes of engineering histidine codons, it is more efficient not to use the stop reading frame. As between hydrophilic and hydrophobic reading frames, the hydrophilic reading frame appears to be preferred. Thus, in one embodiment, the hydrophilic reading frame of human D gene segments is engineered to contain one or more histidine codons (as compared with the stop frame or with the hydrophobic frame).

Methods of introducing a mutation in vitro, e.g., site-directed mutagenesis, are well known in the art. In some embodiments of the described invention, histidine codons are enriched by designing histidine-substituted human D gene segments in silico (e.g., mutation of Y, D, and N codons to H codons, e.g., CAT, CAC), which are synthesized (e.g., chemical synthesis) with (unique) restriction enzyme sites for ligating them back together. The synthesized D gene segments are made with the appropriate recombination signal sequences (RSS) upstream and downstream. In one embodiment, when ligated to one another, the synthesized histidine-substituted D gene segments include the intergenic sequences observed in a human between each D gene segment.

It is understood that the codons that encode the one or more histidines, upon rearrangement and/or somatic hypermutation, may change such that one or more of the histidines will be changed to another amino acid. However, this may not occur for each and every codon encoding histidine, in each and every rearrangement in the non-human animal. If such changes occur, the changes may occur in some but not all B cells or in some but not all heavy chain variable sequences.

In various aspects, the genetically modified immunoglobulin locus comprises a human heavy chain V, D, and J gene segment, wherein at least one of the human D gene segment has been inverted 5' to 3' with respect to a corresponding wild-type sequence, and wherein at least one reading frame of the inverted human D gene segment comprises a histidine codon.

In various embodiments, the nucleotide sequence comprises one or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more of histidine codons.

There are 25 functional human D gene segments in 6 families of 3-5 members each (one family—the D7 family—has a single member). Direct recombination of human D gene segments is much more frequent than inversion, although inverted reading frames exhibit more histidine codons. Certain D gene segments and reading frames are used more frequently than others. All three direct reading frames and all three inverted orientation reading frames for all the functional D gene segments are presented in FIGS. 10A-10E. As shown in FIGS. 10A-10E, there are many more histidine codons in inverted reading frames than in direct reading frames. More specifically, there are 34 histidines in inverted reading frames and only four in direct reading frames. In addition, of the four in direct reading frames, three histidines are encoded by pseudogenes or present in alternate alleles. Therefore, there is only a single direct reading frame of a germline human D gene segment that contains a histidine codon, with further histidine codons possibly encountered in alternate alleles (presumably in subsets of the human population).

Inverted D rearrangements are extremely rare. Tuaillon et al. (J. Immunol., 154(12): 5453-6465, incorporated by reference herein in its entirety) showed that usage of inverted reading frames (as measured by limiting dilution PCT) is very rare, i.e., that the ratio of direct to indirect rearrangements are, in most cases, 100 to 1000. To the extent that the ratio of direct to indirect rearrangement was low, it was only observed in those D segments that exhibit very low usage. It was also shown that D gene segment family 7, which is located adjacent to J1 (far down from other D family members) is mostly used in fetuses, but exhibits a low usage in adults (Schroeder et al., Immunology 30, 2006, 119-135, incorporated by reference herein in its entirety). Therefore, in one embodiment, D family 7 sequences are not inverted 5' to 3'.

In one embodiment, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, or all or substantially all of the human functional D gene segments are inverted 5' to 3' with respect to corresponding wild type sequences.

In one embodiment, the human immunoglobulin heavy chain variable domain comprising at least one non-naturally occurring histidine residue exhibits pH-dependent antigen binding characteristics. For example, an antibody comprising the modified immunoglobulin heavy chain variable domain binds a target with sufficient affinity at around a neutral pH (e.g., pH of about 7.0 to about 7.4), but either does not bind or binds weaker to the same target at an acidic pH (e.g., pH of about 5.5 to about 6.0). In one embodiment, the acidic pH is selected from about 5.5, about 5.6, about 5.7, about 5.8, about 5.9, and about 6.0. In one embodiment, the neutral pH is selected from about 7.0, about 7.1, about 7.2, about 7.3, and about 7.4.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, antigen binding proteins comprising the genetically modified human immunoglobulin heavy chain variable domain is capable of specifically binding an antigen of interest with an affinity ($K_D$) lower than $10^{-6}$, $10^{-7}$, $10^{-8}$, $10^{-9}$ or $10^{-10}$, $10^{-11}$, $10^{-12}$ at a neutral or physiological pH (pH of about 7.0 to about 7.4).

The altered binding property of the immunoglobulin heavy chain variable domain at an acidic pH (e.g., pH of about 5.5 to about 6.0) would, in some circumstances, allow faster turnover of the antibody because the therapeutic antibody will bind a target on a cell's surface, be internalized into an endosome, and more readily or more rapidly dissociate from the target in the endosome, so that the therapeutic can be recycled to bind yet another molecule of target present in another cell. This would allow one to administer a therapeutic antibody at a lower dose, or administer the therapeutic antibody less frequently. This is particularly useful in a situation where it is not desirable to administer a therapeutic antibody frequently, or administer at a level above a certain dosage for safety or toxicity reasons.

In various embodiments, the human immunoglobulin heavy chain variable region nucleotide sequence as described herein is operably linked to a human or non-human heavy chain constant region nucleotide sequence (e.g., a heavy chain constant region nucleotide sequence that encodes an immunoglobulin isotype selected from IgM, IgD, IgG, IgE, and IgA). In various embodiments, the human or non-human heavy chain constant region nucleotide sequence is selected from the group consisting of a $C_H1$, a hinge, a $C_H2$, a $C_H3$, and a combination thereof. In one embodiment, the constant region nucleotide sequence comprises a $C_H1$, a hinge, a $C_H2$, and a $C_H3$ (e.g., $C_H1$-hinge-a $C_H2$-$C_H3$).

In various embodiments, the heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

The neonatal Fc receptor for IgG (FcRn) has been well characterized in the transfer of passive humoral immunity from a mother to her fetus across the placenta and proximal small intestine (Roopenian, D. and Akilesh, S., Nat. Rev. Immun., 2007, 7:715-725, which is incorporated by reference herein in its entirety). FcRn binds to the Fc portion of IgG at a site that is distinct from the binding sites of the classical FcγRs or the C1q component of complement, which initiates the classical pathway of complement activation. More specifically, it was shown that FcRn binds the $C_H2$-$C_H3$ hinge region of IgG antibodies—a versatile region of Fc that also binds Staphylococcal protein A, Streptococcal protein G, and the rheumatoid factor. In contrast to other Fc-binding proteins, however, FcRn binds the Fc region of IgG in a strictly pH-dependent manner; at physiological pH 7.4, FcRn does not bind IgG, whereas at the acidic pH of the endosome (e.g., where the pH ranges from about 5.5 to about 6.0), FcRn exhibits a low micromolar to nanomolar affinity for the Fc region of IgG. This pH-dependent interaction has been shown to be mediated by the titration of histidine residues in the $C_H2$-$C_H3$ region of IgG and their subsequent interaction with acidic residue on the surface of FcRn (Roopenian, D. and Akilesh, S., Nat. Rev. Immun., 2007, 7:715-725, incorporated by reference in its entirety).

Various mutations in the $C_H2$-$C_H3$ region of IgG that can increase the affinity of Fc region to FcRn at an acidic pH are known in the art. These include, but are not limited to, modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/S/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 52Y, 254T, and 256E) modification; a 250Q and 428L modification, or a combination thereof.

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the human constant region amino acid sequence encoded by the heavy chain constant region nucleotide sequence described herein comprises a mutation selected from the group consisting of M428L, N434S, and a combination thereof. In one embodiment, the human constant region amino acid sequence comprises a mutation selected from the group consisting of M428L, V259I, V308F, and a combination thereof. In one embodiment, the human constant region amino acid sequence comprises an N434A mutation. In one embodiment, the human constant region amino acid sequence comprises a mutation selected from the group consisting of M252Y, S254T, T256E, and a combination thereof. In one embodiment, the human constant region amino acid sequence comprises a mutation selected from the group consisting of T250Q, M248L, or both. In one embodiment, the human constant region amino acid sequence comprises a mutation selected from the group consisting of H433K, N434Y, or both.

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

Engineered Histidine Residues in Immunoglobulin Light Chain Genes

In various embodiments, genetically modified non-human animals (e.g., mammals, e.g., mice, rats, rabbits, etc.) are provided that comprise in their genome, e.g., in their germline, nucleotide sequence(s) encoding human antibody molecules that exhibit pH-dependent antigen binding, e.g., a nucleotide sequence of immunoglobulin light chain comprising rearranged human immunoglobulin light chain variable region sequence encoding antibodies that exhibits pH-dependent antigen binding; embryos, cells, and tissues comprising the same; methods of making the same; as well as methods of using the same.

The inventors have discovered that non-human animals that express antibodies that are capable of binding to an antigen in a pH dependent manner can be made by making modifications of an immunoglobulin light chain variable region at one or more positions along the sequence of the light chain. Methods of making modifications in the germline of a non-human animal so that the animal would express histidines in CDRs of antibodies are described. In particular, methods for making modifications in an immunoglobulin light chain variable sequence in the germline of the mouse are described. Variable region sequence, e.g., of light chains, typically show somatic hypermutation along the variable region sequence, and, in some cases, such mutations can result in a substitution of histidine residues (see, e.g., FIG. 15). Such mutations can even occur in complementary determining regions (CDRs), which are the regions of variable domains responsible for antigen binding. In some cases, such mutations can result in antibodies that display pH-dependent antigen binding, e.g., reduced antigen binding at an acidic pH as compared to antigen binding at a neutral pH. Such pH-dependent antigen binding is desired because it may enable the antibody to bind to the antigen outside the cell, and, when internalized into an endosome, release the antigen and recycle back to the surface to bind another antigen, avoiding target-mediated clearance. Approaches for introducing histidine residues to achieve this effect by using a random his-scanning mutagenesis to engineer pH-dependent binding properties in anti-IL-6R antibodies have been reported (US 2011/0111406 A1). However, random mutagenesis of antibody residues may result in decreased affinity of antibody to the antigen. A non-human animal genetically modified to express a histidine substitution in antibody sequence enables generation of high-affinity antibodies in response to an antigen of interest that, due to histidine modification(s), would also display pH-dependent antigen binding.

Thus, in various embodiments, provided herein is a genetically modified non-human animal (e.g., rodent, e.g., a mouse or a rat) that comprises in its genome, e.g., its germline, a human immunoglobulin light chain variable region sequence comprising modifications that result in the animal expressing antibodies capable of binding to antigens in a pH-dependent manner. In one embodiment, the non-human animal comprises modifications in the human immunoglobulin light chain variable region sequence (e.g., $V_L$ and/or $J_L$ segment sequence) that comprise substitutions in at least one non-histidine codon with a histidine codon (in some cases, also may be referred to as "histidine substitution," "histidine codon substitution," or the like). In one embodiment, the animal comprises at least one substitution of a non-histidine codon with a histidine codon in a nucleotide sequence of a complementary determining region (CDR; e.g., CDR1, CDR2, and/or CDR3) of a human immunoglobulin light chain. In one embodiment, the substitution is in a CDR3 codon. In one embodiment, the light chain is a κ light chain. In one embodiment, the animal expresses an immunoglobulin light chain, e.g., a light chain CDR, e.g., a light chain CDR3, comprising a substitution of at least one amino acid with a histidine. In another embodiment, the light chain is a λ light chain. In yet another embodiment, the mouse comprises a substitution of at least one non-histidine codon with a histidine codon in both κ and λ light chains.

A histidine residue is encoded by two different codons, CAT and CAC (deoxyribonucleic acid residues). Thus, a non-histidine codon may be substituted with a CAT or a CAC. The substitution is engineered in a codon that in its germline configuration (i.e., non-somatically mutated state) does not encode a histidine residue.

In one embodiment a light chain is a universal light chain (also termed a common light chain). As described in U.S. patent application Ser. Nos. 13/022,759, 13/093,156, 13/412,936 and 13/488,628 (U.S. Application Publication Nos. 2011/0195454, 2012/0021409, 2012/0192300 and 2013/0045492, all incorporated herein by reference), a non-human animal (e.g., a mouse) that selects a common light chain for a plurality of heavy chains has a practical utility. In various embodiments, antibodies expressed in a non-human animal comprising only a common light chain will have heavy chains that can associate and express with an identical or substantially identical light chain. This is particularly useful in making bispecific antibodies. For example, such an animal can be immunized with a first immunogen to generate a B cell that expresses an antibody that specifically binds a first epitope. The animal (or an animal genetically the same) can be immunized with a second immunogen to generate a B cell that expresses an antibody that specifically binds the second epitope. Variable heavy chain regions can be cloned from the B cells and expressed with the same heavy chain constant region and the same light chain (e.g., a common light chain) in a cell to make a bispecific antibody, wherein the heavy chain component of the bispecific antibody has been selected by an animal to associate and express with the same light chain component. In various embodiments described, the variable regions of the genetically engineered mice are human variable regions.

Thus, a mouse was engineered that is capable of generating immunoglobulin light chains that will suitably pair with a rather diverse family of heavy chains, including heavy chains whose human variable regions depart from germline sequences, e.g., affinity matured or somatically mutated variable regions. In various embodiments, the mouse is devised to pair human light chain variable domains with human heavy chain variable domains that comprise somatic mutations, thus enabling a route to high affinity binding proteins suitable for use as human therapeutics.

The genetically engineered mouse, through the long and complex process of antibody selection within an organism, makes biologically appropriate choices in pairing a diverse collection of human heavy chain variable domains with a limited number of human light chain options. In order to achieve this, the mouse is engineered to present a limited number of human light chain variable domain options in conjunction with a wide diversity of human heavy chain variable domain options. Upon challenge with an immunogen, the mouse maximizes the number of solutions in its repertoire to develop an antibody to the immunogen, limited largely or solely by the number or light chain options in its repertoire. In various embodiments, this includes allowing the mouse to achieve suitable and compatible somatic mutations of the light chain variable domain that will nonetheless be compatible with a relatively large variety of human heavy chain variable domains, including in particular somatically mutated human heavy chain variable domains.

The engineered common light chain mouse described in U.S. Application Publication Nos. 2011/0195454, 2012/0021409, 2012/0192300 and 2013/0045492 comprised nucleic acid sequence encoding a limited repertoire of light chain options, e.g., common or universal light chain "ULC" that comprised no more than two $V_L$ segments or a single rearranged human immunoglobulin light chain variable region sequence. To achieve such limited repertoire, a mouse was engineered to render nonfunctional or substantially nonfunctional its ability to make, or rearrange, a native mouse light chain variable domain. In one aspect, this was achieved, e.g., by deleting the mouse's light chain variable region gene segments. As previously described, the endogenous mouse locus can then be modified by exogenous suitable human light chain variable region gene segments of choice, operably linked to the endogenous mouse light chain constant domain, in a manner such that the exogenous human variable region gene segments can combine with the endogenous mouse light chain constant region gene and form a rearranged reverse chimeric light chain gene (human variable, mouse constant). In various embodiments, the light chain variable region is capable of being somatically mutated. In various embodiments, to maximize ability of the light chain variable region to acquire somatic mutations, the appropriate enhancer(s) is retained in the mouse. In one aspect, in modifying a mouse κ light chain locus to replace endogenous mouse κ light chain gene segments with human κ light chain gene segments, the mouse κ intronic enhancer and mouse κ 3' enhancer are functionally maintained, or undisrupted.

Thus, provided was a genetically engineered mouse that expresses a limited repertoire of reverse chimeric (human variable, mouse constant) light chains associated with a diversity of reverse chimeric (human variable, mouse constant) heavy chains. In various embodiments, the endogenous mouse κ light chain gene segments are deleted and replaced with a single (or two) rearranged human light chain region, operably linked to the endogenous mouse Cκ gene. In embodiments for maximizing somatic hypermutation of the rearranged human light chain region, the mouse κ intronic enhancer and the mouse κ 3' enhancer are maintained. In various embodiments, the mouse also comprises a nonfunctional λ light chain locus, or a deletion thereof or a deletion that renders the locus unable to make a λ light chain.

The universal light chain mouse generated antibodies in response to various antigens that were capable of utilizing a diverse repertoire of heavy chain variable region sequences, comprising a diverse repertoire of $V_H$, $D_H$, and $J_H$ segments. Antibodies generated in such genetically engineered ULC mouse are useful for designing bispecific therapeutic antibodies; however, as with any other antibody, each bispecific antibody may only bind to one target during its lifetime in the plasma; the antibody is internalized into an endosome and targeted for lysosomal degradation. Studies have shown that MHC-class-I-like Fcγ receptor FcRn is capable of rescuing immunoglobulins from lysosomal degradation by recycling it back to the cell surface from the sorting endosome. Simister and Mostov (1989) An Fc receptor structurally related to MHC class I antigens. Nature 337: 184-87. As explained above, to improve efficiency of antibody recycling, further modifications to antibody sequences, e.g., modifications that result in decreased antigen binding at acidic pH (e.g., pH of the endosome), while retaining antibody-antigen affinity and specificity at neutral pH (e.g., pH of body fluids such as blood) are beneficial. The non-human animals described herein, wherein histidine residues are substituted for non-histidine residues in the a universal light chain sequence are beneficial because they are capable of producing high-affinity antibodies based on universal light chain format that also display pH-dependent binding, e.g., display reduced binding to the antigen at acidic versus neutral pH.

Thus, in one embodiment, provided herein is a non-human animal (e.g., a rodent, e.g., a mouse or a rat) that comprises in its genome, e.g., in its germline, a limited repertoire of human light chain variable regions, or a single human light chain variable region, from a limited repertoire of human light chain variable gene segments, wherein the human light chain variable region(s) comprise at least one substitution of a non-histidine codon for a histidine codon. In some embodiments, provided non-human animals are genetically engineered to include a single unrearranged human light chain variable region gene segment (or two human light chain variable region gene segments) that rearranges to form a rearranged human light chain variable region gene (or two rearranged light chain variable region genes) that expresses a single light chain (or that express either or both of two light chains), wherein the light chain variable region gene(s) comprise a substitution of at least one non-histidine codon with a histidine codon. The rearranged human light chain variable domains encoded by these histidine-substituted light chain variable region gene (s) are capable of pairing with a plurality of affinity-matured human heavy chains selected by the animals, wherein the heavy chain variable regions specifically bind different epitopes. In various embodiments, the at least one substitution of a non-histidine residue with a histidine residue results in a rearranged human light chain that, when expressed with a cognate heavy chain, binds to its antigen in a pH-dependent manner.

Genetically engineered animals are provided that express a limited repertoire of human light chain variable domains, or a single human light chain variable domain, from a limited repertoire of human light chain variable region gene sequences, wherein the variable region gene sequences comprise at least one substitution of a non-histidine codon with a histidine codon. In some embodiments, provided animals are genetically engineered to include a single V/J human light chain sequence (or two V/J sequences) that comprises a substitution of at least one non-histidine codon with a histidine codon and expresses a variable region of a single light chain (or that express either or both of two variable regions). In one aspect, a light chain comprising the variable sequence is capable of pairing with a plurality of affinity-matured human heavy chains clonally selected by the animal, wherein the heavy chain variable regions specifically bind different epitopes. In one embodiment, the antibody binds to its antigen(s) in a pH-dependent manner. In one embodiment, the single V/J human light chain sequence is selected from Vκ1-39Jκ5 and Vκ3-20Jκ1. In one embodiment, the two V/J sequences are Vκ1-39Jκ5 and Vκ3-20Jκ1. In one embodiment, the Vκ1-39Jκ5 and Vκ3-20Jκ1 sequences are rearranged V/J sequences.

In one aspect, a genetically modified non-human animal is provided that comprises a single human immunoglobulin light chain $V_L$ gene segment that is capable of rearranging with a human $J_L$ gene segment (selected from one or a plurality of $J_L$ segments) and encoding a human variable domain of an immunoglobulin light chain, wherein the single human immunoglobulin light chain $V_L$ gene segment and/or human $J_L$ gene segment comprise a substitution of at least one non-histidine codon with a histidine codon. In another aspect, a genetically modified mouse is provided that comprises no more than two human $V_L$ gene segments, each of which is capable of rearranging with a human $J_L$ gene segment (selected from one or a plurality of $J_L$ segments) and encoding a human variable domain of an immunoglobulin light chain, wherein each of the no more than two $V_L$ gene segments and/or the $J_L$ gene segment comprise a substitution of at least one non-histidine residue with a histidine residue.

Also provided herein is a genetically modified non-human animal that comprises in its genome, e.g., in its germline, a single rearranged human immunoglobulin light chain variable region sequence comprising a human $V_L$ and $J_L$ sequences wherein the single rearranged human immunoglobulin light chain variable region comprises a substitution of at least one non-histidine codon with a histidine codon. In one aspect, the single rearranged human immunoglobulin light chain variable region sequence is derived from human germline $V_L$ and $J_L$ gene sequences, but for the histidine substitution(s). In one embodiment, the human immunoglobulin light chain is a human immunoglobulin κ chain. Thus, in one embodiment, the human $V_L$ gene sequence is selected from Vκ1-39 and Vκ3-20. In one embodiment, the single rearranged human immunoglobulin light chain variable region sequence comprises rearranged Vκ1-39/J or Vκ3-20/J sequence. In one embodiment, the human $J_L$ gene sequence is selected from Jκ1, Jκ2, Jκ3, Jκ4, and Jκ5. In one embodiment the human $J_L$ sequence is selected from Jκ1 and Jκ5. In one embodiment, the single rearranged human immunoglobulin light chain variable region sequence is selected from Vκ1-39Jκ5 and Vκ3-20Jκ1 (e.g., but for the histidine substitution(s)). In an alternative embodiment, the human immunoglobulin light chain is a human λ chain.

In one embodiment, the substitution of at least one non-histidine codon for a histidine codon is in the nucleotide sequence encoding a complementary determining region (CDR) of the light chain variable domain. In one embodiment, the substitution of at least one non-histidine codon for a histidine codon is in the nucleotide sequence encoding CDR1, CDR2 or CDR3 of the light chain variable domain. In one specific embodiment, the substitution is in the nucleotide sequence encoding CDR3.

In one aspect, the substitution is of at least one non-histidine codon for a histidine codon in the CDR3 codon of the human light chain variable region gene sequence. In one embodiment, the substitution is of one, two, three, four, or more CDR3 codons. In the embodiment wherein the single rearranged human immunoglobulin light chain variable region is a Vκ1-39Jκ5 variable region, the replacement of at least one non-histidine codon with a histidine codon comprises a replacement at a position in the immunoglobulin light chain gene sequence encoding CDR3 designed to express histidine at position selected from 105, 106, 108, 111, and a combination thereof. In one embodiment, the replacement is designed to express histidine at positions 105 and 106. In one embodiment, the replacement is designed to express histidine at positions 105 and 111. In one embodiment, the replacement is designed to express histidine at positions 105 and 108. In one embodiment, the replacement is designed to express histidine at positions 105, 108 and 111. In one embodiment, the replacement is designed to express histidine at positions 105, 106, and 108. In one embodiment, the replacement is designed to express histidine at positions 106 and 108. In one embodiment, the replacement is designed to express histidine at positions 106 and 111. In one embodiment, the replacement is designed to express histidine at positions 108 and 111. In one embodiment, the replacement is designed to express histidine at positions 106, 108, and 111. In yet another embodiment, the replacement is designed to express histidine at positions 106, 108 and 111. In one embodiment, the replacement is designed to express histidine at positions 105, 106, and 111. In one embodiment, the replacement is designed to express histidine at positions 105, 106, 108, and 111. The nucleic acid and amino acid sequences of the histidine-substituted regions are depicted in sequence alignment of FIG. 16 and set forth in SEQ ID NOs: 327-357.

In the embodiment wherein the single rearranged human immunoglobulin light chain variable region is a Vκ3-20Jκ1 variable region, the replacement of at least one non-histidine codon with a histidine codon comprises a replacement at a position in the immunoglobulin light chain gene sequence encoding CDR3 region that is designed to express histidine at position selected from 105, 106, 107, 109, and a combination thereof. In one embodiment, the replacement is designed to express histidine at positions 105 and 106. In one embodiment, the replacement is designed to express histidine at positions 105 and 107. In one embodiment, the replacement is designed to express histidine at positions 105 and 109. In one embodiment, the replacement is designed to express histidine at positions 106 and 107. In one embodiment, the replacement is designed to express histidine at positions 106 and 109. In one embodiment, the replacement is designed to express histidine at positions 107 and 109. In one embodiment, the replacement is designed to express histidine at positions 105, 106, and 107. In one embodiment, the replacement is designed to express histidine at positions 105, 107, and 109. In one embodiment, the replacement is designed to express histidine at positions 106, 108, and 111. In one embodiment, the replacement is designed to express histidine at positions 105, 106 and 109. In another embodiment, the replacement is designed to express histidine at positions 105, 106, 107, and 109. The nucleic acid and amino acid sequences of exemplary histidine-substituted regions are depicted in sequence alignment of FIG. 27 and set forth in SEQ ID NOs: 398-403.

Amino acid positions (105, 106, etc.) are based on a unique numbering described in Lefranc et al. (2003) Dev. Comp. Immunol. 27:55-77, and can also be viewed on the website of the International Immunogenetics Information System (IMGT).

In one embodiment, the human $V_L$ gene segment is operably linked to a human or non-human leader sequence. In one embodiment, the leader sequence is a non-human leader sequence. In a specific embodiment, the non-human leader sequence is a mouse Vκ3-7 leader sequence. In a specific embodiment, the leader sequence is operably linked to an unrearranged human $V_L$ gene segment. In a specific embodiment, the leader sequence is operably linked to a rearranged human $V_L/J_L$ sequence. Thus, in one specific embodiment, the single rearranged Vκ1-39/Jκ5 or Vκ3-20/Jκ1 variable region gene sequence comprising at least one histidine substitution is operably linked to a mouse Vκ3-7 leader sequence.

In one embodiment, the $V_L$ gene segment is operably linked to an immunoglobulin promoter sequence. In one embodiment, the promoter sequence is a human promoter sequence. In a specific embodiment, the human immunoglobulin promoter is a human Vκ3-15 promoter. In a specific embodiment, the promoter is operably linked to an unrearranged human $V_L$ gene segment. In a specific embodiment, the promoter is operably linked to a rearranged human $V_L/J_L$ sequence. Thus, in one specific embodiment, the single rearranged Vκ1-39/Jκ5 or Vκ3-20/Jκ1 variable region gene sequence comprising at least one histidine substitution is operably linked to the human Vκ3-15 promoter.

In one embodiment, the light chain locus comprises a leader sequence flanked 5' (with respect to transcriptional direction of a $V_L$ gene segment) with a human immunoglobulin promoter and flanked 3' with a human $V_L$ gene segment that rearranges with a human $J_L$ segment and encodes a variable domain of a reverse chimeric light chain comprising an endogenous non-human light chain constant region ($C_L$). In a specific embodiment, the $V_L$ and $J_L$ gene segments are at the non-human Vκ locus, and the non-human $C_L$ is a non-human Cκ (e.g., mouse Cκ). In one specific embodiment, the variable region sequence is operably linked to the non-human constant region sequence, e.g., the non-human Cκ gene sequence.

In one embodiment, the light chain locus comprises a leader sequence flanked 5' (with respect to transcriptional direction of a $V_L$ gene segment) with a human immunoglobulin promoter and flanked 3' with a rearranged human variable region sequence ($V_L/J_L$ sequence) and encodes a variable domain of a reverse chimeric light chain comprising an endogenous non-human light chain constant region ($C_L$). In a specific embodiment, the rearranged human $V_L/J_L$ sequence is at the non-human kappa (κ) locus, and the non-human $C_L$ is a non-human Cκ. In one specific embodiment, the rearranged human variable region sequence is operably linked to the non-human immunoglobulin light chain constant region sequence, e.g., the non-human Cκ gene sequence. In one embodiment, the non-human immunoglobulin light chain constant region sequence is an endogenous non-human sequence. In one embodiment, the non-human animal is a mouse and the Cκ gene sequence is a mouse Cκ gene sequence. In one embodiment, the rearranged human immunoglobulin light chain variable region sequence comprising a substitution of at least one non-histidine codon with a histidine codon is at the endogenous non-human (e.g., mouse) immunoglobulin light chain locus (κ locus). Exemplary embodiments of the locus are presented in FIGS. 23C, 23E, 29C, and 29D.

In one embodiment, the genetically modified non-human animal is a mouse, and the variable region locus of the mouse is a κ light chain locus, and the κ light chain locus comprises a mouse κ intronic enhancer, a mouse κ 3' enhancer, or both an intronic enhancer and a 3' enhancer.

In one embodiment, the non-human animal (e.g., a rodent, e.g., a rat or a mouse) comprises a nonfunctional immunoglobulin lambda (λ) light chain locus. In a specific embodiment, the λ light chain locus comprises a deletion of one or more sequences of the locus, wherein the one or more deletions renders the λ light chain locus incapable of rearranging to form a light chain gene. In another embodiment, all or substantially all of the $V_L$ gene segments of the λ light chain locus are deleted. In one embodiment, the non-human animal (e.g., rodent, e.g. mouse or rat) comprises a rearranged human immunoglobulin light chain variable region sequence comprising a substitution of at least one non-histidine codon with a histidine codon, and lacks a functional unrearranged immunoglobulin light chain variable region, e.g., endogenous unrearranged light chain variable region. In one embodiment, the rearranged, histidine-substituted human immunoglobulin light chain variable region gene sequence replaces endogenous unrearranged immunoglobulin light chain variable region gene sequence.

In one embodiment, the animal makes a light chain that comprises a somatically mutated variable domain derived from a human variable region sequence that comprises a substitution of at least one non-histidine codon with a histidine codon. In one embodiment, the light chain comprises a somatically mutated variable domain derived from a human variable region sequence that comprises a substitution of at least one non-histidine codon with a histidine codon, and a non-human Cκ region. In one embodiment, the non-human animal does not express a λ light chain.

One skilled in the art would appreciate that although substitution(s) of at least one non-histidine residue with a histidine residue is genetically engineered into the human immunoglobulin light chain variable region, due to somatic hypermutations, not all antibodies that are generated in the genetically modified non-human animal will harbor that histidine residue(s) at engineered position(s). However, generation of a wide repertoire of antibodies in the non-human animal will allow to select for in vivo generated antigen-specific antibodies that display high affinity for an antigen of interest while retaining histidine modifications introduced into the germline and, thus, exhibiting pH-dependent antigen binding.

Thus, in one embodiment, the animal retains at least one substitution of a non-histidine amino acid with a histidine. In one embodiment, the animal retains all or substantially all histidine substitutions in its somatically mutated light chain variable domain that were introduced into its variable region gene.

In one embodiment, the genetically modified non-human animal described herein also comprises in its genome, e.g., its germline, an unrearranged immunoglobulin heavy chain variable region comprising $V_H$, $D_H$, and $J_H$ gene segment sequences. In one embodiment, the $V_H$, $D_H$, and $J_H$ gene segment sequences are human $V_H$, $D_H$, and $J_H$ gene segment sequences, and the unrearranged immunoglobulin heavy chain variable region is a human heavy chain variable region. In one embodiment, the human $V_H$, $D_H$, and $J_H$ gene segment sequences are operably linked to non-human heavy chain constant region sequence. In one embodiment, the non-human heavy chain constant region sequence is an endogenous non-human heavy chain constant region sequence. In one embodiment, the human heavy chain gene segment sequences are at the endogenous non-human immunoglobulin heavy chain locus. In one embodiment, the human immunoglobulin heavy chain variable region sequence comprised in a non-human animal also comprises a substitution of at least one non-histidine codon for a histidine codon.

In one embodiment, the non-human animal described herein expresses an immunoglobulin light chain that comprises a non-human light chain constant region sequence. In one embodiment, the non-human animal expresses an immunoglobulin light chain that comprises a human light chain constant region sequence.

In one embodiment, the non-human animal described herein expresses an immunoglobulin heavy chain that comprises a non-human sequence selected from a $C_H1$ sequence, a hinge sequence, a $C_H2$ sequence, a $C_H3$ sequence, and a combination thereof.

In one embodiment, the non-human animal expresses an immunoglobulin heavy chain that comprises a human sequence selected from a $C_H1$ sequence, a hinge sequence, a $C_H2$ sequence, a $C_H3$ sequence, and a combination thereof.

In the embodiment where the animal comprises a single rearranged immunoglobulin light chain variable region comprising a substitution of at least one non-histidine codon with a histidine codon, the rearranged immunoglobulin light chain sequence in the germline of the animal is at an endogenous non-human immunoglobulin light chain locus. In a specific embodiment, the rearranged immunoglobulin light chain sequence comprising a substitution of at least one non-histidine codon with a histidine codon in the germline of the animal replaces all or substantially all endogenous non-human light chain V and J segment sequences at the endogenous non-human immunoglobulin light chain locus.

In one embodiment, the non-human animal comprises a replacement of endogenous $V_H$ gene segments with one or more human $V_H$ gene segments, wherein the human $V_H$ gene segments are operably linked to a non-human $D_H$ region gene, such that the non-human animal rearranges the human $V_H$ gene segments and expresses a reverse chimeric immunoglobulin heavy chain that comprises a human $V_H$ domain and a non-human $D_H$. In one embodiment, 90-100% of unrearranged non-human $V_H$ gene segments are replaced with at least one unrearranged human $V_H$ gene segment. In a specific embodiment, all or substantially all (e.g., 90-100%) of the endogenous non-human $V_H$ gene segments are replaced with at least one unrearranged human $V_H$ gene segment. In one embodiment, the replacement is with at least 19, at least 39, or at least 80 or 81 unrearranged human $V_H$ gene segments. In one embodiment, the replacement is with at least 12 functional unrearranged human $V_H$ gene segments, at least 25 functional unrearranged human $V_H$ gene segments, or at least 43 functional unrearranged human $V_H$ gene segments. In one embodiment, the non-human animal comprises a replacement of all non-human $D_H$ and $J_H$ segments with at least one unrearranged human $D_H$ segment and at least one unrearranged human $J_H$ segment. In one embodiment, the non-human animal comprises a replacement of all non-human $D_H$ and $J_H$ segments with all unrearranged human $D_H$ segments and all unrearranged human $J_H$ segments.

A non-human animal, e.g., a mouse, comprising in its genome, e.g., its germline, a limited repertoire of human immunoglobulin light chain variable regions, e.g., a single rearranged human immunoglobulin light chain variable region (e.g., Vκ1-39/Jκ5 or Vκ3-20/Jκ1), with a substitution of at least one non-histidine codon with a histidine codon and a diverse repertoire of unrearranged human $V_H$, $D_H$, and $J_H$ segments is capable of generating antigen binding proteins encoded by heavy chain variable region sequences derived from various permutations of unrearranged human $V_H$, $D_H$, and $J_H$ segments, wherein the $V_H$, $D_H$, and $J_H$ segments present in the heavy chain variable sequences are derived from all or substantially all functional human $V_H$, $D_H$, and $J_H$ segments present in the genome of the animal. Various available possibilities for heavy chain variable domain sequences expressed in the cells, e.g., B cells, of the genetically modified animals described herein (i.e., derived from combinations of various functional human V, D, and J segments) are described in U.S. Application Publication Nos. 2011/0195454, 2012/0021409, 2012/0192300 and 2013/0045492, all incorporated herein by reference. In various embodiments, the rearranged human immunoglobulin light chain variable region sequence comprising substitution(s) of at least one non-histidine codon with a histidine codon and the unrearranged human immunoglobulin heavy chain variable region sequence are comprised in the germline of the non-human animal.

In one embodiment, the non-human animal comprises one copy of one or both of the rearranged human immunoglobulin light chain variable region sequence comprising substitution(s) of at least one non-histidine codon with a histidine codon and the unrearranged human immunoglobulin heavy chain variable region sequence. In another embodiment, the non-human animal comprises two copies of one or both of the rearranged human immunoglobulin light chain variable region sequence comprising substitution(s) of at least one non-histidine codon with a histidine codon and the unrearranged human immunoglobulin heavy chain variable region sequence. Thus, the non-human animal may be homozygous or heterozygous for one or both the rearranged human immunoglobulin light chain variable region sequence comprising substitution(s) of at least one non-histidine codon with a histidine codon and the unrearranged human immunoglobulin heavy chain variable region sequence.

In addition to genetically modified non-human animals comprising in their genome an immunoglobulin light chain variable region gene sequence (e.g., a single rearranged immunoglobulin light chain variable region gene sequence) comprising substitution of at least one non-histidine codon with a histidine codon (e.g., in CDR3 of the light chain), also provided herein are genetically modified non-human animals comprising an immunoglobulin light chain variable region gene sequence with one or more additions of histidine codon(s), such that the expressed variable domain comprises an additional amino acid(s) which, if not subject to somatic hypermutation, is a histidine.

The genetically modified non-human animal comprising a human immunoglobulin light chain variable region gene sequence with a substitution of at least one non-histidine codon with a histidine codon described herein may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, methods distinct from those described herein are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/Svlm), 129S2, 129S4, 12955, 129S9/SvEvH, 129S6 (129/SvEvTac), 12957, 12958, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment, the genetically modified non-human animal is a rodent. In one embodiment, the genetically modified non-human animal is a rat or a mouse. In one embodiment, the animal is a mouse. Thus, in one embodiment, provided herein is a genetically modified mouse comprising in its genome, e.g., its germline, a single rearranged human immunoglobulin light chain variable region comprising human $V_L$ and $J_L$ gene sequences, wherein the single rearranged human immunoglobulin light chain variable region comprises a substitution of at least non-histidine codon with a histidine codon. In one embodiment, the mouse lacks a functional unrearranged immunoglobulin light chain variable region (e.g., lacks functional unrearranged V and J gene segment sequences). In one embodiment, the rearranged human immunoglobulin light chain variable region with histidine codon substitution(s) is Vκ1-39/Jκ or Vκ3-20/Jκ variable region. In one embodiment the J segment sequence is selected from Jκ1, Jκ2, Jκ3, Jκ4, and Jκ5. In one embodiment the J segment sequence is Jκ1 or Jκ5. In one embodiment, the substitution of at least one non-histidine codon with a histidine codon is in the nucleotide sequence encoding a CDR3 region. In one embodiment, wherein the rearranged variable region sequence is Vκ1-39/Jκ5 sequence, the histidine substitution(s) is designed to express at a position selected from 105, 106, 108, 111, and a combination thereof. In another embodiment, wherein the rearranged variable region sequence is Vκ3-20/Jκ1 sequence, the histidine substitution(s) is designed to express at a position selected from 105, 106, 107, 109, and a combination thereof. In one embodiment, the rearranged immunoglobulin light chain variable region with substituted histidine codon(s) is operably linked to an endogenous mouse immunoglobulin constant region gene sequence (e.g., Cκ gene sequence). In one embodiment, the mouse further comprises in its genome, e.g., its germline, an unrearranged immunoglobulin heavy chain variable region comprising human $V_H$, $D_H$, and $J_H$ segments. In one embodiment, human $V_H$, $D_H$, and $J_H$ segments are operably linked to an endogenous mouse immunoglobulin heavy chain constant region gene sequence. In various embodiments, the rearranged human immunoglobulin light chain variable region sequence comprising substitution(s) of at least one non-histidine codon with a histidine codon and the unrearranged human immunoglobulin heavy chain variable region sequence are comprised in the germline of the mouse.

Also provided herein are targeting vectors for generating genetically modified non-human animals, e.g., mice, described herein. In one aspect, provided is a targeting vector comprising, from 5' to 3' in transcriptional direction with reference to the sequences of the 5' and 3' mouse homology arms of the vector, a 5' mouse homology arm, a human or mouse immunoglobulin promoter, a human or mouse leader sequence, a human variable region selected from a rearranged human Vκ1-39Jκ5 or a rearranged human Vκ3-20Jκ1 and comprising a substitution of at least one non-histidine codon with a histidine codon, and a 3' mouse homology arm. In one embodiment, the 5' and 3' homology arms target the vector to a sequence 5' with respect to an enhancer sequence that is present 5' and proximal to the mouse Cκ gene. In another embodiment, the targeting vector comprises a 5' mouse homology arm followed by a selection cassette flanked by recombination sites, human or mouse immunoglobulin promoter, human or mouse leader sequence, a human variable region selected from a rearranged human Vκ1-39Jκ5 or a rearranged human Vκ3-20Jκ1 and comprising a substitution of at least one non-histidine codon with a histidine codon, followed by the 3' mouse homology arm that comprises mouse enhancers and constant region (Cκ) sequences.

A selection cassette is a nucleotide sequence inserted into a targeting construct to facilitate selection of cells (e.g., ES cells) that have integrated the construct of interest. A number of suitable selection cassettes are known in the art. Commonly, a selection cassette enables positive selection in the presence of a particular antibiotic (e.g., Neo, Hyg, Pur, CM, Spec, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art.

In one embodiment, the promoter is a human immunoglobulin variable region gene segment promoter. In a specific embodiment, the promoter is a human Vκ3-15 promoter. In one embodiment, the leader sequence is a mouse leader sequence. In a specific embodiment, the mouse leader sequence is a mouse Vκ3-7 leader sequence. Exemplary embodiments of the targeting vectors are presented in FIGS. 23B and 29B.

In one aspect, a targeting vector is provided as described above, but in place of the 5' mouse homology arm the human or mouse promoter is flanked 5' with a site-specific recombinase recognition site (SRRS), and in place of the 3' mouse homology arm the human $V_L$ region is flanked 3' with an SRRS.

Also provided herein are methods of making genetically modified non-human animals (e.g., rodents, e.g., mice or rats) described herein. In one aspect, the method for making a genetically modified non-human animal described herein utilizes a targeting vector, made using VELOCIGENE® technology, introducing the construct into ES cells, and introducing targeted ES cell clones into a mouse embryo using VELOCIMOUSE® technology, as described in the Examples. Histidine modifications may be introduced into the targeting vector using a variety of molecular biology techniques, e.g., site directed mutagenesis or de novo DNA synthesis. Upon completion of gene targeting, ES cells of genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCT (e.g., real-time PCR using TAQMAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6): 652-659. Other assays that identify a specific nucleotide or amino acid sequence in the genetically modified animals are known to those skilled in the art.

Thus, in one embodiment, the method of generating genetically modified non-human animals comprises replacing an immunoglobulin light chain variable region gene sequence in the animal with a human immunoglobulin light chain variable region gene sequence (comprising human $V_L$ and $J_L$ gene segments) wherein the human immunoglobulin variable region gene sequence comprises a substitution of at least one non-histidine codon with a histidine codon. In one embodiment, the substitution of at least one non-histidine codon with a histidine codon is in the nucleotide sequence encoding a CDR region, e.g., a CDR3 region.

In one embodiment, the method of generating genetically modified non-human animals described herein comprises replacing an immunoglobulin light chain variable region gene sequence in the animal with a single rearranged human immunoglobulin light chain variable region gene sequence comprising human $V_L$ and $J_L$ gene segment sequences, wherein the single rearranged human immunoglobulin variable region gene sequence comprises a substitution of at least one non-histidine codon with a histidine codon. In one embodiment, the substitution is in a CDR codon. In one embodiment, the substitution is of one, two, three, four, or more CDR3 codon(s). In one embodiment, the single rearranged human immunoglobulin light chain variable region gene sequence is based on the human germline rearranged light chain variable region sequence selected from Vκ1-39Jκ5 and Vκ3-20Jκ1. Thus, in one embodiment, where the single rearranged human immunoglobulin light chain variable region gene sequence is derived from Vκ1-39Jκ5, replacement of at least one non-histidine codon with histidine codon is designed to express a histidine at positions selected from 105, 106, 108, 111, and a combination thereof. In one embodiment, where the single rearranged human immunoglobulin light chain variable region gene sequence is derived from Vκ3-20κ1, replacement of at least one non-histidine codon with a histidine codon is designed to express a histidine at position selected from 105, 106, 107, 109, and a combination thereof.

In another embodiment, the method of generating a non-human animal described herein (i.e., comprising a genetically modified immunoglobulin light chain locus described herein) comprises modifying a genome of a non-human animal to delete or render non-functional endogenous immunoglobulin light chain V and J segments in an immunoglobulin light chain locus, and placing in the genome a single rearranged human light chain variable region gene sequence comprising a substitution of at least one non-histidine codon with a histidine codon. In one embodiment, the method results in a genetically modified non-human animal that comprises a population of B cells enriched for antibodies exhibiting pH dependent binding to an antigen of interest.

In some embodiments, the methods of generating genetically modified non-human animals described herein comprise replacing an immunoglobulin light chain variable region gene sequence with human sequence in the animal that also comprises a replacement of endogenous non-human immunoglobulin heavy chain variable region gene sequence with a human immunoglobulin heavy chain variable region gene sequence comprising at least one of each or a repertoire of human $V_H$, $D_H$, and $J_H$ sequences, as described above. In one embodiment, in order to generate a non-human animal comprising a replacement of endogenous immunoglobulin light chain variable region gene sequence human light chain variable region gene sequence comprising a substitution of at least one non-histidine codon with a histidine codon and a replacement of endogenous non-human immunoglobulin heavy chain variable region gene sequence with a human immunoglobulin heavy chain variable region gene sequence, the animal with replacement of light chain variable region gene sequence is bred to an animal with replacement of heavy chain variable region gene sequence.

Inventors presently provide genetically engineered non-human animals (e.g., rodents, e.g., rats or mice) that express antigen-binding proteins, e.g., antibodies, that comprise a universal light chain, e.g., a human universal light chain (e.g., a light chain derived from a single rearranged human immunoglobulin light chain variable region) that comprises one or more histidine modifications, wherein the antigen-binding proteins exhibit a pH-dependent antigen binding of a target antigen. The animals are genetically engineered to include a light chain CDR3 that comprises one or more histidine modifications. In various embodiments, the light chain CDR3 comprises two, three, or four or more histidine residues in a cluster.

In one embodiment, provided herein is a genetically engineered non-human animal that comprises a population of antigen-specific antibodies that express histidine residue(s) as a result of codon modifications in the light chain variable region gene sequence, and display pH-dependent binding of target antigen. In one embodiment, these animals comprise a population of B cells that are enriched for antibodies, e.g., antigen-specific antibodies, that display pH-dependent binding properties (e.g., decreased dissociative half-life ($t_{1/2}$), at acidic pH vs neutral pH) as compared to a population of antigen-specific antibodies generated in animals that do not comprise a substitution of at least one non-histidine codon with a histidine codon in immunoglobulin light chain variable region described herein. In one embodiment, the enrichment of antigen-specific antibodies displaying pH-dependent antigen binding properties generated in the genetically engineered animals described herein as compared to similar animals that do comprise histidine substitutions in light chain variable region is greater than about 2 fold, e.g., greater than about 5 fold, e.g., greater than about 10 fold. Thus, the genetically modified animals of the invention are enriched for antibodies with improved antibody recycling properties, which is desired in order to reduce target-mediated clearance as well as to reduce the dose and/or dosing frequency of a therapeutic antigen-binding protein developed based on such in vivo generated antibody format.

Thus, provided herein is an antigen-binding protein, generated in genetically modified non-human animals described herein, wherein the antigen-binding protein displays pH-dependent antigen binding. In one embodiment, the antigen-binding protein is an antibody, e.g., antigen-specific antibody. In one embodiment, the antibody comprises a light chain which comprises a human light chain variable domain derived from a rearrangement of human immunoglobulin light chain variable gene segments where at least one non-histidine codon was substituted for a histidine codon in the germline gene sequence, and wherein the antibody retains at least one histidine substitution in its expressed human light chain variable domain. In one embodiment, the antibody comprises a light chain which comprises a human light chain variable domain derived from a single rearranged human light chain variable region gene sequence, wherein the single rearranged light chain variable region gene sequence comprises a substitution of at least one non-histidine codon with a histidine codon, and wherein the antibody retains at least one histidine substitution in its expressed light chain variable domain. In one embodiment, the antibody comprises a light chain derived from a human Vκ1-39Jκ5 or $Vκ^3$-20Jκ1 rearrangement, wherein the human Vκ1-39Jκ5 or Vκ3-20Jκ1 gene sequence comprises a substitution of at least one non-histidine codon with a histidine codon, and wherein the antibody retains at least one histidine substitution in its expressed light chain variable domain. In some embodiments, the antibody retains all or substantially all histidine substitutions in its expressed light chain variable domain. In one embodiment, the substitution is of three non-histidine codons with three histidine codons in the nucleotide sequence encoding CDR3 of the light chain variable region gene sequence, and the antibody retains all three histidine substitutions in its expressed light chain variable domain. In one embodiment, the substitution is of four non-histidine codons with four histidine codons in the nucleotide sequence encoding CDR3 of the light chain variable region gene sequence, and the antibody retains three or four histidine substitutions in its expressed light chain variable domain.

In one embodiment, the light chain of the antibody further comprises a non-human light chain constant region amino acid sequence, e.g., endogenous light chain constant region amino acid sequence. In addition, the antibody, e.g., antigen-specific antibody, generated in a genetically modified non-human animal described herein also comprises a heavy chain which comprises a human heavy chain variable domain derived from a rearrangement of human heavy chain V, D, and J segments. Human heavy chain V, D, and J segments may be selected from a repertoire of human heavy chain segments present at the endogenous non-human heavy chain locus, e.g., at least one functional V, at least one functional D, and at least one functional J segment, e.g., up to a complete repertoire of functional human V, D, and J segments. Exemplary possible rearrangements of human heavy chain variable segments may be gleaned from a listing of functional human V, D, and J segments in IMGT database, and from U.S. Application Publication Nos. 2011/0195454, 2012/0021409, 2012/0192309, and 2013/0045492, incorporated herein by reference. Furthermore, in one embodiment, the heavy chain of the antibody comprises a non-human heavy chain constant region amino acid sequence, e.g., an endogenous non-human heavy chain constant region amino acid sequence. In one embodiment, the non-human heavy chain constant region comprises $C_H1$, hinge, $C_H2$, and $C_H^3$ domains. In one embodiment, the antibody is an IgG, IgE, IgD, IgM, or IgA isotype.

Thus, in one embodiment, provided herein is a binding protein generated in the genetically modified non-human animals described herein, wherein the binding protein comprises a reverse chimeric light chain comprising (a) a light chain variable domain derived from a human Vκ1-39Jκ5 rearrangement comprising a substitution of at least one non-histidine codon with a histidine codon, wherein the light chain retains at least one histidine substitution in its expressed light chain variable domain and (b) a non-human, e.g., a mouse, light chain constant region amino acid sequence, wherein the light chain is associated with a reverse chimeric heavy chain comprising (a) a heavy chain variable domain derived from a rearrangement of human V, D, and J segments, wherein the V, D, and J segments are selected from a repertoire of human V, D, and J segments present in the animal, and (b) a non-human, e.g., mouse, heavy chain constant region amino acid sequence. In one embodiment, the repertoire of human V, D, and J segments comprises at least one functional V, at least one functional D, and at least one functional J segment, e.g., up to a complete repertoire of functional human V, D, and J segments. In one embodiment, the heavy and the light chain constant domains are endogenous heavy and light chain constant regions. In one embodiment, the heavy and light chain variable domains are somatically mutated domains. In one embodiment, the somatically mutated light chain domain retains at least one histidine substitution introduced into the germline sequence. In some embodiments, the somatically mutated light chain domain retains all or substantially all histidine substitutions introduced into the germline sequence. In one embodiment, the antigen-binding protein displays pH-dependent antigen binding properties.

In another embodiment, provided herein is a binding protein generated in the genetically modified non-human animals described herein, wherein the binding protein comprises a reverse chimeric light chain comprising (a) a light chain variable domain derived from a human Vκ3-20Jκ1 rearrangement comprising a substitution of at least one non-histidine codon with a histidine codon, wherein the light chain retains at least one histidine substitution in its expressed light chain variable domain and (b) a non-human, e.g., a mouse, light chain constant region amino acid sequence, wherein the light chain is associated with a reverse chimeric heavy chain comprising (a) a heavy chain variable domain derived from a rearrangement of human V, D, and J segments, wherein the V, D, and J segments are selected from a repertoire of human V, D, and J segments present in the animal, and (b) a non-human, e.g., mouse, heavy chain constant region amino acid sequence. In one embodiment, the repertoire of human V, D, and J segments comprises at least one functional V, at least one functional D, and at least one functional J segment, e.g., up to a complete repertoire of functional human V, D, and J segments. In one embodiment, the heavy and the light chain constant regions are endogenous heavy and light chain constant regions. In one embodiment, the heavy and light chain variable domains are somatically mutated domains. In one embodiment, the somatically mutated light chain domain retains at least one histidine substitution introduced into the germline sequence. In some embodiments, the somatically mutated light chain domain retains all or substantially all histidine substitutions introduced into the germline sequence. In one embodiment, the antigen-binding protein displays pH-dependent antigen binding properties.

In one embodiment, also provided herein is a B cell of the genetically modified animal described herein, that comprises in its germline a histidine-modified human light chain variable region sequence, e.g., a histidine-modified single rearranged human light chain variable region sequence, described herein, and expresses an antigen-binding protein described herein. In one embodiment, the antigen-binding protein, e.g., an antibody, expressed in the B cell retains at least one histidine residue introduced into the germline, and displays pH-dependent antigen-binding properties. In some embodiments, the antigen-binding protein, e.g., an antibody, expressed in the B cell retains all or substantially all histidine residues introduced into the germline, and displays pH-dependent antigen-binding properties.

In various embodiments, the genetically modified non-human animal described herein comprises a human light chain variable region gene sequence, e.g., a single rearranged human light chain variable region gene sequence (e.g., Vκ1-39Jκ5 or Vκ3-20Jκ1 sequence) that comprises a substitution of at least one non-histidine codon with a histidine codon (or an addition of a histidine codon into the germline sequence). These additions or substitutions result in a non-human animal that comprises a population of B cells enriched for antigen-binding proteins with pH dependent binding properties for their antigens. In one embodiment, antigen-binding proteins, e.g., antibodies, generated in the non-human animals described herein in response to antigen stimulation display pH dependent antigen binding while exhibiting high affinity for the antigen at neutral pH, e.g., pH between about 7.0 and about 8.0, e.g., pH between about 7.0 and about 7.4, e.g., between about 7.2 and about 7.4, e.g., pH of the body fluids such as blood. In one embodiment, the affinity of the antigen-binding protein to its antigen, expressed as a dissociation constant ($K_D$) at a neutral pH is less than $10^{-6}$ M, e.g., less than $10^{-8}$ M, e.g., less than $10^{-9}$ M, e.g., less than $10^{-10}$ M, e.g., less than $10^{-11}$ M, e.g., less than $10^{-12}$ M.

In one embodiment, an antigen-binding protein, e.g., an antibody, generated in the genetically modified non-human animal described herein, exhibits reduced binding to its antigen in acidic pH (e.g., pH of 6.0 or lower, e.g., pH between about 5.0 and about 6.0, pH between about 5.75 and about 6.0, e.g., pH of endosomal or lysosomal compartments) as compared to neutral pH. In one embodiment, the antigen-binding protein, e.g., the antibody, generated in the genetically modified non-human animal described herein, exhibits no binding to the antigen in acidic pH, while retaining binding to the antigen at neutral pH. In one embodiment, an antigen-binding protein generated by the genetically modified non-human animal described herein, has a decrease in dissociative half-life ($t_{1/2}$) at an acidic pH as compared to the dissociative half-life ($t_{1/2}$) of the antigen-binding protein at a neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, an antigen-binding protein expressed by the genetically modified non-human animal described herein has a $t_{1/2}$ at an acidic pH and 37° C. of about 2 min or less. In one embodiment, an antigen-binding protein expressed by the genetically modified non-human animal described herein has a $t_{1/2}$ at an acidic pH and 37° C. of less than about 1 min. In one embodiment, an antigen-binding protein expressed by the genetically modified non-human animal described herein has a $t_{1/2}$ at an acidic pH and 25° C. of about 2 min or less. In one embodiment, an antigen-binding protein expressed by the genetically modified non-human animal described herein has a $t_{1/2}$ at an acidic pH and 25° C. of less than about 1 min.

Kinetic parameters, such as equilibrium dissociation constants ($K_D$) and dissociative half-lives ($t_{1/2}$) can be calculated from kinetic rate constant as: $K_D$ (M)=$k_d/k_a$; and $t_{1/2}$ (min) ln 2/(60*$k_d$).

In one embodiment, the antigen-binding protein, e.g., an antibody, generated in the genetically modified non-human animals described herein, exhibits increased binding to FcRn molecule. As described above, FcRn is a receptor present inside the endosomal compartment that is capable of binding immunoglobulins at an acidic pH and recycling them back to the surface. Screening antibody molecules in the genetically modified non-human animals described herein presents a unique opportunity to select for antibodies with three beneficial parameters: high affinity for an antigen, pH-dependent antigen binding (with weaker antigen binding at acidic pH) and increased binding to FcRn.

In one embodiment, a genetically modified non-human animal described herein comprises a population of B cells in response to an antigen that produces and is enriched for antigen-binding proteins, e.g., antibodies, that, when reformatted into therapeutics, exhibit increased serum half life upon administration of a therapeutic dose to a subject over an equivalent B cell population produced in response to the same antigen in non-human animals that do not comprise histidine modification(s) in their human light chain variable region gene sequences. Thus, in one embodiment, an antigen-binding protein, e.g., an antibody, produced in response to an antigen of interest in a genetically modified non-human animal described herein, when reformatted into a therapeutic, exhibits increased serum half life upon administration of a therapeutic dose to a subject over a serum half life of an antigen-binding protein (when reformatted into a therapeutic and administered at the same therapeutic dose) that was produced in response to the same antigen in a non-human animal that does not comprise histidine modification(s) in its human light chain variable region gene sequence. In some embodiments, the increase in serum half life is about 2 fold, e.g., about 5 fold, e.g., about 10 fold, e.g., about 15 fold, e.g., about 20 fold, or greater.

In one aspect, a pluripotent, induced pluripotent, or totipotent cell derived from a non-human as described herein is provided. In a specific embodiment, the cell is an embryonic stem (ES) cell.

In one aspect, a tissue derived from a non-human animal as described herein is provided. In one embodiment, the tissue is derived from spleen, lymph node or bone marrow of a non-human animal as described herein.

In one aspect, a nucleus derived from a non-human animal as described herein is provided. In one embodiment, the nucleus is from a diploid cell that is not a B cell.

In one aspect, a non-human cell is provided that is isolated from a non-human animal (e.g., a rodent, e.g., a mouse or a rat) as described herein. In one embodiment, the cell is an ES cell. In one embodiment, the cell is a lymphocyte. In one embodiment, the lymphocyte is a B cell. In one embodiment, the B cell expresses a chimeric heavy chain comprising a variable domain derived from a human gene segment; and a light chain derived from a rearranged human Vκ1-39/J sequence with a substitution of at least one non-histidine codon with histidine codon, rearranged human Vκ3-20/J sequence with a substitution of at least one non-histidine codon with histidine codon, or a combination thereof and further comprising a substitution of at least one amino acid encoded in the germline for a histidine; wherein the heavy chain variable domain is fused to a non-human constant region and the light chain variable domain is fused to a non-human or a human constant region.

In one aspect, a hybridoma is provided, wherein the hybridoma is made with a B cell of a non-human animal as described herein. In a specific embodiment, the B cell is from a mouse as described herein that has been immunized with an immunogen comprising an epitope of interest, and the B cell expresses a binding protein that binds the epitope of interest, the binding protein has a somatically mutated human variable heavy chain domain and a mouse $C_H$, and has a human variable light chain domain derived from a rearranged human Vκ1-39Jκ5 with a substitution of at least one non-histidine codon with histidine codon or a rearranged human Vκ3-20Jκ1 with a substitution of at least one non-histidine codon with histidine codon and a mouse $C_L$, wherein the human light chain domain comprises a substitution of at least one amino acid encoded in the germline with a histidine.

Also provided is a cell expressing an antigen-binding protein generated in the non-human animals described herein. In one embodiment, the cell is selected from CHO, COS, 293, HeLa, and a retinal cell expressing a viral nucleic acid sequence (e.g., a PERC.6™ cell).

In one aspect, a non-human embryo is provided, wherein the embryo comprises a donor ES cell that is derived from a non-human animal as described herein.

The non-human animals described herein are useful to generate B cells that express antibodies having histidines in a CDR3. An animal that places histidines in a CDR3 is useful for making antibodies in general, and in particular useful for developing antibodies that bind a target with sufficient affinity at or around a neutral pH, but that either do not bind or that bind weaker to the same target at an acidic pH.

The non-human animal is useful to generate variable regions of antibodies that can be used to make, e.g., human therapeutic binding proteins that bind their targets by human immunoglobulin variable domains that comprise the histidines in a CDR3. The altered binding at a lower pH will in some circumstances allow faster turnover because the therapeutic will bind a target on a cell's surface, be internalized in an endosome, and more readily or more rapidly dissociate from the target in the endosome, so that the therapeutic can be recycled to bind yet another molecule of target (e.g., on another cell or the same cell). In some circumstances, this will result in the ability to dose the therapeutic at a lower dose, or dose the therapeutic less frequently. This is particularly useful where it is not desirable to dose frequently, or to administer above a certain dosage, for safety or toxicity reasons. As a result, the serum half life of the antibody therapeutic when administered to a subject will be increased.

The non-human animal, e.g., rodent, e.g., mouse or rat, is useful in a method for increasing the number of B cells in a animal that exhibit an antibody variable region having a CDR3 with one or more histidines in it. The non-human animal is useful for generating antibody sequences that will exhibit pH-dependent antigen binding. The non-human animal is useful for generating a greater number of antibody sequences, resulting from a single immunization, wherein the antibodies will exhibit a pH-dependent antigen binding.

Antigen-Binding Proteins and Methods of Generating the Same

In one aspect, also provided herein are methods for generating human antigen-binding proteins, e.g., antibodies, which exhibit pH-dependent antigen binding, from the genetically modified non-human animals described herein with standard methods used in the art.

Several techniques for the producing antibodies have been described. For example, in various embodiments chimeric antibodies are produced in mice as described herein. Antibodies can be isolated directly from B cells of an immunized mouse (e.g., see U.S. 2007/0280945A1) and/or the B cells of the immunized mouse can be used to make hybridomas (Kohler and Milstein, 1975, *Nature* 256:495-497). DNA encoding the antibodies (human heavy and/or light chains) from non-human animals as described herein is readily isolated and sequenced using conventional techniques.

Hybridoma and/or B cells derived from non-human animals as described herein serve as a preferred source of such DNA. Once isolated, the DNA may be placed into expression vectors, which are then transfected into host cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the non-human sequences. Thus, once nucleic acid sequences of antibodies with desired characteristics, e.g., affinity, epitope, pH-dependent antigen binding, etc., are determined, the non-human constant region gene sequences are replaced with a desired human constant region sequences to generate a fully human antibody containing a non-IgM isotype, for example, IgG1, IgG2, IgG3 or IgG4.

Thus, in one embodiment provided herein is a method of generating an antibody that exhibits pH-dependent antigen binding properties comprising generating a non-human animal (e.g., a mouse) as described herein, immunizing a mouse with an antigen of interest, allowing a non-human animal to mount an immune response to the antigen, and selecting in the non-human animal an antigen-specific antibody that exhibits pH dependent antigen binding properties, e.g., weaker binding to the antigen at an acidic than at neutral pH.

Also provided herein are methods of making multi-specific antigen binding proteins, e.g., bispecific antigen-binding proteins. These are molecules capable of binding more than one epitope with high affinity. Advantages of the invention include the ability to select suitably high binding (e.g., affinity matured) heavy chain immunoglobulin chains each of which will associate with a single light chain. In addition, advantages of the invention include the ability to generate a multi-specific, e.g., a bispecific, antigen-binding protein that exhibits pH-dependent antigen binding.

Because of the dual nature of bispecific antibodies (i.e., may be specific for different epitopes of one polypeptide or may contain antigen-binding domains specific for more than one target polypeptide, see, e.g., Tutt et al., 1991, *J. Immunol.* 147:60-69; Kufer et al., 2004, *Trends Biotechnol.* 22:238-244), they offer many useful advantages for therapeutic application. For example, the bispecific antibodies can be used for redirected cytotoxicity (e.g., to kill tumor cells), as a vaccine adjuvant, for delivering thrombolytic agents to clots, for converting enzyme activated prodrugs at a target site (e.g., a tumor), for treating infectious diseases, targeting immune complexes to cell surface receptors, or for delivering immunotoxins to tumor cells.

The bispecific antibodies described herein can also be used in several therapeutic and non-therapeutic and/or diagnostic assay methods, such as, enzyme immunoassays, two-site immunoassays, in vitro or in vivo immunodiagnosis of various diseases (e.g., cancer), competitive binding assays, direct and indirect sandwich assays, and immunoprecipitation assays. Other uses for the bispecific antibodies will be apparent to those skilled in the art.

Several techniques for making bispecific antibody fragments from recombinant cell culture have been reported. However, synthesis and expression of bispecific binding proteins has been problematic, in part due to issues associated with identifying a suitable light chain that can associate and express with two different heavy chains, and in part due to isolation issues. In various embodiments, compositions and methods described herein provide the advantage of full length bispecific antibodies that do not require special modification(s) to maintain traditional immunoglobulin structure by increasing stability/interaction of the components. In various embodiments, such modification(s) has proven cumbersome and served as an obstacle to development of bispecific antibody technology and their potential use in treating for human disease. Thus, in various embodiments, through providing a natural immunoglobulin structure (i.e., full length) having the added property of multiple specificities, full length bispecific antibodies maintain their critical effector functions that previous bispecific fragments lacked, and further provide therapeutics that demonstrate the important pharmacokinetic parameter of a longer half-life.

Methods and compositions described herein allow for a genetically modified mouse to select, through otherwise natural processes, a suitable light chain that can associate and express with more than one heavy chain, including heavy chains that are somatically mutated (e.g., affinity matured), wherein the light chain further confers upon the antigen-binding protein its pH-dependent antigen binding property. Human heavy and light chain variable region sequences from suitable B cells of immunized mice as described herein that express affinity matured antibodies having reverse chimeric heavy chains (i.e., human variable and mouse constant) can be identified and cloned in frame in an expression vector with a suitable human constant region gene sequence (e.g., a human IgG1). Two such constructs can be prepared, wherein each construct encodes a human heavy chain variable domain that binds a different epitope. One of the human light chain variable regions (e.g., human Vκ1-39Jκ5 or human Vκ3-20Jκ1), comprising a substitution of at least one non-histidine codon with a histidine codon, can be fused in frame to a suitable human light chain constant region gene (e.g., a human κ constant gene). These three fully human heavy and light constructs can be placed in a suitable cell for expression. The cell will express two major species: a homodimeric heavy chain with the identical light chain, and a heterodimeric heavy chain with the identical light chain. To allow for a facile separation of these major species, one of the heavy chains is modified to omit a Protein A-binding determinant, resulting in a differential affinity of a homodimeric binding protein from a heterodimeric binding protein. Compositions and methods that address this issue are described in U.S. Ser. No. 12/832,838, filed 25 Jun. 2010, entitled "Readily Isolated Bispecific Antibodies with Native Immunoglobulin Format," published as US 2010/0331527A1, hereby incorporated by reference. Once the specie comprising heterodimeric heavy chain with an identical light chain is selected, this bi-specific antigen binding protein can be screened to confirm the retention of its pH-dependent antigen binding property.

In one aspect, an epitope-binding protein as described herein is provided, wherein human light chain and heavy chain variable region sequences are derived from animals described herein that have been immunized with an antigen comprising an epitope of interest.

In one embodiment, an epitope-binding protein is provided that comprises a first and a second polypeptide, the first polypeptide comprising, from N-terminal to C-terminal, a first epitope-binding region that selectively binds a first epitope, followed by a constant region that comprises a first $C_H3$ region of a human IgG selected from IgG1, IgG2, IgG4, and a combination thereof; and, a second polypeptide comprising, from N-terminal to C-terminal, a second epitope-binding region that selectively binds a second epitope, followed by a constant region that comprises a second $C_H3$ region of a human IgG selected from IgG1, IgG2, IgG4, and a combination thereof, wherein the second $C_H3$ region comprises a modification that reduces or eliminates binding of the second $C_H3$ domain to protein A. Various such modifications are described in, e.g., U.S. Application Publication Nos. 2010/0331527 and 2011/0195454, incorporated herein by reference.

One method for making an epitope-binding protein that binds more than one epitope and exhibits pH-dependent epitope binding property is to immunize a first mouse in accordance with the invention with an antigen that comprises a first epitope of interest, wherein the mouse comprises (1) an endogenous immunoglobulin light chain variable region locus that does not contain an endogenous mouse light chain variable region gene sequence that is capable of rearranging and forming a light chain, wherein at the endogenous mouse immunoglobulin light chain variable region locus is a single rearranged human light chain variable region operably linked to the mouse endogenous light chain constant region gene, and the rearranged human light chain variable region is selected from a human Vκ1-39Jκ5 and a human Vκ3-20Jκ1 comprising a substitution of at least one non-histidine codon with a histidine codon, and (2) the endogenous mouse $V_H$ gene segments have been replaced in whole or in part with human $V_H$ gene segments, such that immunoglobulin heavy chains made by the mouse are solely or substantially heavy chains that comprise human variable domains and mouse constant domains. When immunized, such a mouse will make a reverse chimeric antibody, comprising only one of two human light chain variable domains (e.g., one of human Vκ1-39Jκ5 or human Vκ3-20Jκ1, e.g., comprising a substitution of at least one amino acid with a histidine). Commonly, at least some of the substituted histidine residues introduced into the germline sequence will be retained in the reverse chimeric antibody. Once a B cell is identified that encodes a heavy chain variable domain that binds the epitope of interest and expresses an antibody that exhibits pH-dependent antigen binding properties, the nucleotide sequence of the heavy chain variable region (and, optionally, the light chain variable region) can be retrieved (e.g., by PCR) and cloned into an expression construct in frame with a suitable human immunoglobulin heavy chain constant region sequence. This process can be repeated to identify a second heavy chain variable domain that binds a second epitope, and a second heavy chain variable region gene sequence can be retrieved and cloned into an expression vector in frame to a second suitable human immunoglobulin heavy chain constant region sequence. The first and the second immunoglobulin constant domains encoded by the constant region gene sequence can be the same or different isotype, and one of the immunoglobulin constant domains (but not the other) can be modified as described herein or in US 2010/0331527A1, and epitope-binding protein can be expressed in a suitable cell and isolated based on its differential affinity for Protein A as compared to a homodimeric epitope-binding protein, e.g., as described in US 2010/0331527A1.

Thus, in various embodiments, following isolation of the DNA and selection of the first and second nucleic acid sequences that encode the first and second human heavy chain variable domains having the desired specificities/affinities, and a third nucleic acid sequence that encodes a human light chain domain (a germline rearranged sequence or a light chain sequence isolated from a non-human animal as described herein) and comprises a substitution of at least one non-histidine codon with a histidine codon, the three nucleic acids sequences encoding the molecules are expressed to form the bispecific antibody using recombinant techniques which are widely available in the art. Often, the expression system of choice will involve a mammalian cell expression vector and host so that the bispecific antibody is appropriately glycosylated (e.g., in the case of bispecific antibodies comprising antibody domains which are glycosylated). However, the molecules can also be produced in the prokaryotic expression systems. Normally, the host cell will be transformed with DNA encoding both the first human heavy chain variable domain, the second human heavy chain variable domain, the human light chain domain on a single vector or independent vectors. However, it is possible to express the first human heavy chain variable domain, second human heavy chain variable domain, and human light chain domain (the bispecific antibody components) in independent expression systems and couple the expressed polypeptides in vitro. In various embodiments, the human light chain domain derived from a germline sequence but for the substitution of at least one non-histidine coding with a histidine codon, e.g., in a CDR codon. In various embodiments, the human light chain domain comprises no more than one, no more than two, no more than three, no more than four, or no more than five somatic hypermutations within the light chain variable sequence of the light chain domain. In some embodiments, the somatic hypermutations do not alter the presence of at least one histidine residue introduced into the germline sequence of the light chain variable region.

In various embodiments, the nucleic acid(s) (e.g., cDNA or genomic DNA) encoding the two heavy chains and single human light chain with a substitution of at least one non-histidine with a histidine is inserted into a replicable vector for further cloning (amplification of the DNA) and/or for expression. Many vectors are available, and generally include, but are not limited to, one or more of the following: a signal sequence, an origin of replication, one or more marker genes, an enhancer element, a promoter, and a transcription termination sequence. Each component may be selected individually or based on a host cell choice or other criteria determined experimentally. Several examples of each component are known in the art.

Expression and cloning vectors usually contain a promoter that is recognized by the host organism and is operably linked to the nucleic acid sequences that encode each or all the components of the bispecific antibody. A large number of promoters recognized by a variety of potential host cells are well known. These promoters are operably linked to bispecific antibody-encoding DNA by removing the promoter from the source DNA by restriction enzyme digestion and inserting the isolated promoter sequence into the vector.

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the bispecific antibody components. Suitable expression vectors for various embodiments include those that provide for the transient expression in mammalian cells of DNA encoding the bispecific antibody. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of bispecific antibodies having desired binding specificities/affinities or the desired gel migration characteristics relative to the parental antibodies having homodimers of the first or second human heavy chain variable domains.

In various embodiments, once the DNA encoding the components of the bispecific antibody are assembled into the desired vector(s) as described above, they are introduced into a suitable host cell for expression and recovery. Transfecting host cells can be accomplished using standard techniques known in the art appropriate to the host cell selected (e.g., electroporation, nuclear microinjection, bacterial protoplast fusion with intact cells, or polycations, e.g., polybrene, polyornithine, etc.).

A host cell is chosen, in various embodiments, that best suits the expression vector containing the components and allows for the most efficient and favorable production of the bispecific antibody species. Exemplary host cells for expression include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In various embodiments, the cell is a human, monkey, ape, hamster, rat, or mouse cell. In various embodiments, the cell is eukaryotic cell selected from CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In various embodiments, the cell comprises one or more viral genes, e.g. a retinal cell that expresses a viral gene (e.g., a PER.C6™ cell).

Mammalian host cells used to produce the bispecific antibody may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. Media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™), trace elements (defined as inorganic compounds usually present at final concentrations in the micromolar range), and glucose or an equivalent energy source. Any other supplements may also be included at appropriate concentrations as known to those skilled in the art. The culture conditions, such as temperature, pH, and the like, are, in various embodiments, those previously used with the host cell selected for expression, and will be apparent to those skilled in the art.

The bispecific antibody may be recovered from the culture medium as a secreted polypeptide, although it also may be recovered from host cell lysate when directly produced without a secretory signal. If the bispecific antibody is membrane-bound, it can be released from the membrane using a suitable detergent solution (e.g., Triton-X 100).

Following isolation, a bispecific antibody comprising a two human heavy chains and a single human light chain derived from a rearranged human light chain variable region gene sequence selected from Vκ1-39Jκ5 and Vκ3-20Jκ1 sequences that comprise a substitution of at least one non-histidine codon with a histidine codon, is screened for its ability to exhibit pH dependent binding of one, preferably both of its antigens. The ability of bispecific antibodies to bind its antigens differently at neutral and acidic pH's (e.g., their ability to demonstrate decreased $t_{1/2}$ at acidic pH compared to neutral pH) can be determined by a variety of techniques available in the art and described in the following examples, e.g., BIACORE™ assay.

Additional Methods for Generating Antigen-Binding Proteins with pH-Dependent Antigen Binding Various methods of generating antigen-binding proteins with pH-dependent antigen binding properties in genetically modified non-human animals described herein are provided. Also provided are methods of generating antigen binding proteins with pH-dependent antigen binding properties in vitro. Such methods may involve generating various components of the antigen-binding proteins in vivo in genetically modified non-human animals, and then modifying them and reassembling them in vitro outside an organism as protein complexes expressed in mammalian cell culture.

In one embodiment, the method of generating antigen-binding proteins with pH-dependent antigen binding properties utilizes an antigen-binding protein sequence, e.g., an antibody sequence, that is generated in a mouse comprising a limited repertoire of light chain variable region V and J segments, e.g., human light chain variable region V and J segments, "universal light chain" or "common light chain" mouse ("ULC" mouse), such as the mouse described in U.S. Application Publication Nos. 2011/0195454, 2012/0021409, 2012/0192300 and 2013/0045492, all incorporated herein by reference. In one embodiment, the method of generating antigen-binding proteins with pH-dependent antigen binding properties utilizes an antigen binding protein sequence that is generated in a mouse comprising a single rearranged human light chain variable region gene sequence. In one embodiment, the method utilizes an antigen binding protein generated in a mouse comprising a single rearranged human light chain variable region gene sequence selected from human Vκ1-39Jκ5 and human Vκ3-20Jκ1.

In one embodiment, the method for generating an antigen-binding protein, e.g., an antibody, with pH dependent antigen binding properties comprises selecting a first antibody that binds to an antigen of interest (e.g., binds to an antigen of interest with a desired affinity), modifying an immunoglobulin light chain nucleotide sequence of the first antibody to comprise a substitution of at least one non-histidine codon with a histidine codon, expressing an immunoglobulin heavy chain of the first antibody and the modified immunoglobulin light chain in a cells, and selecting a second antibody expressed in the cell that retains binding to the antigen of interest (e.g., retains desired affinity for the antigen of interest) at neutral pH and displays reduced binding to the antigen of interest at an acidic pH.

In one embodiment, the method for generating an antigen-binding protein, e.g., an antibody, with pH dependent antigen binding properties comprises selecting an immunoglobulin heavy chain from an antibody (e.g., obtained from a non-human animal, e.g., a mouse, e.g., a ULC mouse) that comprises an immunoglobulin light chain having a single rearranged human immunoglobulin light chain variable region sequence wherein the antibody binds to an antigen of interest (e.g., binds to an antigen of interest with a desired affinity); modifying the nucleic acid sequence of the immunoglobulin light chain such that the single rearranged human immunoglobulin light chain variable region sequence comprises a substitution of at least one non-histidine codon with a histidine codon; expressing the selected immunoglobulin heavy chain and the immunoglobulin light chain comprising the substitution of at least one amino acid with a histidine in its variable domain; and selecting an antibody that retains binding to the antigen of interest at a neutral pH (e.g., retains desired affinity to the antigen of interest) while displaying reduced binding to the antigen of interest at an acidic pH. In various embodiments, the immunoglobulin heavy chain is derived from a rearrangement of human heavy chain variable gene segments (human V, D, and J segments).

In one embodiment, the method for generating an antigen-binding protein, e.g., an antibody, with pH-dependent antigen binding properties comprises (1) immunizing a non-human animal, e.g., a mouse, comprising a single rearranged human light chain variable region gene sequence and a repertoire of unrearranged human heavy chain variable gene segments (V, D, and J segments) with an antigen of interest and allowing a mouse to mount an immune response to said antigen, (2) selecting in the non-human animal, e.g., in the mouse, an antibody that binds to the antigen of interest with a desired affinity, (3) isolating from the non-human animal, e.g., from the mouse, a nucleotide sequence of an immunoglobulin heavy chain of the antibody that binds to the antigen of interest with a desired affinity, (4) determining the nucleotide sequence of said heavy chain, (5) modifying a nucleotide sequence of an immunoglobulin light chain containing the single rearranged human immunoglobulin light chain variable region to comprise a substitution of at least one non-histidine codon with a histidine codon, (6) expressing the immunoglobulin heavy chain of the antibody that binds to the antigen of interest with desired affinity and the immunoglobulin light chain comprising the histidine modification in a cell, and (7) determining whether the antibody expressed in the cell retains binding to the antigen at a neutral pH while displaying reduced binding at an acidic pH. In one embodiment, the antibody expressed in the cell exhibits desired affinity to the antigen at neutral pH. In various embodiments, the immunoglobulin heavy chain is derived from a rearrangement of human heavy chain variable gene segments (human V, D, and J segments).

In one embodiment, the mouse comprising a single rearranged human light chain variable region gene sequence is a universal light chain or common light chain "ULC" mouse described in, e.g., U.S. Application Publication Nos. 2011/0195454, 2012/0021409, 2012/0192300 and 2013/0045492. In one embodiment, the single rearranged human light chain variable region gene sequence is selected from human Vκ1-39Jκ5 and human Vκ3-20Jκ1 sequence.

In one embodiment, the antigen of interest is selected from a soluble antigen, a cell surface antigen (e.g., a tumor antigen) and a cell surface receptor. In a specific embodiment, the cell surface receptor is an immunoglobulin receptor. In a specific embodiment, the immunoglobulin receptor is an Fc receptor.

In one embodiment, the desired affinity of an antibody for an antigen expressed as a dissociation constant ($K_D$) at a neutral pH is less than $10^{-6}$ M, e.g., less than $10^{-8}$ M, e.g., less than $10^{-9}$ M, e.g., less than $10^{-10}$ M, e.g., less than $10^{-11}$ M, e.g., less than $10^{-12}$ M.

As explained above, the ULC mice, in one embodiment, comprise a single rearranged human immunoglobulin light chain variable gene sequence, and express antibodies in response to the antigen where the affinity of antibodies to the antigen is primarily mediated through the heavy chains of their antibodies. These mice comprise a repertoire of human heavy chain variable (V, D, and J) segments, that rearrange to encode a human heavy chain variable domain of an antibody that also comprises the light chain derived from the single rearranged human light chain variable sequence. In one embodiment, upon antigen exposure, these mice utilize the diverse repertoire of human heavy chain variable (V, D, and J) segments to generate an antibody with affinity to and specificity for the antigen. Thus, upon exposure to the antigen, the nucleotide sequence of an immunoglobulin heavy chain of the antibody generated in the ULC mice may be isolated and utilized to generate a desired binding protein also comprising an immunoglobulin light chain derived from the single rearranged human immunoglobulin light chain variable region sequence (e.g., the single rearranged human immunoglobulin light chain variable region sequence with a substitution of at least one non-histidine codon with a histidine codon).

In one embodiment of the ULC mice, 90-100% of unrearranged non-human $V_H$ gene segments are replaced with at least one unrearranged human $V_H$ gene segment. In a specific embodiment, all or substantially all (e.g., 90-100%) of the endogenous non-human $V_H$ gene segments are replaced with at least one unrearranged human $V_H$ gene segment. In one embodiment, the replacement is with at least 19, at least 39, or at least 80 or 81 unrearranged human $V_H$ gene segments. In one embodiment, the replacement is with at least 12 functional unrearranged human $V_H$ gene segments, at least 25 functional unrearranged human $V_H$ gene segments, or at least 43 functional unrearranged human $V_H$ gene segments. In one embodiment, the non-human animal comprises a replacement of all non-human $D_H$ and $J_H$ segments with at least one unrearranged human $D_H$ segment and at least one unrearranged human $J_H$ segment. In one embodiment, the non-human animal comprises a replacement of all non-human $D_H$ and $J_H$ segments with all unrearranged human $D_H$ segments and all unrearranged human $J_H$ segments. Thus, the ULC mouse utilizes a diverse repertoire of human variable region gene segments (V, D, and J segments) to generate an antibody in response to the antigen of interest.

Once the heavy chain of the antibody that binds to the antigen of interest with the desired affinity is determined, the nucleotide sequence of the heavy chain is isolated and sequenced. The sequence is cloned into a vector for expression in suitable host cells, e.g., eukaryotic cells, e.g., CHO cells. In one embodiment, the sequence of a human heavy chain constant region is cloned downstream of the human heavy chain variable region sequence isolated from the mouse (e.g., the ULC mouse).

In one embodiment, the generating an antigen-binding protein with pH-dependent antigen-binding properties comprises modifying a nucleotide sequence the immunoglobulin light chain, particularly the sequence of the single rearranged human immunoglobulin light chain variable region, to comprise a substitution of at least one non-histidine codon with a histidine codon. Various techniques for modifying a nucleotide sequence are known in the art, e.g., site directed mutagenesis. In addition, a nucleotide sequence comprising the desired histidine substitution may be synthesized de novo.

In one embodiment, the substitution of at least one non-histidine codon with a histidine codon comprises a substitution resulting in expression of one, two, three, four, or more histidine residues. In one embodiment, the substitution(s) results in expression of three or four histidine residues. In one embodiment, the substitution(s) is in the immunoglobulin light chain variable region. In one embodiment, the substitution(s) is in the CDR codon, e.g., CDR1, CDR3, and/or CDR3. In one embodiment, the substitution(s) is in the CDR3 codon.

In one embodiment, wherein the immunoglobulin light chain nucleic acid sequence comprises Vκ1-39Jκ5 gene sequence, and the substitution(s) is in the CDR3 codon, the substitution results in expression of histidine at position selected from 105, 106, 108, 111, and combinations thereof. In one embodiment, the substitutions result in expression of histidines at positions 105, 106, 108, and 111. In one embodiment, the substitutions result in expression of histidines at positions 105 and 106. In one embodiment, the substitutions result in expression of histidines at positions 105 and 108. In one embodiment, the substitutions result in expression of histidines at positions 105 and 111. In one embodiment, the substitutions result in expression of histidines at positions 106 and 108. In one embodiment, the substitutions result in expression of histidines at positions 106 and 111. In one embodiment, the substitutions result in expression of histidines at positions 108 and 111. In one embodiment, the substitutions result in expression of histidines at positions 105, 106, and 108. In one embodiment, the substitutions result in expression of histidines at positions 105, 106, and 111. In one embodiment, the substitutions result in expression of histidines at positions 105, 108, and 111. In one embodiment, the substitutions result in expression of histidines at positions 106, 108, and 111. Amino acid and nucleic acid sequences of Vκ1-39Jκ5 CDR3 regions comprising various histidine substitutions are depicted in FIG. 16 and included in the sequence listing.

In one embodiment, wherein the immunoglobulin light chain nucleic acid sequence comprises Vκ3-20Jκ1 gene sequence, and the substitution(s) is in the CDR3 codon, the substitution results in expression of histidine at position selected from 105, 106, 107, 109, and combinations thereof. In one embodiment, the substitutions result in expression of histidines at positions 105, 106, 107, and 109. In one embodiment, the substitutions result in expression of histidines at positions 105 and 106. In one embodiment, the substitutions result in expression of histidines at positions 105 and 107. In one embodiment, the substitutions result in expression of histidines at positions 105 and 109. In one embodiment, the substitutions result in expression of histidines at positions 106 and 107. In one embodiment, the substitutions result in expression of histidines at positions 106 and 109. In one embodiment, the substitutions result in expression of histidines at positions 107 and 109. In one embodiment, the substitutions result in expression of histidines at positions 105, 106, and 107. In one embodiment, the substitutions result in expression of histidines at positions 105, 106, and 109. In one embodiment, the substitutions result in expression of histidines at positions 105, 107, and 109. In one embodiment, the substitutions result in expression of histidines at positions 106, 107, and 109. Selected amino acid and nucleic acid sequences of Vκ3-20Jκ1 CDR3 regions comprising various histidine substitutions are depicted in FIG. 27 and included in the sequence listing.

Once the sequence of immunoglobulin light chain, e.g., human immunoglobulin light chain variable domain, is modified to include histidine residues at desired positions, the nucleotide sequence of the light chain is cloned into a vector for expression in suitable host cells, e.g., eukaryotic cells, e.g., CHO cells. In one embodiment, the sequence of a human light chain constant region is cloned downstream of the modified nucleotide sequence of human variable region.

In one embodiment, vectors comprising nucleotide sequence encoding modified human immunoglobulin light chain and selected human immunoglobulin heavy chain are co-expressed in a suitable host cell, e.g., eukaryotic host cell, e.g., CHO cell, to generate an antigen-binding protein. Various host cells that can be used for expression are known in the art and are mentioned throughout this specification.

An antigen-binding protein, e.g., an antibody, generated in the host cell may be secreted into cell supernatant, which is screened for proper expression and affinity for the original antigen at neutral pH. The antigen-binding protein may also be recovered from cell lysate, or, if membrane bound, released from the membrane using a suitable detergent (e.g., Triton-X). The antigen-binding protein with desired characteristics may be purified.

In one embodiment, the antigen-binding protein comprising histidine modification(s) retains the affinity to the antigen that is comparable to the affinity to the antigen of the same (original) antigen-binding protein that does not comprise histidine modification(s). In one embodiment, the affinity of the histidine-modified antigen-binding protein for the antigen of interest expressed as a dissociation constant ($K_D$) at a neutral pH is less than $10^{-6}$ M, e.g., less than $10^{-8}$ M, e.g., less than $10^{-9}$ M, e.g., less than $10^{-10}$ M, e.g., less than $10^{-11}$ M, e.g., less than $10^{-12}$ M.

In one embodiment, the antigen-binding protein, e.g., an antibody, comprising histidine modifications described herein exhibits pH dependent antigen binding properties. In one embodiment, the antigen-binding protein comprising histidine modifications possesses enhanced pH dependent properties over an equivalent antigen-binding protein without the histidine modifications (antigen-binding protein of the same amino acid sequence but for the histidine modifications). In one embodiment, the antigen-binding protein described herein retains binding to the antigen at neutral pH (e.g., retains desired affinity for the antigen at neutral pH) while displaying reduced binding at an acidic pH. In one embodiment, the antigen-binding protein, e.g., the antibody, described herein, exhibits no binding to the antigen in acidic pH, while retaining binding to the antigen at neutral pH. In one embodiment, an antigen-binding protein described herein, has a decrease in dissociative half-life ($t_{1/2}$) at an acidic pH as compared to the dissociative half-life ($t_{1/2}$) of the antigen-binding protein at a neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, an antigen-binding protein described herein has a $t_{1/2}$ at an acidic pH and 37° C. of about 2 min or less. In one embodiment, an antigen-binding protein described herein has a $t_{1/2}$ at an acidic pH and 37° C. of less than about 1 min. In one embodiment, an antigen-binding protein described herein has a $t_{1/2}$ at an acidic pH and 25° C. of about 2 min or less. In one embodiment, an antigen-binding protein described herein has a $t_{1/2}$ at an acidic pH and 25° C. of less than about 1 min.

In one embodiment, the antigen-binding protein e.g., the antibody, comprising histidine modifications described herein, exhibits increased serum half life upon administration of a therapeutic dose to a subject as compared to a serum half life upon administration of an equivalent therapeutic dose of antigen-binding protein that does not comprise histidine modifications (e.g., the original antigen-binding protein that does not comprise histidine modifications). In some embodiments, the increase in serum half life upon administration of a dose of the antigen-binding protein comprising histidine modifications described herein over a serum half life upon administration of the same dose of the antigen-binding protein not comprising histidine modifications is about 2 fold, e.g., about 5 fold, e.g., about 10 fold, e.g., about 15 fold, e.g., about 20 fold, or greater. In one embodiment, serum half-life is at least about 1 day, e.g., at least about 2 days, e.g., at least about 7 days, e.g., at least about 14 days, e.g., at least about 30 days, e.g., at least about 60 days.

In addition to the in vitro methods for generating antigen-binding proteins with pH-dependent antigen binding properties described above, also provided herein are antigen-binding proteins, e.g., antibodies, generated by said method. In addition, said method may be utilized to generate multi-specific, e.g., bispecific, antigen-binding proteins, by selecting two different human immunoglobulin heavy chains that bind to a common (universal) light chain in a mouse, determining nucleotide sequences of the heavy chains, modifying universal light chain to comprise histidine substitutions as described above, and co-expressing two human heavy chains with a single histidine-modified universal light chain in a host cell. Various steps for generating an antigen-binding protein described above may be applicable to the method of generating a bispecific antigen-binding protein. Bispecific antigen binding protein, confirmed to possess desired affinity for the antigen(s) and pH-dependent antigen binding properties may be purified. Thus, bispecific antibodies comprising two human heavy chains and a single human light chain comprising a human light chain variable domain sequence encoded by a human variable region gene, e.g., Vκ1-39Jκ5 or Vκ3-20Jκ1 variable region gene comprising a substitution of at least one non-histidine codon with a histidine codon, is provided.

Also provided are constructs utilized in making an antigen-binding protein comprising human immunoglobulin heavy chain and human immunoglobulin light chain comprising histidine substitutions. Host cells expressing antigen-binding proteins, e.g., antibodies, described herein are also provided.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Construction of Humanized Immunoglobulin Heavy Chain Loci Comprising Histidine-Substituted D Gene Segments Construction of immunoglobulin heavy chain loci comprising histidine-substituted human D gene segments was carried out by series of homologous recombination reactions in bacterial cells (BHR) using Bacterial Artificial Chromosome (BAC) DNA. Several targeting constructs for creation of a genetically engineered mouse that expresses a heavy chain variable domain comprising one or more histidine residues were generated using VELOCIGENE® genetic engineering technology (see, e.g., U.S. Pat. No. 6,586,251 and Valenzuela, D. M. et al. (2003), High-throughput engineering of the mouse genome coupled with high-resolution expression analysis, Nature Biotechnology 21(6):652-659, incorporated herein by reference in their entireties).

Figure 3:
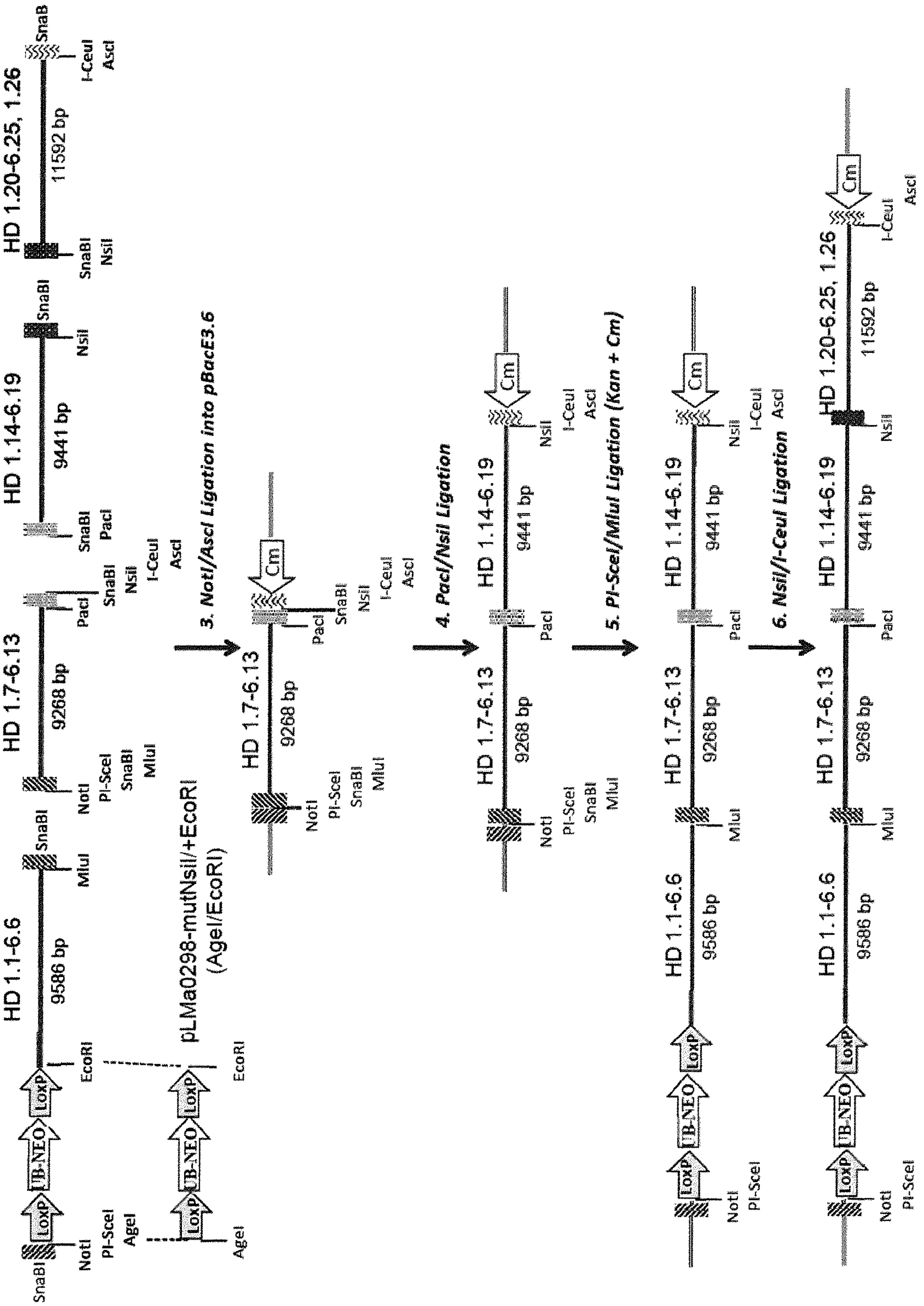
FIG. 3 illustrates schemes for assembling histidine-substituted human D gene segments via sequential ligation.

Initially, human D gene segments were synthesized in silico as four pieces (4 repeats) in which the codons encoding tyrosine (Y), asparagine (N), serine (S), glycine (G), and aspartate (D) in the hydrophilic frame were substituted with histidine codons (hereinafter "histidine-substituted human D gene segments", i.e., HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4) (FIG. 3). The four repeats also contained unique restriction enzyme sites at the ends for ligating them back together. The specific location of the histidine substitutions (labeled in bold type) in each human D gene segment is shown in FIGS. 1A and 1B in the column labeled "Hydrophilic." As shown in FIG. 1, while the modification introduced histidine codons in the hydrophilic reading frame, it also changed some stop codons to serine codons in the "Stop" reading frame. The modification, however, made few changes in the "Hydrophobic" reading frame. The detailed procedure for ligating the four synthesized D segment repeats is illustrated in FIG. 3 (sequential ligation). The resulting clone contained, from 5' to 3', a 5' mouse homology arm, a floxed neomycin cassette, human D gene segments comprising histidine substitutions (i.e., HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)), a chloramphenicol selection cassette, and a 3' homology arm.

The following six genetic modifications were carried out in order to replace the endogenous human D gene segments in the VELOCIMMUNE® humanized mouse with the histidine-substituted human D gene segments described above.

First, pLMa0174, containing a spectinomycin selection cassette and an AsiSI restriction site, was targeted into the 5' end of the MAID 1116 clone (Step 1. BHR (Spec); FIG. 2). During Step 1, a chloramphenicol selection cassette, a neomycin selection cassette, a loxP site, two $V_H$ gene segments (h$V_H$1-3 and h$V_H$1-2), and the human Adam6p gene, all of which are located 5' upstream of h$V_H$6-1, were deleted from the MAID 1116 clone and replaced by a spectinomycin cassette to yield the V1433 clone.

Second, in Step 2 (BHR (Hyg+Spec); FIG. 2), pNTu0002 containing a hygromycin cassette flanked by FRT sites was targeted into a region comprising human immunoglobulin $D_H$ gene segments. During Step 2, all human heavy chain D gene segments were deleted from VI433 and replaced with the hygromycin cassette to yield MAID6011 VI 434 (clone 1). The modification also introduced the PI-SceI and the I-CeuI restriction sites at the 5' and 3' end of the hygromycin cassette.

Figure 4:
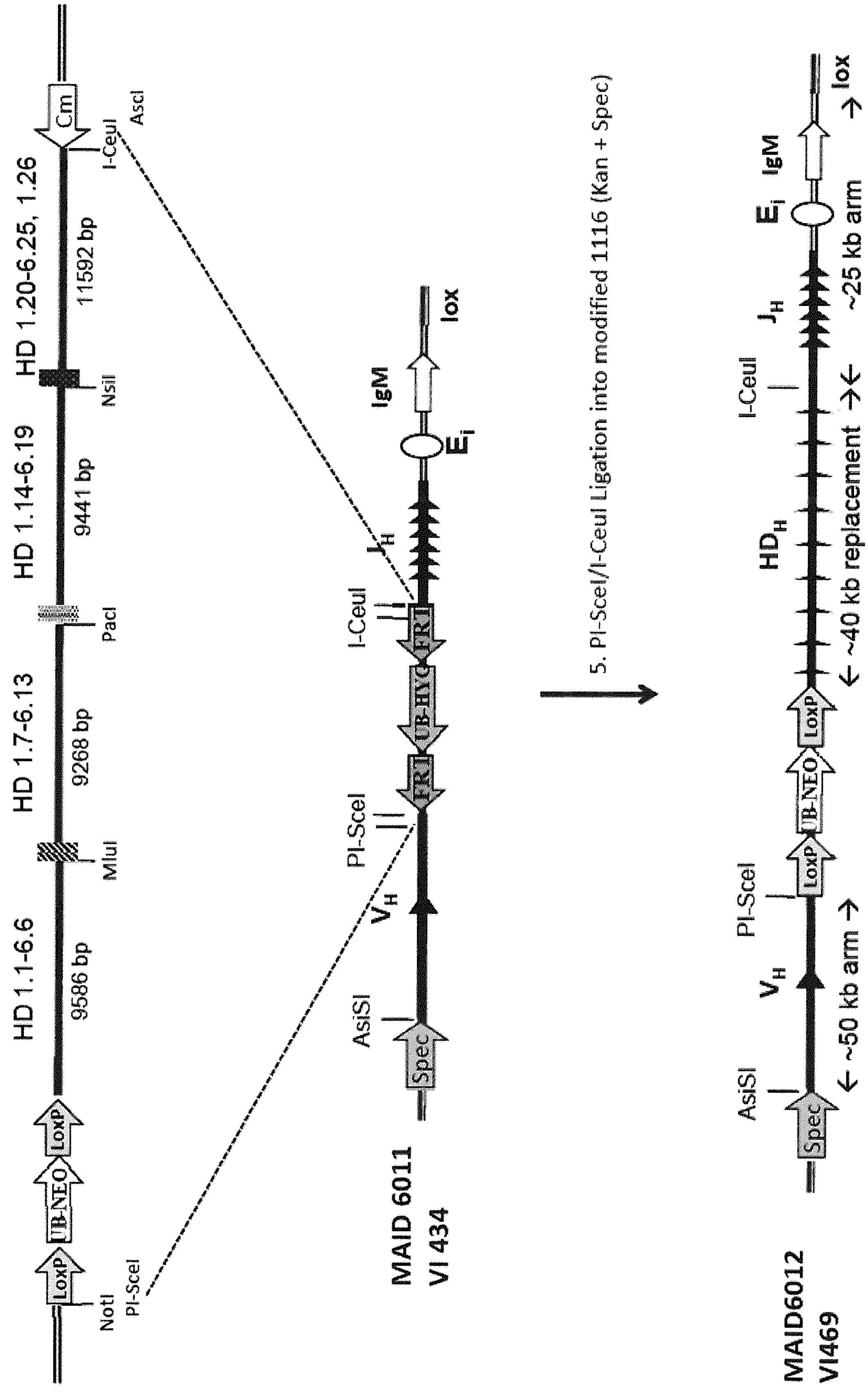
FIG. 4 illustrates the introduction of pre-assembled, histidine-substituted human D gene segments containing a neomycin cassette into a region between the most D-proximal $V_H$ gene segment ($V_H$ 6-1) and the most D-proximal $J_H$ gene segment ($J_H1$) via enzyme-mediated digestion (PI-SceI and I-CeuI) and ligation. This process removes the hygromycin cassette from MAID 6011 VI434 and introduces pre-assembled human histidine-substituted D gene segments into the clone. Bacterial cells comprising a successfully targeted clone are selected based on both neomycin and spectinomycin resistance. The resulting clone (MAID6012 VI469) comprises, from 5' to 3', (1) a spectinomycin selection cassette, (2) a 50 kb arm comprising a human $V_H$ gene segment ($V_H$ 6-1), (3) a neomycin cassette flanked by loxP sites, (4) human D gene segments containing histidine substitutions (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)), (5) about 25 kb of a genomic region containing human $J_H$ gene segments, (6) a mouse $E_i$ sequence (SEQ ID NO: 5; an intronic enhancer that promotes $V_H$ to $DJ_H$ rearrangement in developing B cells), and (7) a mouse IgM constant region nucleotide sequence (mIgM exon 1; SEQ ID NO: 7).

Third, the genomic region comprising histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)) were introduced into a region between the PI-SceI and the I-CeuI sites of MAID 6011 V1434 via restriction digestion and ligation (PI-SceI/1-CeuI Ligation modified 1116 (Kan+Spec); FIG. 4). This yielded MAID6012 V1469 containing, from 5' to 3', a spectinomycin cassette, about 50 kb of a genomic region comprising $V_H$6-1, a floxed neomycin cassette, about 40 kb of the histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)), and about 25 kb of a genomic region containing human $J_H$ gene segments, followed by a mouse $E_i$ (mIgH intronic enhancer; SEQ ID NO: 5), a mouse switch region (SEQ ID NO: 6), and a mouse IgM constant region nucleotide sequence (mIgM exon 1; SEQ ID NO: 7). Bacterial cells containing the modification were selected based on Kanamycin and Spectinomycin selection.

Figure 5:
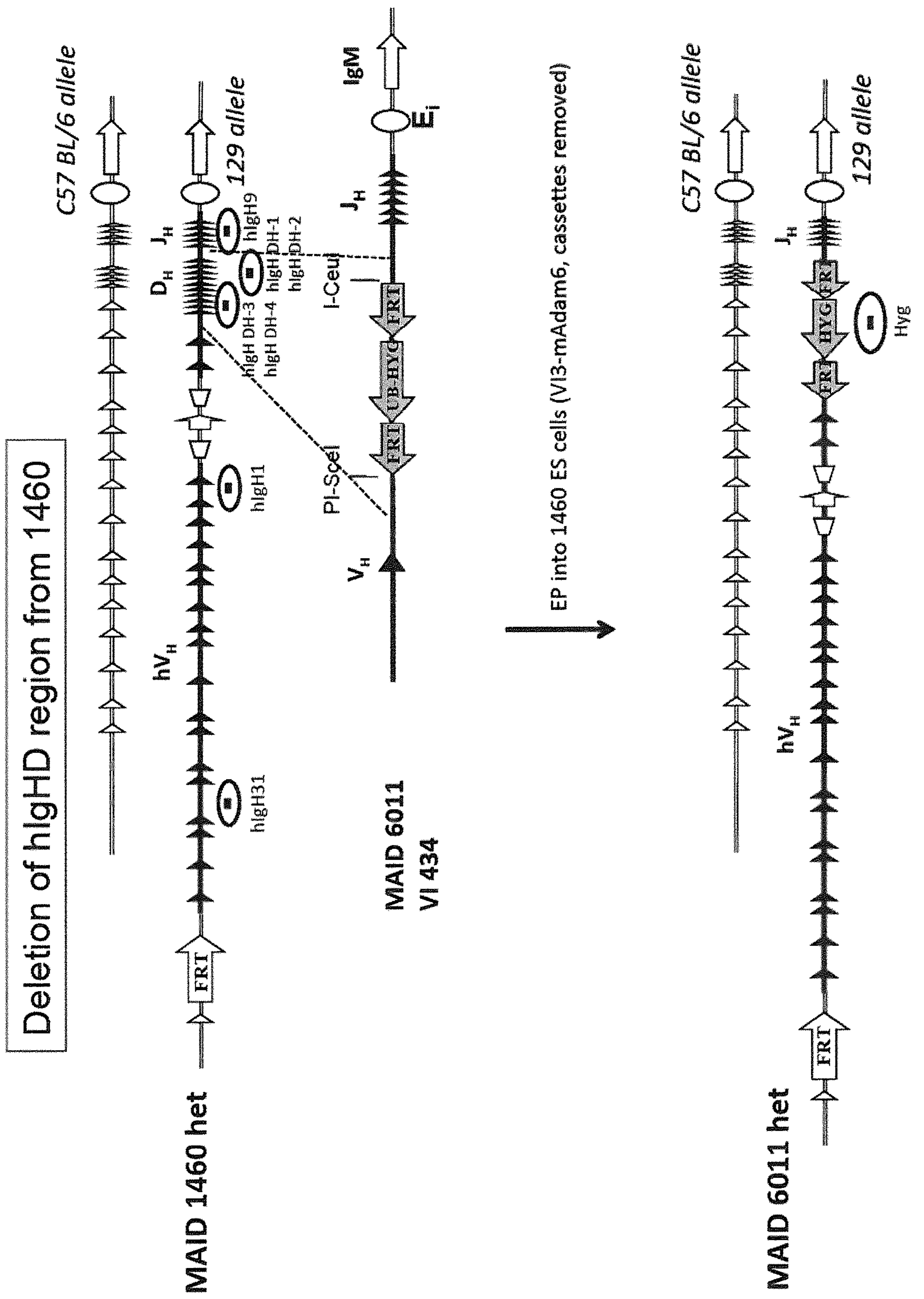
FIG. 5 illustrates schemes for deleting the human immunoglobulin heavy chain D gene region from the MAID 1460 heterozygous ES cells by targeting the 129 strain-derived chromosome of MAID 1460 het with the hygromycin selection cassette in MAID 6011 V1434.

Fourth, MAID 1460 heterozygous mouse ES cells were targeted with MAID 6011 V1434 via electroporation in order to remove all endogenous human D gene segments from the MAID 1460 clone as illustrated in FIG. 5. This yielded MAID 6011 heterozygous mouse ES cells comprising in its immunoglobulin heavy chain locus (at the 129 strain-derived chromosome), from 5' to 3', an FRT site, human $V_H$ gene segments, a mouse genomic region encompassing adam6a/b genes, a hygromycin cassette flanked by FRT sites, and human $J_H$ segments, followed by a mouse $E_i$ sequence and an IgM constant region nucleotide sequence. The genetic modification of MAID 6011 (a loss of alleles, a gain of alleles, and presence of parental alleles) was confirmed by using the probes and primers as shown in FIG. 6.

Figure 7:
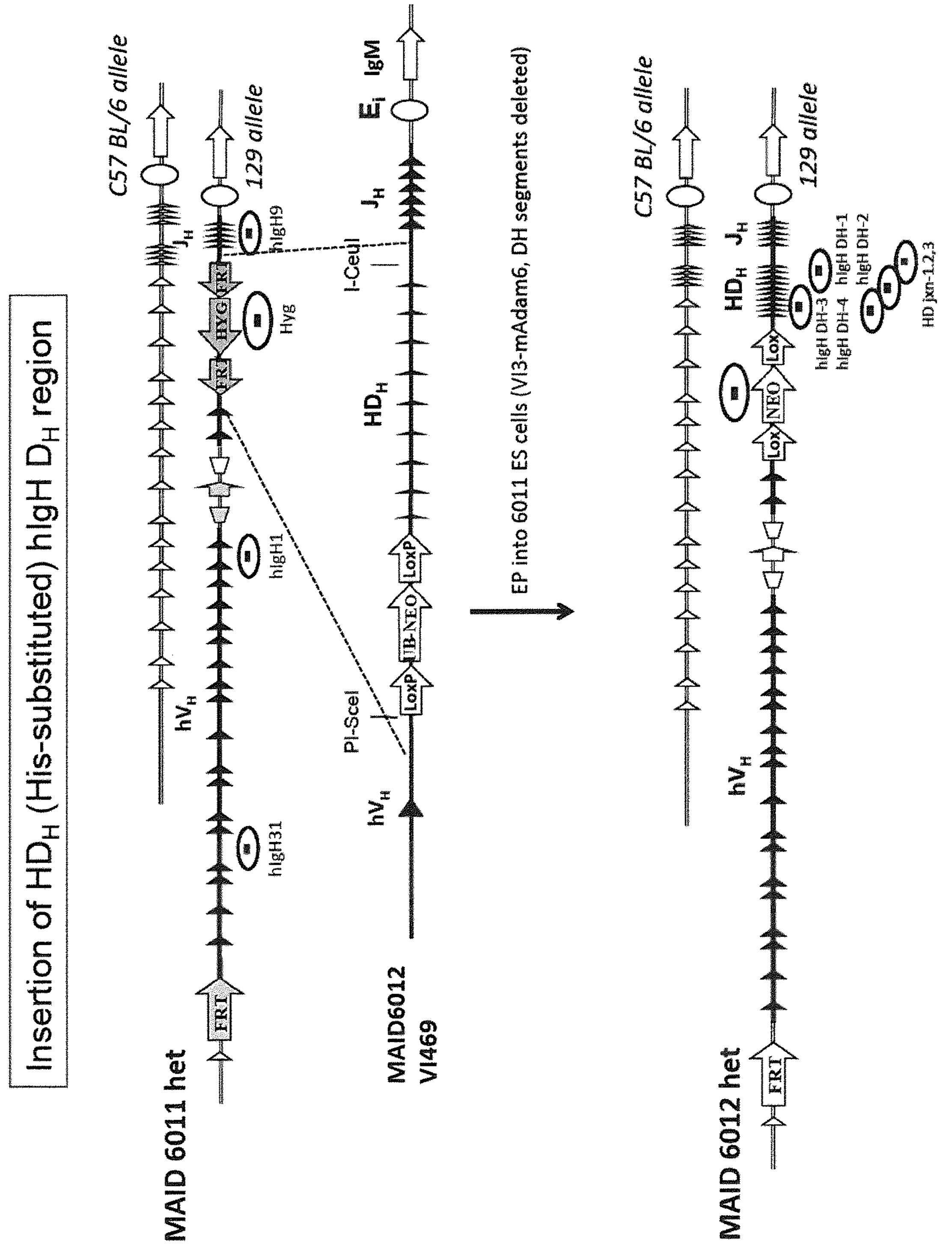
FIG. 7 illustrates schemes for constructing MAID 6012 het by targeting MAID 6011 heterozygous ES cells with MAID 6012 VI469. Electroporation of the MAID 6012 VI469 construct into the MAID 6011 heterozygous ES cells yielded MAID 6012 heterozygous ES cells in which the 129 strain-derived chromosome is modified to contain, from 5' to 3' direction, an FRT site, human $V_H$ gene segments, a mouse genomic region comprising adam6 genes, a floxed neomycin selection cassette, human D gene segments comprising histidine substitutions (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)), human $J_H$ gene segments, a mouse $E_i$ sequence (SEQ ID NO: 5; an intronic enhancer that promotes $V_H$ to $DJ_H$ rearrangement in developing B cells), and a mouse IgM constant region nucleotide sequence (mIgM exon 1; SEQ ID NO: 7).

Fifth, MAID 6011 heterozygous mouse ES cells were electroporated with MAID 6012 VI469 in order to introduce histidine-substituted human D gene segments (i.e., HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)) into MAID 6011. The targeting step removed the floxed hygromycin selection cassette from MAID 6011 and replaced the sequence with the histidine-substituted human D gene segments. This lead to MAID 6012 heterozygous ES cells comprising a wild-type C57BL/6 strain-derived chromosome and a genetically modified 129 strain-derived chromosome comprising human wild-type $V_H$ and $J_H$ gene segments and the histidine-substituted human D gene segments described herein. In addition, the ES cells contained a mouse genomic region encompassing adam6a/b genes and a floxed neomycin cassette between the $V_H$ and D segments (FIG. 7). The genetic modification of MAID 6012 (a loss of alleles, a gain of alleles, and presence of parental alleles) was confirmed by using the probes and primers as shown in FIG. 8.

Figure 9:
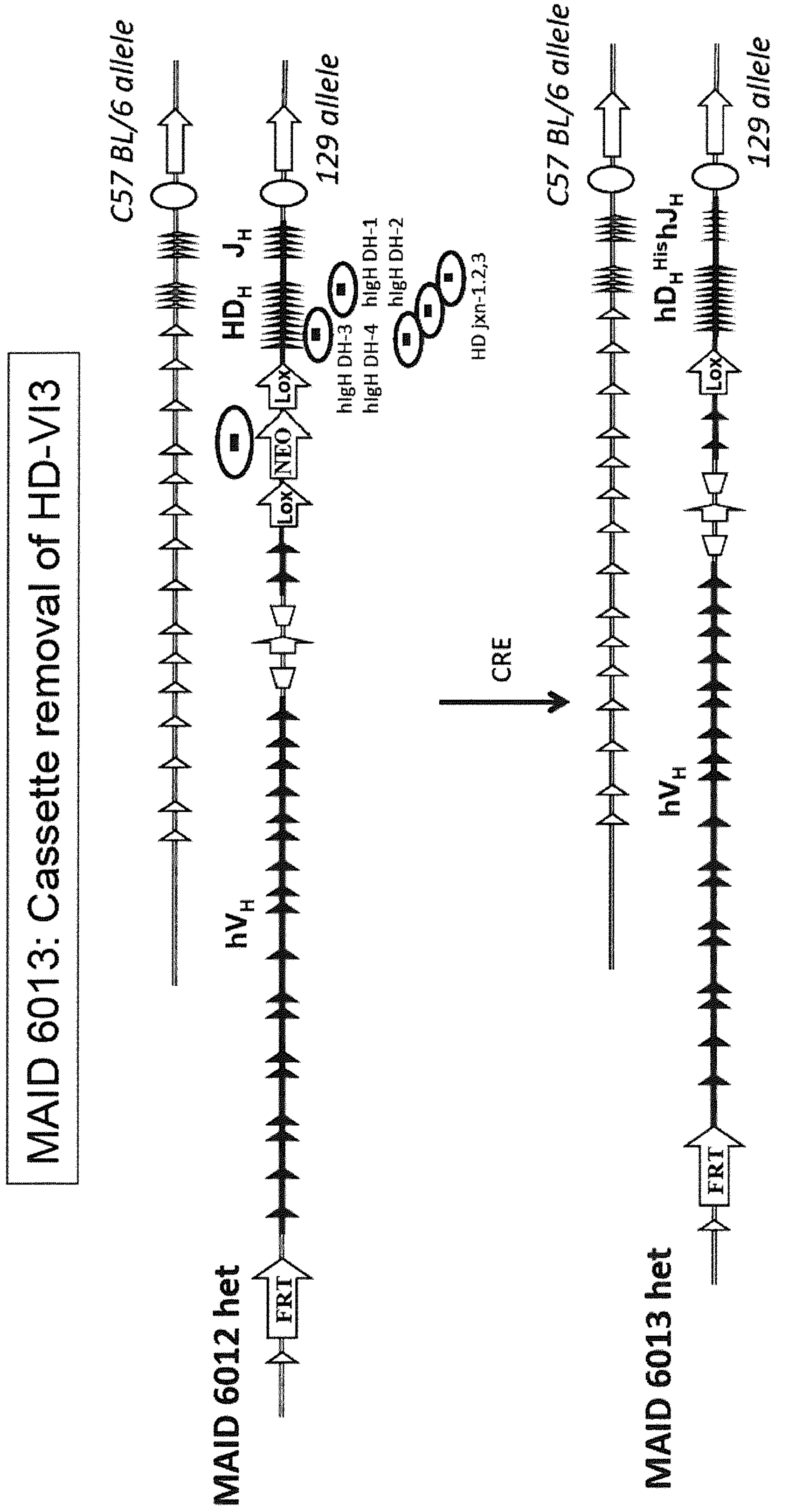
FIG. 9 illustrates schemes for removing a neomycin cassette from MAID 6012 heterozygous ES cells. Electroporation of a Cre-expressing plasmid into the MAID 6012 ES cells lead to recombination and deletion of the floxed neomycin cassette, yielding MAID 6013 heterozygous ES cells.
Figure 14:
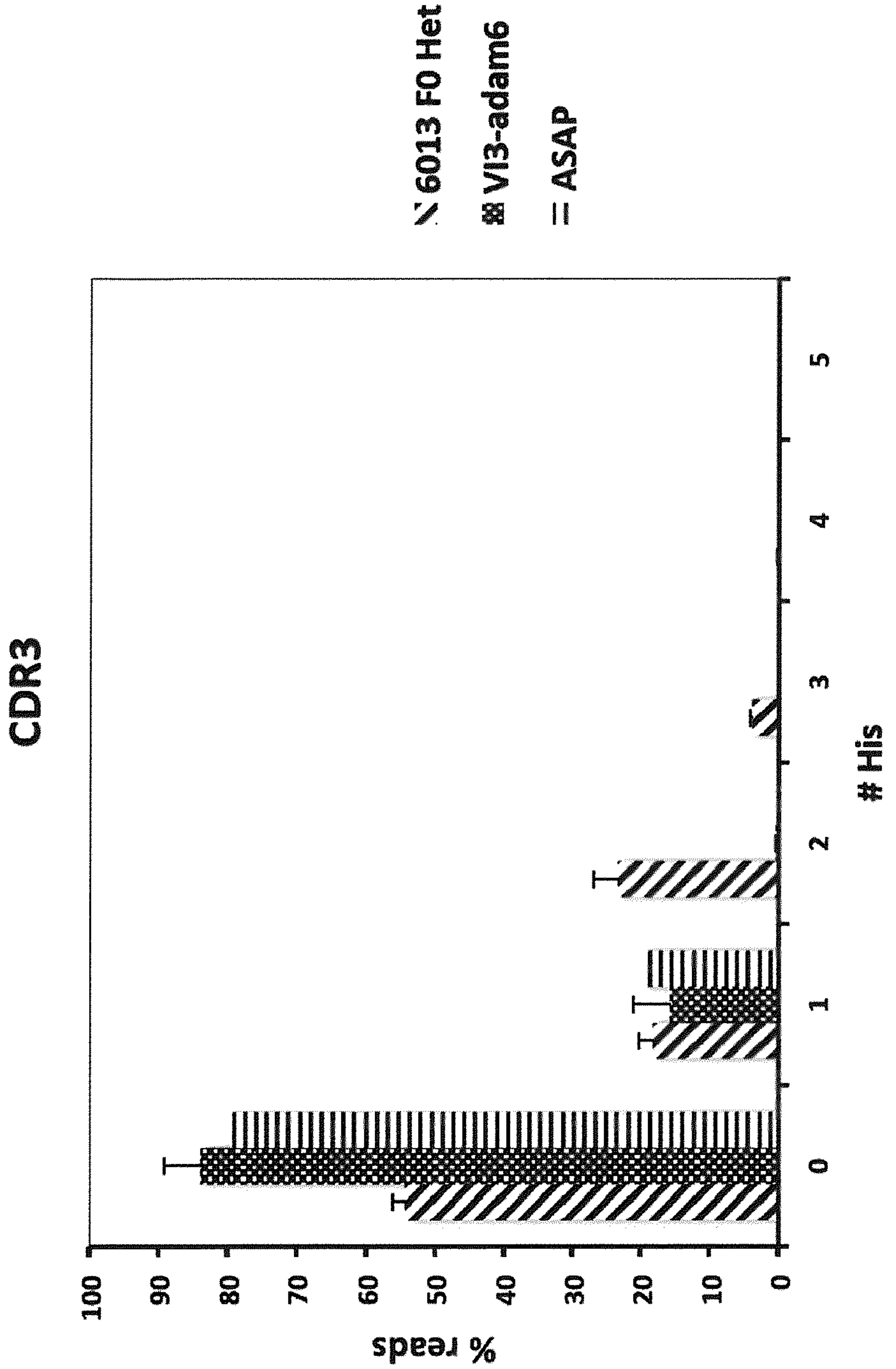
FIG. 14 illustrates histidine incorporation frequency in immunoglobulin heavy chain CDR3 sequences. The X-axis represents the number of histidine codons appeared in each CDR3 sequence, and the Y-axis represents the corresponding proportion of reads. The "6013 F0 het" indicates CDR3 sequences expressed by the 6013 heterozygous mice comprising histidine-substituted D gene segments. The "V13-Adam6" indicates CDR3 sequences obtained from control mice comprising human VH, D, and JH gene segments without the histidine modification as described herein. The "ASAP" indicates CDR3 sequences obtained from the Regeneron antibody database, which was used as another control.

Lastly, MAID 6012 ES cells were electroporated with a plasmid that expresses a Cre recombinase in order to remove the neomycin selection cassette from the MAID 6012 ES cells, resulting in MAID 6013 heterozygous ES cells (FIG. 9). The final MAID 6013 heterozygous ("MAID 6013 het") ES cell contains a wild-type C57BL/6 strain-derived chromosome and a genetically modified, 129 strain-derived chromosome comprising in its immunoglobulin heavy chain locus, from 5' to 3', (1) an FRT site; (2) human $V_H$ gene segments; (3) a mouse genomic region encompassing adam6a/b genes; (4) a floxed neomycin selection cassette; (5) histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)); (6) human $J_H$ gene segments; followed by (7) a mouse $E_i$ sequence (mIgH intronic enhancer; SEQ ID NO: 5), (8) a switch region (SEQ ID NO: 6); and (9) a mouse IgM constant region nucleotide sequence (mIgM exon 1; SEQ ID NO: 7) as illustrated in FIG. 9.

The targeted ES cells (MAID 6013) described above were used as donor ES cells and introduced into an 8-cell stage mouse embryo by the VELOCIMOUSE® method (see, e.g., U.S. Pat. Nos. 7,576,259, 7,659,442, 7,294,754, US 2008-0078000 A1, all of which are incorporated by reference herein in their entireties). Mice bearing the genetically modified immunoglobulin heavy chain locus comprising the histidine-substituted human heavy chain D gene segments described herein were identified by genotyping using the primers and probes set forth in FIG. 8. The resulting genetically modified F0 mouse was crossed to a wild-type mouse to obtain F1 offspring. F1 pups were genotyped, and the F1 pups that are heterozygous for the genetically modified immunoglobulin locus comprising histidine-substituted human heavy chain D gene segments were selected for further characterization.

Example 2. Analysis of Rearranged Heavy Chain Variable Region Nucleotide Sequences Next, it was examined whether the genetically modified mouse comprising histidine-substituted human D gene segments described herein, e.g., 6013 F0 heterozygous mouse, which comprises in its germline a 129 strain-derived chromosome comprising human $V_H$, $J_H$ gene segments, and histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4), can express rearranged heavy chain V(D)J sequences comprising one or more histidine codons derived from the genetically modified immunoglobulin heavy chain locus.

To this end, mRNA sequences isolated from splenic B cells of the 6013 F0 heterozygous mice were analyzed by reverse-transcriptase polymerase chain reaction (RT-PCR) for the presence of IgM CDR3 sequences derived from the histidine-substituted human D gene segments.

Briefly, spleens were harvested and homogenized in 1×PBS (Gibco) using glass slides. Cells were pelleted in a centrifuge (500×g for 5 minutes), and red blood cells were lysed in ACK Lysis buffer (Gibco) for 3 minutes. Cells were washed with 1×PBS and filtered using a 0.7 μm cell strainer. B-cells were isolated from spleen cells using MACS magnetic positive selection for CD19 (Miltenyi Biotec). Total RNA was isolated from pelleted B-cells using the RNeasy Plus kit (Qiagen). PolyA+ mRNA was isolated from total RNA using the Oligotex® Direct mRNA mini kit (Qiagen).

Double-stranded cDNA was prepared from splenic B cell mRNA by 5' RACE using the SMARTer™ Pico cDNA Synthesis Kit (Clontech). The Clontech reverse transcriptase and dNTPs were substituted with Superscript II and dNTPs from Invitrogen. Heavy chain variable region ($V_H$) antibody repertoires were amplified from the cDNA using primers specific for IgM constant regions and the SMARTer™ 5' RACE primer (Table 1). PCR products were cleaned up using a QIAquick® PCR Purification Kit (Qiagen). A second round of PCR was done using the same 5' RACE primer and a nested 3' primer specific for the IgM constant regions (Table 2). Second round PCR products were purified using a SizeSelect™ E-gel® system (Invitrogen). A third PCR was performed with primers that added 454 adapters and barcodes. Third round PCR products were purified using Agencourt® AMPure® XP Beads. Purified PCR products were quantified by SYBR®-qPCR using a KAPA Library Quantification Kit (KAPA Biosystems). Pooled libraries were subjected to emulsion PCR (emPCR) using the 454 GS Junior Titanium Series Lib-A emPCR Kit (Roche Diagnostics) and bidirectional sequencing using Roche 454 GS Junior instrument according to the manufacturer's protocols.

TABLE 1

| NAME | SEQUENCE |
|---|---|
| 3' mIgM CH1 outer | TCTTATCAGACAGGGGGCTCTC (SEQ ID NO: 318) |

TABLE 2

| NAME | |
|---|---|
| 3' mIgM CH1 inner | GGAAGACATTTGGGAAGGACTG (SEQ ID NO: 319) |

Bioinformatic Analysis

The 454 sequences were sorted based on the sample barcode perfect match and trimmed for quality. Sequences were annotated based on alignment of rearranged Ig sequences to human germline V, D and J segments database using local installation of igblast (NCBI, v2.2.25+). A sequence was marked as ambiguous and removed from analysis when multiple best hits with identical score were detected. A set of perl scripts was developed to analyze results and store data in mysql database. The CDR3 region was defined between conserved C codon and FGXG motif (SEQ ID NO: 320) for light chains and WGXG motif (SEQ ID NO: 321) for heavy chains. CDR3 length was determined using only productive antibodies.

As shown in FIGS. 11-13, 6013 F0 heterozygous mice expressed a diverse repertoire of rearranged heavy chain variable region mRNA sequences (rearranged V-D-J sequences) encoding one or more histidine codons in CDR3. The sequencing data suggested that the histidine codons appeared in CDR3 were derived from various histidine-substituted human D gene segments present in the genetically modified immunoglobulin heavy chain locus of the 6013 mice described herein.

Example 3. Histidine Usage in Antigen-Specific Human Light Chains

Amino acid sequences of selected light chains from antigen-specific human antibodies were aligned. Histidine mutations in the CDRs of human Vκ1-39-derived light chains for a selected number of antigen-specific human antibodies were identified (FIG. 15). The human Vκ1-39-derived light chains were isolated from immunized mice engineered to contain a single rearranged human Vκ1-39 light chain (see US 2011/0195454A1, herein incorporated by reference), and bear somatic hypermutations as generated in the antibody repertoire of the mouse.

Histidine residues were engineered into a rearranged human Vκ1-39 light chain using molecular mutagenesis techniques known in the art. Locations of the engineered residues are shown in FIG. 16.

Human Vκ1-39-derived light chain variable regions containing engineered histidine residues were constructed and paired with various human heavy chain variable regions in an antibody format, specific for a human cell surface receptor, to analyze expression in CHO cells.

CHO cells having a particular heavy chain and a light chain with indicated his modifications (e.g., 105, 106, 108, 111) were seeded into wells of a 48-well plate. The next day, DNA corresponding to heavy chain and light chain, in equal weight (400 ng), were mixed with transfection reagent (Lipofectin 2000), allowed to form a complex by incubation, and the complex added to the plated cells. Four days later, media was collected. The media contained the expressed antibody.

CHO cells having different heavy chains paired with the same light chain having one or more his substitutions in CDR3 express well. Level (ng/mL) of antibody expression in ng/mL detected in supernatants of CHO cells transfected with antibody genes having histidine residues engineered at selected locations in the CDR3 of the light chains was determined.

Figure 18:
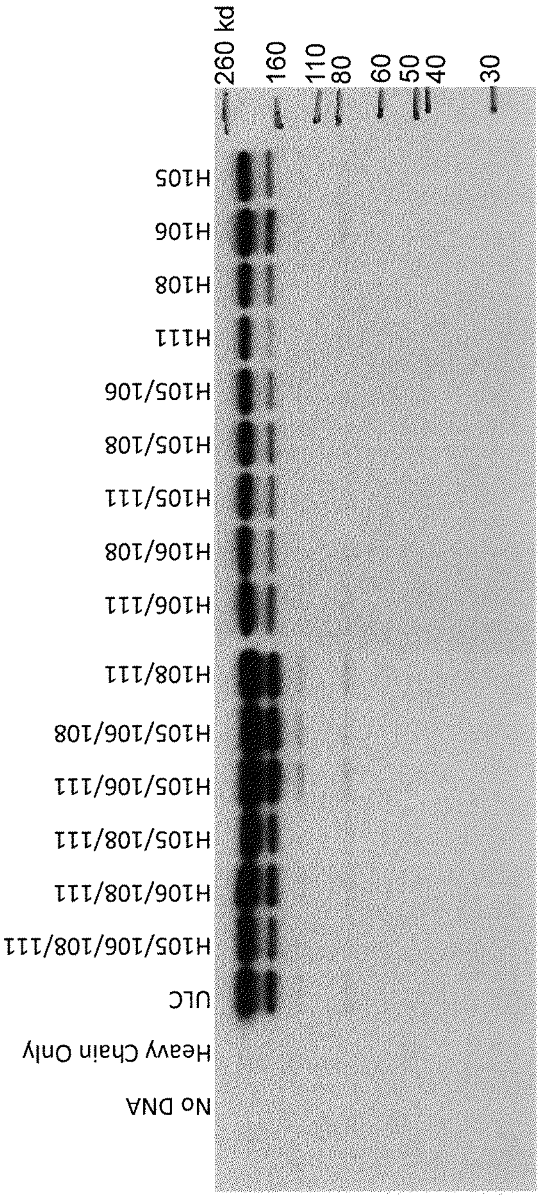
FIG. 18 is a western blot showing expression of selected antigen-specific human antibodies containing histidine engineered light chains in CHO cell supernatants.

Expression in supernatants of CHO cells of paired antigen-specific heavy chains with histidine engineered light chains using selected heavy chains, measured by protein blots, is shown in FIG. 18. ULC refers to a rearranged human Vκ1-39-derived light chain.

An aliquot of media was subjected to analysis on a BIACORE™ instrument using the target antigen for the antibody (a cell surface receptor sequence). Antibody was captured on the chip. Antibody capture level is shown in FIG. 19A-19J as RU. Captured antibody on the BIACORE™ chip was subjected to flow containing the sequence of the target antigen. Antibody capture of the target antigen was measured, as well as association rate and other parameters as shown. Antigen flow was stopped and dissociation rate was determined as antigen disengaged from the bound antibody.

Equilibrium dissociation constants ($K_D$) (apparent) for selected antibody supernatants were determined by SPR (Surface Plasmon Resonance) using a BIACORE™ T100 instrument (GE Healthcare). Kinetics were measured at pH 7.4 and at pH 5.75. Results are shown in FIG. 19A-19J.

As shown in FIG. 19A-19J, data for antibody binding to a cell surface receptor, where the light chains have been modified to encode histidine residues a specific positions in a CDR, for Vκ1-30/Jκ5 light chains paired with the indicated heavy chains, demonstrates that the histidine modifications directly influence binding of the antigen (e.g., a cell surface receptor) with different affinities at pH 7.4 and pH 5.75. Histidine modifications that retain binding at pH 7.4, but that exhibit a low binding or no detectable binding at pH 5.75, are desirable.

Example 4. Identification of Histidine Residues in Antigen-Specific Human Light Chains Generation of a common light chain mouse (e.g., Vκ1-39 or Vκ3-20 common light chain mouse) and antigen-specific antibodies in those mice is described in U.S. patent application Ser. Nos. 13/022,759, 13/093,156, and 13/412,936 (Publication Nos. 2011/0195454, 2012/0021409, and 2012/0192300, respectively), incorporated by reference herein in their entireties. Briefly, rearranged human germline light chain targeting vector was made using VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6): 652-659) to modify mouse genomic Bacterial Artificial Chromosome (BAC) clones, and genomic constructs were engineered to contain a single rearranged human germline light chain region and inserted into an endogenous κ light chain locus that was previously modified to delete the endogenous κ variable and joining gene segments. Targeted BAC DNA was then used to electroporate mouse ES cells to create modified ES cells for generating chimeric mice that express a rearranged human germline Vκ1-39Jκ5 or Vκ3-20Jκ1 region. Targeted ES cells were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1): 91-99). VELOCIMICE® independently bearing an engineered human germline Vκ1-39Jκ5 or Vκ3-20Jκ1 light chain region were identified by genotyping using a modification of allele assay (Valenzuela et al., supra) that detects the presence of the unique rearranged human germline light chain region.

Mice bearing an engineered human germline light chain locus (ULC mice) were bred with mice that contain a replacement of the endogenous mouse heavy chain variable gene locus with the human heavy chain variable gene locus (see U.S. Pat. No. 6,596,541; the VELOCIMMUNE® mouse, Regeneron Pharmaceuticals, Inc.).

VELOCIMMUNE® mouse containing a single rearranged human germline light chain region is challenged with an antigen of interest and antibodies comprising a universal light chain (e.g., Vκ1-39Jκ5) are isolated and sequenced. Amino acid sequences of selected light chains (A-K) from antigen-specific human antibodies generated in a common Vκ1-39Jκ5 light chain mouse were aligned. Histidine mutations in the CDRs of human Vκ1-39-derived light chains for a selected number of antigen-specific human antibodies were identified (FIG. 15). The partial amino acid sequence of germline Vκ1-39Jκ5 variable domain is shown above the alignments and set forth in SEQ ID NO:325, the complete variable domain amino acid sequence is set forth in SEQ ID NO:404.

Example 5. Engineering and Characterization of Histidine-Substituted Human Universal Light Chain Antibodies

Example 5.1. Engineering of Histidine Residues into a Germline Human Rearranged Light Chain Histidine residues were engineered into a rearranged human Vκ1-39Jκ5 light chain using site directed mutagenesis primers specifically designed to introduce engineered histidine residues at Q105, Q106, Y108, and P111 positions of the human Vκ1-39Jκ5 light chain. Site directed mutagenesis was performed using molecular techniques known in the art (e.g., QuikChange II XL Site Directed Mutagenesis Kit, Agilent Technologies). Locations of the engineered residues in the CDR3 are shown in FIG. 16, the nucleic acid sequences of histidine-substituted CDR3's depicted in FIG. 16 are set forth in SEQ ID NOs: 328, 330, 332, 334, 336, 338, 340, 342, 344, 346, 348, 350, 352, 354, and 356 (corresponding amino acid sequences are set forth in SEQ ID NOs: 329, 331, 333, 335, 337, 339, 341, 343, 345, 347, 349, 351, 353, 355, and 357). The nucleic acid and amino acid sequences of germline rearranged Vκ1-39Jκ5 CDR3 are set forth in SEQ ID NOs: 326 and 327, respectively.

Example 5.2. Construction and Expression of Histidine Engineered Light Chains Human Vκ1-39-derived light chains containing germline engineered histidine residues made according to Example 2 were constructed and paired with various human heavy chains (labeled 1-5), specific for a human cell surface receptor, to analyze expression in CHO cells. The five human heavy chains specific for a human cell surface receptor that were paired with histidine-substituted Vκ1-39-derived light chains were obtained from mice that have a single rearranged human light chain (a human Vκ1-39/Jκ5 rearranged light chain; see US2011/0195454A1).

Figure 17:
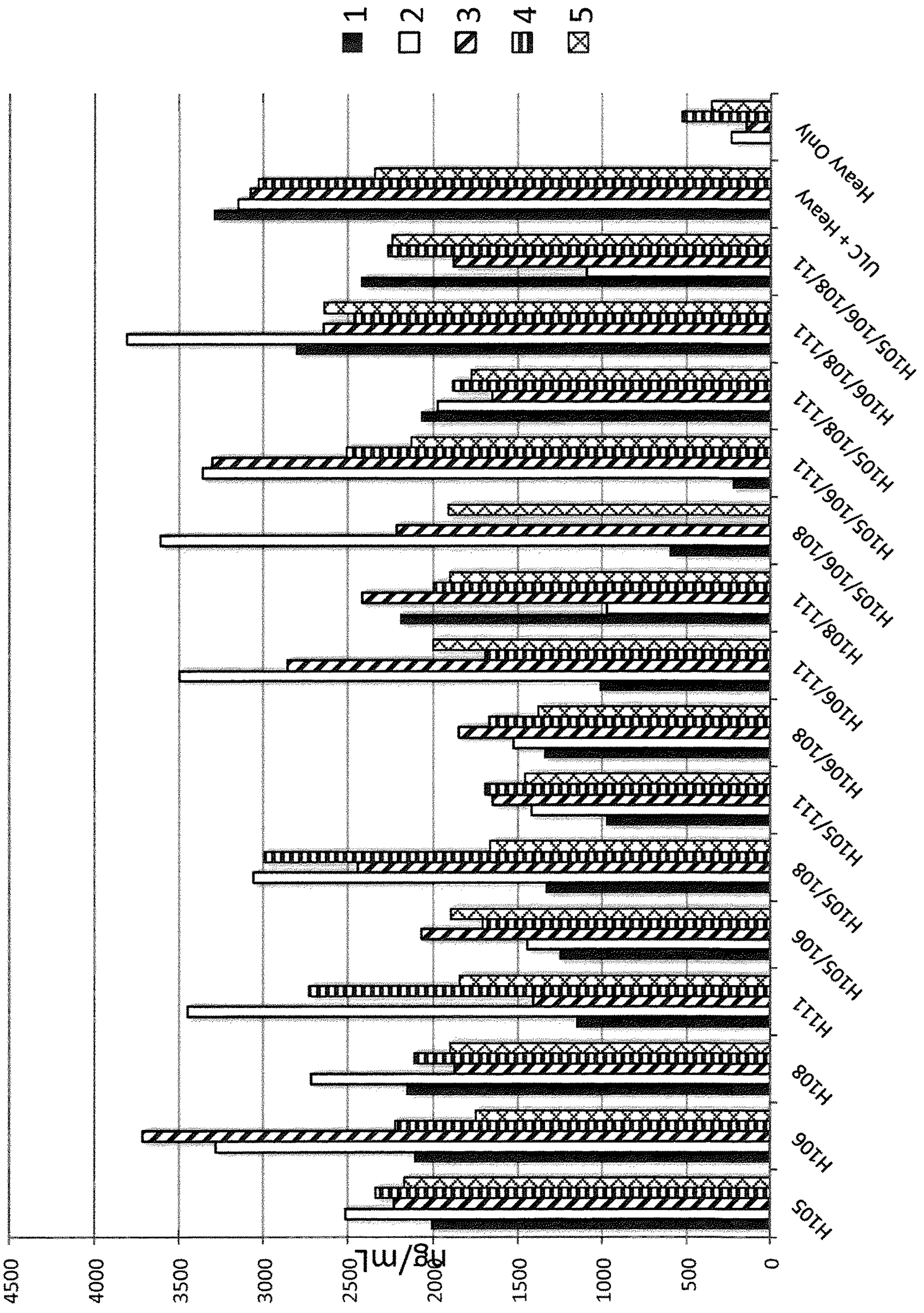
FIG. 17 illustrates the level of antibody expression in ng/mL detected in the supernatants of CHO cells transfected with nucleic acids encoding five (1-5) different heavy chains and Vκ1-39-derived light chains having histidine residues engineered at indicated locations (see Y axis) in the CDR3.

Enzyme-linked Immunosorbent assay (ELISA): Antibody secretion from CHO cells was detected using an Fc ELISA, for light chains with indicated histidine modifications with five different heavy chains. The light and heavy chain sequences (but for the modifications) were generated in mice that have a single rearranged human light chain (e.g., a human Vκ1-39/Jκ5 rearranged light chain; see US2011/0195454A1). Capture antibody was goat anti-human IgG and detection antibody was goat anti-human (Fc gamma-specific)-HRP. The results are shown in FIG. 17. ULC+heavy: specific heavy chain and unmodified human Vκ1-39-derived light chain. As shown in FIG. 17, expression was detected in about all mutants.

Protein Immunoblot. Expression in supernatants of CHO cells of paired antigen-specific heavy chains with histidine engineered light chains was further analyzed by western blot. Samples were run on a 4-12% tris-glycine gel. Results using a selected heavy chain (heavy chain 3) are shown in FIG. 18. ULC refers to a rearranged human Vκ1-39-derived light chain (as described above).

Example 5.3. Determination of Binding Affinity of Histidine Engineered Light Chains Equilibrium dissociation constants ($K_D$), dissociative half-lives ($t_{1/2}$), and other kinetic parameters for selected antibody supernatants were determined by SPR (Surface Plasmon Resonance) using a BIACORE™ T200 instrument (GE Healthcare). Kinetics were measured at pH 7.4 and at pH 5.75. Results are shown in FIGS. 20A-20E.

Numerical values for the kinetic binding properties (e.g., $k_a$, $k_d$, $K_D$, $t_{1/2}$, etc.) of antibodies binding to immunogen at neutral pH (pH 7.4) and at acidic pH (pH 5.75) were obtained using a real-time surface plasmon resonance biosensor (Biacore T200.) A Biacore CM5 sensor chip was derivatized with a mouse anti-human Fc antibody to capture antibodies from the supernatant. A single concentration (50 nM) of immunogen was then injected over the antibody-captured surface at a flow rate of 30 μl/min. Antibody-antigen association was monitored for 2.5 minutes and then the dissociation of antigen from the captured antibody was monitored for 8 minutes. Kinetic association (ka) and dissociation (kd) rate constants were determined by processing and fitting the data to a 1:1 binding with a mass transport model using Biacore T200 Evaluation software version 1.0. Equilibrium dissociation constants ($K_D$) and dissociative half-lives ($t_{1/2}$) were calculated from the kinetic rate constants as: $K_D$ (M)=$k_d/k_a$; and $t_{1/2}$ (min)=(ln 2/(60*$k_d$).

As shown in FIG. 20, in a binding assay of antibody to a cell surface receptor, two out of five antibodies with histidine-modified common light chains (histidine modified CDR3's of Vκ1-39/Jκ5 light chains) that were paired with the antigen-specific human heavy chains, exhibited binding to the antigen (e.g., to a cell surface receptor) with different affinities at pH 7.4 and pH 5.75. Antibodies with histidine modifications that retain binding at pH 7.4, but that exhibit a low binding or no detectable binding at pH 5.75, are desirable. Antibodies with histidine modification that exhibit reduced $t_{1/2}$ at pH 5.75 as compared to pH 7.4 are desirable.

Antigen binding data for three antibodies comprising histidine-modified common light chains and three antigen-specific heavy chains (labeled 2, 3, and 6) at different pHs is summarized further in FIG. 21. These antibodies exhibited significant drop in antigen binding at pH 5.75 in comparison to pH 7.4, as demonstrated, e.g., by reduction in $t_{1/2}$ or no binding detected at pH 5.75.

Example 6. Engineering and Characterization of Genetically Modified Mouse Comprising a Histidine-Substituted Vκ1-39Jκ5 Universal Light Chain

Example 6.1. Constructing of Targeting Vector for Engineering Histidine Residues in a Rearranged Human Light Chain Variable Region A genetically modified mouse containing a rearranged human light chain gene having histidine residues engineered into a CDR region of the human light chain is made using targeting vectors made by standard molecular cloning techniques known in the art.

Briefly, various rearranged human germline light chain targeting vectors are made using VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6):652-659) to modify mouse genomic Bacterial Artificial Chromosome (BAC) DNA to contain a single rearranged human germline light chain region and inserted into an endogenous κ light chain locus that was previously modified to delete the endogenous κ variable and joining gene segments. The rearranged human germline light chain region is modified at one or more nucleotide positions within the sequence of the light chain to encode histidine residues that are not normally present at the respective locations of the germline sequence. The targeting vectors are electroporated into mouse embryonic stem (ES) cells to create and confirmed using a quantitative PCR assay (e.g., TAQMAN™).

Figure 23A:
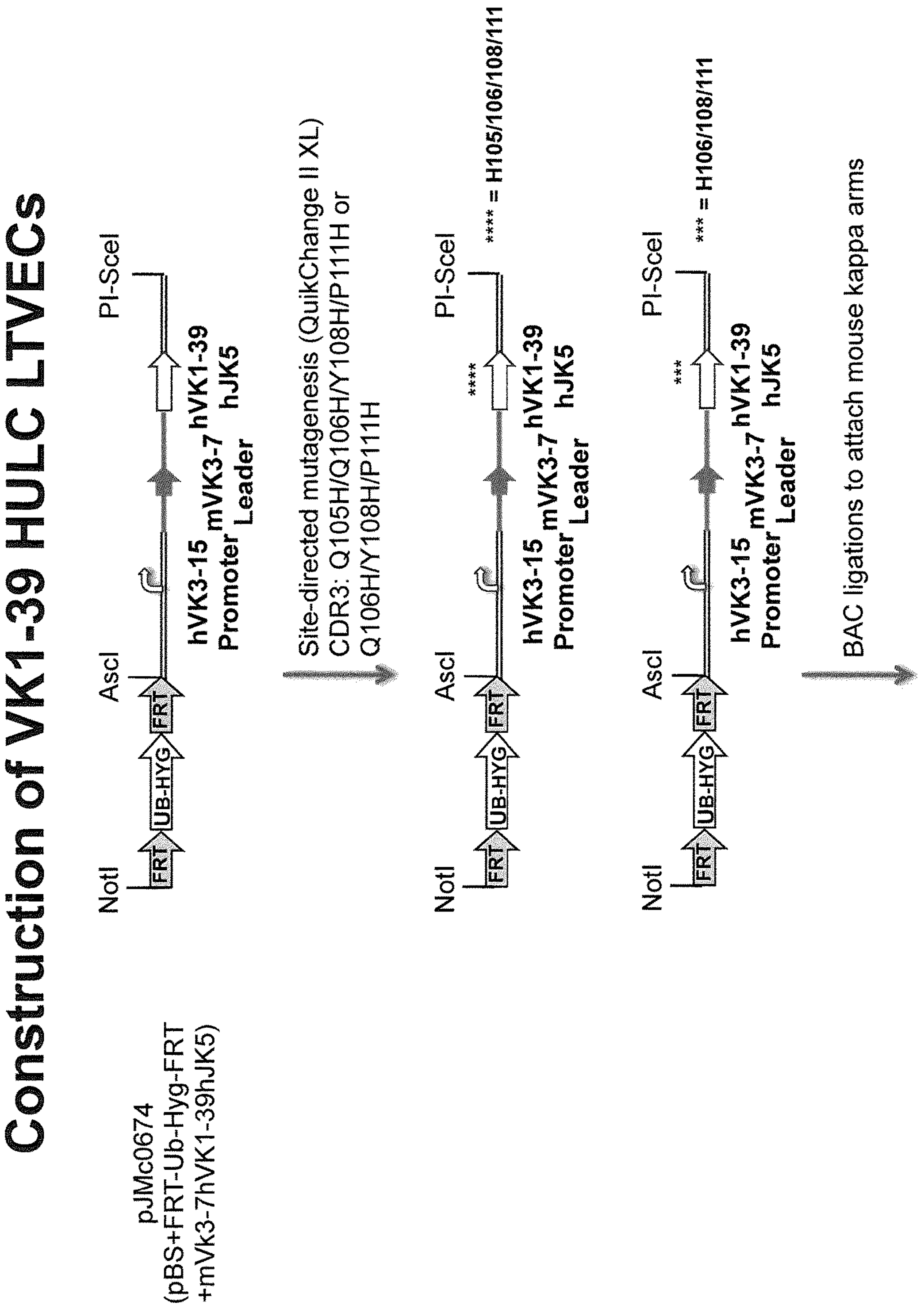
FIGS. 23A-23B show a general strategy for construction of targeting vectors for engineering of histidine residues into a rearranged human light chain variable region sequence derived from Vκ1-39/Jκ5 variable region for making a genetically modified mouse that expresses antibodies containing the modified human light chain.
Figure 23B:
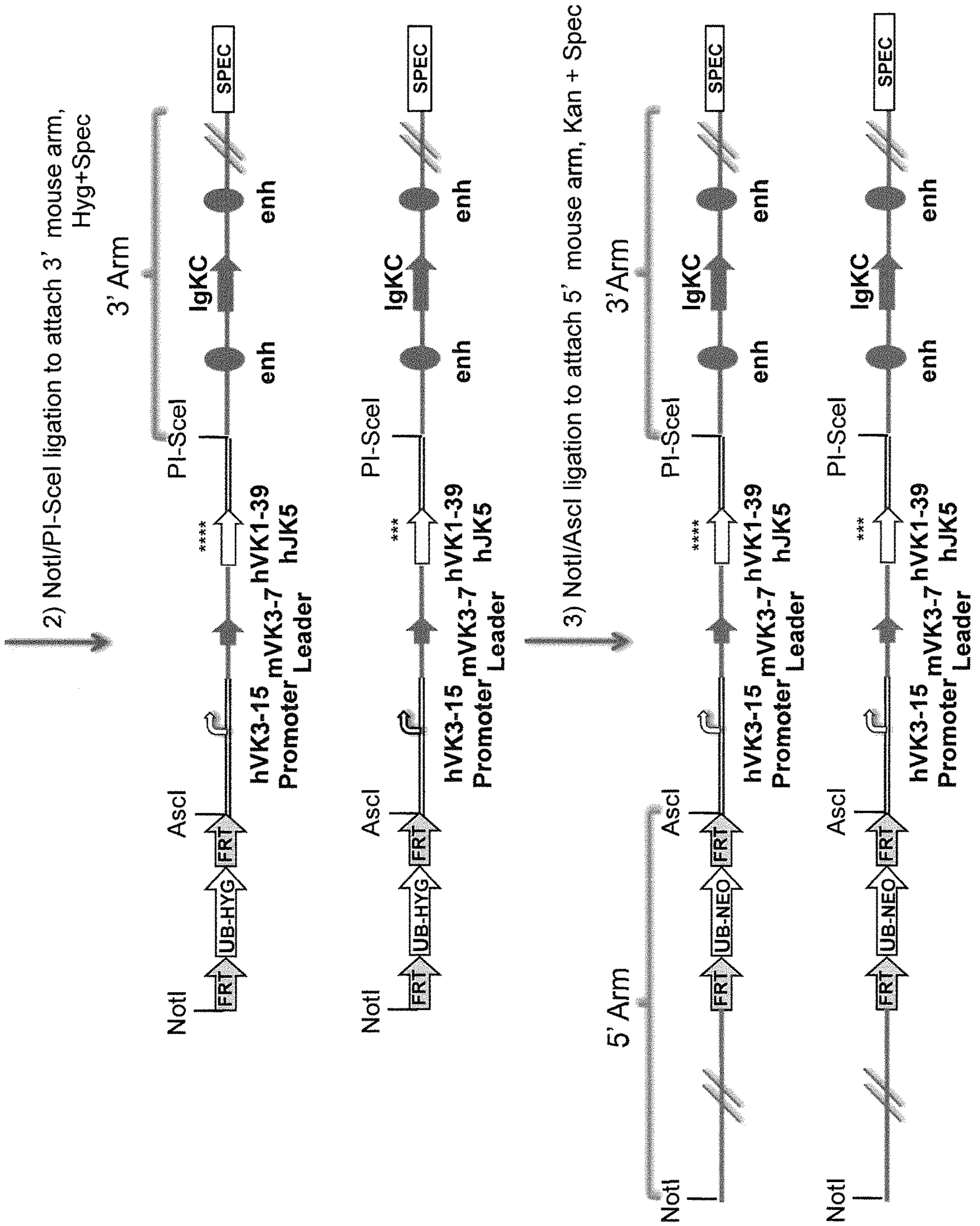

Specifically, a strategy for constructing these targeting vectors is shown in FIGS. 23A-23F. A plasmid used for generating a targeting vector for common (universal) light chain mouse ("ULC mouse," described in, e.g., US2011/0195454A1), containing pBS+FRT-Ub-Hyg-FRT+mouse Vκ3-7 leader+human Vκ1-39Jκ5 was modified by site directed mutagenesis (QuickChange II XL Kit) to replace Q105, Q106, Y108 and P111 or Q106, Y108 and P111 with histidine residues in the CDR3 region using site-directed mutagenesis primers shown in FIG. 22 (See FIG. 23A for this engineering step). Resultant vectors (H105/106/108/111 and H106/108/111) were modified further and ligated into a vector comprising mouse IgK constant region, mouse enhancers, a mouse 3' homology arm and a SPEC cassette (FIG. 23B). Further modification involved ligation into a vector carrying 5' mouse arm and comprising Frt-Ub-NEO-Frt cassette (FIG. 23B). Resultant targeting vectors were electroporated into ES cells comprising deletion of the mouse Igκ variable locus (comprising κ variable and joining gene segments) (FIGS. 23C-23F).

Positive ES cell clones were confirmed by using a modification of allele assay (Valenzuela et al.) using probes specific for the engineered Vκ1-39Jκ5 light chain region inserted into the endogenous κ light chain locus. Primers and probes used in the assay are shown in Table 3 below and set forth in the Sequence Listing; the locations of the probes are depicted in FIGS. 23C-23F.

TABLE 3

Primers and Probes Used for ES Cell Screening

| Probe Name | Assay | Probe Sequence | 5' Primer | 3' Primer |
|---|---|---|---|---|
| Neo | GOA | TGGGCACAAC AGACAATCGGC TG (SEQ ID NO: 362) | GGTGGAGAG GCTATTCGGC (SEQ ID NO: 363) | GAACACGGCGG CATCAG (SEQ ID NO: 364) |
| ULC-m1 | GOA | CCATTATGATG CTCCATGCCTC TCTGTTC (SEQ ID NO: 365) | AGGTGAGGG TACAGATAAG TGTTATGAG (SEQ ID NO: 366) | TGACAAATGCCC TAATTATAGTGAT CA (SEQ ID NO: 367) |
| 1633h2 (Vκ1-39Jκ5-specific) | GOA | ATCAGCAGAAA CCAGGGAAAGC CCCT (SEQ ID NO: 368) | GGGCAAGTC AGAGCATTAG CA (SEQ ID NO: 369) | TGCAAACTGGAT GCAGCATAG (SEQ ID NO: 370) |
| mIgKd2 | Retention | GGCCACATTCC ATGGGTTC (SEQ ID NO: 371) | GCAAACAAAA ACCACTGGCC (SEQ ID NO: 372) | CTGTTCCTCTAAA ACTGGACTCCAC AGTAAATGGAAA (SEQ ID NO: 373) |
| mIgKp15 | Retention | GGGCACTGGAT ACGATGTATGG (SEQ ID NO: 374) | CACAGCTTGT GCAGCCTCC (SEQ ID NO: 375) | AGAAGAAGCCTG TACTACAGCATC CGTTTTACAGTCA (SEQ ID NO: 376) |

Figure 23C:
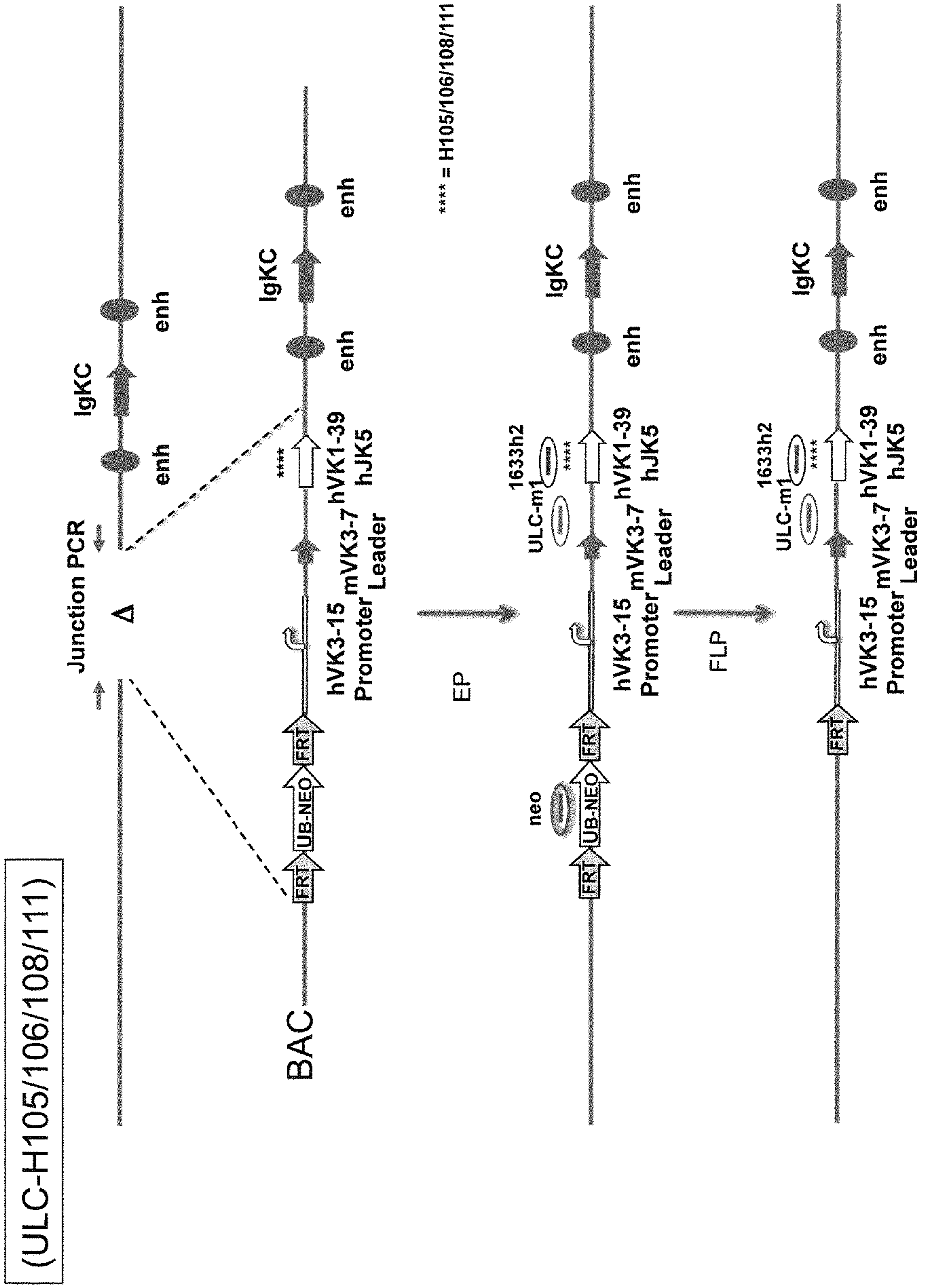
Figure 23D:
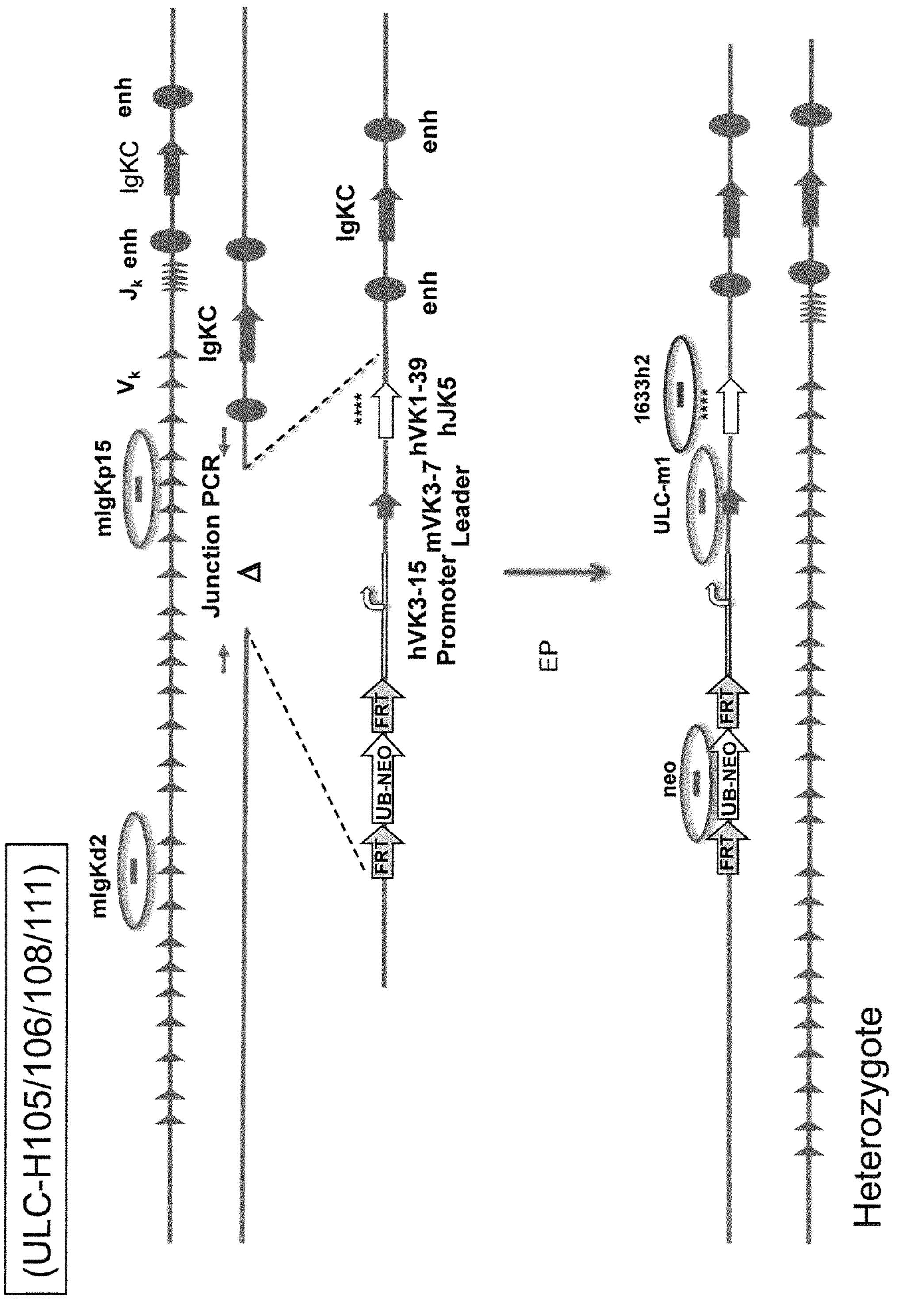
Figure 23E:
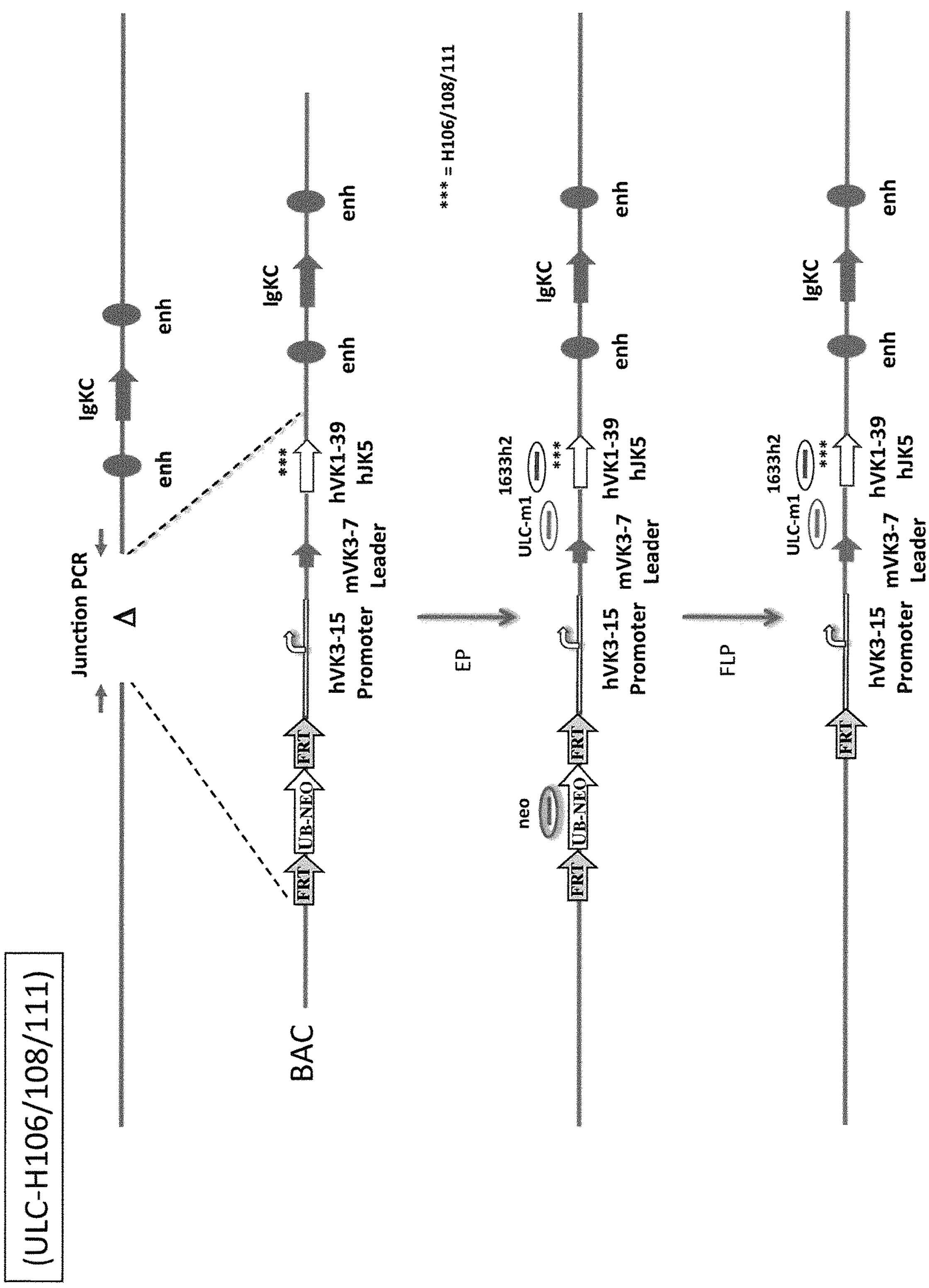
FIGS. 23E-23F show introduction of the targeting vector for ULC-H106/108/111 substitutions into ES cells and generation of heterozygous mice from the same. The diagrams are not presented to scale. Unless indicated otherwise, filled shapes and solid lines represent mouse sequence, empty shapes and double lines represent human sequence.
Figure 23F:
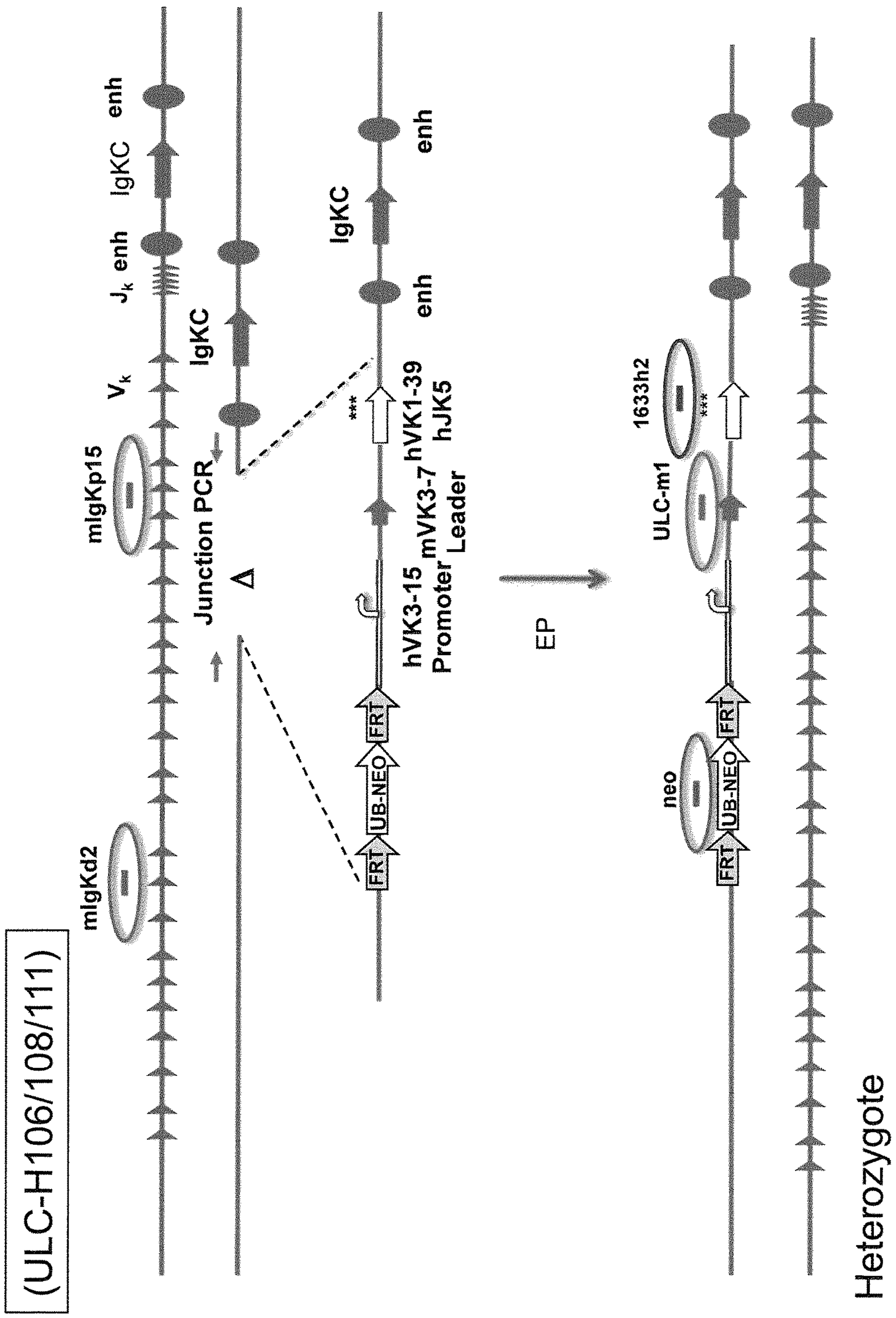

The NEO selection cassette introduced by the targeting constructs was deleted by transfecting ES cells with a plasmid that expresses FLP (FIGS. 23C and 23E). Optionally, the neomycin cassette may be removed by breeding to mice that express FLP recombinase (e.g., U.S. Pat. No. 6,774,279). Optionally, the neomycin cassette is retained in the mice.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99. VELOCIMICE® independently bearing an engineered human light chain gene that contains histidine residues mutated into one or more positions along the sequence were made from the targeted ES cells described above.

Pups were genotyped and pups heterozygous for the engineered histidine-modified human light chain were selected for characterizing expression of the light chain and binding capabilities of the expressed antibodies. Primers and probes for genotyping of mice specifically comprising a universal light chain gene with either three (H106/108/111; "1930") or four (H105/105/108/111; "1927") histidine modifications are listed in Table 4 below and set forth in the Sequence Listing. Mice containing histidine modification in their universal light chains are referred herein as "HULC" mice (histidine universal light chain mice).

Antibody serum titers against immunogen were determined by a standard ELISA. To perform the ELISA, 96-well microtiter plates (Thermo Scientific) were coated at 2 μg/ml with Antigen A in phosphate-buffered saline (PBS, Irvine Scientific) overnight at 4° C. The next day, plates were washed with phosphate-buffered saline containing 0.05% Tween 20 (PBS-T, Sigma-Aldrich) four times using a plate washer (Molecular Devices). Plates were then blocked with 250 μl of 0.5% bovine serum albumin (BSA, Sigma-Aldrich) in PBS and incubated for 1 hour at room temperature. The plates were then washed four times with PBS-T. Sera from immunized mice and pre-immune sera were serially diluted three-fold in 0.5% BSA-PBS starting at 1:300 or 1:1000, added to the blocked plates in duplicate, and then incubated for 1 hour at room temperature. The last two wells were left blank to be used as a secondary antibody control (background control). The plates were again washed four times with PBS-T in a plate washer. Goat anti-mouse IgG-Fc-Horse Radish Peroxidase (HRP) conjugated secondary antibody (Jackson Immunoresearch) was then added to the plates at 1:5000/1:10,000 dilution and incubated for 1 hour at room temperature. Plates were then washed eight times with PBS-T and developed using TMB/$H_2O_2$ as substrate. The substrate was incubated for 20 min and the reaction was stopped with 2 N sulfuric acid ($H_2SO_4$, VWR, cat #BDH3500-1) or 1 N phosphoric acid (JT Baker, Cat #7664-38-2). Plates were read on a spectrophotometer (Victor, Perkin Elmer) at 450 nm. Antibody titers were computed using Graphpad PRISM software.

TABLE 4

Primers and Probes Used for Genotyping

| Probe Name | Assay | Probe Sequence | 5' Primer | 3' Primer |
|---|---|---|---|---|
| 1927jxn3 | GOA 1927 (4 His) mouse-specific | ACCATAGTCACAGTACCCA (SEQ ID NO: 377) | AGCAGTCTGCAACCTGAAGATTT (SEQ ID NO: 378) | CCCTTGGCCGAAGGTGAT (SEQ ID NO: 379) |
| 1930jxn3 | GOA 1930 (3 His) mouse-specific | ATAGTCACAGTACCCATCC (SEQ ID NO: 380) | AGTCTGCAACCTGAAGATTTTGC (SEQ ID NO: 381) | CCCTTGGCCGAAGGTGAT (SEQ ID NO: 382) |

Example 6.2. Analysis of Immune Response to Antigen in Mice with Histidine-Substituted Universal Light Chains Cell surface receptor ("Antigen A") was used as the immunogen to immunize mice that were either heterozygous for expression of a pre-arranged human kappa light chain utilizing Vk1-39 and Jk5 that has 4 histidine substitutions in CDR3 (hereinafter "HULC 1927") or heterozygous for expression of a pre-arranged human kappa light chain utilizing Vk1-39 and Jk5 that has 3 histidine substitutions in CDR3 (hereinafter "HULC1930"), or homozygous WT mice. Pre-immune serum was collected from the mice prior to the initiation of immunization. The immunogen was administered at 2.35 μg of protein for the initial priming immunization mixed with 10 μg of CpG oligonucleotide as an adjuvant (Invivogen) in a volume of 25 μl via footpad (f.p.). Subsequently, mice were boosted via the same route with 2.35 μg of Antigen A along with 10 μg of CpG and 25 μg of Adju-Phos (Brenntag) as adjuvants on days 3, 6, 11, 13, 17, 20 for a total of 6 boosts. The mice were bled on days 15 and 22 after the $4^{th}$ and $6^{th}$ boost, respectively. Their antiserum was assayed for antibody titers to Antigen A.

Figure 24:
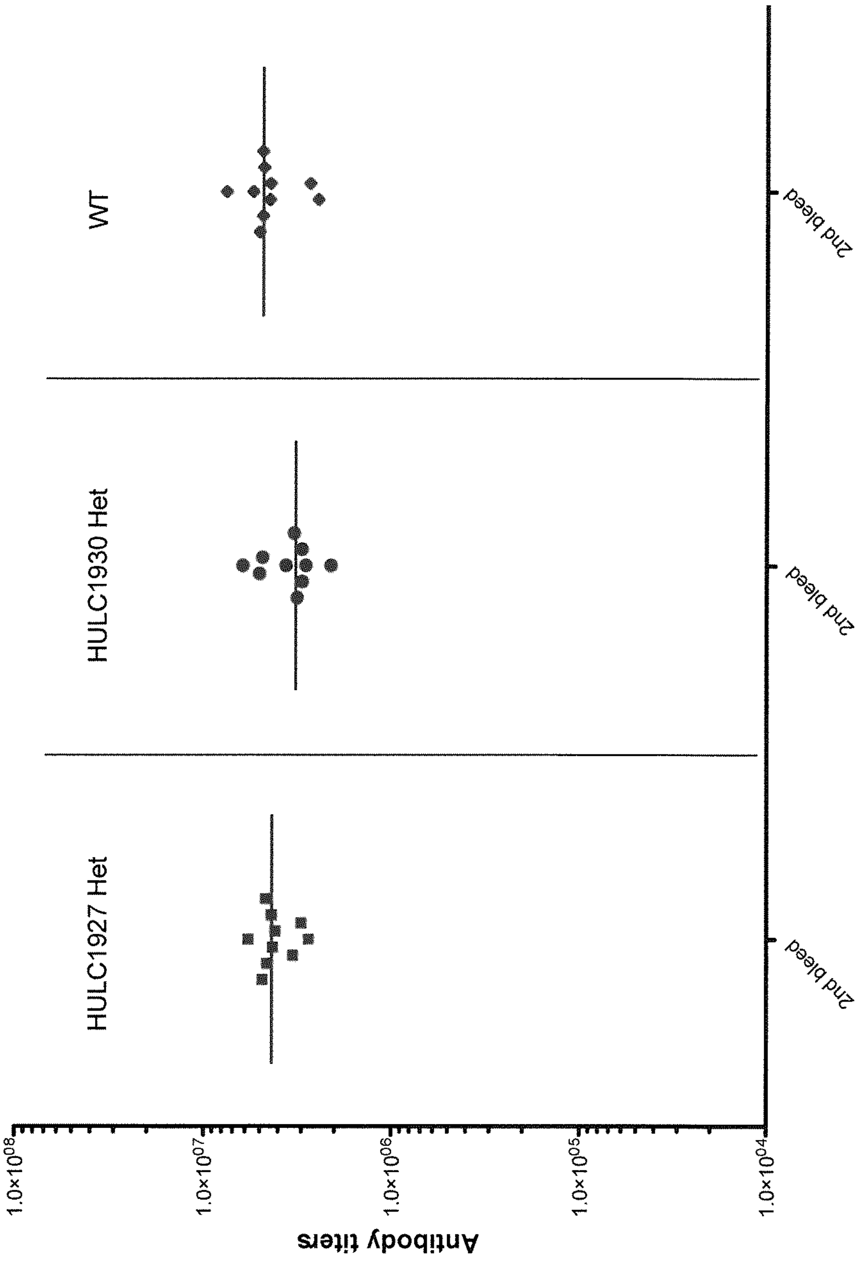
FIG. 24 shows antiserum titers against immunogen from mice heterozygous for histidine universal light chain (HULC) (with 4 His substitutions—HULC 1927 mice; with 3 His substitutions—HULC 1930 mice) and wild type animals in a second bleed.

The immune response induced in mice to the injected immunogen is represented as antibody titers, which is defined as the reciprocal of the highest serum dilution at which antigen binding absorbance is two-fold higher over background. Therefore, the higher the number, the greater the humoral immune response to the immunogen. Antibody titers induced to the immunogen were very high in both strains of HULC mice and in the WT mice, with no significant differences observed among the strains (FIG. 24).

Example 6.3. Generation of pH-Sensitive Monoclonal Antibodies

When a desired immune response to the immunogen was achieved in both strains of HULC mice and in the WT mice, splenocytes from each mouse strain were harvested and fused with mouse myeloma cells to generate hybridoma cells, which were allowed to grow in 96-well plates. After 10 days of growth, supernatants from each hybridoma cell-containing well were screened via immunogen-specific ELISA to identify positive antigen binding samples. For the ELISA, 96 well micro-titer plates were coated with 1 ug/mL of an anti-myc polyclonal antibody (Novus Biologicals, #NB600-34) overnight at 4° C. to immobilize the myc-tagged antigen, followed by blocking with a solution of 0.5% (w/v) BSA in PBS. The plates were washed, the antigen solutions were added to the plates at a concentration of 1 μg/mL and allowed to bind to the coated plate for 1 hour at room temperature. Subsequently, supernatants from hybridoma cells were added to the wells at 1:50 dilution and allowed to bind for 1 hour at room temperature. The plate bound antibodies were detected using an anti-mouse IgG polyclonal antibody conjugated with HRP (Jackson Immunoresearch, #115-035-164). TMB substrates were added to the plates (BD Biosciences, #51-2606KC/51-2607KC) and colorimetric signals were developed according to manufacturer recommended protocol. The absorbance was recorded at 450 nm on a Victor Wallac plate reader. Antigen positive samples defined as having an OD equal to or greater than 0.5 (with the baseline having OD of about 0.1) were subject to affinity screening using a real-time surface plasmon resonance biosensor (Biacore 4000).

Figure 25:
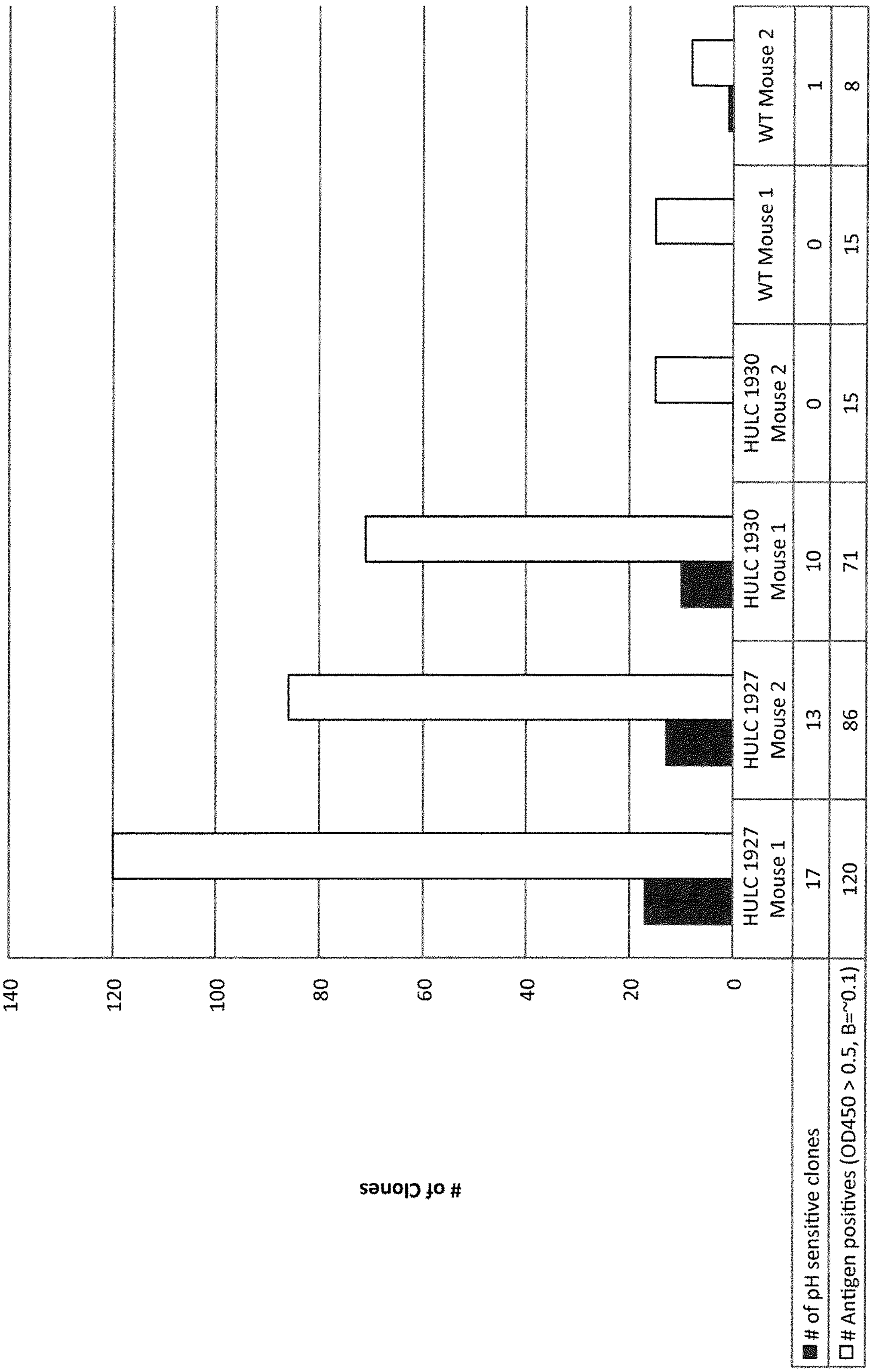
FIG. 25 is a comparison of the number of total antigen positive clones and the number of antigen positive clones displaying pH sensitive antigen binding obtained from hybridoma fusions from HULC (1927 vs 1930) and WT mice. Figure includes data for two mice for each mouse type ("mouse 1" and "mouse 2").

Kinetic binding parameters (e.g., $k_a$, $k_d$, $K_D$, $t_{1/2}$, etc.) for antibody binding to the immunogen at neutral pH (pH 7.4) and at acidic pH (pH 6.0) were recorded. A Biacore CM4 sensor chip was derivatized with a polyclonal goat anti-mouse Fc antibody to capture antibodies from the supernatant. A single concentration (100 nM) of immunogen was then injected over the antibody-captured surface at a flow rate of 30 μl/min. Antibody-antigen association was monitored for 1.5 minutes and then the dissociation of antigen from the captured antibody was monitored for 2.5 minutes. Kinetic association ($k_a$) and dissociation ($k_d$) rate constants were determined by processing and fitting the data to a 1:1 binding with a mass transport model using Biacore 4000 Evaluation software version 1.0. Equilibrium dissociation constants ($K_D$) and dissociative half-lives ($t_{1/2}$) were calculated from the kinetic rate constants as: $K_D$ (M)=$k_d/k_a$; and $t_{1/2}$ (min)=ln 2/(60*$k_d$). A set of samples that displayed decreased binding at pH 6.0 as compared to that at pH 7.4 (pH sensitive) as well as a set of control samples that displayed no significant rate changes between the pH 7.4 and pH 6.0 (pH insensitive controls) were selected to be produced clonally. FIG. 25 depicts comparison of the number of total antigen positives and the number of antigen positives displaying pH-sensitive antigen binding from HULC and WT mice.

Among the antigen positives, 18 and 7 clones isolated from two heterozygous HULC1927 mice and two HULC1930 respectively, and 1 clone from the WT mouse, were made monoclonal. Supernatants of the monoclonal hybridomas were subject to neutral and low pH antigen dissociation rate (off-rate) analysis and cell pellets were used for light chain variable domain DNA sequencing.

Example 6.4. Sequencing and Somatic Hypermutations in CDR3 Region of Vκ1-39Jκ5-Based Histidine Universal Light Chain Mice Cell pellets from monoclonal hybridomas from HULC and WT mice were used for light chain variable domain DNA sequencing. From the 26 clones made monoclonal (see Example 6.3 above) and subjected to sequencing, 15 were confirmed as using either a HULC or WT mouse light chain (MM and NN, see Table 6). 14 clones were derived from HULC heterozygous mice (1927 or 1930 mice) and 1 was derived from a WT mouse.

From the 14 antigen positive samples derived from HULC heterozygous mice, 12 of the monoclonal antibodies utilized their corresponding HULC light chain, while 2 utilized a WT mouse light chain. All but one of the HULC utilizing antibodies retained all of the introduced histidine mutations as shown in Table 6. Sequencing of clone AA produced 2 different HULC sequences, which is reflected by two entries in Table 5.

TABLE 5

Number of conserved histidine insertions and somatic hypermutations in light sequences from clones utilizing the HULC light chain

| | | Light Chain Sequences from mice utilizing HULC | | |
|---|---|---|---|---|
| Clone Name | Mouse Strain | # Conserved His Mutations in CDR3 | # Somatic Hypermutations in Framework | # Somatic Hypermutations in CDRs |
| AA (Sequence 1) | 1927 | 4 | 3 | 0 |
| AA (Sequence 2) | 1927 | 4 | 1 | 1 |
| BB | 1927 | 4 | 3 | 3 |
| CC | 1927 | 4 | 0 | 0 |
| DD | 1927 | 3 | 1 | 1 |
| EE | 1927 | 4 | 2 | 2 |
| FF | 1927 | 4 | 0 | 1 |
| GG | 1927 | 4 | 1 | 1 |
| HH | 1927 | 4 | 2 | 0 |
| II | 1930 | 3 | 1 | 1 |
| JJ | 1930 | 3 | 4 | 5 |
| KK | 1930 | 3 | 1 | 2 |
| LL | 1930 | 3 | 1 | 0 |

Example 6.5. pH-Dependent Binding of Monoclonal Antibodies Generated in Vκ1-39Jκ5-Based Histidine Universal Light Chain Mice In order to further assess the pH-dependent binding characteristics of the monoclonal antibodies isolated from HULC and WT mice, binding experiments were carried out in which the antibody/antigen association phase was observed at neutral pH and the antibody/antigen dissociation phase was observed at either neutral or acidic pHs.

Figure 26A:
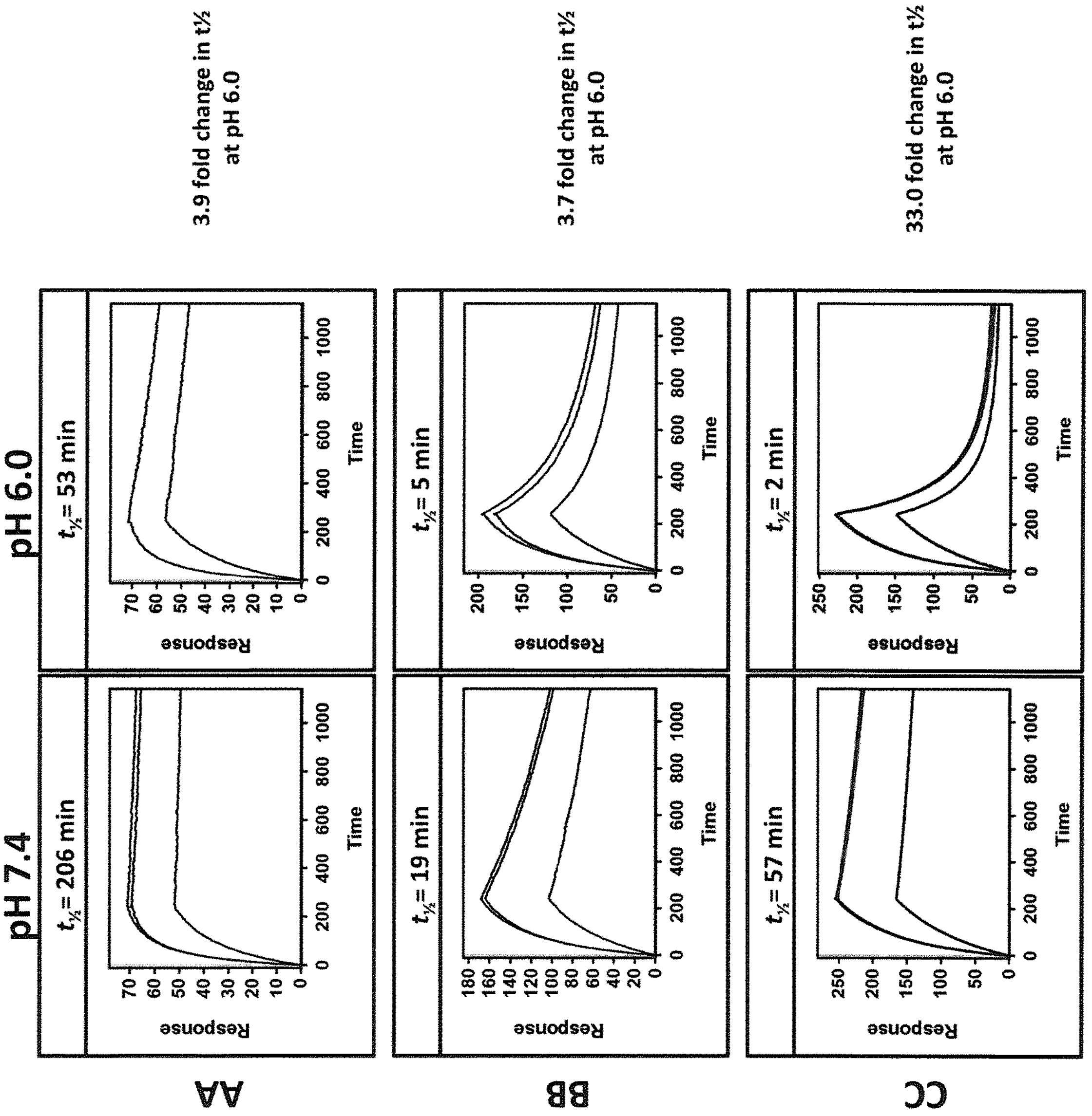
FIGS. 26A-26C show sensorgrams from surface plasmon resonance binding experiments in which monoclonal antibodies (AA, BB, CC, DD, HH, GG, NN, and OO) from either heterozygous HULC or WT mice were allowed to associate with the immunogen at neutral pH (pH 7.4) followed by a shift to a buffer with pH of either 7.4 or 6.0 for the dissociation phase. The individual lines in each graph represent the binding responses at different concentrations of the respective antibodies. All experiments were carried out at 25° C. Dissociative half-life values ($t_{1/2}$) are noted above the respective sensorgrams, and fold change in $t_{1/2}$ is included to the right of each sensorgram. Antibodies AA, BB, CC, DD, HH, and GG were from HULC 1927 mice using His-substituted light chain, NN is from HULC 1927 mouse using WT light chain, and OO is from a WT mouse (See Table 5 for clarification).
Figure 26B:
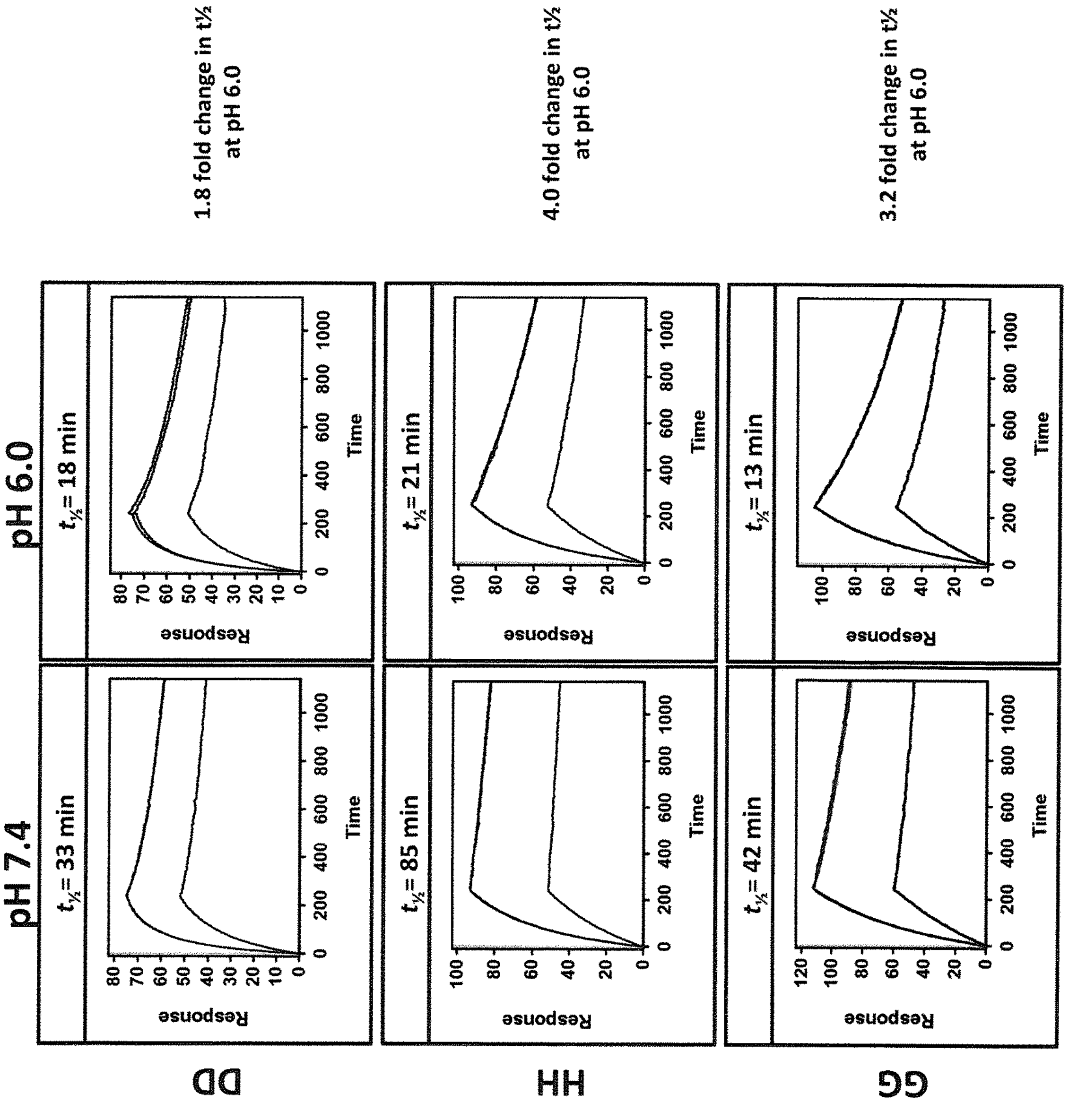
Figure 26C:
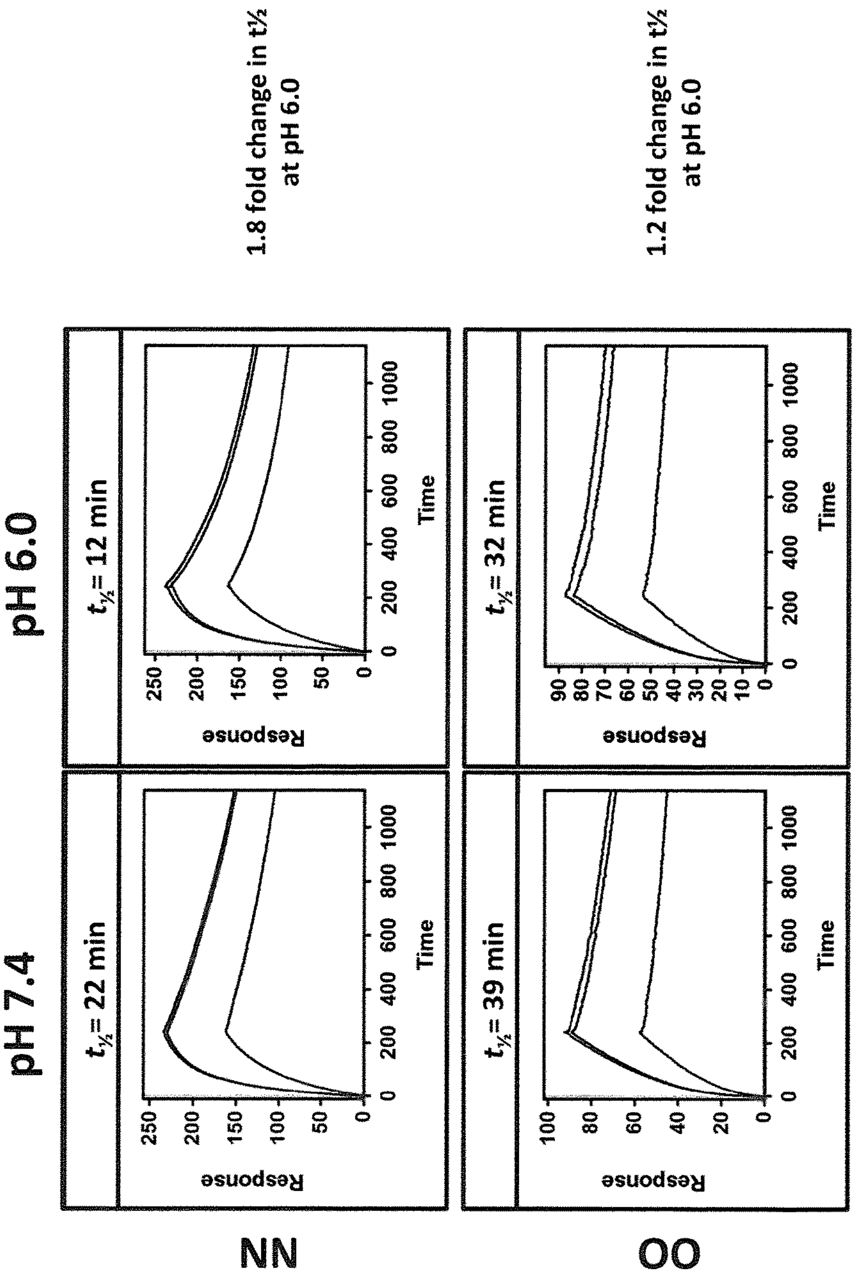

A Biacore CM4 sensor chip was derivatized with a polyclonal rabbit anti-mouse Fc antibody. Monoclonal antibody supernatants were captured onto the anti-mouse Fc sensor surface. Two concentrations, 50 nM (in duplicate) and 16.7 nM, of the immunogen were injected over the monoclonal antibody captured surface at a flow rate of 30 μl/min. Antibody-antigen association was monitored at pH 7.4 for 4 minutes and then the dissociation of antigen from the captured monoclonal antibody was monitored for 15 minutes at either pH 7.4 or 6.0. Dissociation ($k_d$) rate constants were determined by processing and fitting the data using Scrubber version 2.0 curve fitting software and are shown in Table 6. Dissociative half-lives ($t_{1/2}$) were calculated from the dissociation rate constants as: $t_{1/2}$ (min)=(ln 2/$k_d$)/60, and are shown in Table 6. Sensorgrams depicting the association/dissociation characteristics of several antibodies listed in Table 4 under the various pH conditions are shown graphically in FIG. 26. The individual lines in each graph represent the binding responses at different concentrations of the respective antibodies. All experiments were carried out at 25° C. Dissociative half-life values ($t_{1/2}$) are noted above the respective sensorgrams. Response is measured in RU.

TABLE 6

Dissociation ($k_d$) rate constants and dissociative half-lives ($t_{1/2}$) of monoclonal HULC or WT antibodies binding to their immunogen at neutral and low pH.

| | | pH 7.4 Association/pH 7.4 Dissociation | | | | pH 7.4 Association/pH 6.0 Dissociation | | | | pH 6.0/pH7.4 ratio | |
|---|---|---|---|---|---|---|---|---|---|---|---|
| Clone Name | Light chain used | neutral mAb capture | 50 nM immunogen bound (RU) | $k_d$ (1/s) | $t_{1/2}$ (min) | low mab capture | 50 nM immunogen bound (RU) | $k_d$ (1/s) | $t_{1/2}$ (min) | $k_d$ | $t_{1/2}$ |
| AA | HULC (1927) | 129 | 70 | 5.60E−05 | 206 | 122 | 73 | 2.18E−04 | 53 | 3.9 | 0.3 |
| BB | HULC (1927) | 350 | 165 | 6.00E−04 | 19 | 378 | 185 | 2.20E−03 | 5 | 3.7 | 0.3 |
| CC | HULC (1927) | 611 | 251 | 2.03E−04 | 57 | 545 | 226 | 6.68E−03 | 2 | 33.0 | 0.03 |
| DD | HULC (1927) | 182 | 75 | 3.55E−04 | 33 | 168 | 74 | 6.44E−04 | 18 | 1.8 | 0.6 |
| HH | HULC (1927) | 268 | 92 | 1.36E−04 | 85 | 251 | 91 | 5.39E−04 | 21 | 4.0 | 0.3 |
| GG | HULC (1927) | 353 | 110 | 2.78E−04 | 42 | 328 | 102 | 8.97E−04 | 13 | 3.2 | 0.3 |
| FF | HULC (1927) | 334 | 202 | 4.79E−05 | 241 | 364 | 220 | 6.90E−05 | 167 | 1.4 | 0.7 |
| EE | HULC (1927) | 339 | 124 | 5.08E−04 | 23 | 299 | 120 | 4.66E−04 | 25 | 0.9 | 1.1 |
| II | HULC (1930) | 387 | 174 | 1.22E−04 | 95 | 334 | 147 | 2.14E−04 | 54 | 1.8 | 0.6 |
| JJ | HULC (1930) | 363 | 14 | 9.83E−04 | 12 | 333 | 12 | 5.30E−04 | 22 | 0.5 | 1.9 |
| KK | HULC (1930) | 490 | 303 | 7.41E−05 | 156 | 484 | 295 | 1.29E−04 | 90 | 1.7 | 0.6 |
| LL | HULC (1930) | 636 | 41 | 3.09E−04 | 37 | 597 | 36 | 5.77E−04 | 20 | 1.9 | 0.5 |
| MM* | WT (from 1927 mouse) | 245 | 6 | NA | NA | 203 | 6 | NA | NA | NA | NA |
| NN | WT (from 1927 mouse) | 394 | 231 | 5.26E−04 | 22 | 378 | 231 | 9.35E−04 | 12 | 1.8 | 0.6 |
| OO | WT | 413 | 89 | 2.94E−04 | 39 | 400 | 83 | 3.57E−04 | 32 | 1.2 | 0.8 |

*$k_d$ and $t_{1/2}$ values could not be determined due to low antigen binding signal

Example 7. Engineering of Genetically Modified Mouse Comprising a Histidine-Substituted Vκ3-20Jκ1 Universal Light Chain A mouse comprising a common Vκ3-20Jκ1 light chain was generated as described in, e.g., U.S. patent application Ser. Nos. 13/022,759, 13/093,156, 13/412,936, and 13/488,628 (Publication Nos. 2011/0195454, 2012/0021409, 2012/0192300, and 2013/0045492, respectively), and in Example 1 above. The amino acid sequence of the germline universal Vκ3-20Jκ1 light chain variable domain is set forth in SEQ ID NO:383.

Histidine substitutions were introduced into the Vκ3-20Jκ1 universal light chain targeting vector and mice generated from the same using a similar strategy to the one described above in Example 3 for Vκ1-39Jκ5 histidine modified universal light chain mice (HULC 1927 and 1930).

Figure 29A:
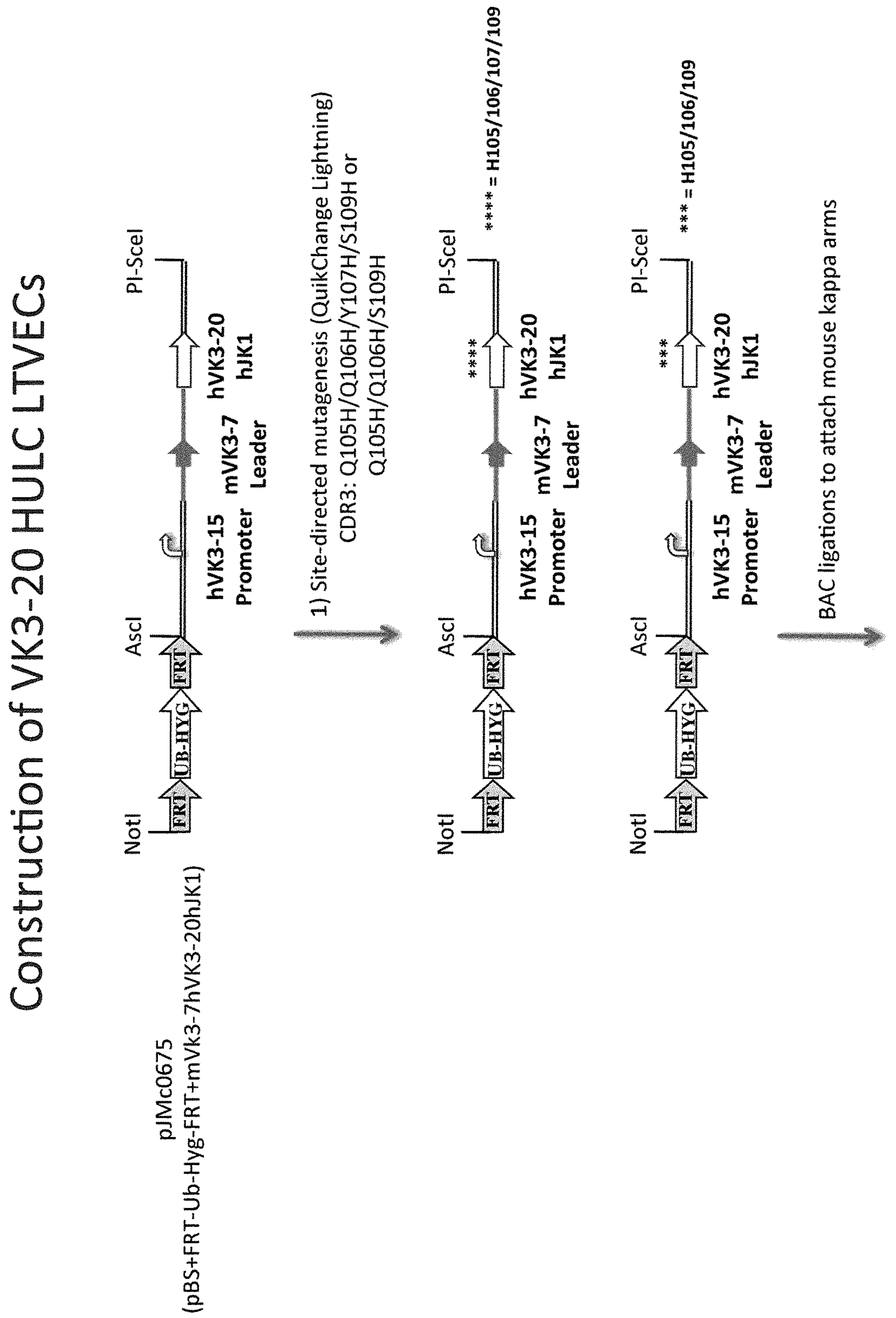
FIGS. 29A-29B show a general strategy for construction of targeting vectors for the engineering of histidine residues into a rearranged human light chain variable region sequence derived from Vκ3-20/Jκ1 light chain variable region for making a genetically modified mouse that expresses antibodies containing the modified human light chain.
Figure 29B:
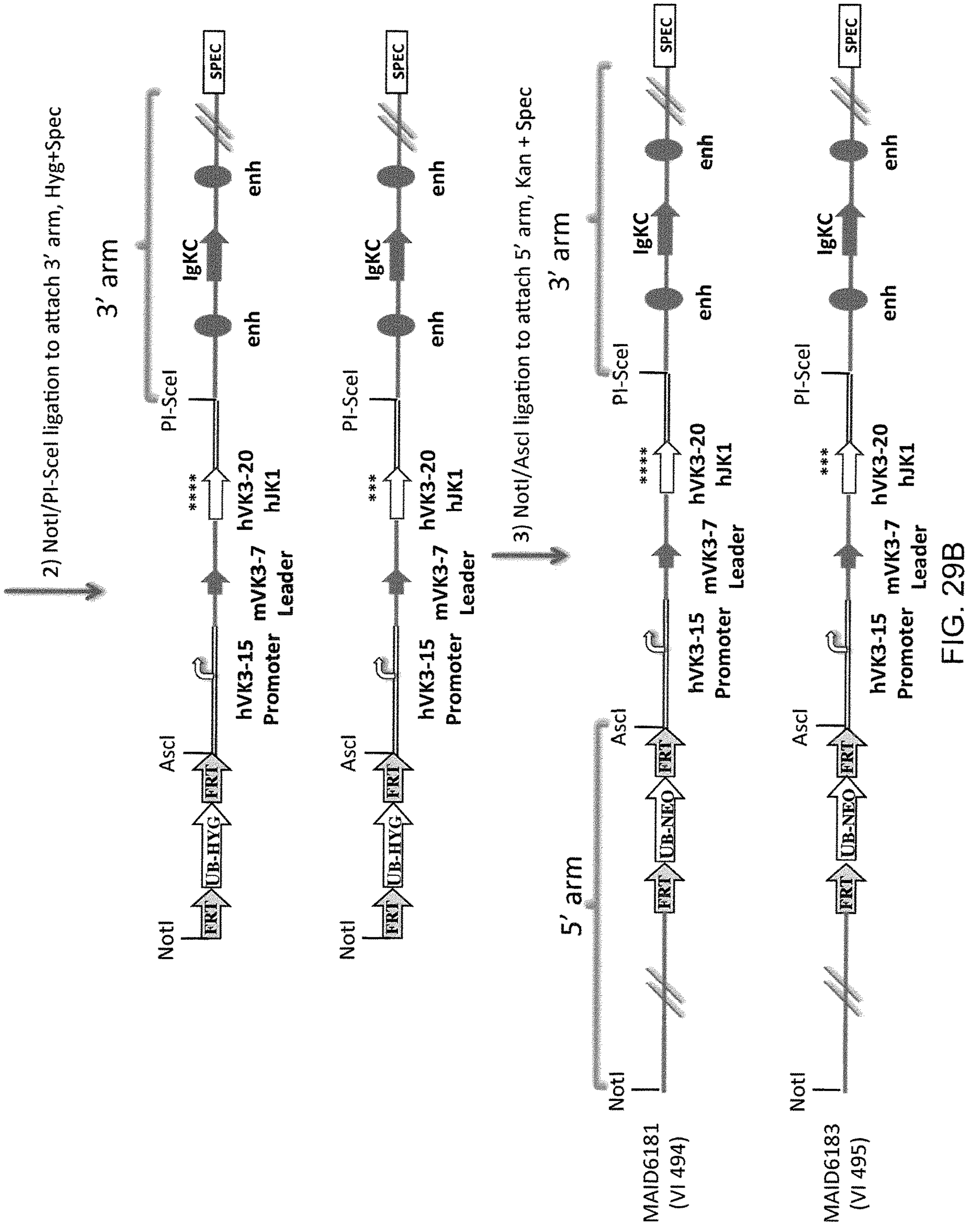
Figure 29C:
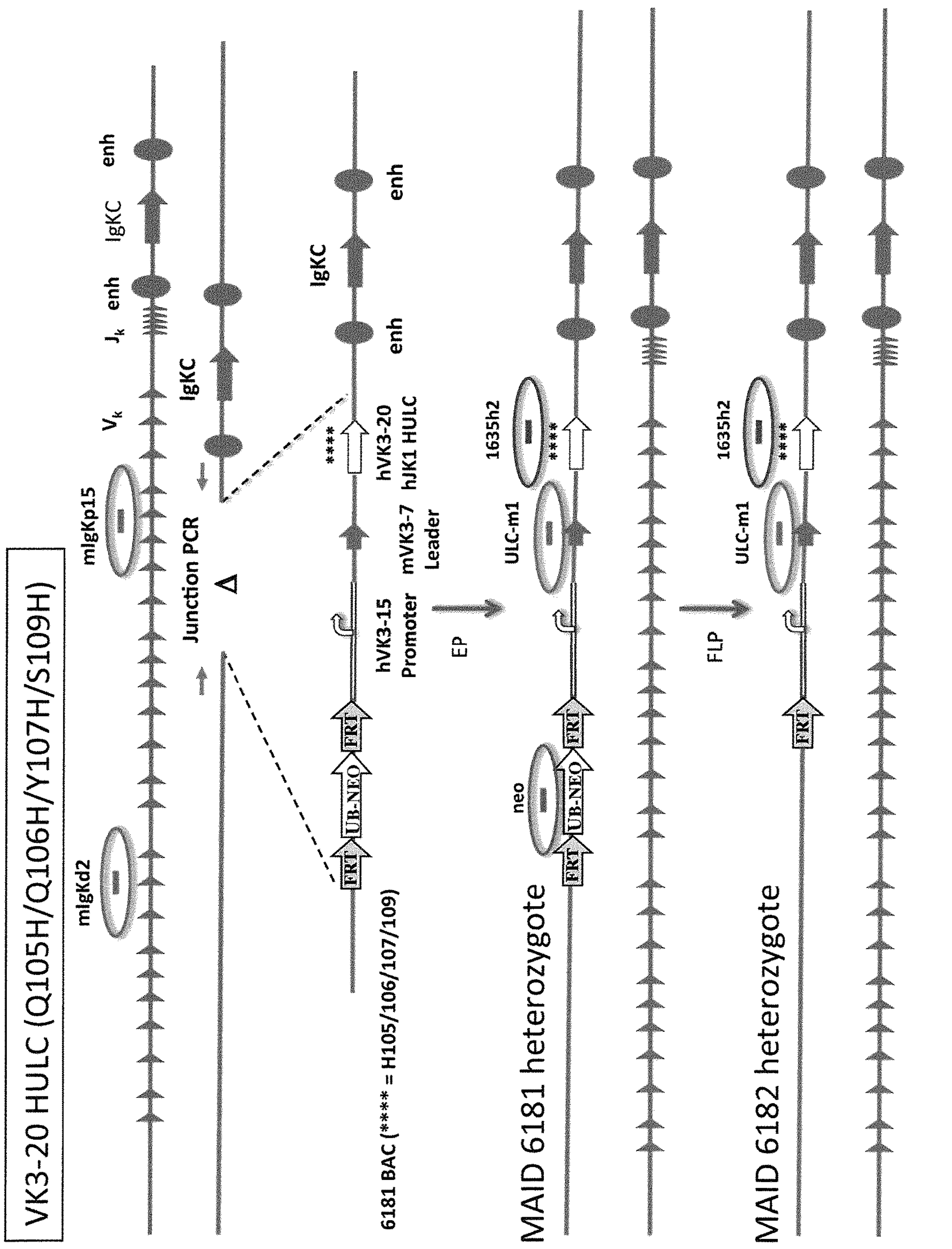
Figure 29D:
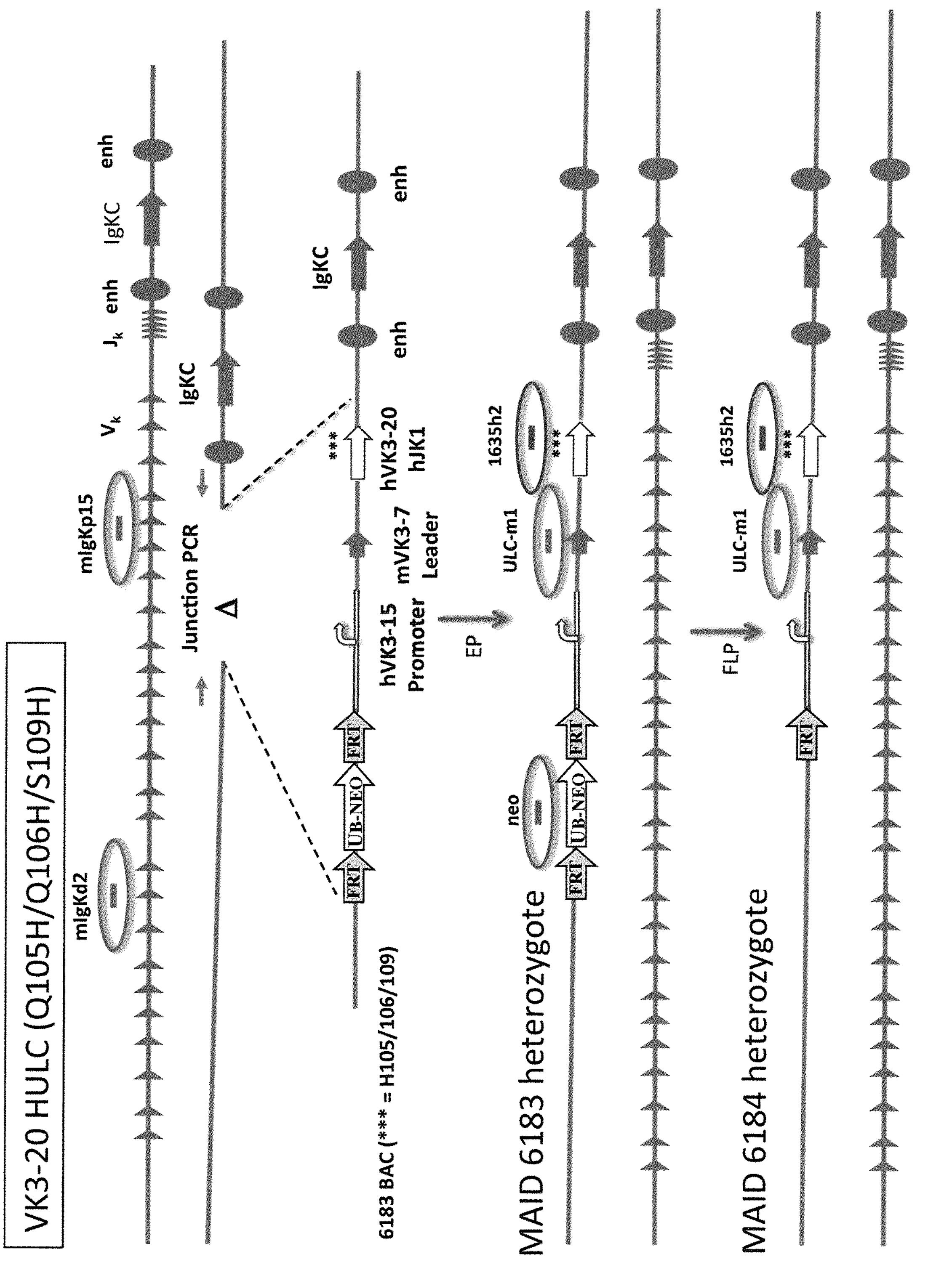
FIG. 29D shows introduction of the targeting vector for ULC-Q105H/Q106H/S109H substitutions into ES cells and generation of heterozygous mice from the same. The diagrams are not presented to scale. Unless indicated otherwise, filled shapes and solid lines represent mouse sequence, empty shapes and double lines represent human sequence.

Briefly, the strategy for generating a histidine-modified Vκ3-20Jκ1 universal light chain targeting vector is summarized in FIGS. 29A-129D. A plasmid used for generating a targeting vector for common (universal) light chain mouse ("ULC mouse," described in, e.g., US2011/0195454A1), containing pBS+FRT-Ub-Hyg-FRT+mouse Vκ3-7 leader+human Vκ3-20Jκ1 was modified by site directed mutagenesis (QuickChange Lightning Kit) to replace Q105, Q106, Y107 and S109 or Q105, Q106 and S109 (see alignment in FIG. 27) with histidine residues in the CDR3 region using site-directed mutagenesis primers shown in FIG. 28 (See FIG. 29A for this engineering step). Resultant vectors (H105/106/107/109 and H105/106/109) were modified further and ligated into a vector comprising mouse Igκ constant region, mouse enhancers, a mouse 3' homology arm and a SPEC cassette (FIG. 29B). Further modification involved ligation into a vector carrying 5' mouse arm and comprising Frt-UB-NEO-Frt cassette (FIG. 29B). Resultant targeting vectors were electroporated into ES cells comprising deletion of the mouse Igκ variable locus (comprising κ variable and joining gene segments) (FIGS. 29C-29D).

Positive ES cell clones were confirmed by using a modification of allele assay (Valenzuela et al.) using probes specific for the engineered Vκ3-20κJ1 light chain region inserted into the endogenous κ light chain locus. Primers and probes used in the assay are shown in Table 7 below and set forth in the Sequence Listing; the locations of the probes are depicted in FIGS. 29C-29D.

TABLE 7

| Primers and Probes Used for ES Cell Screening | | | | |
|---|---|---|---|---|
| Probe Name | Assay | Probe Sequence | 5' Primer | 3' Primer |
| Neo | GOA | TGGGCACAAC AGACAATCGG CTG (SEQ ID NO: 362) | GGTGGAGAG GCTATTCGGC (SEQ ID NO: 363) | GAACACGGC GGCATCAG (SEQ ID NO: 364) |
| ULC-m1 | GOA | CCATTATGATG CTCCATGCCT CTCTGTTC (SEQ ID NO: 365) | AGGTGAGGG TACAGATAAG TGTTATGAG (SEQ ID NO: 366) | TGACAAATGC CCTAATTATA GTGATCA (SEQ ID NO: 367) |
| 1635h2 (Vκ3-20Jκ1 specific) | GOA | AAAGAGCCAC CCTCTCCTGC AGGG (SEQ ID NO: 389) | TCCAGGCACC CTGTCTTTG (SEQ ID NO: 390) | AAGTAGCTGC TGCTAACACT CTGACT (SEQ ID NO: 391) |
| mIgKd2 | Retention | GGCCACATTC CATGGGTTC (SEQ ID NO: 371) | GCAAACAAAA ACCACTGGCC (SEQ ID NO: 372) | CTGTTCCTCT AAAACTGGAC TCCACAGTAA ATGGAAA (SEQ ID NO: 373) |
| mIgKp15 | Retention | GGGCACTGGA TACGATGTATG G (SEQ ID NO: 374) | CACAGCTTGT GCAGCCTCC (SEQ ID NO: 375) | AGAAGAAGCC TGTACTACAG CATCCGTTTT ACAGTCA (SEQ ID NO: 376) |

The NEO selection cassette introduced by the targeting constructs is deleted by transfecting ES cells with a plasmid that expresses FLP (FIGS. 29C and 29D). Optionally, the neomycin cassette may be removed by breeding to mice that express FLP recombinase (e.g., U.S. Pat. No. 6,774,279). Optionally, the neomycin cassette is retained in the mice.

Targeted ES cells described above are used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® independently bearing an engineered human light chain gene that contains histidine residues mutated into one or more positions along the sequence are made from the targeted ES cells described above.

Pups are genotyped and pups heterozygous for the engineered histidine-modified human light chain are selected for characterizing expression of the light chain and binding capabilities of the expressed antibodies. Primers and probes for genotyping of mice specifically comprising a universal light chain gene with either three (H105/106/109; “6183”) or four (H105/105/108/111; “6181”) histidine modifications are listed in Table 6 below and set forth in the Sequence Listing. Mice containing histidine modification in their universal light chains are referred herein as “HULC” mice (histidine universal light chain mice).

TABLE 8

| Primers and Probes Used for Genotyping | | | | |
|---|---|---|---|---|
| Probe Name | Assay | Probe Sequence | 5' Primer | 3' Primer |
| hVI494-1 | GOA 6181 (4 His) mouse-specific | CTGTCATCACC ATGG (SEQ ID NO: 392) | GCAGACTGGA GCCTGAAGAT TTT (SEQ ID NO: 393) | CCGAACGTCCAA GGTGAGTG (SEQ ID NO: 394) |
| hVI495-1 | GOA 6183 (3 His) mouse-specific | TACTGTCATCA CTATGG (SEQ ID NO: 395) | GCAGACTGGA GCCTGAAGAT TT (SEQ ID NO: 396) | CCGAACGTCCAA GGTGAGTG (SEQ ID NO: 397) |

Mice are immunized with antigen of interest and tested for ability to generate antibodies with pH-dependent binding.

Example 8. Breeding of Mice Comprising a Histidine-Substituted Single Rearranged Human Universal Light Chain Mouse (HULC)

This Example describes several other genetically modified mouse strains that can be bred to any one of the HULC mice described herein to create multiple genetically modified mouse strains harboring multiple genetically modified immunoglobulin loci.

Endogenous Igλ Knockout (KO). To optimize the usage of the engineered light chain locus, any one of the HULC animals described above (e.g., comprising Vκ1-39Jκ5 or Vκ3-20Jκ1 histidine-substituted universal light chain) may be bred to another mouse containing a deletion in the endogenous λ light chain locus. In this manner, the progeny obtained will express, as their only light chain, the rearranged histidine-substituted human germline light chain region as described in Examples 3 and 4 above. Breeding is performed by standard techniques recognized in the art and, alternatively, by a commercial breeder (e.g., The Jackson Laboratory). Mouse strains bearing an engineered histidine-substituted light chain locus and a deletion of the endogenous λ light chain locus are screened for presence of the unique light chain region and absence of endogenous mouse λ light chains.

Humanized Endogenous Heavy Chain Locus. Mice bearing an engineered human germline light chain locus (HULC mice) are bred with mice that contain a replacement of the endogenous mouse heavy chain variable gene locus with the human heavy chain variable gene locus (see U.S. Pat. No. 6,596,541; the VELOCIMMUNE® mouse, Regeneron Pharmaceuticals, Inc.). The VELOCIMMUNE® mouse comprises a genome comprising human heavy chain variable regions operably linked to endogenous mouse constant region loci such that the mouse produces antibodies comprising a human heavy chain variable domain and a mouse heavy chain constant region in response to antigenic stimulation.

Mice bearing a replacement of the endogenous mouse heavy chain variable region locus with the human heavy chain variable region locus and a histidine-substituted single rearranged human light chain variable region at the endogenous κ light chain locus are obtained. Reverse chimeric antibodies containing somatically mutated heavy chains (human heavy chain variable domain and mouse $C_H$) with a histidine-substituted single human light chain (HULC, human light chain variable domain and mouse $C_L$) are obtained upon immunization with an antigen of interest. pH-dependent human antibodies generated in such mice are identified using antibody isolation and screening methods known in the art or described above. Variable light and heavy chain region nucleotide sequences of B cells expressing the antibodies, e.g., pH-sensitive antibodies, are identified, and fully human antibodies are made by fusion of the variable heavy and light chain region nucleotide sequences to human $C_H$ and $C_L$ nucleotide sequences, respectively, in a suitable expression system.

Example 9. Progeny of Genetically Modified Mice

Mice bearing an engineered human germline light chain locus comprising a limited repertoire of rearranged human light chain variable region sequences or a single rearranged human light chain variable region sequence (HULC mice) described herein are bred with mice that contain a histidine-modified human heavy chain variable gene locus described herein. Mice are obtained, and the presence of a light chain sequence containing histidine-modified human light chain variable region and a heavy chain sequence containing a histidine-modified human heavy chain variable region is confirmed by genotyping.

Reverse chimeric antibodies containing histidine-modified heavy chains (human histidine-modified heavy chain variable domain and mouse $C_H$) and histidine-modified single human light chain (HULC, human histidine-modified light chain variable domain and mouse $C_L$) are obtained upon immunization with an antigen of interest. pH-dependent human antibodies generated in such mice are identified using antibody isolation and screening methods known in the art or described above. Variable light and heavy chain region nucleotide sequences of B cells expressing the antibodies, e.g., pH-sensitive antibodies, are identified, and fully human antibodies are made by fusion of the variable heavy and light chain region nucleotide sequences to human $C_H$ and $C_L$ nucleotide sequences, respectively, in a suitable expression system.

EQUIVALENTS

Those skilled in the art will recognize, or be able to ascertain using no more than routine experimentation, many equivalents of the specific embodiments of the invention described herein. Such equivalents are intended to be encompassed by the following claims. While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

Entire contents of all non-patent documents, patent applications and patents cited throughout this application are incorporated by reference herein in their entirety. U.S. patent application Ser. Nos. 13/832,309 and 13/832,247, each filed 15 Mar. 2013, are hereby incorporated by reference.

What is claimed is:

1. A method of obtaining a lymphocyte that expresses an antigen-specific immunoglobulin variable domain with histidines encoded by germline histidine codons, comprising harvesting the lymphocyte from a non-human animal, wherein the non-human animal comprises in its germline genome either or both (i) at an endogenous immunoglobulin heavy chain locus, an unrearranged immunoglobulin heavy chain variable region gene sequence comprising an unrearranged human $V_H$ gene segment, an unrearranged $D_H$ gene segment, and an unrearranged human $J_H$ gene segment operably linked to an immunoglobulin heavy chain constant region gene sequence, wherein one or more of the unrearranged human $V_H$, unrearranged $D_H$, and unrearranged human $J_H$ gene segments comprise, in a complementarity determining region 3 (CDR3) encoding sequence, a substitution of at least one non-histidine codon with a histidine codon or an insertion of at least one histidine codon and (ii) at an endogenous immunoglobulin light chain locus, an unrearranged human immunoglobulin light chain variable region gene sequence comprising unrearranged human $V_L$ and unrearranged human $J_L$ gene segments operably linked to an endogenous immunoglobulin light chain constant region gene sequence, wherein one or more of the unrearranged human $V_L$ and $J_L$ gene segments comprise, in a CDR3 encoding sequence, a substitution of at least one non-histidine codon with a histidine codon or an insertion of at least one histidine codon;

wherein the non-human animal further comprises in vivo a diverse repertoire of antibodies that bind an antigen of interest, wherein each of the diverse repertoire of antibodies comprises (a) an immunoglobulin heavy chain variable domain that retains, in a CDR3, at least one histidine amino acid encoded by the substituted or inserted histidine codon in the germline genome and/or (b) an immunoglobulin light chain variable domain that retains, in a CDR3, at least one histidine amino acid encoded by the substituted or inserted histidine codon in the germline genome; and wherein the lymphocyte expresses one of the diverse repertoire of antibodies.

2. The method of claim 1, wherein the unrearranged $D_H$ gene segment comprises a synthetic D segment.

3. The method of claim 1, wherein the unrearranged human $D_H$ gene segment comprises an inverted human $D_H$ segment.

4. The method of claim 1, wherein an endogenous non-human immunoglobulin heavy chain variable region gene sequence is replaced with the unrearranged immunoglobulin heavy chain variable region gene sequence such that the unrearranged immunoglobulin heavy chain variable region gene sequence is operably linked to an endogenous non-human immunoglobulin heavy chain constant region gene sequence, and/or wherein an endogenous non-human immunoglobulin light chain variable region gene sequence is replaced with the unrearranged human immunoglobulin light chain variable region gene-sequence such that the unrearranged human immunoglobulin light chain variable region gene sequence is operably linked to an endogenous non-human immunoglobulin light chain constant region gene sequence.

5. The method of claim 1, wherein the unrearranged immunoglobulin heavy chain variable region gene sequence and/or the unrearranged human immunoglobulin light chain variable region gene sequence further comprises a substituted or inserted histidine codon in a CDR1 encoding sequence, a CDR2 encoding sequence, and/or an N terminal encoding sequence or a loop encoding sequence.

6. The method of claim 1, wherein the non-human animal is a rat, a mouse, or a hamster.

7. The method of claim 1, further comprising a step of producing a hybridoma from the harvested lymphocyte.

8. A hybridoma produced according to the method of claim 7.

9. The method of claim 1, further comprising obtaining from the harvested lymphocyte, or a hybridoma produced therefrom, a first nucleotide sequence that encodes the immunoglobulin heavy chain variable domain that retains at least one histidine amino acid encoded by the substituted or inserted histidine codon in the germline genome and/or a second nucleotide sequence that encodes the immunoglobulin light chain variable domain that retains at least one histidine amino acid encoded by the substituted or inserted histidine codon in the germline genome; and expressing in a cell a first nucleic acid operably linked to a human heavy chain constant region gene sequence and/or a second nucleic acid operably linked to a human light chain constant region gene sequence, wherein the first nucleic acid comprises a sequence identical to the first nucleotide sequence, and wherein the second nucleic acid comprises a sequence identical to the second nucleotide sequence.

10. A nucleic acid comprising a sequence identical to the first nucleotide sequence or the second nucleotide sequence obtained according to the method of claim 9.

11. A cell comprising the nucleic acid of claim 10.

12. An immunoglobulin variable domain made by the lymphocyte obtained by the method of claim 1.

13. A method of obtaining a lymphocyte that expresses an antigen-specific immunoglobulin variable domain with histidines encoded by germline histidine codons, comprising harvesting the lymphocyte from a non-human animal;

wherein the non-human animal comprises in its germline genome both (i) at an endogenous immunoglobulin heavy chain locus, an unrearranged human immunoglobulin heavy chain variable region gene sequence comprising unrearranged human $V_H$, unrearranged human $D_H$, and unrearranged human $J_H$ gene segments operably linked to an immunoglobulin heavy chain constant region gene sequence, wherein one or more of the unrearranged human $V_H$, unrearranged human $D_H$, and unrearranged human $J_H$ gene segments comprise, in a CDR3 encoding sequence, a substitution of at least one non-histidine codon with a histidine codon or an insertion of at least one histidine codon, and (ii) at an endogenous immunoglobulin light chain locus, a rearranged human immunoglobulin light chain variable region gene sequence comprising a human $V_L$ gene segment rearranged with a human $J_L$ gene segment operably linked to an endogenous immunoglobulin light chain constant region gene sequence, wherein the rearranged human immunoglobulin light chain variable region gene sequence comprises, in a CDR3 encoding sequence, a substitution of at least one non-histidine codon with a histidine codon or an insertion of at least one histidine codon;

wherein the non-human animal further comprises in vivo a diverse repertoire of antibodies that bind an antigen of interest, wherein each of the diverse repertoire of antibodies comprises an immunoglobulin light chain variable domain that is encoded by the rearranged human immunoglobulin light chain variable region gene sequence, wherein the immunoglobulin light chain variable domain retains, in a CDR3, at least one histidine amino acid encoded by the substituted or inserted histidine codon in the germline genome; and wherein the lymphocyte expresses one of the diverse repertoire of antibodies.

14. The method of claim 13, wherein an endogenous non-human immunoglobulin heavy chain variable region gene is replaced with the unrearranged human immunoglobulin heavy chain variable region gene sequence such that the unrearranged human immunoglobulin heavy chain variable region gene sequence is operably linked to an endogenous non-human immunoglobulin heavy chain constant region gene sequence, and wherein an endogenous non-human immunoglobulin light chain variable region gene is replaced with the rearranged human immunoglobulin light chain variable region gene sequence such that the rearranged human immunoglobulin light chain variable region gene sequence is operably linked to an endogenous non-human immunoglobulin light chain constant region gene sequence.

15. The method of claim 13, wherein the rearranged human immunoglobulin light chain variable region gene sequence comprises a rearranged human Vκ1-39 gene segment or a rearranged human Vκ3-20 gene segment.

16. The method of claim 13, wherein the unrearranged human immunoglobulin heavy chain variable region gene sequence and/or the rearranged human immunoglobulin light chain variable region gene sequence further comprises a substituted or inserted histidine codon in a CDR1 encoding sequence, a CDR2 encoding sequence, and/or an N terminal encoding sequence or a loop encoding sequence.

17. The method of claim 13, wherein the non-human animal is a rat, a mouse, or a hamster.

18. The method of claim 13, further comprising a step of producing a hybridoma from the harvested lymphocyte.

19. A hybridoma formed according to the method of claim 18.

20. The method of claim 13, further comprising obtaining from the harvested lymphocyte, or a hybridoma produced therefrom, a first nucleotide sequence that encodes the immunoglobulin heavy chain variable domain that is cognate to the immunoglobulin light chain variable domain, and the immunoglobulin heavy chain variable domain comprises at least one histidine amino acid that is encoded by the substituted or inserted histidine codon in the germline; and expressing in a cell a first nucleic acid operably linked to a human heavy chain constant region gene sequence and a second nucleic acid operably linked to a human light chain constant region gene sequence, wherein the first nucleic acid comprises a sequence identical to the first nucleotide sequence, and wherein the second nucleic acid comprises a sequence identical to the rearranged human immunoglobulin light chain variable region gene sequence.

21. The method of claim 20, wherein the cell further comprises a third nucleic acid operably linked to a human heavy chain constant region gene sequence, wherein the third nucleic acid encodes a different immunoglobulin heavy chain variable domain that is cognate to the immunoglobulin light chain variable domain, and wherein the cell expresses the first, second and third nucleic acids as a bi-specific antibody.

22. The method of claim 21, wherein one of the human heavy chain constant region genes is modified to omit a Protein A-binding determinant.

23. A nucleic acid comprising a sequence identical to the first nucleotide sequence obtained according to the method of claim 20.

24. A cell comprising the nucleic acid of claim 23.

25. An antigen-specific antibody made by the lymphocyte obtained according to the method of claim 13.

26. The method of claim 13, wherein the unrearranged human $D_H$ gene segment comprises a synthetic D segment.

27. The method of claim 13, wherein the unrearranged human $D_H$ gene segment comprises an inverted human $D_H$ segment.

* * * * *